(12) United States Patent
Stark et al.

(10) Patent No.: US 11,642,415 B2
(45) Date of Patent: May 9, 2023

(54) HYDROGEL CROSS-LINKED HYALURONIC ACID PRODRUG COMPOSITIONS AND METHODS

(71) Applicant: Ascendis Pharma A/S, Hellerup (DK)

(72) Inventors: Sebastian Stark, Heidelberg (DE); Thomas Knappe, Heidelberg (DE); Harald Rau, Heidelberg (DE); Nicola Bisek, Heidelberg (DE); Burkhardt Laufer, Heidelberg (DE); Samuel Weisbrod, Heidelberg (DE); Tobias Voigt, Heidelberg (DE)

(73) Assignee: Ascendis Pharma A/S, Hellerup (DK)

(*) Notice: Subject to any disclaimer, the term of this patent is extended or adjusted under 35 U.S.C. 154(b) by 0 days.

(21) Appl. No.: 16/575,749

(22) Filed: Sep. 19, 2019

(65) Prior Publication Data

US 2020/0222547 A1    Jul. 16, 2020

Related U.S. Application Data

(63) Continuation of application No. PCT/US2018/023857, filed on Mar. 22, 2018.

(60) Provisional application No. 62/475,094, filed on Mar. 22, 2017.

(51) Int. Cl.
| A61K 47/61 | (2017.01) |
| A61K 47/69 | (2017.01) |
| A61K 9/00 | (2006.01) |
| A61K 39/395 | (2006.01) |

(52) U.S. Cl.
CPC ........... *A61K 47/61* (2017.08); *A61K 9/0019* (2013.01); *A61K 9/0048* (2013.01); *A61K 39/395* (2013.01); *A61K 47/6903* (2017.08)

(58) Field of Classification Search
CPC ............. A61K 47/6903; A61K 9/0019; A61K 9/0048; A61K 39/395
USPC ...................................................... 424/136.1
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,128,326 A | 7/1992 | Balazs et al. |
| 5,571,894 A | 11/1996 | Wels et al. |
| 5,587,458 A | 12/1996 | King et al. |
| 5,591,828 A | 1/1997 | Bosslet et al. |
| 5,648,237 A | 7/1997 | Carter |
| 5,690,961 A | 11/1997 | Nguyen |
| 5,731,168 A | 3/1998 | Carter et al. |
| 5,750,373 A | 5/1998 | Garrard et al. |
| 5,789,199 A | 8/1998 | Joly et al. |
| 5,821,337 A | 10/1998 | Carter et al. |
| 5,837,747 A | 11/1998 | Soon-Shiong et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,248,516 B1 | 6/2001 | Winter et al. |
| 6,417,429 B1 | 7/2002 | Hein et al. |
| 6,420,548 B1 | 7/2002 | Vezina et al. |
| 6,982,321 B2 | 1/2006 | Winter |
| 7,087,409 B2 | 8/2006 | Barbas et al. |
| 7,125,978 B1 | 10/2006 | Vezina et al. |
| 7,527,791 B2 | 5/2009 | Adams et al. |
| 7,585,837 B2 | 9/2009 | Shechter et al. |
| 7,758,859 B2 | 7/2010 | Fuh et al. |
| 8,618,124 B2 | 12/2013 | Greenwald et al. |
| 8,679,536 B2 | 3/2014 | Arthur |
| 8,754,190 B2 | 6/2014 | Ashley et al. |
| 8,946,405 B2 | 2/2015 | Ashley et al. |
| 9,044,515 B2 | 6/2015 | Baldwin et al. |
| 2005/0003013 A1 | 1/2005 | Yui et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2006/0025576 A1 | 2/2006 | Miller et al. |
| 2006/0110458 A1 | 5/2006 | Hahn et al. |
| 2007/0117126 A1 | 5/2007 | Sidhu et al. |
| 2007/0160598 A1 | 7/2007 | Dennis et al. |
| 2007/0224277 A1 | 9/2007 | Borbely et al. |
| 2007/0237764 A1 | 10/2007 | Birtalan et al. |
| 2007/0292936 A1 | 12/2007 | Barthelemy et al. |

(Continued)

FOREIGN PATENT DOCUMENTS

| CA | 2988010 A1 | 12/2016 |
| CN | 101538377 A | 9/2009 |

(Continued)

OTHER PUBLICATIONS

Almagro et al., "Humanization of Antibodies," Frontiers in Bioscience, 13(1): 1619-1633 (2008).
Baca et al., "Antibody Humanization Using Monovalent Phage Display," Journal of Biological Chemistry, 272(16): 10678-10684 (1997).
Brennan et al., "Preparation of Bispecific Antibodies by Chemical Recombination of Monoclonal Immunoglobulin G1 Fragments," Science, 229(4708): 81-83 (1985).
Brezski et al., "Human Anti-IgG1 Hinge Autoantibodies Reconstitute the Effector Functions of Proteolytically Inactivated IgGs," Journal of Immunology, 181(5): 3183-3192 (2008).

(Continued)

*Primary Examiner* — Yih-Horng Shiao
(74) *Attorney, Agent, or Firm* — Armstrong Teasdale LLP

(57) ABSTRACT

The present invention relates to hydrogel prodrug compositions comprising cross-linked hyaluronic acid (HA), or a derivative or a salt thereof, wherein the cross-linker system comprises a biodegradable spacer, wherein the cross-linked HA comprises a conjugated drug-linker, and wherein the linker is capable of releasing the drug under physiological conditions. The present invention further relates to methods for preparing the hydrogel prodrug compositions. The present invention further relates to methods for treating an ocular condition using the hydrogel compositions.

28 Claims, 15 Drawing Sheets

Specification includes a Sequence Listing.

(56) References Cited

U.S. PATENT DOCUMENTS

| | | | |
|---|---|---|---|
| 2008/0069820 A1 | 3/2008 | Fuh et al. | |
| 2009/0002360 A1 | 1/2009 | Chen et al. | |
| 2010/0098772 A1* | 4/2010 | Robinson | A61K 9/19 424/501 |
| 2011/0039764 A1 | 2/2011 | Matsuno et al. | |
| 2011/0053848 A1 | 3/2011 | Cleemann et al. | |
| 2011/0236486 A1 | 9/2011 | Giammona et al. | |
| 2012/0156259 A1 | 6/2012 | Rau et al. | |
| 2013/0231474 A1 | 9/2013 | Auzely et al. | |
| 2014/0017244 A1 | 1/2014 | Duerr et al. | |
| 2014/0187487 A1 | 7/2014 | Shoichet et al. | |
| 2014/0341842 A1 | 11/2014 | Zarembinski et al. | |
| 2015/0010634 A1 | 1/2015 | Knappe et al. | |
| 2015/0157563 A1 | 6/2015 | Wirostko | |
| 2015/0297740 A1 | 10/2015 | Rau et al. | |

FOREIGN PATENT DOCUMENTS

| | | |
|---|---|---|
| CN | 102226009 A | 10/2011 |
| CN | 102911380 A | 2/2013 |
| CN | 102942699 A | 2/2013 |
| EP | 0326111 A2 | 8/1989 |
| EP | 0404097 A2 | 12/1990 |
| EP | 0161887 B1 | 9/1991 |
| EP | 0712635 A1 | 5/1996 |
| EP | 0749982 B1 | 9/2000 |
| EP | 1082963 A1 | 3/2001 |
| EP | 1536334 A2 | 6/2005 |
| EP | 1368309 B1 | 12/2005 |
| EP | 1905456 A1 | 4/2008 |
| EP | 1942117 A1 | 7/2008 |
| EP | 1994945 A1 | 11/2008 |
| EP | 2090592 A1 | 8/2009 |
| EP | 2353612 A1 | 8/2011 |
| EP | 1548004 B1 | 8/2012 |
| EP | 2435101 B1 | 2/2013 |
| EP | 2682409 A1 | 1/2014 |
| EP | 2716662 A1 | 4/2014 |
| EP | 2737908 B1 | 6/2014 |
| IN | 242539 B | 5/2007 |
| JP | 07-097401 A | 4/1995 |
| JP | 3130234 A | 2/1999 |
| JP | 11033104 A | 2/1999 |
| JP | 2000119196 A | 4/2000 |
| KR | 20080073419 A | 8/2008 |
| KR | 20090013696 A | 2/2009 |
| KR | 20130123080 A | 11/2013 |
| WO | 198902445 A1 | 3/1989 |
| WO | 198910941 A1 | 11/1989 |
| WO | 199009401 A1 | 8/1990 |
| WO | 199119470 A1 | 12/1991 |
| WO | 199201477 A1 | 2/1992 |
| WO | 199219579 A1 | 11/1992 |
| WO | 199301161 A1 | 1/1993 |
| WO | 199308829 A1 | 5/1993 |
| WO | 199311161 A1 | 6/1993 |
| WO | 199316185 A2 | 8/1993 |
| WO | 199402517 A1 | 2/1994 |
| WO | 199403155 A1 | 2/1994 |
| WO | 199403269 A1 | 2/1994 |
| WO | 199637519 A1 | 11/1996 |
| WO | 199728828 A1 | 8/1997 |
| WO | 199728833 A1 | 8/1997 |
| WO | 199901143 A1 | 1/1999 |
| WO | 2000001733 A1 | 1/2000 |
| WO | 2000016818 A1 | 3/2000 |
| WO | 200027887 A2 | 5/2000 |
| WO | 200033764 A1 | 6/2000 |
| WO | 200054762 A2 | 9/2000 |
| WO | 200140314 A1 | 6/2001 |
| WO | 200209787 A1 | 2/2002 |
| WO | 200218450 A1 | 3/2002 |
| WO | 200249501 A2 | 6/2002 |
| WO | 2002089789 A1 | 11/2002 |
| WO | 2002100440 A1 | 12/2002 |
| WO | 2003076475 A2 | 9/2003 |
| WO | 2003082316 A1 | 10/2003 |
| WO | 2003101972 A1 | 12/2003 |
| WO | 2004022603 A1 | 3/2004 |
| WO | 2004056311 A2 | 7/2004 |
| WO | 2004066704 A1 | 8/2004 |
| WO | 2004092223 A1 | 10/2004 |
| WO | 2004096127 A2 | 11/2004 |
| WO | 2005012359 A2 | 2/2005 |
| WO | 2005034852 A2 | 4/2005 |
| WO | 2005067994 A1 | 7/2005 |
| WO | 2005087201 A1 | 9/2005 |
| WO | 2005099768 A2 | 10/2005 |
| WO | 2005110436 A2 | 11/2005 |
| WO | 2005110505 A2 | 11/2005 |
| WO | 2005116084 A1 | 12/2005 |
| WO | 2006003014 A2 | 1/2006 |
| WO | 2006113668 A1 | 10/2006 |
| WO | 2006136586 A2 | 12/2006 |
| WO | 2007026362 A2 | 3/2007 |
| WO | 2007035080 A1 | 3/2007 |
| WO | 2007035296 A2 | 3/2007 |
| WO | 2007043702 A1 | 4/2007 |
| WO | 2007047922 A2 | 4/2007 |
| WO | 2007070546 A2 | 6/2007 |
| WO | 2007100745 A2 | 9/2007 |
| WO | 2007124132 A2 | 11/2007 |
| WO | 2008031525 A1 | 3/2008 |
| WO | 2008034122 A2 | 3/2008 |
| WO | 2008060359 A2 | 5/2008 |
| WO | 2009009712 A1 | 1/2009 |
| WO | 2009018076 A1 | 2/2009 |
| WO | 2009021701 A2 | 2/2009 |
| WO | 2009047346 A1 | 4/2009 |
| WO | 2009047347 A1 | 4/2009 |
| WO | 2009073437 A1 | 6/2009 |
| WO | 2009073508 A2 | 6/2009 |
| WO | 2009077620 A1 | 6/2009 |
| WO | 2009082354 A1 | 7/2009 |
| WO | 2009089004 A1 | 7/2009 |
| WO | 2009095479 A2 | 8/2009 |
| WO | 2009115579 A1 | 9/2009 |
| WO | 2009120893 A2 | 10/2009 |
| WO | 2009143412 A2 | 11/2009 |
| WO | 2010009034 A2 | 1/2010 |
| WO | 2010015900 A1 | 2/2010 |
| WO | 2010029344 A2 | 3/2010 |
| WO | 2010048086 A1 | 4/2010 |
| WO | 2010061005 A1 | 6/2010 |
| WO | 2010069532 A1 | 6/2010 |
| WO | 2010074958 A1 | 7/2010 |
| WO | 2010138074 A1 | 12/2010 |
| WO | 2010145821 A1 | 12/2010 |
| WO | 2011002249 A2 | 1/2011 |
| WO | 2011002888 A2 | 1/2011 |
| WO | 2011012715 A1 | 2/2011 |
| WO | 2011012722 A1 | 2/2011 |
| WO | 2011018902 A1 | 2/2011 |
| WO | 2011028031 A2 | 3/2011 |
| WO | 2011077388 A1 | 6/2011 |
| WO | 2011082368 A2 | 7/2011 |
| WO | 2011089214 A1 | 7/2011 |
| WO | 2011089215 A1 | 7/2011 |
| WO | 2011089216 A1 | 7/2011 |
| WO | 2011109129 A1 | 9/2011 |
| WO | 2011126839 A1 | 10/2011 |
| WO | 2011136645 A1 | 11/2011 |
| WO | 2011148116 A2 | 12/2011 |
| WO | 2011161172 A1 | 12/2011 |
| WO | 2011163069 A2 | 12/2011 |
| WO | 2012014180 A1 | 2/2012 |
| WO | 2012054311 A1 | 4/2012 |
| WO | 2012103445 A2 | 8/2012 |
| WO | 2012146218 A1 | 11/2012 |
| WO | 2012149358 A1 | 11/2012 |
| WO | 2012167079 A2 | 12/2012 |
| WO | 2012171335 A1 | 12/2012 |
| WO | 2013024053 A1 | 2/2013 |

(56) References Cited

FOREIGN PATENT DOCUMENTS

| | | |
|---|---|---|
| WO | 2013036748 A1 | 3/2013 |
| WO | 2013036847 A1 | 3/2013 |
| WO | 2013036857 A1 | 3/2013 |
| WO | 2013055832 A1 | 4/2013 |
| WO | 2013071216 A1 | 5/2013 |
| WO | 2013158661 A1 | 10/2013 |
| WO | 2013160340 A1 | 10/2013 |
| WO | 2013171485 A1 | 11/2013 |
| WO | 2014023272 A1 | 2/2014 |
| WO | 2014028209 A1 | 2/2014 |
| WO | 2014048564 A1 | 4/2014 |
| WO | 2014056923 A1 | 4/2014 |
| WO | 2014072330 A1 | 5/2014 |
| WO | 2014096257 A1 | 6/2014 |
| WO | 2014099997 A1 | 6/2014 |
| WO | 2014106116 A2 | 7/2014 |
| WO | 2014138897 A1 | 9/2014 |
| WO | 2014154804 A1 | 10/2014 |
| WO | 2014169298 A1 | 10/2014 |
| WO | 2014169299 A1 | 10/2014 |
| WO | 2014169300 A1 | 10/2014 |
| WO | 2014169301 A1 | 10/2014 |
| WO | 2014172784 A1 | 10/2014 |
| WO | WO 2014/173759 * | 10/2014 |
| WO | 2014198406 A1 | 12/2014 |
| WO | 2014198683 A2 | 12/2014 |
| WO | 2014206500 A1 | 12/2014 |
| WO | 2015001087 A1 | 1/2015 |
| WO | 2015048408 A1 | 4/2015 |
| WO | 2015052155 A1 | 4/2015 |
| WO | 2015088198 A1 | 6/2015 |
| WO | 2016020373 A1 | 2/2016 |
| WO | 2016073157 A1 | 5/2016 |
| WO | 2016073890 A1 | 5/2016 |
| WO | 2016191850 A1 | 12/2016 |
| WO | 2016193371 A1 | 12/2016 |
| WO | 2016196124 A2 | 12/2016 |
| WO | 2015053281 A1 | 3/2017 |
| WO | 2015053282 A1 | 3/2017 |
| WO | 2017053807 A2 | 3/2017 |
| WO | 2017100470 A1 | 6/2017 |
| WO | 2018100174 A1 | 6/2018 |

OTHER PUBLICATIONS

Brezski et al., "Cleavage of IgGs by Proteases Associated with Associated with Invasive Diseases," MAbs, 2(3): 212-220 (2010).
Burdick et al., "Hyaluronic Acid Hydrogels for Biomedical Applications," Advanced Materials, 23(12): H41-H56 (2011).
Carmeliet et al., "Angiogenesis in Cancer and Other Diseases," Nature, 407(6801): 249-257 (2000).
Carter et al., "Humanization of an Anti-p185$^{HER2}$ Antibody for Human Cancer Therapy," 89(10): 4285-4289 (1992).
Charlton, "Expression and Isolation of Recombinant Antibody Fragments in *E. coli*," in Methods in Molecular Biology, Antibody Engineering: Methods and Protocols, Edited by B.K.C. Lo, Humana Press, vol. 248: 245-254 (2003).
Chen et al., "Selection and Analysis of an Optimized anti-VEGF Antibody: Crystal Structure of an Affinity-Matured Fab in Complex with Antigen," Journal of Molecular Biology, 293(4): 865-881 (1999).
Chothia et al., "Canonical Structures for the Hypervariable Regions of Immunoglobulins," Journal of Molecular Biology, 196(4): 901-917, (1987).
Chowdhury, "Engineering Hot Spots for Affinity Enhancement of Antibodies," in Methods in Molecular Biology, Recombinant Antibodies for Cancer Therapy: Methods and Protocols, Edited by M. Welschof et al., Humana Press, vol. 207: 179-196 (2008).
Clackson et al., "Making Antibody Fragments Using Phage Display Libraries," Nature, 352(6336): 624-628 (1991).
Cunningham et al., "High-Resolution Epitope Mapping of hGH-Receptor Interactions by Alanine-Scanning Mutagenesis," Science, 244(4908): 1081-1085 (1989).

Dall'Acqua et al., "Antibody Humanization by Framework Shuffling," Methods, 36(1): 43-60 (2005).
Fellouse et al., "Synthetic Antibodies form a Four-Amino-Acid Code: A Dominant Role for Tyrosine in Antigen Recognition," PNAS, 101(34): 12467-12472 (2004).
Ferrara, N. "Binding to the Extracellular Matrix and Proteolytic Processing : Two Key Mechanisms Regulating Vascular Endothelial Growth Factor Action," Molecular Biology of the Cell, 21(5): 687-690 (2010).
Gerngross, T. "Advances in the Production of Human Therapeutic Proteins in Yeasts and Filamentous Fungi," Nature Biotechnology, 22(11): 1409-1404 (2004).
Graham et al., "Characteristics of a Human Cell Line Transformed by DNA From Human Adenovirus Type 5," Journal of General Virology, 36(1): 59-72 (1977).
Griffiths et al., "Human Anti-Self Antibodies with High Specificity from Phage Display Libraries," EMBO Journal, 12(2): 725-734 (1993).
Gruber et al., "Efficient Tumor Cell Lysis Mediated by a Bispecific Single Chain Antibody Expressed in *Escherichia coli*," Journal of Immunology, 152(11): 5368-5374 (1994).
Holliger et al., ""Diabodies": Small Bivalent and Bispecific Antibody Fragments," PNAS, 90(14): 6444-6448 (1993).
Hoogenboom et al., "Overview of Antibody Phage-Display Technology and its Applications," in Methods in Molecular Biology, Antibody Phase Display: Methods and Protocols, Edited by P.M. O'Brien et al., Humana Press, vol. 178: 1-37 (2001).
Hoogenboom et al., "By-Passing Immunisation: Human Antibodies from Synthetic Repertoires of Germline $V_H$ Gene Segments Rearranged in vitro," Journal of Molecular Biology, 227(2): 381-388 (1992).
Houck et al., "The Vascular Endothelial Growth Factor Family: Identification of a Fourth Molecular Species and Characterization of Alternative Splicing of RNA," Molecular Endocrinology, 5(12): 1806-1814 (1991).
Hudson et al., "Engineered Antibodies," Nature Medicine, 9(1): 129-134 (2003).
Ito et al., "Anti-Inflammatory Function of an in situ Cross-linkable Conjugate Hydrogel of Hyaluronic Acid and Dexamethasone," Biomaterials, 28(10): 1778-1786 (2007).
Jones et al., "Replacing the Complementarity-Determining Regions in a Human Antibody with Those from a Mouse," Nature, 321(6069): 522-525 (1986).
Kashmiri et al., "SDR Grafting—A New Approach to Antibody Humanization," Methods, 36(1): 25-34 (2005).
Klimka et al., "Human Anti-CD30 Recombinant Antibodies by Guided Phage Antibody Selection Using Cell Planning," British Journal of Cancer, 83(2): 252-260 (2000).
Kostelny et al., "Formation of a Bispecific Antibody by the Use of Leucine Zippers," Journal of Immunology, 145(5): 1547-1553 (1992).
Lee et al., "Bivalent Antibody Phage Display Miimics Natural Immunoglobulin," Journal of Immunological Methods, 284(1-2): 119-132 (2004).
Lee et al., "High-Affinity Human Antibodies from Phage-Displayed Synthetic Fab Libraries with a Single Framework Scaffold," Journal of Molecular Biology, 340(5): 1073-1093 (2004).
Leung et al., "Vascular Endothelial Growth Factor is a Secreted Angiogenic Mitogen," Science, 246(4935): 1306-1309 (1989).
Li et al., "Optimization of Humanized IgGs in Glycoengineered Pichia Pastoris," Nature Biotechnology, 24(2): 210-215 (2006).
Marks et al., "By-passing Immunization. Human Antibodies From V-gene Libraries Displayed on Phage," Journal of Molecular Biology, 222(3): 581-597 (1991).
Marks et al., "Selection of Human Antibodies from Phage Display Libraries," In Antibody Engineering Methods and Protocols, Methods in Molecular Biology, Humana Press, vol. 248, pp. 161-175 (2003).
Mather et al., "Culture of Testicular Cells in Hormone-Supplemented Serum-Free Medium," Annals of the NY Academy of Sciences, 383(1): 44-68 (1982).
Mather, J., "Establishment and Characterization of Two Distinct Mouse Testicular Epithelial Cell Line," Biology of Reproduction, 23(1): 243-252 (1980).

(56) References Cited

OTHER PUBLICATIONS

McCafferty et al., "Phage Antibodies: Filamentous Phage Displaying Antibody Variable Domains," Nature, 348(6301): 552-554 (1990).
Mero et al., "Hyaluronic Acid Bioconjugates for the Delivery of Bioactive Molecules," Polymers, 6(2): 346-369 (2014).
Milstein et al., "Hybrid Hybridomas and Their Use in Immunohistochemistry," Nature, 305(5934): 537-540 (1983).
Morrison et al., "Chimeric Human Antibody Molecules: Mouse Antigen-Binding Domains with Human Constant Region Domains," PNAS, 81(21): 6851-6855 (1984).
Osbourn et al., "From Rodent Reagents to Human Therapeutics Using Antibody Guided Selection," Methods, 36(1): 61-68 (2005).
Padlan, E., "A Possible Procedure for Reducing the Immunogenicity of Antibody Variable Domains While Preserving Their Ligand-Binding Properties," Molecular Immunology, 28(4-5): 489-498 (1991).
Pluckthun, A. "Antibodies from *Escherichia coli*," The Pharmacology of Monoclonal Antibodies, Springer-Verlag, M. Rosenberg et al., Editors, Chapter 11, pp. 269-315 (1994) (Submitted in 5 parts due to size).
Pouyani, et al. "Functionalized Derivatives of Hyaluronic Acid Oligosaccharides: Drug Carriers and Novel Biomaterials," Bioconjugate Chem., 5(4): 339-347 (1994).
Presta et al., "Humanization of an Anti-Vascular Endothelial Growth Factor Monoclonal Antibody for the Therapy of Solid Tumors and Other Disorders," Cancer Research, 57(20): 4593-4599 (1997).
Presta et al., "Humanization of an antibody directed against IgE," Journal of Immunology, 151(5): 2623-2632 (1993).
Presta, L. "Antibody Engineering," Current Opinion in Structural Biology, 2(4): 593-596 (1992).
Queen et al. "A Humanized Antibody that Binds to the Interleukin 2 Receptor," PNAS, 86(24): 10029-10033 (1989).
Riechmann et al., "Reshaping Human Antibodies for Therapy," Nature, 332(6162): 323-327 (1988).
Rosok et al., "A Combinatorial Library Strategy for the Rapid Humanization of Anticarcinoma BR96 Fab," Journal of Biological Chemistry, 271(37): 22611-22618 (1996).
Shatz et al., "Contribution of Antibody Hydrodynamic Size to Vitreal Clearance Revealed through Rabbit Studies Using a Species-Matched Fab," Molecular Pharmaceutics, 13(9): 2996-3003 (2016).
Shendi et al., "Tunable, Bioactive Protein Conjugated Hyaluronic Acid Hydrogel for Neural Engineering Applications," Journal of Materials Chemistry B, 4(16): 2803-2818 (2016).
Sidhu et al., "Phage-displayed Antibody Libraries of Synthetic Heavy Chain Complementarity Determining Regions," Journal of Molecular Biology, 338(2): 299-310 (2004).
Sims et al., "A Humanized CD18 Antibody Can Block Function Without Cell Destruction," Journal of Immunology, 151(4): 2296-2308 (1993).
Traunecker et al., "Bispecific Single Chain Molecules (Janusins) Target Cytotoxic Lymphocytes on HIV Infected Cells," EMBO Journal, 10(12): 3655-3659 (1991).
Tutt et al., "Trispecific F(ab')3 Derivatives that Use Cooperative Signaling via the TCR/CD3 Complex and CD2 to Activate and Redirect Resting Cytotoxic T Cells," Journal of Immunology, 147(1): 60-69 (1991).
Urlaub et al., "Isolation of Chinese Hamster Cell Mutants Deficient in Dihydrofolate Reductase Activity" PNAS, 77(7): 4216-4220 (1980).
Winter et al., "Making Antibodies by Phage Display Technology," Annual Review of Immunology, 12(1): 433-455 (1994).
Yazaki et al., "Expression of Recombinant Antibodies in Mammalian Cell Lines," in Methods in Molecular Biology, Antibody Engineering: Methods and Protocols, Edited by B.K.C. Lo, Humana Press, vol. 248: 255-268 (2004).
International Search Report and Written Opinion for PCT/US2018/023857 dated Jul. 13, 2018 (9 pages).
Flatman et al., "Process Analytics for Purification of Monoclonal Antibodies," Journal of Chromatography B, 848(1): 79-87 (2007).
Varghese et al., "In Situ Cross-Linkable High Molecular Weight Hyaluronan-Bisphosphonate Conjugate for Localized Delivery and Cell-Specific Targeting: A Hydrogel Linked Prodrug Approach," J American Chemical Society, 131(25): 8781-8783 (2009).

* cited by examiner

1

HYDROGEL CROSS-LINKED HYALURONIC ACID PRODRUG COMPOSITIONS AND METHODS

CROSS REFERENCE TO RELATED APPLICATIONS

This application is a continuation of International Application No. PCT/US2018/023857, which claims priority to U.S. Provisional Application Ser. No. 62/475,094 filed on Mar. 22, 2017, the disclosures of which are incorporated herein by reference.

SEQUENCE LISTING

The instant application contains a Sequence Listing which has been submitted via EFS-Web and is hereby incorporated by reference in its entirety. Said ASCII copy, created on Mar. 22, 2017, is named P34128_US_03.22.2017.TXT and is 37,974 bytes in size.

FIELD OF THE INVENTION

The present invention relates to pharmaceutical compositions, related preparation methods, and methods for use of the pharmaceutical compositions for the treatment of one or more ocular conditions.

BACKGROUND OF THE INVENTION

A leading cause of blindness is the inability to sufficiently treat certain diseases of the eye. A major limitation is the lack of suitable options of introducing drugs or therapeutic agents into the eye and maintain these drugs or agents at a therapeutically effective concentration therein for the necessary duration. Systemic administration may not be an ideal solution because, often, unacceptably high levels of systemic dosing are needed to achieve effective intraocular concentrations, with the increased incidence of unacceptable side effects of the drugs. Simple ocular instillation or application is not an acceptable alternative in many cases because the drug may be quickly washed out by tear-action or is depleted from within the eye into the general circulation. Topical eye drop therapy is limited by poor absorption, a need for frequent and/or chronic dosing over periods of days to years, rapid turnover of aqueous humor, production and movement of the tear film and other causes, which may effectively remove therapeutic agents long before therapy has been completed or the proper dose delivered.

Intraocular injections have the advantage that they can provide enhanced bioavailability to a target location (e.g., the retina) of the eye relative to other delivery mechanisms such as topical delivery. However, they also have drawbacks and can present various different complications. For example, intravitreal injections can result in delivery of undesirably high concentrations of therapeutic agent to a target location or elsewhere particularly when the therapeutic agent is relatively soluble. In addition, intraocular injections are highly unpleasant for the patient. Furthermore, as the intraocular injection itself may cause complications, such as endophthalmitis and retinal detachment, it is highly desirable to have the longest possible duration between injections, while retaining therapeutic levels of drug in the eye.

In addition to the above, therapeutic agents delivered by intravitreal injections can lack duration of action since the agents can often rapidly disperse within the eye after injection. Such lack of duration is particularly undesirable since it can necessitate greater injection frequency. Ranibizumab and pegaptanib, for example, are administered to a patient via intraocular injection every 4 and 6 weeks, respectively, which is a highly unpleasant experience for the patient.

Thus, there is widespread recognition that the field of ophthalmology would benefit from longer lasting formulations. They would benefit patient care and ocular health by providing extended delivery of therapeutic agents to the eye while minimizing the problems associated with patient compliance to prescribed therapeutic medical regimens.

Expression of vascular endothelial growth factor (VEGF), a signal protein produced by cells that stimulates vasculogenesis and angiogenesis, plays an important role in various ocular conditions, such as in certain forms of macular degeneration and retinopathies.

Various medicaments to treat such ocular conditions are on the market, such as ranibizumab, aflibercept and pegaptanib. Application to the patient occurs via intraocular injections every 4 and 8 weeks.

In view of the above, there exists a need to provide a form of administration that overcomes these drawbacks at least partially.

BRIEF DESCRIPTION OF THE INVENTION

The invention provides cross-linked hyaluronic acid (HA) drug conjugates, pharmaceutical compositions and methods of using such conjugates for treatment of ocular indications, and methods of making the conjugates.

In certain embodiments the invention provides a cross-linked HA drug conjugate comprising a plurality of hyaluronic acid polymers 2A and a plurality of hyaluronic acid polymers 2B, wherein:

each 2A comprises a plurality of linearly connected units, the units consisting essentially of:

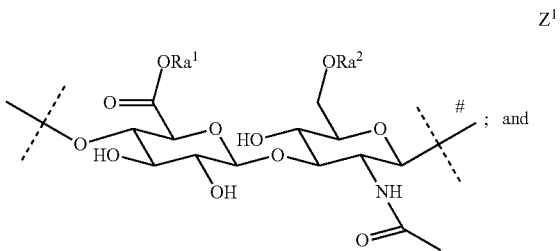

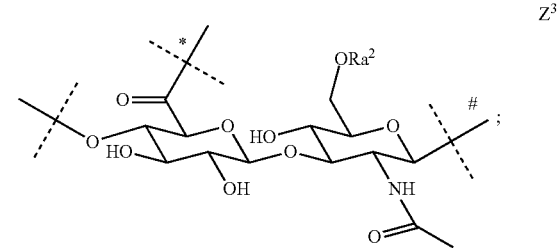

each 2B comprises a plurality of linearly connected units, the units consisting essentially of:

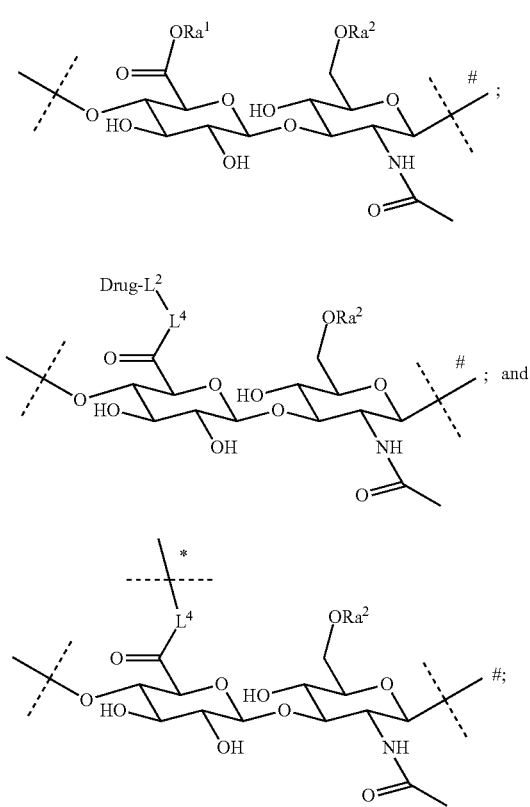

wherein
an unmarked dashed line indicate a point of attachment to an adjacent unit at a dashed line marked with #, or to a hydrogen, a dashed line marked with # indicate a point of attachment to an adjacent unit at an unmarked dashed line, or to a hydroxyl; and a dashed line marked with * indicates a point of cross-linking attachment between a unit $Z^3$ of 2A and a unit $Z^4$ of 2B, such that at least one 2A is cross-linked to at least one 2B;

Drug is a therapeutic agent;

$Ra^1$ and $Ra^2$ are each independently is hydrogen; $C_{1-4}$ alkyl; an alkali metal ion, an ammonium ion, an alkaline earth metal ion, or other suitable counterion;

$L^2$ is a reversible prodrug linker;

$L^4$ is an optionally biodegradable spacer and may be the same or different in $Z^2$ and $Z^4$;

2A comprises a total of s units wherein s is from 25 to 2500, wherein;
  the number of $Z^1$ units in 2A is from about 0.8 s to about 0.99 s, and
  the number of $Z^3$ units is from about 0.2 s to about 0.01 s;

2B comprising a total of t units wherein t is from 25 to 2500, wherein;
  the number of $Z^1$ units in 2B is from about 0.75 t to about 0.94 t;
  the combined number of $Z^2$ and $Z^4$ units is from about 0.25 t to about 0.06 t;
  the number of $Z^2$ units is at least 0.01 t; and
  the number of $Z^4$ units is at least 0.01 t.

In certain embodiments, s is from 50 to 2000.
In certain embodiments, s is from 75 to 1500.
In certain embodiments, s is from 75 to 1000.
In certain embodiments, s is from 80 to 500.
In certain embodiments, s is from 100 to 250.
In certain embodiments, s is from 100 to 200.
In certain embodiments, s is from 200 to 800, or from 300 to 600.
In certain embodiments, t is from 50 to 2000.
In certain embodiments, t is from 75 to 1500.
In certain embodiments, t is from 75 to 1000.
In certain embodiments, t is from 80 to 500.
In certain embodiments, t is from 100 to 250.
In certain embodiments, t is from 100 to 200.
In certain embodiments, t is from 200 to 800, or from 300 to 600.
In certain embodiments, the number of $Z^1$ units in 2A is from about 0.91 s to about 0.98 s.
In certain embodiments, the number of $Z^1$ units in 2A is from about 0.8 s to about 0.99 s.
In certain embodiments, the number of $Z^1$ units in 2A is from about 0.82 s to about 0.99 s.
In certain embodiments, the number of $Z^1$ units in 2A is from about 0.84 s to about 0.99 s.
In certain embodiments, the number of $Z^1$ units in 2A is from about 0.86 s to about 0.99 s.
In certain embodiments, the number of $Z^1$ units in 2A is from about 0.88 s to about 0.99 s.
In certain embodiments, the number of $Z^1$ units in 2A is from about 0.9 s to about 0.99 s. In certain embodiments, the number of $Z^1$ units in 2A is from about 0.92 s to about 0.97 s.
In certain embodiments, the number of $Z^1$ units in 2A is from about 0.93 s to about 0.96 s.
In certain embodiments, the number of $Z^1$ units in 2A is from about 0.94 s to about 0.95 s.
In certain embodiments, the number of $Z^3$ units in 2A is from about 0.2 s to about 0.01 s.
In certain embodiments, the number of $Z^3$ units in 2A is from about 0.18 s to about 0.01 s.
In certain embodiments, the number of $Z^3$ units in 2A is from about 0.16 s to about 0.01 s.
In certain embodiments, the number of $Z^3$ units in 2A is from about 0.14 s to about 0.01 s. In certain embodiments, the number of $Z^3$ units in 2A is from about 0.12 s to about 0.01 s.
In certain embodiments, the number of $Z^3$ units in 2A is from about 0.10 s to about 0.01 s.
In certain embodiments, the number of $Z^3$ units is from about 0.09 s to about 0.02 s.
In certain embodiments, the number of $Z^3$ units is from about 0.08 s to about 0.03 s.
In certain embodiments, the number of $Z^3$ units is from about 0.07 s to about 0.04 s.
In certain embodiments, the number of $Z^1$ units in 2B is from about 0.88 s to about 0.92 s.
In certain embodiments, the number of $Z^1$ units in 2B is from about 0.86 s to about 0.94 s.
In certain embodiments, the number of $Z^1$ units in 2B is from about 0.89 s to about 0.91 s.
In certain embodiments, the number of $Z^1$ units in 2B is from about 0.86 s to about 0.94 s.
In certain embodiments, the combined number of $Z^2$ and $Z^4$ units in 2B is from about 0.25 t to about 0.05 t.

In certain embodiments, the combined number of $Z^2$ and $Z^4$ units in 2B is from about 0.23 t to about 0.05 t.

In certain embodiments, the combined number of $Z^2$ and $Z^4$ units in 2B is from about 0.21 t to about 0.05 t.

In certain embodiments, the combined number of $Z^2$ and $Z^4$ units in 2B is from about 0.19 t to about 0.05 t.

In certain embodiments, the combined number of $Z^2$ and $Z^4$ units in 2B is from about 0.17 t to about 0.05 t.

In certain embodiments, the combined number of $Z^2$ and $Z^4$ units in 2B is from about 0.15 t to about 0.05 t.

In certain embodiments, the combined number of $Z^2$ and $Z^4$ units in 2B is from about 0.13 t to about 0.05 t.

In certain embodiments, the combined number of $Z^2$ and $Z^4$ units is from about 0.12 t to about 0.06 t.

In certain embodiments, the combined number of $Z^2$ and $Z^4$ units is from about 0.11 t to about 0.07 t.

In certain embodiments, the combined number of $Z^2$ and $Z^4$ units is from about 0.25 t to about 0.06 t.

In certain embodiments, the number of $Z^2$ units is from 0.02 t to 0.12 t.

In certain embodiments, the number of $Z^2$ units is from 0.04 t to 0.10 t.

In certain embodiments, the number of $Z^2$ units is from 0.06 t to 0.08 t.

In certain embodiments, the number of $Z^2$ units is from 0.07 t to 0.08 t.

In certain embodiments, the number of $Z^2$ units is from 0.075 t to 0.08 t.

In certain embodiments, the number of $Z^2$ units is 0.077 t.

In certain embodiments, the number of $Z^4$ units is from 0.01 t to 0.12 t.

In certain embodiments, the number of $Z^4$ units is from 0.02 t to 0.12 t.

In certain embodiments, the number of $Z^4$ units is from 0.04 t to 0.10 t.

In certain embodiments, the number of $Z^4$ units is from 0.06 t to 0.08 t.

In certain embodiments, the number of $Z^4$ units is from 0.01 t to 0.04 t.

In certain embodiments, the number of $Z^4$ units is from 0.02 t to 0.03 t.

In certain embodiments, the number of $Z^4$ units is from 0.02 t to 0.025 t.

In certain embodiments, the number of $Z^4$ units is 0.023 t.

In certain embodiments, the reversible prodrug linker $L^2$ coupling the drug to spacer $L^4$ is of formula XIIa

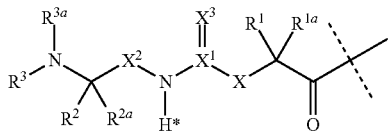

(XIIa)

wherein
the dashed line indicates the attachment to a nitrogen of a drug compound (not shown) by forming an amide bond;
—X— is —C($R^4R^{4a}$)—; —N($R^4$)—; —O—; —C($R^4R^{4a}$)—C($R^5R^{5a}$)—; —C($R^5R^{5a}$)—C($R^4R^{4a}$)—; —C($R^4R^{4a}$)—N($R^6$)—; —N($R^6$)—C($R^4R^{4a}$)—; —C($R^4R^{4a}$)—O—; —O—C($R^4R^{4a}$)—; or —C($R^7R^{7a}$)—; $X^1$ is C; or S(O);
—$X^2$— is —C($R^8R^{8a}$)—; or —C($R^8R^{8a}$)—C($R^9R^{9a}$)—;
=$X^3$ is =O; =S; or =N—CN;
—$R^1$, —$R^{1a}$, —$R^2$, —$R^{2a}$, —$R^4$, —$R^{4a}$, —$R^5$, —$R^{5a}$, —$R_6$, —$R^8$, —$R^{8a}$, —$R^9$, —$R^{9a}$ are independently selected from the group consisting of —H; and $C_{1-6}$ alkyl;
—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;
—$R^7$ is —N($R^{10}R^{10a}$); or —N$R^{10}$—(C=O)—$R^{11}$;
—$R^{7a}$, —$R^{10}$, —$R^{10a}$, —$R^{11}$ are independently of each other —H; or $C_{1-10}$ alkyl;
optionally, one or more of the pairs —$R^{1a}/$—$R^{4a}$, —$R^{1a}/$—$R^{5a}$, —$R^{1a}/$—$R^{7a}$, —$R^{4a}/$—$R^{5a}$, —$R^{8a}/$—$R^{9a}$ form a chemical bond;
optionally, one or more of the pairs —$R^1/$—$R^{1a}$, —$R^2/$—$R^{2a}$, —$R^4/$—$R^{4a}$, —$R^5/$—$R^{5a}$, —$R^8/$—$R^{8a}$, —$R^9/$—$R^{9a}$ are joined together with the atom to which they are attached to form a $C_{3-10}$ cycloalkyl; or 3- to 10-membered heterocyclyl;
optionally, one or more of the pairs —$R^1/$—$R^4$, —$R^1/$—$R^5$, —$R^1/$—$R^6$, —$R^1/$—$R^{7a}$, —$R^4/$—$R^5$, —$R^4/$—$R^6$, —$R^8/$—$R^9$, —$R^2/$—$R^3$ are joined together with the atoms to which they are attached to form a ring A;
optionally, $R^3/R^{3a}$ are joined together with the nitrogen atom to which they are attached to form a 3- to 10-membered heterocycle;
Ring A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein the group of formula XIIa is substituted with -$L^4$ provided that the hydrogen marked with the asterisk in formula (XIIa) is not replaced by -$L^4$ or other substituent;
wherein -$L^4$- is a single chemical bond or a spacer moiety as defined herein.

In certain embodiments, the reversible prodrug linker $L^2$ is of the formula (VIIa)

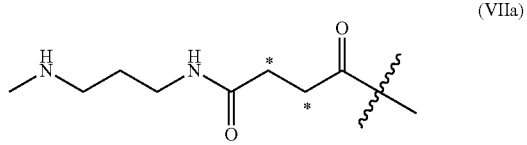 [SMILES: *C(=O)CCC(=O)NCCCNC]

(VIIa)

wherein:
each asterisk represents an independent site of attachment to the spacer $L^4$.

In certain embodiments, the reversible prodrug linker $L^2$ together with spacer $L^4$ is of the formula VIIc:

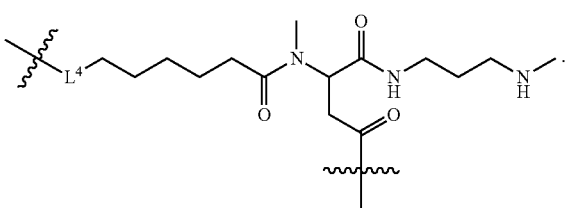

VIIc wherein:
  the right-most wavy line represents the point of attachment to the nitrogen atom of Drug; and
  the left-most wavy line represents the point of attachment to a unit $Z^2$ of hyaluronic acid 2B.

In certain embodiments, the spacer $L^4$ connecting hyaluronic acid polymer 2A to hyaluronic acid polymer 2B (by connecting unit $Z^3$ of polymer 2A to unit $Z^4$ of polymer 2B) is of the formula:

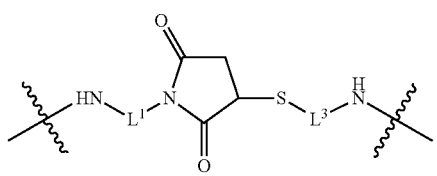

wherein:
  the right-most wavy line represents the point of attachement to a unit $Z^3$ on hyaluronic acid polymer 2A; and
  the left-most wavy line represents the point of attachment to a unit $Z^4$ on hyaluronic acid polymer 2B.

The spacer $L^4$ connecting hyaluronic acid polymer 2A to hylauronic acid polymer 2B may, in certain embodiments, be reversed in orientation such that the right-most wavy line of the above formula represents the point of attaehement to a unit $Z^4$ on hyaluronic acid polymer 2B; and the left-most wavy line represents the point of attachment to a unit $Z^3$ on hyaluronic acid polymer 2A.

In certain embodiments, the spacer $L_4$ joining reversible prodrug linker $L^2$ to hyaluronic acid polymer 2B is of the formula

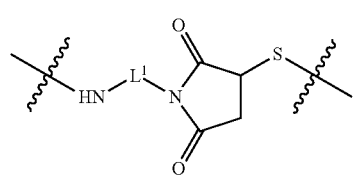

wherein:
  the right-most wavy line represents the point of attachement to $L^2$; and
  the left-most wavy line represents the point of attachment to a unit $Z^2$ on hyaluronic acid polymer 2B;
wherein:
  $L^1$ is a spacer; and
  $L^3$ is a biodegradable spacer.

In certain embodiments, the unit $Z^4$ is

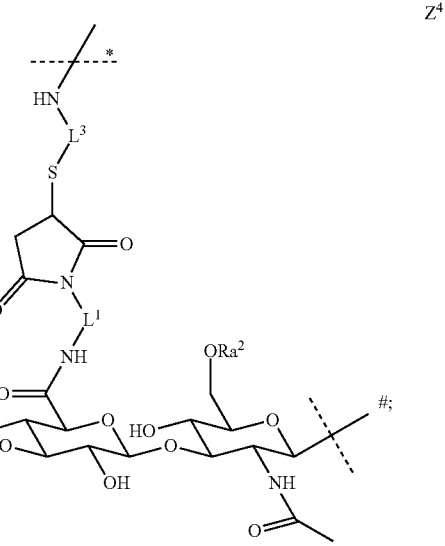

wherein $L^1$, $L^3$ and $Ra^2$ are as defined herein.

In certain embodiments, the unit $Z^2$ is

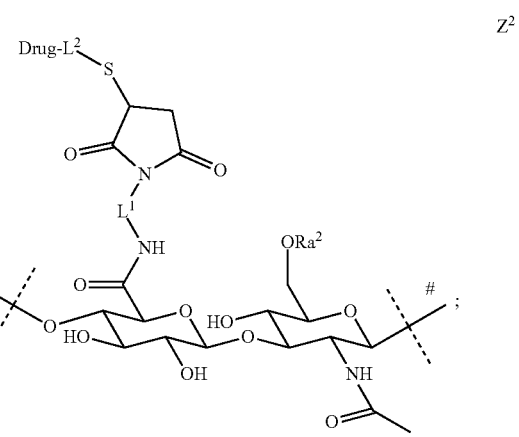

wherein $L^1$, $L^2$, $L^3$ and $Ra^2$ are as defined herein.

In certain embodiments, the spacer $L_4$ connecting hyaluronic acid polymer 2A to Hylauronic acid polymer 2B is of the formula:

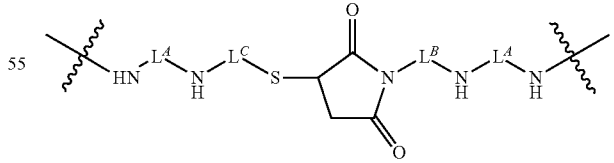

wherein:
  the right-most wavy line represents the point of attachement to a unit $Z^3$ on hyaluronic acid polymer 2B; and
  the left-most wavy line represents the point of attachment to a unit $Z^4$ on hyaluronic acid polymer 2A;
  $L^A$ is a spacer;
  $L^B$ is a spacer; and
  $L^C$ is a biodegradable spacer.

In certain embodiments, the spacer $L^4$ connecting hyaluronic acid polymer 2A to hylauronic acid polymer 2B is of the formula:

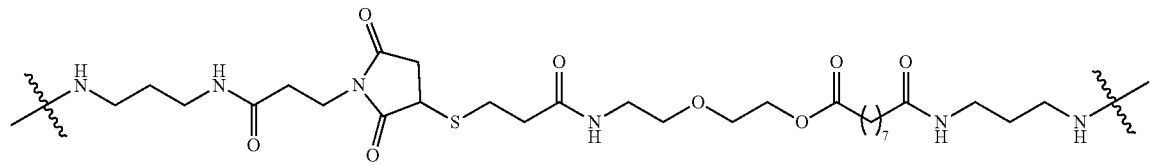

wherein:
the right-most wavy line represents the point of attachement to a unit $Z^3$ on hyaluronic acid polymer 2A; and
the left-most wavy line represents the point of attachment to a unit $Z^4$ on hyaluronic acid polymer 2B.

In certain embodiments the spacer $L^4$ joining reversible prodrug linker $L^2$ to hyaluronic acid polymer 2A is of the formula

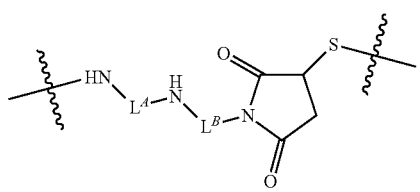

wherein:
the right-most wavy line represents the point of attachement to $L^2$; and
the left-most wavy line represents the point of attachment to a unit $Z^2$ on hyaluronic acid polymer 2B;
wherein:
$L^A$ is a spacer;
$L^B$ is a spacer; and
$L^C$ is a biodegradable spacer.

In certain embodiments, $L^A$ is optionally substituted and/or optionally interrupted $C_{1-10}$ alkylene.

In certain embodiments, $L^A$ is linear $C_{2-4}$ alkylene.

In certain embodiments, $L^B$ is linear —(O)—$C_{1-5}$ alkylene.

In certain embodiments, $L^C$ is:

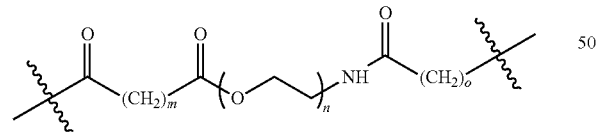

wherein m is from 0 to 10, n is from 1 to 4, and o is from 1 to 4.

In certain embodiments, $L^C$ is:

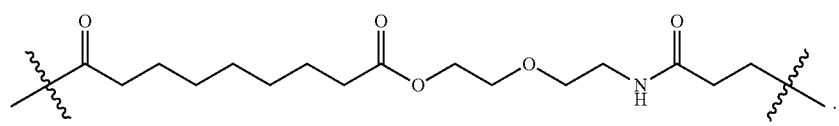 [SMILES: *CCC(=O)NCCOCCOC(=O)CCCCCCCC(*)=O]

In certain embodiments, the spacer $L_4$ joining reversible prodrug linker $L^2$ to hyaluronic acid polymer 2B is of the formula

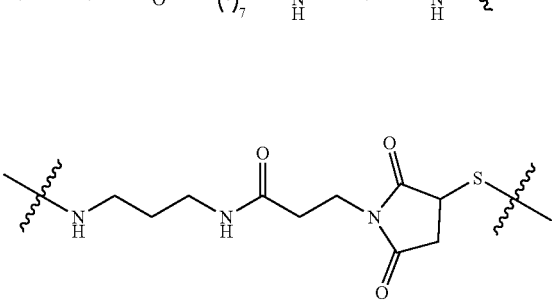

wherein:
the right-most wavy line represents the point of attachement to a unit $Z^3$ on hyaluronic acid polymer 2A; and
the left-most wavy line represents the point of attachment to a unit $Z^4$ on hyaluronic acid polymer 2B.

In certain embodiments, the unit $Z^4$ is:

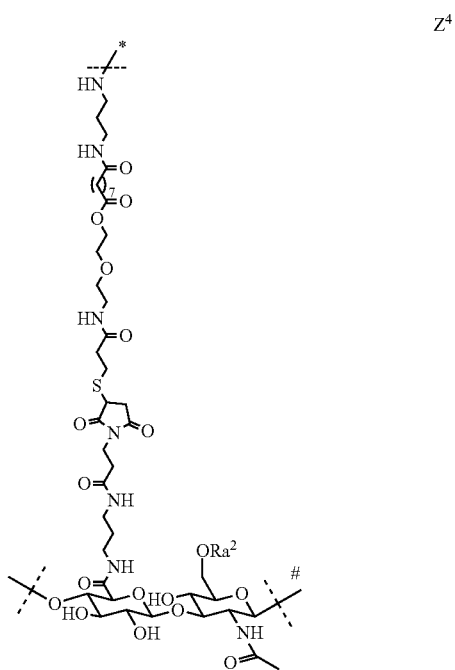

$Z^4$ wherein $Ra^2$ is as defined herein.

In certain embodiments, the unit $Z^2$ is
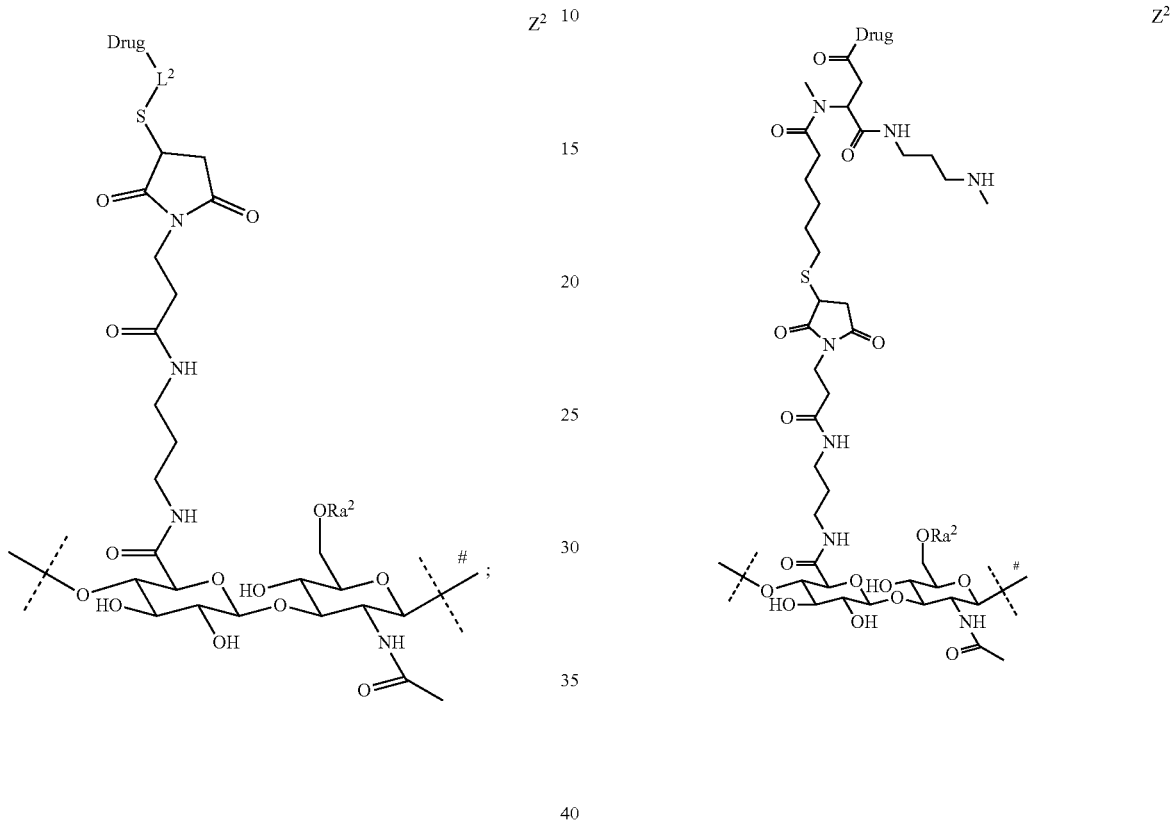
wherein $L^2$, $Ra^2$ and Drug are as defined herein.
wherein $Ra^2$ and Drug are as defined herein.
In certain embodiments, the combined reversible prodrug linker $L^2$ together with spacer $L^4$ is of the formula VIId
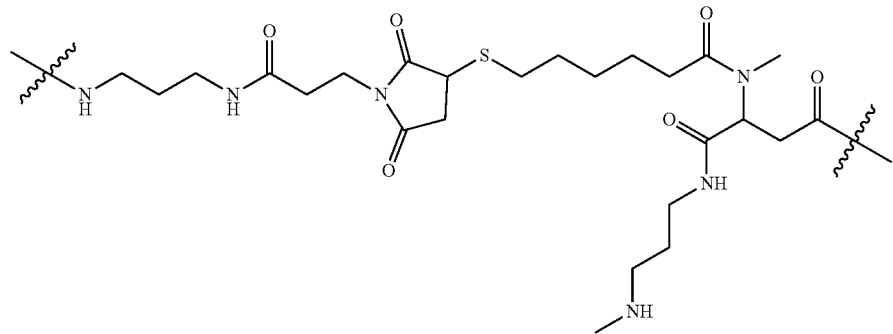

wherein:

the right-most wavy line represents the point of attachment to the nitrogen atom of Drug; and the left-most wavy line represents the point of attachment to a unit $Z^2$ of hyaluronic acid 2B.

In certain embodiments, drug is an antibody.

In certain embodiments, the antibody is a VEGF antagonist.

In certain embodiments, the antibody is an anti-VEGF antibody fragment.

In certain embodiments, the antibody fragment is a Fab antibody fragment.

In certain embodiments, the Fab antibody fragment is ranibizumab or LUCENTIS®.

In certain embodiments, the antibody comprises the following six hypervariable regions (HVRs):
  (a) an HVR-H1 comprising the amino acid sequence of DYWIH (SEQ ID NO: 1);
  (b) an HVR-H2 comprising the amino acid sequence of $GX_1TPX_2GGX_3X_4X_5YX_6DSVX_7X_8$ (SEQ ID NO: 2), wherein $X_1$ is Ile or His, $X_2$ is Ala or Arg, $X_3$ is Tyr or Lys, $X_4$ is Thr or Glu, $X_5$ is Arg, Tyr, Gln, or Glu, $X_6$ is Ala or Glu, $X_7$ is Lys or Glu, and $X_8$ is Gly or Glu;
  (c) an HVR-H3 comprising the amino acid sequence of FVFFLPYAMDY (SEQ ID NO: 3);
  (d) an HVR-L1 comprising the amino acid sequence of RASQX$_1$VSTAVA (SEQ ID NO: 4), wherein $X_1$ is Asp or Arg;
  (e) an HVR-L2 comprising the amino acid sequence of $X_1$ASFLYS (SEQ ID NO: 5), wherein $X_1$ is Ser or Met; and
  (f) an HVR-L3 comprising the amino acid sequence of $X_1$QGYGX$_2$PFT (SEQ ID NO: 6), wherein $X_1$ is Gln, Asn, or Thr and $X_2$ is Ala, Asn, Gln, or Arg.

In certain embodiments, the antibody comprises the following six HVRs:
  (a) an HVR-H1 comprising the amino acid sequence of DYWIH (SEQ ID NO: 1);
  (b) an HVR-H2 comprising the amino acid sequence of GITPAGGYTRYADSVKG (SEQ ID NO: 7), GITPAGGYEYYADSVKG (SEQ ID NO: 21), or GITPAGGYEYYADSVEG (SEQ ID NO: 22);
  (c) an HVR-H3 comprising the amino acid sequence of FVFFLPYAMDY (SEQ ID NO: 3);
  (d) an HVR-L1 comprising the amino acid sequence of RASQDVSTAVA (SEQ ID NO: 8);
  (e) an HVR-L2 comprising the amino acid sequence of SASFLYS (SEQ ID NO: 9); and
  (f) an HVR-L3 comprising the amino acid sequence of QQGYGAPFT (SEQ ID NO: 10) or QQGYGNPFT (SEQ ID NO: 23).

In certain embodiments, the antibody comprises the following six HVRs:
  (a) an HVR-H1 comprising the amino acid sequence of DYWIH (SEQ ID NO: 1);
  (b) an HVR-H2 comprising the amino acid sequence of GITPAGGYTRYADSVKG (SEQ ID NO: 7);
  (c) an HVR-H3 comprising the amino acid sequence of FVFFLPYAMDY (SEQ ID NO: 3);
  (d) an HVR-L1 comprising the amino acid sequence of RASQDVSTAVA (SEQ ID NO: 8);
  (e) an HVR-L2 comprising the amino acid sequence of SASFLYS (SEQ ID NO: 9); and
  (f) an HVR-L3 comprising the amino acid sequence of QQGYGAPFT (SEQ ID NO: 10).

In certain embodiments, the antibody further comprises the following heavy chain variable (VH) domain framework regions (FRs):
  (a) an FR-H1 comprising the amino acid sequence of

EVQLVESGGGLVQPGGSLRLSCAASGFTIS; (SEQ ID NO: 13)

(b) an FR-H2 comprising the amino acid sequence of WVRQAPGKGLEWVA (SEQ ID NO: 14);
  (c) an FR-H3 comprising the amino acid sequence of RFTISADTSKNTAYLQMRSLRAEDTAVYYCAR (SEQ ID NO: 15); and
  (d) an FR-H4 comprising the amino acid sequence of WGQGTLVTVSS (SEQ ID NO: 16).

In certain embodiments, the antibody further comprises the following light chain variable (VL) domain FRs:
  (a) an FR-L1 comprising the amino acid sequence of DIQMTQSPSSLSASVGDRVTITC (SEQ ID NO: 17);
  (b) an FR-L2 comprising the amino acid sequence of WYQQKPGKAPKLLIY (SEQ ID NO: 18);
  (c) an FR-L3 comprising the amino acid sequence of GVPSRFSGSGSGTDFTLTISSLQPEDAATYYC (SEQ ID NO: 19); and
  (d) an FR-L4 comprising the amino acid sequence of FGQGTKVEIK (SEQ ID NO: 20).

In certain embodiments, the antibody comprises the following six HVRs:
  (a) an HVR-H1 comprising the amino acid sequence of DYWIH (SEQ ID NO: 1);
  (b) an HVR-H2 comprising the amino acid sequence of GITPAGGYEYYADSVEG (SEQ ID NO: 22);
  (c) an HVR-H3 comprising the amino acid sequence of FVFFLPYAMDY (SEQ ID NO: 3);
  (d) an HVR-L1 comprising the amino acid sequence of RASQDVSTAVA (SEQ ID NO: 8);
  (e) an HVR-L2 comprising the amino acid sequence of SASFLYS (SEQ ID NO: 9); and
  (f) an HVR-L3 comprising the amino acid sequence of QQGYGNPFT (SEQ ID NO: 23).

In certain embodiments, the antibody further comprises the following VL domain FRs:
  (a) an FR-L1 comprising the amino acid sequence of DIQMTQSPSSLSASVGDRVTITC (SEQ ID NO: 17);
  (b) an FR-L2 comprising the amino acid sequence of WYQQKPGKAPKLLIY (SEQ ID NO: 18);
  (c) an FR-L3 comprising the amino acid sequence of GVPSRFSGSGSGTDFTLTISSLQPEDFATYYC (SEQ ID NO: 24); and
  (d) an FR-L4 comprising the amino acid sequence of FGQGTKVEIK (SEQ ID NO: 20).

In certain embodiments, the antibody comprises the following six HVRs:
  (a) an HVR-H1 comprising the amino acid sequence of DYWIH (SEQ ID NO: 1);
  (b) an HVR-H2 comprising the amino acid sequence of GITPAGGYEYYADSVEG (SEQ ID NO: 22);
  (c) an HVR-H3 comprising the amino acid sequence of FVFFLPYAMDY (SEQ ID NO: 3);
  (d) an HVR-L1 comprising the amino acid sequence of RASQDVSTAVA (SEQ ID NO: 8);
  (e) an HVR-L2 comprising the amino acid sequence of SASFLYS (SEQ ID NO: 9); and
  (f) an HVR-L3 comprising the amino acid sequence of QQGYGAPFT (SEQ ID NO: 10).

In certain embodiments, the antibody further comprises the following VL domain FRs:
(a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26);
(b) an FR-L2 comprising the amino acid sequence of WYQQKPGKAPKLLIY (SEQ ID NO: 18) or WYQQKPGEAPKLLIY (SEQ ID NO: 27);
(c) an FR-L3 comprising the amino acid sequence of GVPSRFSGSGSGTDFTLTISSLQPEDAATYYC (SEQ ID NO: 19) or GVPSRFSGSGSGTDFTLTIES-LQPEDAATYYC (SEQ ID NO: 28); and
(d) an FR-L4 comprising the amino acid sequence of FGQGTKVEIK (SEQ ID NO: 20).

In certain embodiments, the antibody further comprises the following VH domain FRs:
(a) an FR-H1 comprising the amino acid sequence of

```
                                        (SEQ ID NO: 29)
EEQLVEEGGGLVQPGESLELSCAASGFEIS
or
                                        (SEQ ID NO: 51)
EEQLVEEGGGLVQPGESLRLSCAASGFEIS;
```

(b) an FR-H2 comprising the amino acid sequence of WVRQEPGEGLEWVA (SEQ ID NO: 30);
(c) an FR-H3 comprising the amino acid sequence of RFTISADTSENTAYLQMNELRAEDTAVYYCAR (SEQ ID NO: 31); and
(d) an FR-H4 comprising the amino acid sequence of WGQGELVTVSS (SEQ ID NO: 32).

In certain embodiments, the antibody further comprises the following VH domain FRs:
(e) an FR-H1 comprising the amino acid sequence of

```
                                        (SEQ ID NO: 29)
EEQLVEEGGGLVQPGESLELSCAASGFEIS
or
                                        (SEQ ID NO: 52)
EEQLVEEGGGLVQPGESLRLSCAASGFEIS;
```

(f) an FR-H2 comprising the amino acid sequence of WVRQEPGEGLEWVA (SEQ ID NO: 30);
(g) an FR-H3 comprising the amino acid sequence of RFTISADTSENTAYLQMNELRAEDTAVYYCAR (SEQ ID NO: 31); and
(h) an FR-H4 comprising the amino acid sequence of WGQGELVTVSS (SEQ ID NO: 32).

In certain embodiments, the antibody comprises (a) a VH domain comprising an amino acid sequence having at least 95% sequence identity to the amino acid sequence of SEQ ID NO: 11, 40, or 42; (b) a VL domain comprising an amino acid sequence having at least 95% sequence identity to the amino acid sequence of SEQ ID NO: 12, 41, or 46; or (c) a VH domain as in (a) and a VL domain as in (b).

In certain embodiments, the antibody comprises (a) a VH domain comprising the amino acid sequence of SEQ ID NO:11, 40, or 42; (b) a VL domain comprising the amino acid sequence of SEQ ID NO: 12, 41, or 46; or (c) a VH domain as in (a) and a VL domain as in (b).

In certain embodiments, the antibody comprises a VH domain comprising the amino acid sequence of SEQ ID NO:11 and a VL domain comprising the amino acid sequence of SEQ ID NO:12.

In certain embodiments, the antibody comprises a heavy chain comprising the amino acid sequence of SEQ ID NO:48 and a light chain comprising the amino acid sequence of SEQ ID NO:50.

In certain embodiments, the antibody comprises a heavy chain comprising the amino acid sequence of SEQ ID NO:49 and a light chain comprising the amino acid sequence of SEQ ID NO:50.

In certain embodiments, the antibody-hydrogel conjugate has an ocular effective half-life that is increased relative to a reference antibody that is not covalently attached to the hydrogel.

In certain embodiments, the ocular effective half-life is increased at least about 2-fold relative to the reference antibody.

In certain embodiments, the ocular effective half-life is increased at least about 5-fold relative to the reference antibody.

In certain embodiments, the ocular effective half-life is increased at least about 8-fold relative to the reference antibody.

In certain embodiments, the ocular effective half-life is increased at least about 10-fold relative to the reference antibody.

In certain embodiments, the ocular effective half-life is increased at least about 12-fold relative to the reference antibody.

In certain embodiments, the ocular effective half-life is increased at least about 15-fold relative to the reference antibody.

In certain embodiments, the ocular effective half-life is increased at least about 16-fold relative to the reference antibody.

In certain embodiments, the ocular effective half-life is a vitreal half-life.

In certain embodiments, the reference antibody is identical to the antibody of the antibody conjugate.

In certain embodiments, the invention provides a pharmaceutical composition for use as a medicament, for use in the manufacture of a medicament for treating a disorder associated with pathological angiogenesis in a subject, for use in reducing or inhibiting angiogenesis in a subject having a disorder associated with pathological angiogenesis, and/or for use in treating a disorder associated with pathological angiogenesis in a subject.

In certain embodiments, the pharmaceutical composition comprises the hydrogel conjugate and a pharmaceutically acceptable carrier, excipient, or diluent.

In certain embodiments, the pharmaceutical composition further comprising a second agent, wherein the second agent is selected from the group consisting of an antibody, an anti-angiogenic agent, a cytokine, a cytokine antagonist, a corticosteroid, an analgesic, and a compound that binds to a second biological molecule.

In certain embodiments, the pharmaceutical composition further comprising a second agent, wherein the second agent is selected from the group consisting of an antibody, an anti-angiogenic agent, a cytokine, a cytokine antagonist, a corticosteroid, an analgesic, and a compound that binds to a second biological molecule.

In certain embodiments, the anti-angiogenic agent of the pharmaceutical composition is a VEGF antagonist.

In certain embodiments, the VEGF antagonist of the pharmaceutical composition is an anti-VEGF antibody, an anti-VEGF receptor antibody, a soluble VEGF receptor fusion protein, an aptamer, an anti-VEGF DARPin®, or a VEGFR tyrosine kinase inhibitor.

In certain embodiments, the anti-VEGF antibody of of the pharmaceutical composition is ranibizumab (LUCENTIS®), RTH-258, or a bispecific anti-VEGF antibody.

In certain embodiments, the bispecific anti-VEGF antibody is an anti-VEGF/anti-Ang2 antibody.

In certain embodiments, the anti-VEGF/anti-Ang2 antibody is RG-7716.

In certain embodiments, the soluble VEGF receptor fusion protein is aflibercept (EYLEA®).

In certain embodiments, the aptamer is pegaptanib (MACUGEN®).

In certain embodiments, the anti-VEGF DARPin® is abicipar pegol.

In certain embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD 6474), 4-(4-fluoro-2-methylindol-5-yloxy)-6-methoxy-7-(3-pyrrolidin-1-ylpropoxy) quinazoline (AZD2171), vatalanib (PTK787), semaxaminib (SU5416), and SUTENT® (sunitinib).

In certain embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk.

In certain embodiments, the VEGF receptor is VEGFR1, VEGFR2, VEGFR3, mbVEGFR, or sVEGFR.

In certain embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A.

In certain embodiments, the compound that binds a second biological molecule is an antibody or antigen-binding fragment thereof.

In certain embodiments, the antigen-binding antibody fragment is selected from the group consisting of Fab, Fab-C, Fab'-SH, Fv, scFv, and (Fab')2 fragments.

In certain embodiments, the disorder associated with pathological angiogenesis is an ocular disorder.

In certain embodiments, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease.

In certain embodiments, the ocular disorder is AMD, DME, DR, or RVO.

In certain embodiments, the ocular disorder is AMD.

In certain embodiments, AMD is wet AMD.

In certain embodiments, the invention provides a method for treating an ocular indication, the method comprising administering a therapeutic amount of a solution of the pharmaceutical compositions described herein.

In certain embodiments, the administration of the pharmaceutical composition is intraocular.

In certain embodiments, the pharmaceutical composition is injected into the vitreum of the subject.

In certain embodiments, the pharmaceutical composition is injected using a needle having a gauge of 20, 21, 22, 23, 24, 25, 26, 27, 28, 29, 30, 31, or 32.

IIn certain embodiments, the ocular indication is selected from age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease.

In certain embodiments, the invention provides a method for producing a hydrogel drug conjugate, the method comprising:

(a) providing a first hyaluronic acid, or an alkali metal salt or a derivative thereof, having at least three first reactive groups thereon;

(b) providing a second hyaluronic acid, or an alkali metal salt or a derivative thereof, having at least two second reactive group thereon, wherein the first and second reactive groups are capable reacting with each other to form a covalent bond;

(c) coupling at least one drug to one of the first reactive groups; and (d) cross-linking the first and second hyaluronic acids by reaction of a first reactive group and a second reactive group to form a cross-linker and form the hydrogel conjugate.

In certain embodiments, the drug is coupled to the first hyaluronic acid via a reversible prodrug linker.

In certain embodiments, the drug is coupled to the reversible prodrug linker and purified to form a purified drug-reversible prodrug linker conjugate prior to coupling with the first hyaluronic acid, wherein the drug-reversible prodrug linker conjugate is purified by:

(a) tagging the drug-reversible prodrug linker conjugate with a purification tag to form a tagged drug-reversible prodrug linker conjugate mixture;
(b) purifying a tagged drug-reversible prodrug linker monoconjugate from the mixture by chromatographic separation; and
(c) removing the purification tag from the tagged drug-reversible prodrug linker monoconjugate to form the purified drug-reversible prodrug linker conjugate.

In certain embodiments, the cross-linker comprises a biodegradable spacer moiety.

In certain embodiments, the cross-linker comprises an azelaic acid ester moiety.

DETAILED DESCRIPTION OF THE INVENTION

In some aspects, the present disclosure generally relates to methods for preparing hydrogel prodrug compositions comprising cross-linked hyaluronic acid (HA), or a derivative or a salt thereof, wherein the cross-linker system comprises a biodegradable spacer, wherein the cross-linked HA comprises a conjugated drug-linker, and wherein the linker is capable of releasing the drug under physiological conditions. In some such aspects, hydrogel HA prodrug compositions of the present disclosure are of formulae 1, 10, 16 and 26 as shown in FIGS. 1, 3, 5 and 9 respectively. In the formulas, structures and reaction schemes herein, any open valency on a carbon, nitrogen, oxygen or sulfur atom should be understood as representing a hydrogen atom.

Figure 1:
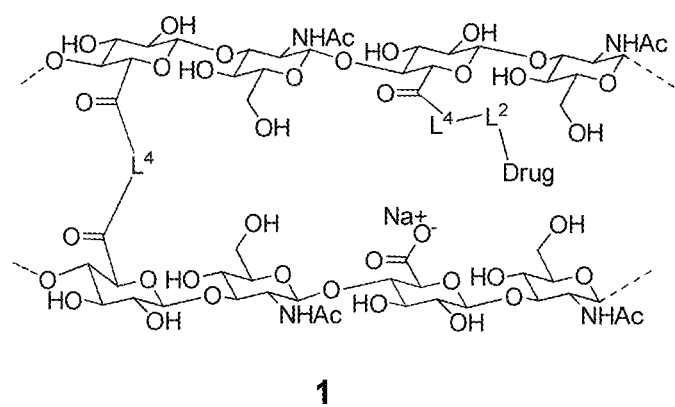
FIG. 1 is a cross-linked hyaluronic acid drug conjugate in accordance with the invention.

Referring to FIG. 1, a cross-linked HA drug conjugate compound 1 in accordance with the invention is shown. Compound 1 may be prepared as described further below. In compound 1, a drug moiety is joined to an HA moiety via a linker $L^2$, which is a reversible prodrug linker moiety, and a spacer $L^4$, as described further herein. The drug moiety may comprise any therapeutic or biologically active moiety as also described further herein. HA moieties are joined or cross-linked together by a spacer $L^4$, and the $L^2$-Drug moiety is joined to an HA moiety by spacer $L^4$. The spacers $L^4$ may be the same or different in each occurrence, and may in many embodiments be biodegradable, as described further herein.

Spacers $L^4$ may vary according to the type of chemistry used for cross-linking the HA moieties and attaching the $L_2$-Drug moiety to an HA moiety. In many embodiments herein the cross-linked HA drug conjugates of the invention are based on thiol-maleimide chemistry and thus spacers $L^4$ comprise thiosuccinimide groups resulting from reaction of thiols and maleimides. It should be understood, however, that various types of chemistry may be used for cross-linking the HA moieties and attaching the $L^2$-Drug moiety to an HA moiety in accordance with the invention are also within the scope of this disclosure. For example, "click" chemistry based on reaction of alkynes with azides as disclosed in WO2003101972, WO2011136645, WO2013036748 and WO2013171485, the disclosures of which are incorporated herein by reference, may be used for cross-linking the HA moieties and attaching the $L^2$-Drug moiety to an HA moiety. Acrylic based cross-linking chemistry, amine-epoxide cross-linking chemistry, and other linkage forming chemistries may also be used with the invention.

Figure 2:
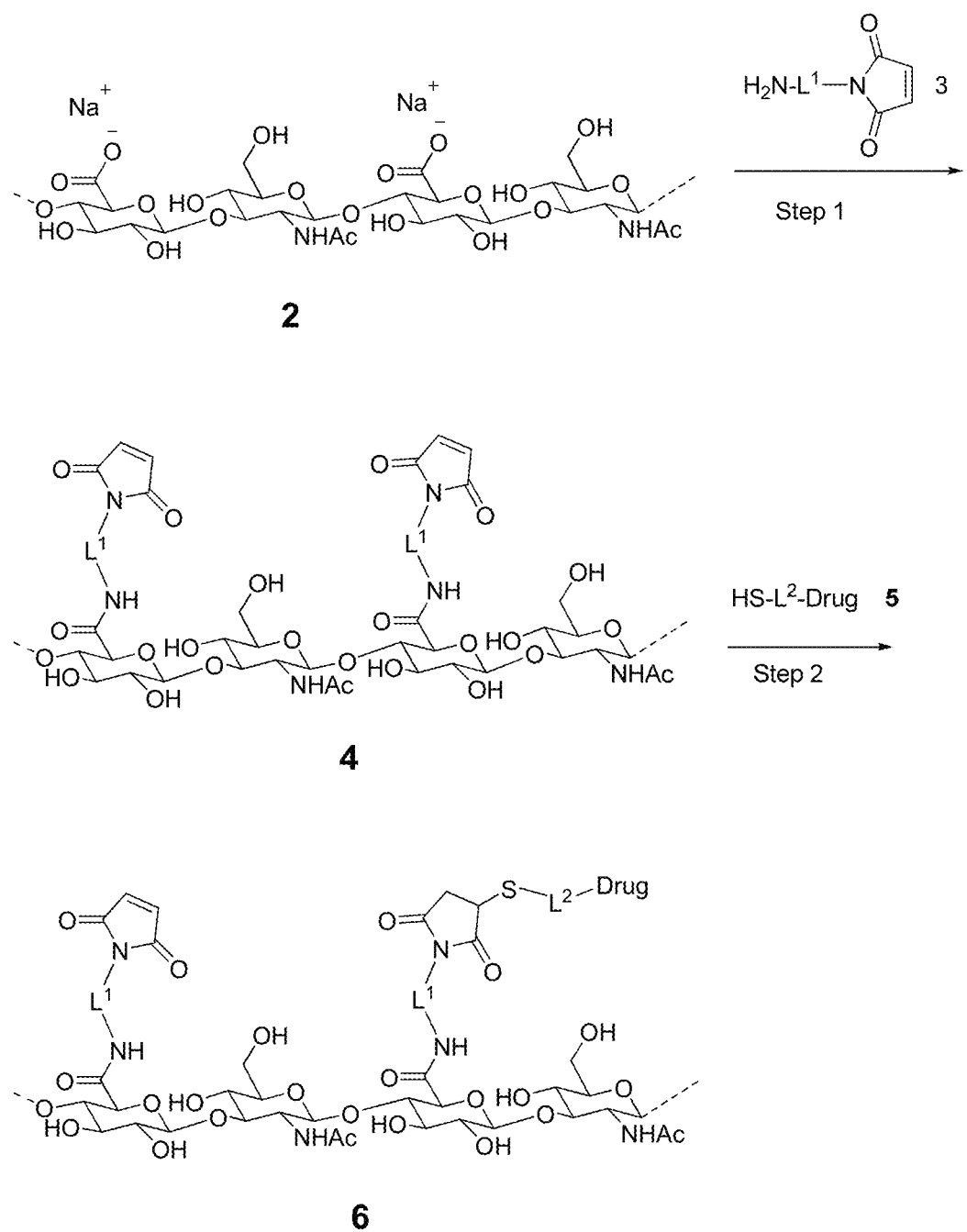
FIG. 2 is a reaction scheme according to one aspect of the present disclosure for the preparation of maleimide functionalized hyaluronic acid (HA) and maleimide functionalized hyaluronic acid having a conjugated drug.
Figure 3:
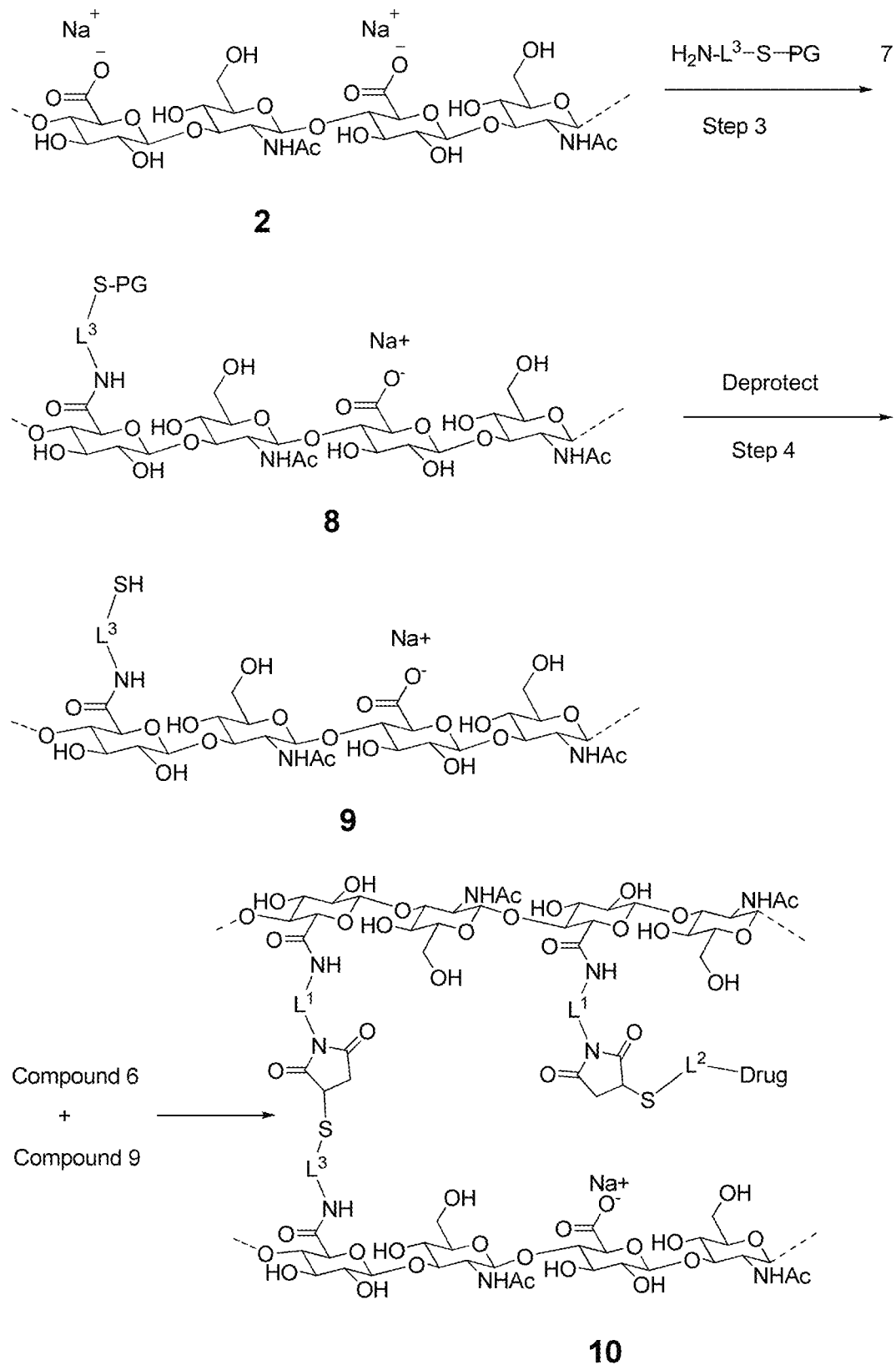
FIG. 3 is a reaction scheme according to one aspect of the present disclosure for the preparation of protected thiol functionalized hyaluronic acid, thiol functionalized hyaluronic acid, and a cross-linked hyaluronic acid prodrug composition.

Referring also FIGS. 2 and 3, there is shown a cross-linked HA drug conjugate hydrogel compound 10 (FIG. 3) in accordance with the invention. In compound 10, the spacer $L^4$ of compound 1 that joins the HA moieties together is more particularly shown as

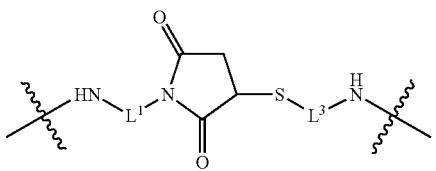

and the spacer $L^4$ joining the $L_2$-Drug moiety to an HA moiety is shown more particularly as

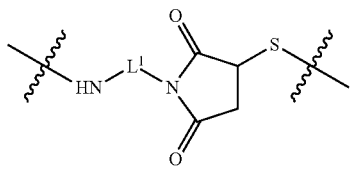

wherein $L^1$ and $L^3$ are as defined herein. In general, compound 10 may be prepared according to the method depicted in FIGS. 2 and 3. In a first step, a first HA compound 2 (or a derivative or a salt thereof) is conjugated with maleimide compound 3 to form compound 4 comprising maleimide reactive groups conjugated to HA by a spacer $L^1$.

In a second step, thiol-$L^2$-drug conjugate compound 5 is reacted with the maleimide reactive groups of compound 4 to form compound 6 comprising conjugated —S-$L^2$-drug conjugate moieties. In some aspects, $L^2$ is a reversible prodrug linker moiety, as described further elsewhere herein, that is capable of controlled release of the drug under physiological conditions. The thiol group in compound 5 may be part of the reversible prodrug linker $L^2$. In some aspects, the drug is a therapeutic such as an anti-VEGF molecule that is useful for treatment of diseases in the eye. The equivalents of maleimide groups on compound 4 exceeds the equivalents of drug conjugate compound 5 such that compound 6 comprises free maleimide groups.

In a third step, a second HA compound 2 (or a derivative or a salt thereof) is conjugated with protected (shown with a protecting group PG) thiol compound 7 to form compound 8 comprising protected thiol groups conjugated to HA by spacer $L^3$. In some aspects, $L^3$ is a biodegradable spacer moiety.

In a fourth step, the protecting groups of compound 8 are removed to generate compound 9 having thiol groups. In certain embodiments the protecting group may form a disulfide with the thiol groups such that removal of the protecting group may be achieved with a reducing agent.

In a fifth step, compound 6 and compound 9 are combined and reacted to form cross-linked HA hydrogel prodrug compound 10.

The degree of functionalization of maleimide and thiol as shown in the Figures is only illustrative and it should be understood that not all of the carboxylate groups in HA compound 2 undergo reaction, and in most embodiments the majority of the carboxylate groups are unreacted. The maleimide functionalized HA compound 4 in FIG. 2 will have a sufficient degree of functionalization such that a portion of the maleimide functional groups in compound 4 are available for attachement of drug (as shown in compound 6) and the remaining maleimide groups are available to undergo cross-linking reaction with thiol groups of compound 9 to ultimately provide the cross-linked HA hydrogel prodrug composition 10 in accordance with the invention. For example, the degree of maleimide functionalization of compound 4 may range from about about 5% to about 15%, while the degree of functionalization of thiol compound 9 may range from about 1% to about 7%.

In certain embodiments, the degree of functionalization of HA compound 4 with maleimide may range from about 6% to about 14%, from about 7% to about 13%, from about 8% to about 12%, from about 10% to about 12%, and from about 9% to about 11%. The degree of functionalization of HA compound 9 with thiol as shown in FIG. 3 may, for example, be varied from about 1% to about 7%, from about 2% to about 6%, and from about 3% to about 5%.

In certain embodiments the degree of maleimide functionalization on HA compound 4 as shown in in FIG. 2 may be about 10%, such that about one out of ten carboxylate groups on first HA compound 2 are derivatized with maleimide. In other words, if HA compound 2 has x number of carboxylate groups thereon, then compound 4 includes 0.1x maleimide groups. The degree of thiol functionalization on HA compound 9 as shown in FIG. 3 may be about 4%, or for x carboxylate groups on HA compound 2, there are 0.04x thiol groups on compound 9 (and correspondingly 0.04x protected thiol groups on compound 8).

In compound 6, about 77% of the maleimides on average will be substituted with Drug, while the remaining approximately 23% are used for the cross-linking reaction with compound 9 to provde the cross-linked gel 10. Thus, for example, a 116 kDa HA that is 10% functionalized with maleimide, there will be approximately 28 maleimide groups thereon, of which approximately 22 maleimide groups will be addressed by Drug. 4.

Figure 4:
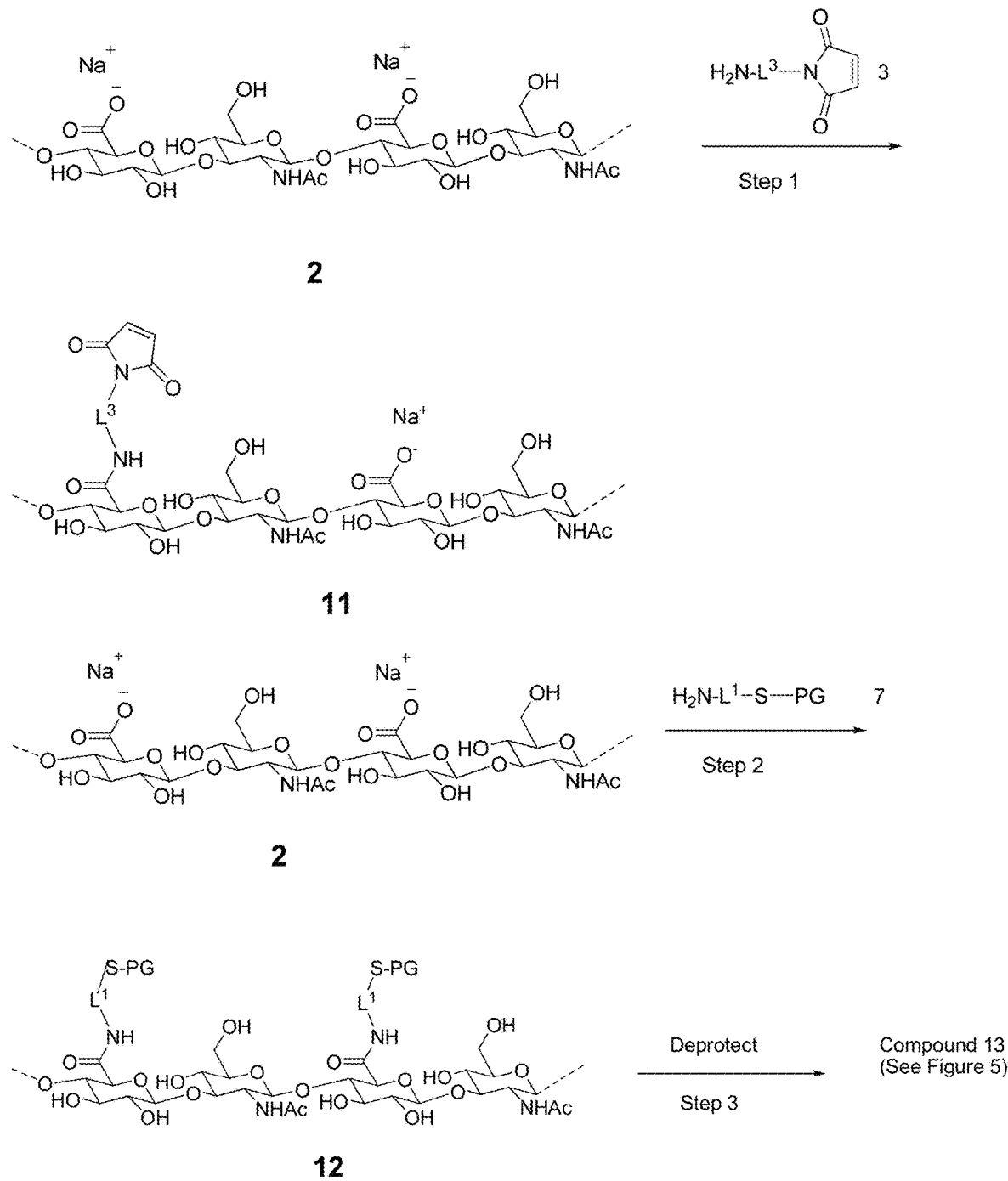
FIG. 4 is a reaction scheme according to one aspect of the present disclosure for the preparation of maleimide functionalized hyaluronic acid and protected disulfide functionalized hyaluronic acid.
Figure 5:
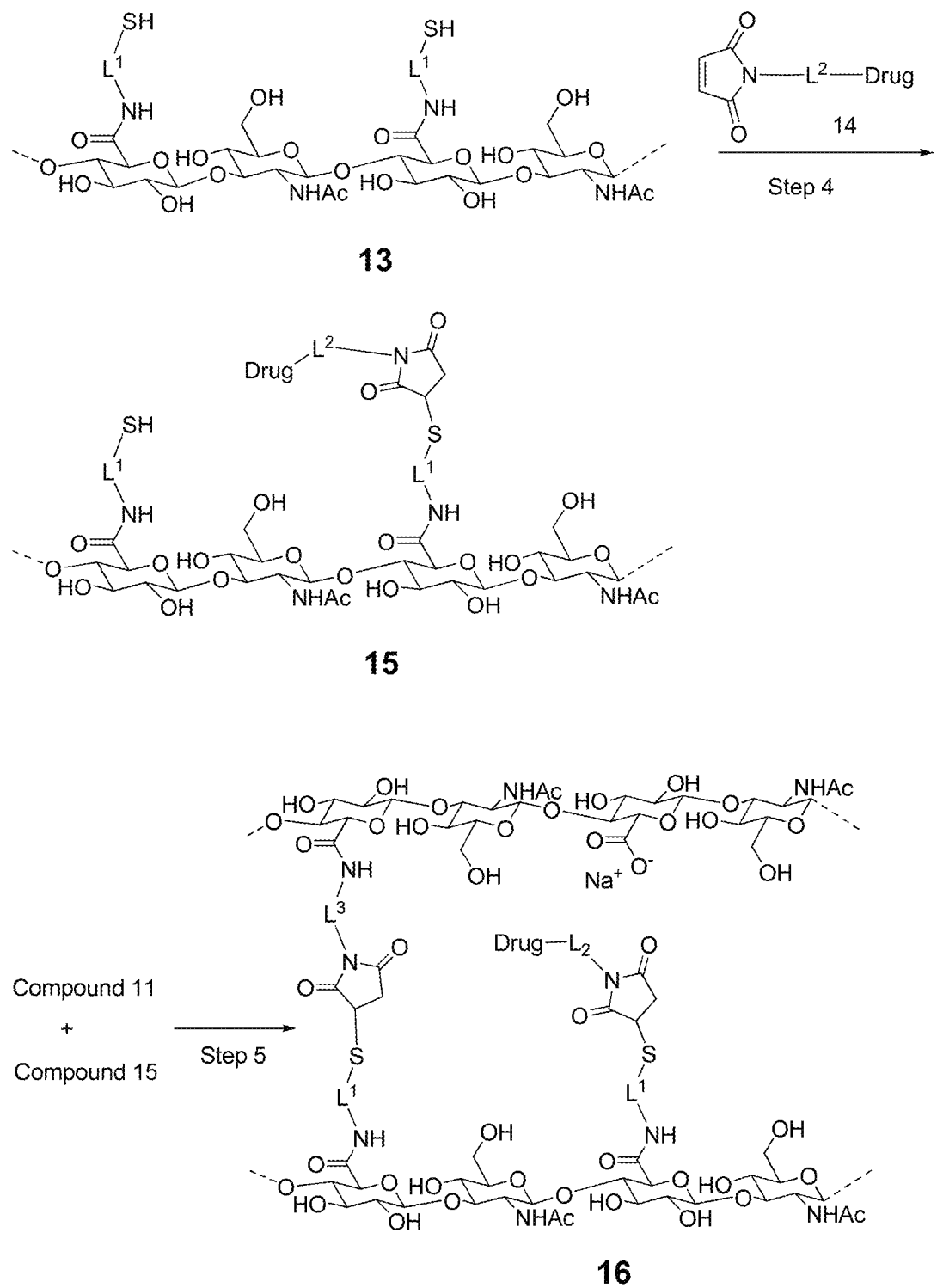
FIG. 5 is a reaction scheme according to one aspect of the present disclosure for the preparation of thiol functionalized hyaluronic acid, thiol functionalized hyaluronic acid having a conjugated drug, and a cross-linked hyaluronic acid prodrug composition.

Referring now to FIGS. 4 and 5, the preparation of compound 16 is shown.

In a first step, a first HA compound 2 (or a derivative or a salt thereof) is conjugated with maleimide compound 3 to form compound 11 comprising maleimide reactive groups conjugated to HA by spacer $L^3$.

In a second step, a second HA compound 2 (or a derivative or a salt thereof) is conjugated with protected (PG) disulfide compound 7 to form compound 12 comprising protected disulfide groups conjugated to HA by spacer $L^1$. In some aspects, $L^1$ is a biodegradable spacer moiety.

In a third step, the protecting groups of compound 12 are removed to generate compound 13 having thiol groups.

In a fourth step, maleimide-$L^2$-drug conjugate compound 14 is reacted with the thiol reactive groups of compound 13 to form compound 15 comprising conjugated drug moieties. The equivalents of thiol groups exceeds the equivalents of compound 14 such that compound 15 comprises free thiol groups. In some aspects, $L^2$ is a reversible prodrug linker moiety that is capable of controlled release of the drug under physiological conditions. In some aspects, the drug is an anti-VEGF molecule.

In step 5, compound 11 and compound 15 are combined such that the free maleimide and thiol groups respectively thereon are reacted to form cross-linked HA hydrogel prodrug compound 16. In compound 16, the spacer $L^4$ as shown in FIG. 1 that joins the HA moieties together is more particularly represented by

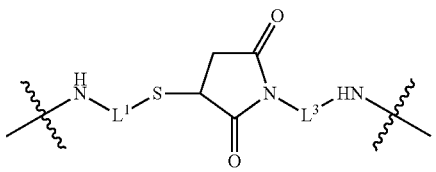

and the spacer L⁴ joining the L²-Drug moiety to an HA moiety is represented more particularly as

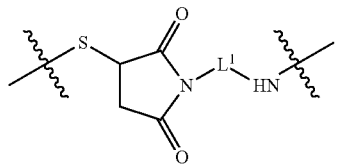

wherein L¹ and L³ are as defined herein.

As described above, the degree of functionalization of the carboxylate groups on HA compounds 2 as shown in the Figures is arbitrary and is for illustrative purposes. The thiol functionalized HA compound 13 (and protected thiol functionalized compound 12) will have a higher degree of functionalization than maleimide functionalized HA compound 11. A portion of the thiol functional groups in compound 13 will be used for attachement of drug and the remaining thiol groups are available to undergo cross-linking reaction with maleimide groups of compound 11 to provide the cross-linked HA hydrogel prodrug composition 16. For example, the degree of thiol functionalization of compound 13 may range from about about 5% to about 15%, while the degree of functionalization of maleimide compound 11 may range from about 1% to about 7%. Variation of the degree of thiol and maleimide functionalization allows different cross-link densities and different degrees of loading of drug in the bioconjugate of the invention as described above.

In some aspects, as depicted in FIGS. 6 to 9, cross-linked HA hydrogel prodrugs may be prepared by (1) preparation of a first amine functionalized HA and preparation of a maleimido-functionalized HA therefrom, (2) preparation of a second amine functionalized HA and preparation of a thiol-functionalized HA therefrom, (3) conjugation of a drug-linker conjugate to the maleimido-functionalized HA wherein a portion of the maleimido groups are not conjugated with the drug-linker conjugate, and (4) formation of cross-linked HA hydrogel prodrugs by reaction of the maleimido groups on the first functionalized HA with the thiol groups on the second functionalized HA.

Figure 6:
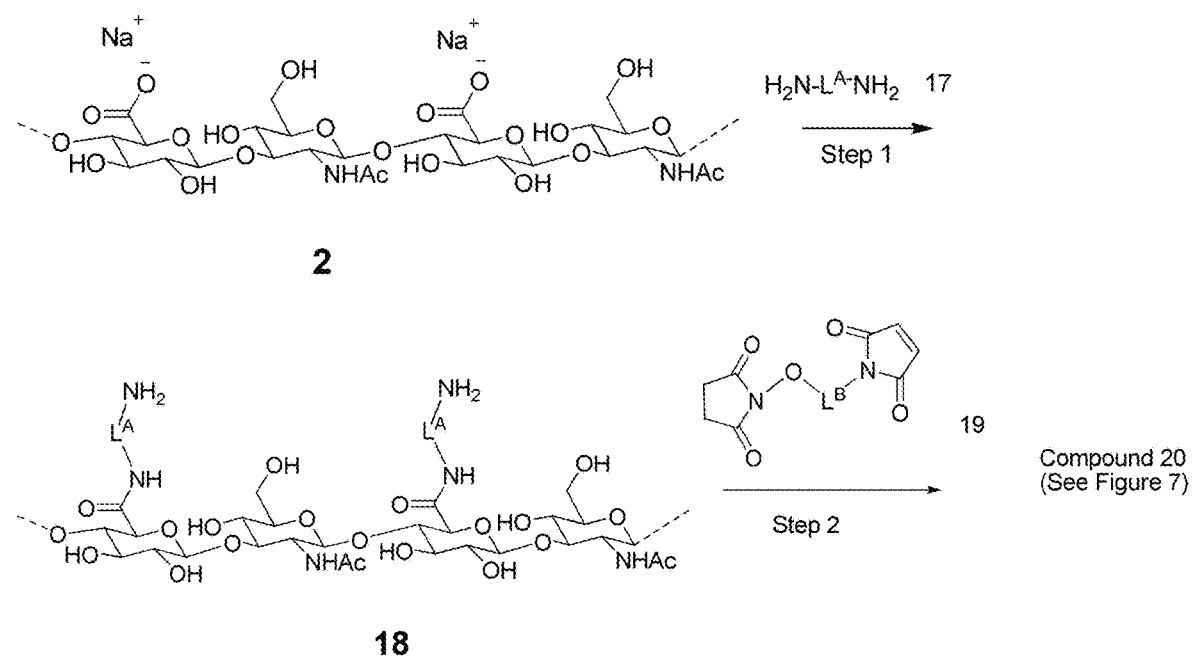
FIG. 6 is a reaction scheme according to one aspect of the present disclosure for the preparation of amine functionalized hyaluronic acid and the preparation of maleimide functionalized hyaluronic acid therefrom.

In FIG. 6, step 1, a first sodium hyaluronate compound 2 (or the acid form or a derivative thereof) is reacted with H₂N-L⁴-NH₂ compound 17 to form amine-functionalized HA compound 18 where the degree of amine functionalization of the HA is from about 5% to about 15%, from about 6% to about 14%, from about 7% to about 13%, from about 8% to about 12%, from about 9% to about 11%, or in some embodiments, about 10%; about 11%; or about 12% In some aspects, LA is a spacer moiety as defined herein.

Figure 7:
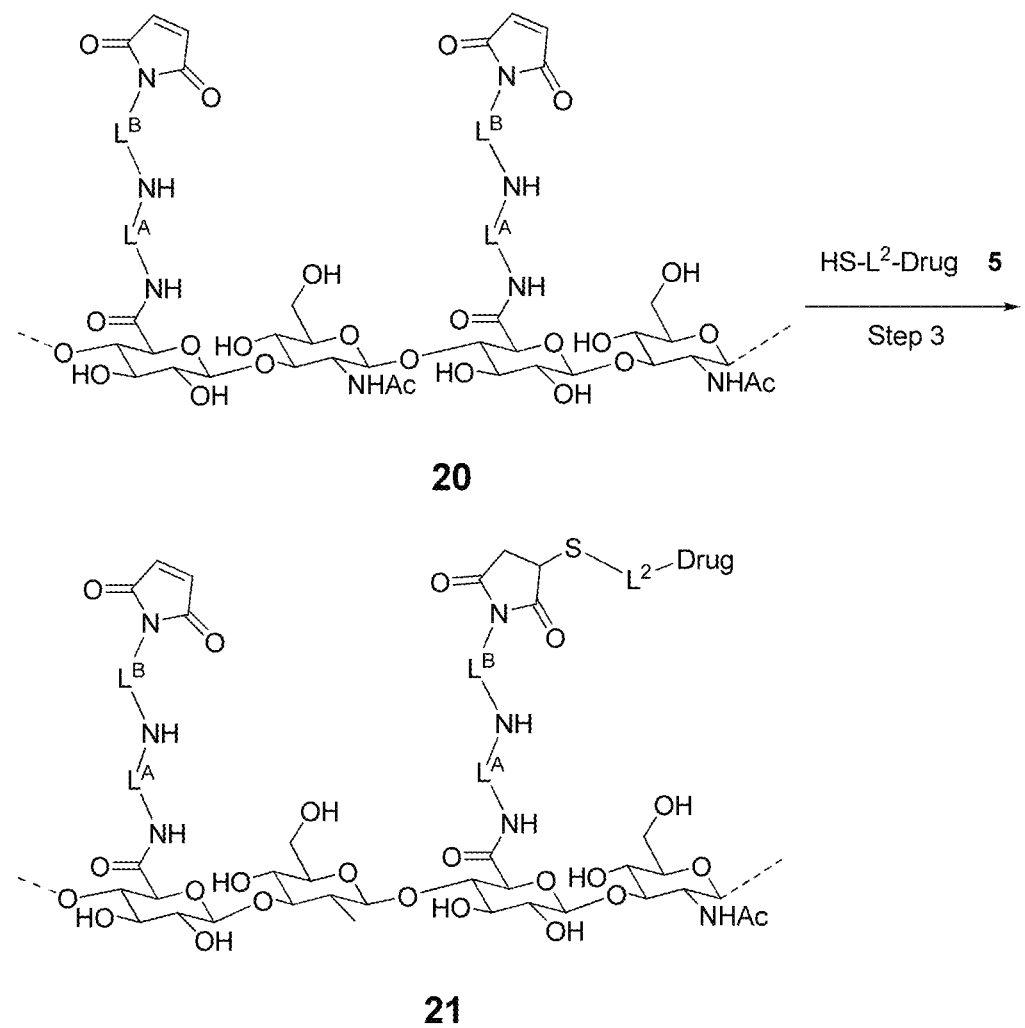
FIG. 7 is a reaction scheme according to one aspect of the present disclosure showing maleimide functionalized hyaluronic acid and maleimide functionalized hyaluronic acid having a conjugated drug.

As depicted in FIG. 6, step 2, compound 18 is reacted with N-hydroxysuccinimide-L_B-maleimide compound 19 to form maleimido-functionalized HA compound 20 depicted in FIG. 7. In some aspects, L_B is a spacer moiety that forms an activated ester with the succinimide portion of reagent 19

As depicted in FIG. 7, step 3, compound 20 is reacted with thiol drug conjugate compound 5 to form a prodrug precursor compound 21. L₂ is a reversible prodrug linker as defined herein.

Figure 8:
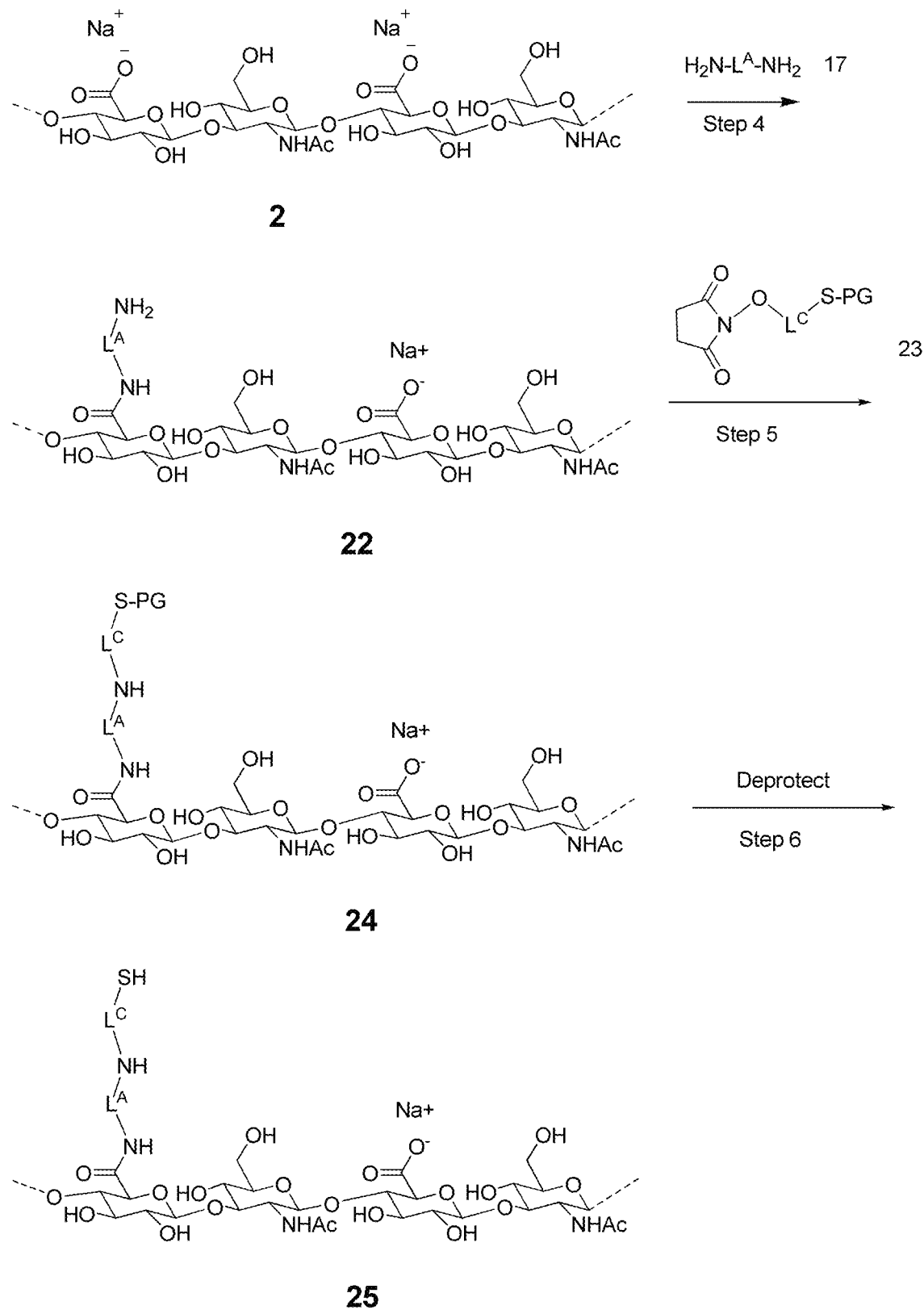
FIG. 8 is a reaction scheme according to one aspect of the present disclosure for the preparation of amine functionalized hyaluronic acid, protected disulfide functionalized hyaluronic acid, and thiol functionalized hyaluronic acid.

As shown in FIG. 8, step 4, a second sodium hyaluronate compound 2 (or the acid form or a derivative thereof) is reacted with H₂H-L⁴-NH₂ compound 17 to form amine-functionalized HA (compound 22) where the degree of amine functionalization of the HA may be varied from about 1% to about 7%, from about 2% to about 6%, from about 3% to about 5%, and in certain embodiments 4%.

Figure 9:
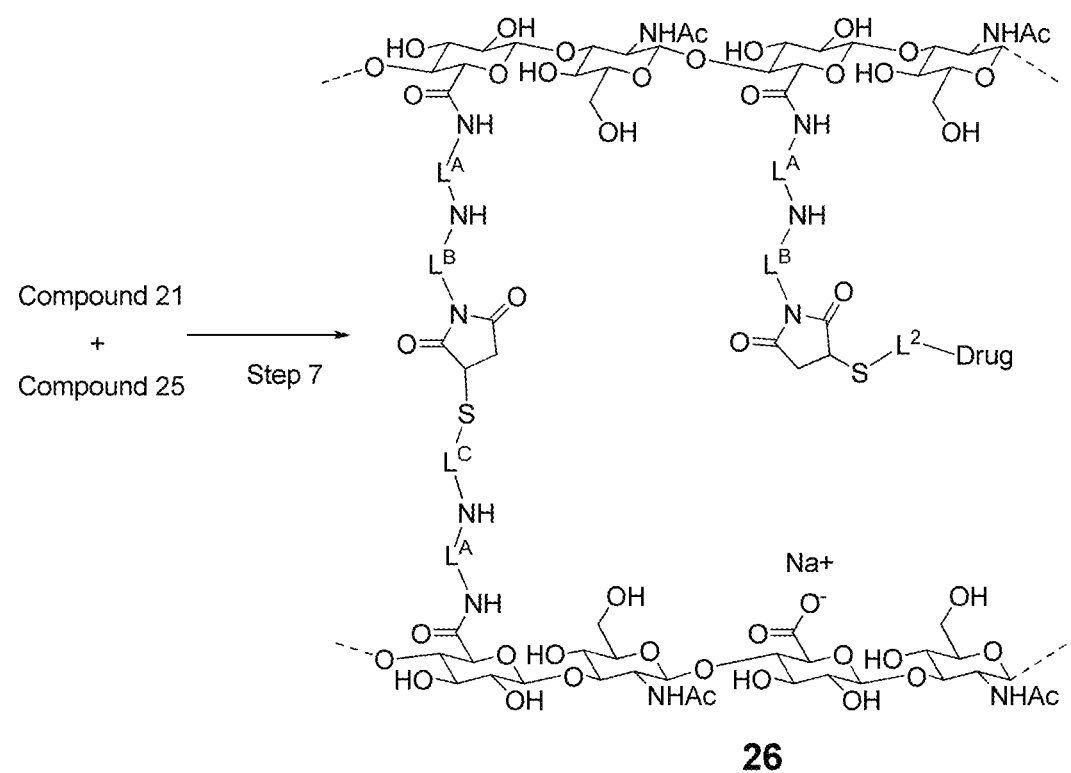
FIG. 9 is a reaction scheme according to one aspect of the present disclosure for the preparation of a cross-linked hyaluronic acid prodrug composition.

As further depicted in FIG. 8, step 5, compound 22 is reacted with N-hydroxysuccinimide-L^C-SProtecting Group (Protecting Group shown as "PG") compound 23 to form compound 24. Compound 24 is then is deprotected in step 6 to remove the protecting group and form thiol-functionalized HA compound 25. In some aspects, L^C is a biodegradable spacer moiety that forms an activated ester with the succinimide portion of reagent 23. As depicted in FIG. 9, prodrug precursor compound 21 is cross-linked with thiol-functionalized HA compound 25 to form cross-linked HA hydrogel prodrug composition 26. In compound 26, the spacer L⁴ as shown in FIG. 1 that joins the HA moieties together is more particularly represented by

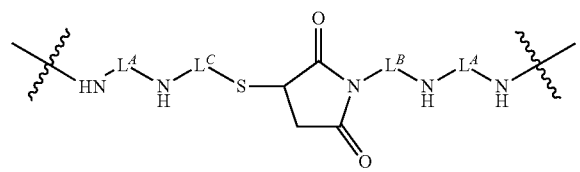

and the spacer L⁴ joining the L²-Drug moiety to an HA moiety is represented more particularly as

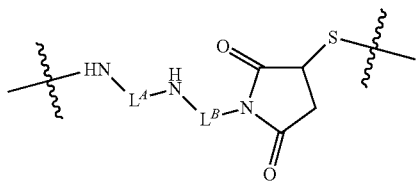

wherein L^A, L^B and and L^C are as defined herein.

As in the embodiment of FIGS. 2-3 described above, in the embodiment of FIGS. 6-9 the maleimide functionalized HA compound 20 in FIG. 7 will have a higher degree of functionalization than thiol functionalized HA compound 25 in FIG. 8. A portion of the maleimide functional groups in compound 20 will be used for attachement of drug (as shown in compound 21) and the remaining maleimide groups are available to undergo cross-linking reaction with thiol groups of compound 25 to provide the cross-linked HA hydrogel prodrug composition 26 in accordance with the invention. The ranges and values of degree of functionalization of maleimide and thiol groups, the ranges and values for cross-link density, and the ranges and values for drug loading related elsewhere herein also apply to the embodiment of FIGS. 6-9.

Definitions

As used herein, hyaluronic acid (HA) refers to HA and any derivatives and salts thereof. In certain embodiments HA may be of the formula:

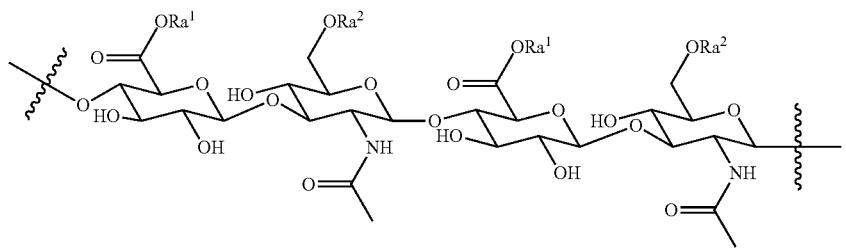

wherein Ra¹ and Ra² each independently represents hydrogen, lower alkyl or other ester forming group, a metal or or ammonium (including mono-, di-, tri- and tetra- alkyl ammonium) counter ion or other type of counter ion. In certain embodiments Ra¹ is independently selected from H, $C_{1-4}$ alkyl and an alkali metal counter-ion, and each Ra² is independently selected from H, $C_{1-4}$ alkyl and an alkali metal counter-ion. In some aspects, each Ra¹ is Na⁻ and each Ra² is H. In some possible derivatives of HA as shown above, the hydroxyl groups may each independently be replaced with $C_{1-4}$ alkyl ethers (not shown) or with $C_{1-4}$ alkyl esters (not shown), and the nitrogen atom of each of the amide functionalities may optionally be substituted (alkylated) with $C_{1-4}$ alkyl (also not shown). The HA number average molecular weight is about 10 kDa, about 25 kDa, about 50 kDa, about 75 kDa, about 100 kDa, about 125 kDa, about 150 kDa, about 175 kDa, about 200 kDa, about 225 kDa, about 250 kDa, about 275 kDa, about 300 kDa, about 325 kDa, about 350 kDa, about 375 kDa, about 400 kDa, about 425 kDa, about 450 kDa, about 475 kDa, about 500 kDa, about 550 kDa, about 600 kDa, about 650 kDa, about 700 kDa, and ranges thereof, such as from about 10 kDa to about 1000 kDa, from about 25 kDa to about 750 kDa, from about 50 kDa to about 250 kDa, from about 75 kDa to about 200 kDa, from about 75 kDa to about 175 kDa, from about 100 kDa to about 150 kDa, or from about 100 kDa to about 125 kDa.

The term "reversible prodrug linker" or simply "linker" refers to a moiety which on its one end is attached to a drug, e.g., a VEGF neutralizing drug, through a reversible linkage and on another end is attached through a permanent bond to a carrier, such as the hydrogels in accordance with the invention, thereby linking the drug to the carrier. Examplary reversible prodrug linkers usable with the invention are disclosed in WO2009095479, the disclosure of which is incorporated herein by reference. In such embodiments the resversible prodrug linker is a group of formula XIIa

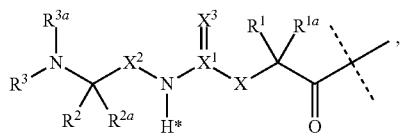

XIIa wherein
the dashed line indicates the attachment to a nitrogen of a drug compound (not shown) by forming an amide bond;
—X— is —C(R⁴R⁴ᵃ)—; —N(R⁴)—; —O—; —C(R⁴R⁴ᵃ)—C(R⁵R⁵ᵃ)—; —C(R⁵R⁵ᵃ)—C(R⁴R⁴ᵃ)—; —C(R⁴R⁴ᵃ)—N(R⁶)—; —N(R⁶)—C(R⁴R⁴ᵃ)—; —C(R⁴R⁴ᵃ)—O—; —O—C(R⁴R⁴ᵃ)—; or —C(R⁷R⁷ᵃ)—;

X¹ is C; or S(O);
—X²— is —C(R⁸R⁸ᵃ)—; or —C(R⁸R⁸ᵃ)—C(R⁹R⁹ᵃ)—;
=X³ is =O; =S; or =N—CN;
—R¹, —R¹ᵃ, —R², —R²ᵃ, —R⁴, —R⁴ᵃ, —R⁵, —R⁵ᵃ, —R⁶, —R⁸, —R⁸ᵃ, —R⁹, —R⁹ᵃ are independently selected from the group consisting of —H; and $C_{1-6}$ alkyl;
—R³, —R³ᵃ are independently selected from the group consisting of —H; and $C_{1-6}$ alkyl, provided that in case one of —R³, —R³ᵃ or both are other than —H they are connected to N to which they are attached through an SP³-hybridized carbon atom;
—R⁷ is —N(R¹⁰, R¹⁰ᵃ); or —NR¹⁰—(C=O)—R¹¹;
—R⁷ᵃ, R¹⁰, R¹⁰ᵃ, —R¹¹ are independently of each other —H; or $C_{1-10}$ alkyl;
optionally, one or more of the pairs —R¹ᵃ/—R⁴ᵃ, —R¹ᵃ/—R⁵ᵃ, —R¹ᵃ/—R⁷ᵃ, —R⁴ᵃ/—R⁵ᵃ, —R⁸ᵃ/—R⁹ᵃ form a chemical bond;
optionally, one or more of the pairs —R¹/R¹ᵃ, —R²/—R²ᵃ, —R⁴/—R⁴ᵃ, —R⁵/—R⁵ᵃ, —R⁸/—R⁸ᵃ, —R⁹/—R⁹ᵃ are joined together with the atom to which they are attached to form a $C_{3-10}$ cycloalkyl; or 3- to 10-membered heterocyclyl;
optionally, one or more of the pairs —R¹/—R⁴, —R¹/—R⁵, —R¹/—R⁶, —R¹/—R⁷ᵃ, —R⁴/—R⁵, —R⁴/—R⁶, —R⁸/—R⁹, —R²/—R³ are joined together with the atoms to which they are attached to form a ring A;
optionally, R³/R³ᵃ are joined together with the nitrogen atom to which they are attached to form a 3- to 10-membered heterocycle;
A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein the group of formula XIIa is substituted with -L⁴ provided that the hydrogen marked with the asterisk in formula (XIIa) is not replaced by -L⁴ or other substituent;
wherein -L⁴- is a single chemical bond or a spacer moiety as defined herein; and
wherein the $C_{1-10}$ alkyl may be optionally interrupted and/or optionally substituted as defined herein.

Additional reversible prodrug linkers usable in other embodiments of the invention are described in WO05099768A2, WO06136586A2, WO2011/012722A1, WO2011/089214A1, WO2011/089216A1, WO2011/089215A1, WO2013/024053A1, WO2013/160340A1, WO2016/020373A1, WO2016/196124A2, EP1536334B1, WO2009/009712A1, WO2008/034122A1, WO2009/143412A2, WO2011/082368A2, US8618124B2, US8946405B2, US8754190B2, WO2013/036857A1, US7585837B2 and WO2002/089789A1, the disclosures of which are incorporated herein by reference.

A spacer or spacer moiety in many embodiments may be selected from -T-, —$C_{1-10}$alkylene, —C(O)O—, —O—, —C(O)—, —C(O)N(R^{y1})—, —S(O)₂N(R^{y1})—, —S(O)N $(R^{y1})$—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

wherein:

—R$^{y1}$ and —R$^{y1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more —R$^{y2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

each —R$^{y2}$ is independently selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —NR$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

Such spacer is a "biodegradable spacer" if the spacer moiety comprises at least one biodegradable linkage.

In certain embodiments a spacer moiety may be selected from -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)NR$^{y1}$)—, C$_{1-50}$ alkyl, C$_{2-50}$ alkenyl, and C$_{2-50}$ alkynyl; wherein C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —NR$^{y3}$)—, —OC(OR$^{y3}$)(R$^{y3a}$)—, —NR$^{y3}$)C(O)NR$^{y3a}$)—, and —OC(O)N(R$^{y3}$)—;

wherein:

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

—R$^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$) C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5a}$, and —R$^{y5b}$ is independently of each other selected from the group consisting of —H, and C$_{1-6}$ alkyl; wherein C$_{1-6}$ alkyl is optionally substituted with one or more halogen, which are the same or different.

Such spacer is a "biodegradable spacer" if the spacer moiety comprises at least one biodegradable linkage.

In still other embodiments a spacer moiety may be selected from -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$NR$^{y1a}$)—, —S—, —NR$^{y1}$)—, —OC (OR$^{y1}$)(R$^{y1a}$)—, —NR$^{y1}$)C(O)R$^{y1a}$)—, —OC(O) NR$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$) S(O)$_2$N(R$^{y3}$)—, —S—, —N(R$^{y3}$)—, —OC(OR$^{y3}$)(R$^{y3a}$)—, —NR$^{y3}$)C(O)NR$^{y3a}$)—, and —OC(O)N(R$^{y3}$)—;

wherein:

R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

Such spacer is a "biodegradable spacer" if the spacer moiety comprises at least one biodegradable linkage. In further embodiments a spacer moiety may be a $C_{1-20}$ alkyl chain, which is optionally interrupted by one or more groups independently selected from —O—, -T- and —C(O)N($R^{y1}$)—; and which $C_{1-20}$ alkyl chain is optionally substituted with one or more groups independently selected from —OH, -T and —C(O)N($R^{y6}R^{y6a}$); wherein —$R^{y1}$, —$R^{y6}$, —$R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Such spacer is a "biodegradable spacer" if the spacer moiety comprises at least one biodegradable linkage.

A biodegradable linkage may be an ester or carbonate linkage, for example.

As used herein, "TAG" and "Purification TAG" refer to a moiety which, when conjugated to a second moiety, confers (a) physical and/or chemical property/properties not present in said second moiety without the tag moiety and which different physical and/or chemical property/properties allow for the purification of such a conjugate.

As used herein, "protecting group" or "PG" refer to a moiety that is used for the reversible protection of functional groups during chemical reaction processes to render these functional groups essentially unreactive in said chemical reaction processes.

As used herein, the term "prodrug" means a conjugate in which a drug is covalently and reversibly conjugated to a reversible linker moiety, which reversible prodrug linker moiety is either directly or indirectly through a spacer moiety attached to a carrier, such as a hydrogel in accordance with the invention. A prodrug releases the drug under physiological conditions (aqueous buffer, 37.4° C., pH 7.4). Such released drug may be unmodified, meaning that no residue from the reversible prodrug linker moiety remains attached to the released drug.

As used herein, the term "drug" refers to any substance which can affect any physical or biochemical properties of a biological organism, including but not limited to viruses, bacteria, fungi, plants, animals, and humans. In particular, as used herein, the terms include any substance intended for diagnosis, cure, mitigation, treatment, or prevention of disease in organisms, in particular humans or animals, or to otherwise enhance physical or mental well-being of organisms, in particular humans or animals. In some aspects, the drug is a biologically active moiety that modulates the activity of one or more protein(s) selected from the group comprising basic fibroblast growth factors (bFGF), acidic fibroblast growth factors (aFGF), transforming growth factors alpha (TGFa), transforming growth factors beta (TGFβ), platelet-derived growth factor (PDGF), angiogenin, platelet-derived endothelial cell growth factor (PD-ECGF), interleukin-1 (IL-1), interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin plasminogen fragment, antiangiogenic anti-thrombin III, cartilage-derived inhibitor (CDI), CDS9 complement fragment, endostatin collagen XVIII fragment, fibronectin fragment, gro-beta, heparinases, heparin hexasaccharide fragment, human chorionic gonadotropin (hCG), interferon alpha/beta/gamma, interferon inducible protein (IP-I0), kringle S plasminogen fragment, metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, vasostatin calreticulin fragment, prostaglandin receptor, growth hormone, insulin-like growth factor-I (IGF-I), sphingosine-1-phosphate, factor D, RTP801, inhibitors of complement, α2 adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), pigment epithelium-derived factor (PEDF), neutrophil-activating protein, monocyte chemoattractant protein, macrophage-inflammatory protein, small inducible secreted (SIS) proteins, platelet factor, platelet basic protein, melanoma growth stimulating activity, epidermal growth factor, nerve growth factor, bone morphogenic proteins, bone growth cartilage-inducing factor, interleukins, interleukin inhibitors, interleukin receptors, hematopoietic factors, granulocyte colony stimulating factor, macrophage colony stimulating factor, granulocyte-macrophage colony stimulating factor, inhibin, and activing. In some aspects the drug is a VEGF antagonist. The term "drug" is also used for the conjugated drug, which compared to the free drug, lacks a hydrogen.

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and VEGF121-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or VEGF165.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib). Additional VEGF antagonists are described below.

A "disorder" is any condition that would benefit from treatment with the antibody conjugates described herein. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include disorders associated with pathological angiogenesis (e.g., ocular disorders and cell proliferative disorders) and disorders associated with undesirable vascular permeability.

An "effective amount" of an agent, e.g., a pharmaceutical formulation, refers to an amount effective, at dosages and for periods of time necessary, to achieve the desired therapeutic or prophylactic result.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibody conjugates of the invention or other compositions that include an antibody conjugate of the invention (e.g., a pharmaceutical formulation) are used to delay development of a disease or to slow the progression of a disease The term "interrupted" means that a moiety is inserted between two carbon atoms or—if the insertion is at one of the moiety's ends—between a carbon or heteroatom and a hydrogen atom, preferably between a carbon and a hydrogen atom. Non-limiting examples of such atoms and moieties include —O—, —S—, —N(H)—, —N(Substituted)-, —NC(O)— and —OC(O)—.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below. Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "alkylene" refers to a bivalent saturated aliphatic radical such as methylene, ethylene, propylene and the like.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=$CH_2$, —CH=CH—$CH_3$, —$CH_2$—CH=$CH_2$, —CH=$CHCH_2$—$CH_3$ and —CH=CH—CH=$CH_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below. Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below. Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more moieties which are preferably selected from the group consisting of

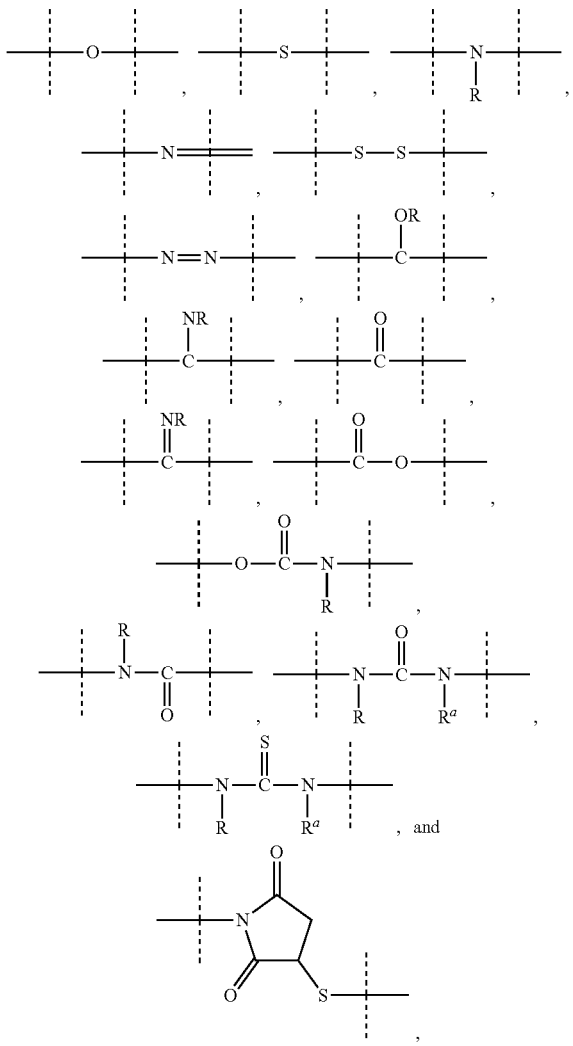

wherein
dashed lines indicate attachment to the remainder of the moiety or reagent; and
—R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or unsaturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, dec ahydroiso quino line, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

As used herein, "halogen" means fluoro, chloro, bromo or iodo. It is generally preferred that halogen is fluoro or chloro.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "biodegradable" as used herein with respect to a spacer moiety or other chemical species means that the spacer moiety or chemical species is capable of undergoing degradation or bond cleavages under biological or physiological conditions. The biodegradation may occur via hydrolysis, enzymatic cleavage or other mechanism. The spacer moieties described herein will in general undergo degradation in vitreal fluid by bond cleavage reaction that occurs with a half-life of no more thann 12 months, in some embodiments with a half-life of no more than six months, of injection into or exposure to the vitreum. The biodegradation of spacer moieties may occur at the chemical bonds attaching the spacer moiety to other groups, as well as at chemical bonds within the spacer moiety.

As used herein, the term "optionally substituted" unless otherwise specified means that a group may be substituted by one or more (e.g., 1, 2, 3 or 4) of the substituents listed for that group in which said substituents may be the same or different. In some aspects, an optionally substituted group has 1 substituent. In another aspect, an optionally substituted group has 2 substituents. In another aspect, an optionally substituted group has 3 substituents.

The term "interrupted" as used herein with alkyl, alkenyl, alkynyl or alkylene, means that one or more carbon atoms are replaced with functional groups or heteroatoms such that the in the alkyl, alkenyl, alkynyl or alkylene are interrupted. Exemplary groups that may interrupt alkyl, alkenyl, alkynyl or alkylene, unless otherwise specified herein, include T, —C(O)O—; —O—; —C(O)—; —C(O)N(R$^{17}$)—; —S(O)$_2$N(R$^{17}$)—; —S(O)N(R$^{17}$)—; —S(O)$_2$—; —S(O)—; —N(R$^{17}$)S(O)$_2$N(R$^{17a}$)—; —S—; —N(R$^7$)—; —OC(O)R$^{17}$; —N(R$^{17}$)C(O)—; N(R$^{17}$)C(O)—; —N(R$^{17}$)S(O)$_2$—; —N(R$^{17}$)S(O)—; —N(R$^{17}$)C(O)O—; —N(R$^{17}$)C(O)N(R$^{17a}$)—; and —OC(O)N(R$^{17}$R$^{17a}$) wherein R$^{17}$ is in each occurrence independently H or C$_{1-50}$ alkyl.

The term "substituted" means that one or more —H atom(s) of a molecule are replaced by a different atom or a group of atoms, which are referred to as "substituent" or "substituents". Suitable substituents are selected from the group consisting of halogen; CN; COOR$^{15}$; OR$^{15}$; C(O)R$^{15}$; C(O)N(R$^{15}$R$^{15a}$); S(O)$_2$N(R$^{15}$R$^{15a}$); S(O)N(R$^{15}$R$^{15a}$); S(O)$_2$R$^{15}$; S(O)R$^{15}$; N(R$^{15}$)S(O)$_2$N(R$^{15a}$R$^{15b}$); SR$^{15}$; N(R$^{15}$R$^{15a}$); NO$_2$; OC(O)R$^{15}$; N(R$^{15}$)C(O)R$^{15a}$; N(R$^{15}$)S(O)$_2$R$^{15a}$; N(R$^{15}$)S(O)R$^{15a}$; N(R$^{15}$)C(O)OR$^{15a}$; N(R$^{15}$)C(O)N(R$^{15a}$R$^{15b}$); OC(O)N(R$^{15}$R$^{15a}$); T; C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{16}$, which are the same or different and wherein C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{17}$)—; —S(O)$_2$N(R$^{17}$)—; —S(O)N(R$^{17}$)—; —S(O)$_2$—; —S(O)—; —N(R$^{17}$)S(O)$_2$N(R$^{17a}$)—; —S—; —N(R$^{17}$)—; —OC(O)R$^{17}$; —N(R$^{17}$)C(O)—; —N(R$^{17}$)S(O)$_2$—; —N(R$^{17}$)S(O)—; —N(R$^{17}$)C(O)O—; —N(R$^{17}$)C(O)N(R$^{17a}$)—; and —OC(O)N(R$^{17}$R$^{17a}$). In some such aspects, R$^{15}$, R$^{15a}$, R$^{15b}$ are independently selected from the group consisting of H; T; and C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{16}$, which are the same or different and wherein C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{17}$)—; —S(O)$_2$N(R$^{17}$)—; —S(O)N(R$^{17}$)—; —S(O)$_2$—; —S(O)—; —N(R$^{17}$)S(O)$_2$N(R$^{17a}$)—; —S—; —N(R$^{17}$)—; —OC(O)R$^{17}$; —N(R$^{17}$)C(O)—; —N(R$^{17}$)S(O)$_2$—; —N(R$^{17}$)S(O)—; —N(R$^{17}$)C(O)O—; —N(R$^{17}$)C(O)N(R$^{17a}$)—; and —OC(O)N(R$^{17}$R$^{17a}$). In some such aspects, T is selected from the group consisting of phenyl; naphthyl; indenyl; indanyl; tetralinyl; C$_{3-10}$ cycloalkyl; 4 to 7 membered heterocyclyl; or 8- to 11- membered heterobicyclyl, wherein T is optionally substituted with one or more R$^{16}$, which are the same or different. In some such aspects, R$^{16}$ is halogen; CN; oxo (=O); COOR$^{18}$; OR$^{18}$; C(O)R$^{18}$; C(O)N(R$^{18}$R$^{18a}$); S(O)$_2$N(R$^{18}$R$^{18a}$); S(O)N(R$^{18}$R$^{18a}$); S(O)R$^{18}$; N(R$^{18}$)S(O)$_2$N(R$^{18a}$R$^{18b}$); SR$^{18}$; N(R$^{18}$R$^{18a}$); NO$_2$; OC(O)R$^{18}$; N(R$^{18}$)C(O)R$^{18a}$; N(R$^{18}$)S(O)$_2$R$^{18a}$; N(R$^{18}$)S(O)R$^{18a}$; N(R$^{18}$)C(O)OR$^{18a}$; N(R$^{18}$)C(O)N(R$^{18a}$R$^{18b}$); OC(O)N(R$^{18}$R$^{18a}$); or C$_{1-6}$ alkyl, wherein C$_{1-6}$ alkyl is optionally substituted with one or more halogen, which are the same or different. In some such aspects, R$^{17}$, R$^{17a}$, R$^{18}$, R$^{18a}$, R$^{18b}$ are independently selected from the group consisting of H; or C$_{1-6}$ alkyl, wherein C$_{1-6}$ alkyl is optionally substituted with one or more halogen, which are the same or different.

As used herein "alkali metal counterion" refers to Na$^+$, K$^+$ and Li$^+$.

As used herein, the term "hydrogel" means a hydrophilic or amphiphilic polymeric network composed of homopolymers or copolymers, which is insoluble due to the presence of covalent chemical cross-links.

As used herein, the term "number average molecular weight" means the ordinary arithmetic mean of the molecular weights of the individual polymers. The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers.

As used herein, the term "pharmaceutical composition" refers to a composition comprising one or more active ingredient(s), and one or more inert ingredient(s), as well as any product which results, directly or indirectly, from combination, complexation or aggregation of any two or more of the ingredients, or from dissociation of one or more of the ingredient(s), or from other types of reactions or interactions of one or more of the ingredients.

As used herein, the term "excipient" refers to a diluent, adjuvant, or vehicle with which the therapeutic, i.e. the VEGF neutralizing prodrug, such as an anti-VEGF antibody, is administered. Such pharmaceutical excipient can be water; oils and petroleum of animal, vegetable or synthetic origin, including but not limited to peanut oil, soybean oil, mineral oil, sesame oil and the like; starch; glucose; lactose; sucrose; mannitol; trehalose; gelatin; malt; rice; flour; chalk; silica gel; sodium stearate; glycerol monostearate; talc; sodium chloride; dried skim milk; glycerol; propylene;

glycol; ethanol; acetate; succinate; tris; carbonate; phosphate; HEPES (4-(2-hydroxyethyl)-1-piperazineethanesulfonic acid); MES (2-(N-morpholino)ethanesulfonic acid); Tween®; poloxamers; poloxamines; CHAPS; Igepal®; amino acids like, for example, glycine, lysine, or histidine; triglycerides; mannitol; lactose; starch; magnesium stearate; sodium saccharine; cellulose; and magnesium carbonate. Examples of suitable pharmaceutical excipients are described in "Remington's Pharmaceutical Sciences" by E. W. Martin. The formulation should suit the mode of administration.

As used herein, the term "pharmaceutically acceptable" means that a molecule or reagent is approved by a regulatory agency, such as the EMA (Europe) and/or the FDA (US) and/or any other national regulatory agency, for use in animals, preferably in humans.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs) and/or framework regions (FRs), compared to a parent antibody which does not possess such alterations, such alterations resulting in an improvement in the affinity of the antibody for antigen.

The term "vascular endothelial growth factor" or "VEGF" refers to vascular endothelial growth factor protein A, as exemplified by SEQ ID NO: 47 (see also Swiss Prot Accession Number P15692, Gene ID (NCBI): 7422). The term "VEGF" encompasses the protein having the amino acid sequence of SEQ ID NO: 47 as well as homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of $VEGF_{165}$ as described in Ferrara Mol. Biol. Cell. 21:687 (2010), Leung et al., Science, 246:1306 (1989), and Houck et al., Mol. Endocrin., 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF109," "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab-C, Fab'-SH, F(ab')$_2$; diabodies; linear antibodies; single-chain antibody molecules (e.g., scFv); and multispecific antibodies formed from antibody fragments. In some instances, examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab-C molecules are Fab molecules that are expressed such that the sequence is truncated at the first hinge cysteine, resulting in a Fab with a free cysteine directly upon expression (see, e.g., Shatz et al. *Mol. Pharmaceutics* 2016; PubMed identifier (PMID) 27244474). For example, a Fab-C molecule may have a free cysteine at position Cys227 of the heavy chain. In other instances, a Fab-C molecule may have a free cysteine at position Cys229 of the heavy chain. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md. (1991).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci.* USA, 90:6444-6448 (1993).

A "blocking" antibody or an "antagonist" antibody is one which inhibits or reduces biological activity of the antigen it binds. Certain blocking antibodies or antagonist antibodies substantially or completely inhibit the biological activity of the antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

A "parent antibody" is an antibody comprising an amino acid sequence from which one or more amino acid residues are replaced by one or more residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g., a biologically important polypeptide, such as VEGF. Any of the antibodies described herein (e.g., anti-VEGF antibodies) may be a parent antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g. B cell receptor); and B cell activation.

"Framework" or "framework region" or "FR" refers to variable domain residues other than hypervariable region (HVR) residues. The FR of a variable domain generally consists of four FR domains FR1, FR2, FR3, and FR4.

The terms "full-length antibody," "intact antibody," and "whole antibody" are used herein interchangeably to refer to an antibody having a structure substantially similar to a native antibody structure or having heavy chains that contain an Fc region as defined herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., Sequences of Proteins of Immunological Interest, 5 th Ed. Public Health Service, National Institutes of Health, Bethesda, Md. (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, J. Mol. Biol. 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5 th Ed. Public Health Service, National Institutes of Health, Bethesda, Md. (1991)). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5 th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Unless otherwise indicated, HVR residues and other residues in the variable domain (e.g., FR residues) are numbered herein according to Kabat et al., supra.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, for example, Flatman et al., J. Chromatogr. B 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SD S-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fab', Fab-C. Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and $CH_3$). Similarly, from N- to C-terminus, each light chain has a variable region (VL), also called a variable light domain or a light chain variable domain, followed by a constant light (CL) domain. The light chain of an antibody may be assigned to one of two types, called kappa (K) and lambda (i), based on the amino acid sequence of its constant domain.

With regard to the binding of a antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of 10-4 M or lower, alternatively 10-5 M or lower, alternatively 10-6 M or lower, alternatively 10-7 M or lower, alternatively 10-8 M or lower, alternatively 10-9 M or lower, alternatively 10-10 M or lower, alternatively 10-11 M or lower, alternatively 10-12 M or lower or a Kd in the range of 10-4 M to 10-6 M or 10 M to 10 10 M or 10 7 M to 10 9 M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, "administering" is meant a method of giving a dosage of a compound (e.g., antibody-hydrogel conjugate of the invention) or a composition (e.g., a pharmaceutical composition, e.g., a pharmaceutical composition including an an antibody-hydrogel conjugate of the invention) to a subject. The compositions utilized in the methods described herein can be administered, for example, intravitreally (e.g., by intravitreal injection), by eye drop, intramuscularly, topically, subconjunctivally, intravesicularly, intraocularly, intraorbitally, by injection, by implantation, by infusion, by continuous infusion, in lipid compositions.

"Angiogenesis" refers to the process through which new blood vessels form from pre-existing blood vessels. Angiogenesis is distinct from vasculogenesis, which is the de novo formation of endothelial cells from mesoderm cell precursors. Disorders associated with pathological angiogenesis can be treated by compositions and methods of the invention. These disorders include both non-neoplastic disorders and cell proliferative disorders. Cell proliferative disorders include but are not limited those described below. Non-neoplastic disorders include but are not limited to ocular conditions (non-limiting ocular conditions include, for example, retinopathy including proliferative diabetic retinopathy, choroidal neovascularization (CNV), age-related macular degeneration (AMD), diabetic and other ischemia-related retinopathies, diabetic macular edema (DME), pathologic myopia, von Hippel-Lindau disease, histoplasmosis of the eye, retinal vein occlusion (including central (CRVO) and branched (BRVO) forms), corneal neovascularization, retinal neovascularization, retinopathy of prematurity (ROP), familial exudative vitreoretinopathy (FEVR), Coats' disease, Norrie Disease, Osteoporosis-Pseudoglioma Syndrome (OPPG), subconjuctival hemorrhage, rubeosis, ocular neovascular disease, neovascular glaucoma, and hypertensive retinopathy), autoimmune diseases (e.g., rheumatoid arthritis (RA), psoriasis, ankylosing spondylitis, and inflammatory bowel disease (e.g., Crohn's disease and ulcerative colitis)), undesired or aberrant hypertrophy, arthritis, psoriatic arthritis, psoriatic plaques, sarcoidosis, atherosclerosis, atherosclerotic plaques, arterial arteriosclerosis, vascular restenosis, arteriovenous malformations (AVM), meningioma, hemangioma, angiofibroma, thyroid hyperplasias (including Grave's disease), corneal and other tissue transplantation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), chronic asthma, uterine fibroids, premature labor, chronic inflammation such as IBD (Crohn's disease and ulcerative colitis), inflammatory renal diseases (including glomerulonephritis, especially mesangioproliferative glomerulonephritis, haemolytic uremic syndrome, diabetic nephropathy and hypertensive nephrosclerosis), diseases occurring after transplants, renal allograft rejection, inflammatory diseases, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion. Additional ocular disorders are described below.

Other disorders which may be associated with pathological angiogenesis include nonunion fractures (fractures that will not heal), pyogenic granuloma, trachoma, hemophilic joints, vascular adhesions and hypertrophic scars, graft rejection, fibrovascular tissue, acne rosacea, acquired immune deficiency syndrome, artery occlusion, atopic keratitis, bacterial ulcers, Bechet's disease, carotid obstructive disease, chronic inflammation, chronic retinal detachment, chronic uveitis, chronic vitritis, contact lens overwear, corneal graft rejection, corneal graft neovascularization, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, optic pits, osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retrolental fibroplasias, sarcoid, scleritis, sickle cell anemia, Sjogren's syndrome, Stargarts disease, Steven's Johnson disease, superior limbic keratitis, syphilis, systemic lupus, Terrien's marginal degeneration, toxoplasmosis, trauma, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

The term "ocular disorder," as used herein, includes any ocular disorder (also referred to interchangeably herein as "ocular condition") associated with pathogical angiogenesis. An ocular disorder may be characterized by altered or unregulated proliferation and/or invasion of new blood vessels into the structures of ocular tissues such as the retina or cornea. Non-limiting ocular disorders include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g, allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disorder is associated with ocular neovascularization, vascular leakage, and/or retinal edema. Additional exemplary ocular disorders include diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, Stargart's disease, pars planitis, retinal detachment (e.g., chronic retinal detachment), hyperviscosity syndromes, toxoplasmosis, trauma, and post-laser complications.

"Disorders associated with undesirable vascular permeability," as used herein, include, for example, edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

A "variant" or "mutant" of a starting or reference polypeptide (e.g., a reference antibody or its variable domain(s)/ HVR(s)), is a polypeptide that (1) has an amino acid sequence different from that of the starting or reference polypeptide and (2) was derived from the starting or reference polypeptide through either natural or artificial (manmade) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

The term "clearance," as used herein, refers to the volume of a substance (e.g., an anti-VEGF antibody, an antibody conjugate, a fusion protein (e.g., a Fab fusion protein), or a polymeric formulation) cleared from a compartment (e.g., the eye (e.g., the vitreous)) per unit time.

The term "half-life" refers to the time required for the concentration of a substance (e.g., an anti-VEGF antibody, an antibody conjugate, a fusion protein (e.g., a Fab fusion protein), or a polymeric formulation) to decrease by one-half, in vivo (e.g., in the eye (e.g., the vitreous)) or in vitro.

The term "effective half-life refers to the time required for the concentration of a conjugate, e.g. a hydrogel-linker-antibody conjugate, to decrease by one half, in vivo (e.g., in the eye, e.g., in the vitreous) or in vitro. It is understood that each of the components of the conjugate, e.g., the hydrogel, the linker, and the antibody may contribute to the effective half life of the conjugate.

HA Purification

HA may optionally be purified prior to derivation according to the methods of the present disclosure. In some such aspects, an aqueous solution is formed comprising HA and from about 0.5 to about 1 mol/L sodium acetate. HA is precipitated from solution by addition of ethanol to about 80% ethanol v/v. Precipitated HA is collected and is washed with about 80% v/v ethanol followed by absolute ethanol. The dissolution/precipitation/washing procedure may be repeated as necessary until the desired purity is achieved.

Preparation of Amine-Functionalized Hyaluronic Acid

In some aspects, hyaluronic acid is functionalized with an amine by reacting a reaction mixture comprising HA of formula I, a primary amine ($H_2N$-LA-$NH_2$), and a carboxyl-activating coupling reagent to form amine-HA of formula II and partially cross-linked amine-HA of formula III according to reaction scheme 1 below.

Reaction Scheme 1

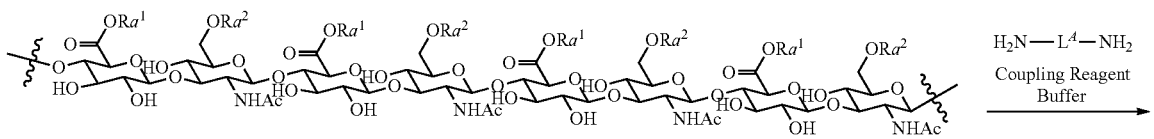

I

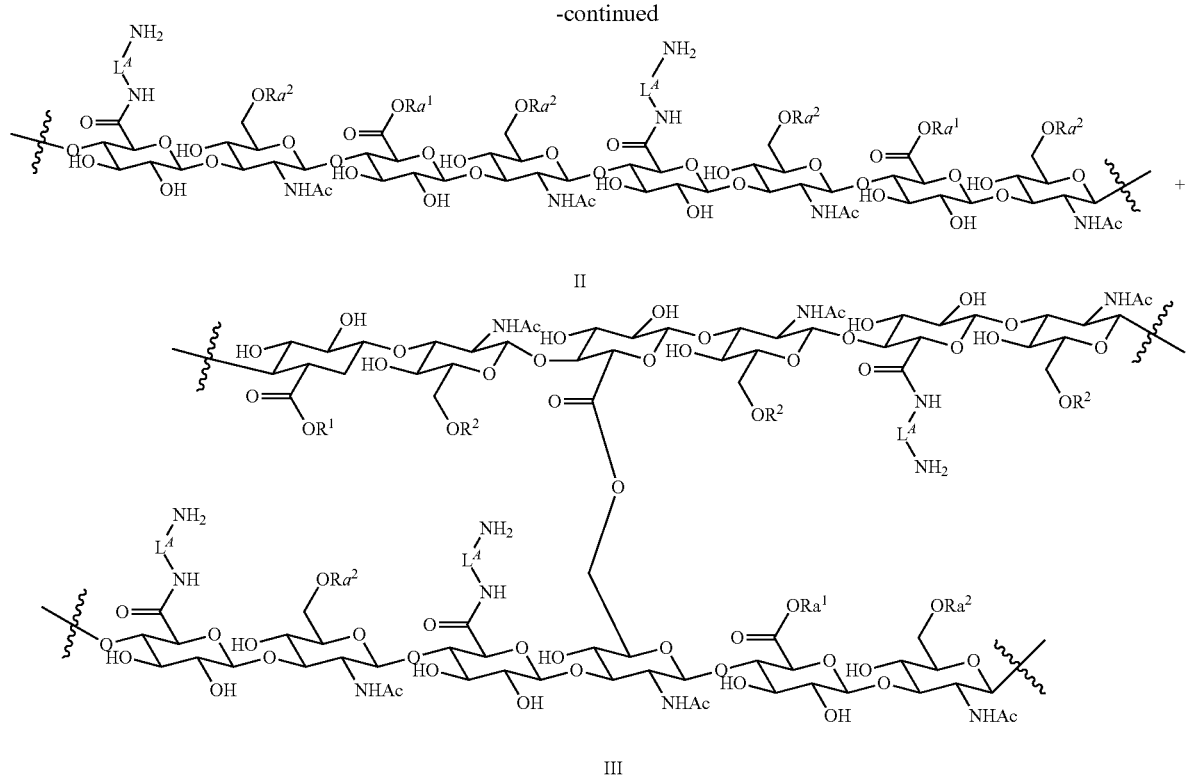

II

III

The degree of functionalization of HA II and III with amine reagent H$_2$N-LA-NH$_2$ as shown in Reaction Scheme 1 is as described elsewhere herein.

In Reaction Scheme 1, each Ra$^1$ is independently selected from H, C$_{1-4}$ alkyl, an alkali metal counter-ion, an ammonium counter-ion, or an alkaline earth metal counter-ion. Each Ra$^2$ is independently selected from H, C$_{1-4}$ alkyl and an alkali metal counter-ion. The cross-linking ester bond in formula III may subsequently be hydroliyzed, as described further below, to provide additional material of formula II, and to render the reaction product of Scheme 1 amenable to sterile filtration.

In some such aspects, L$^A$ is a spacer. In some other aspects, L$_A$ is optionally substituted and/or optionally interrupted C$_{1-10}$ alkylene. In some such aspects, L$_A$ is linear C$_{2-4}$ alkylene, or is n-propylene. In other aspects, L$_A$ may comprise an oxyalkylene oligomer or polymer such as polyethylene glycol (PEG).

The amide formation in Reaction Scheme 1 utilizes a coupling reagent, which in certain embodiments may be selected from 1-ethyl-3-(3-dimethylaminopropyl) carbodiimide (EDC), dicyclohexylcarbodiimide (DCC), diisopropylcarbodiimide (DIC), 4-(4,6-Dimethoxy-1,3,5-triazin-2-yl)-4-methylmorpholinium chloride (DMTMM) and 2-chloro-4,6-dimethoxy-1,3,5-triazine) (CDMT). In some particular aspects, the coupling reagent is EDC.

In some aspects, the reaction mixture may further comprise a coupling additive. In some such aspects, the coupling additive may be selected from 1-hydroxybenzotriazole (HOBt), 1-hydroxy-7-aza-1H-benzotriazole (HOAt), N-hydroxysuccinimide (HOSu), and ethyl 2-cyano-2-(hydroximino)acetate (Oxyma pure®). In some particular aspects, the coupling additive is HOBt. In other embodiments the coupling reagent may be 1-cyano-2-ethoxy-2-oxoethylidenaminooxy)dimethylamino-morpholino-carbenium hexafluorophosphate (COMU). A buffer having a pH of from about 5 to about 6 at a at a concentration of from about 50 mM to 150 mM is generally suitable for the reaction mixture for forming amine-functionalized hyaluronic acid. In some such aspects, the buffer is 2-(N-morpholino)ethanesulfonic acid (MES)

The reaction mixture may in some embodiments further comprise a polar aprotic solvent to improve the solubility of the reactants. In such aspects, suitable ratios of buffer to polar aprotic solvent are about 1:3 v/v, about 1:2 v/v, about 1:1.5 v/v, about 1:1 v/v, about 1.5:1 v/v, about 2:1 v/v, about 3:1 v/v, about 5:1 v/v or about 10:1 v/v. In some such aspects, the polar aprotic solvent may be selected from acetone, N,N-dimethyl formamide (DMF), acetonitrile (ACN), dimethyl sulfoxide (DMSO), and combinations thereof. In one aspect, the solvent is acetonitrile.

Amine functionalization may be done at a temperature of about 10° C., about 15° C., about 20° C., about 25° C., about 30° C., about 35° C., or about 40° C., for a time suitable to achieve essentially complete coupling, such as about 2 hours, about 4 hours, about 6 hours, about 8 hours, about 10 hours, about 12 hours, or longer.

In any of the various aspects of the disclosure, the equivalents of carboxyl groups exceeds the equivalents of primary amine at the formed, functionalized HA, as described above, such that not all of the HA carboxyl groups are functionalized, as depicted in reaction scheme I. More particularly, amine functionalities are introduced to provide a degree of functionalization of the HA (or a derivative thereof or an alkali metal salt thereof) of about 2%, about 3%, about 4%, about 5%, about 6%, about 7%, about 8%, about 9%, about 10%, about 11%, about 12%, about 13%, about 14% or about 15%, and ranges thereof, or as described elsewhere herein. The concentration of hyaluronate, primary amine and coupling additive may be held constant, and said concentrations are independent from the desired amine load of the formed amine-functionalized hyaluronic acid.

Examples of suitable hyaluronate concentrations may range, for example, from 2 g/L to 16 g/L. The number of equivalents of amine reagent and amide coupling additives with respect to the equivalents of carboxylate groups on HA I may be varied as required to provide the desired degree of functionalization. The degree of functionalization in some embodiments may be controlled based on the equivalents of amide coupling reagent in the presence of excess amine reagent.

Preparation of Maleimido-Functionalized HA

In some aspects of the disclosure, amine-functionalized HA described elsewhere herein is reacted with —N-hydroxysuccinimide (NHS)-$L_a$-maleimide or NHS-$L_C$-maleimide to form maleimide-functionalized HA. In some such aspects, the HA derivative of formula II is reacted with NHS-$L_B$-maleimide or NHS-$L_C$-maleimide (where NHS is N-hydroxysuccinimide and is in the form of an activated ester with $L_B$ or $L_C$) to form maleimide-functionalized HA of formula IV according to reaction scheme 2 below.

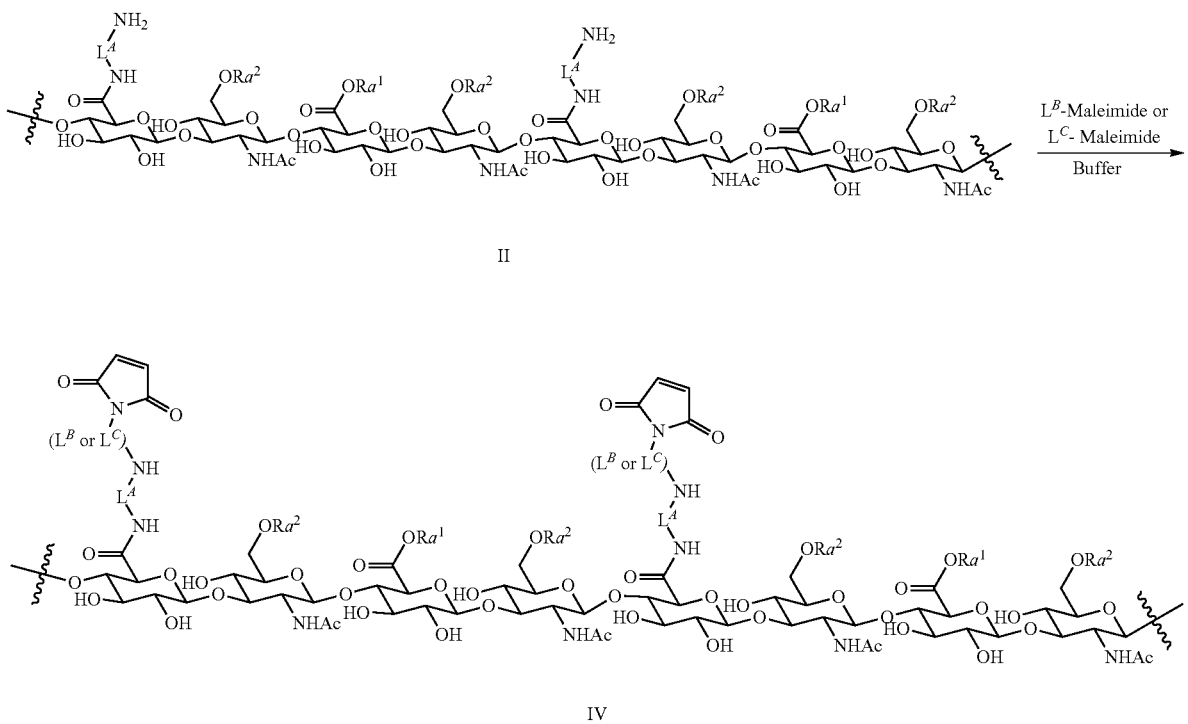

As depicted in Reaction Scheme 1, a portion of the HA may be cross-linked by ester bonds to form partially cross-linked amine-HA. Such partially cross-linked HA is soluble in aqueous systems, but is in most cases not sterile filterable. The cross-linked HA may be incubated in the presence of a base to hydrolyze the ester bonds and provide linear amine-HA. Suitable bases include alkali metal bases such as NaOH, KOH and LiOH. Hydrolysis may be done at a base concentration such as about 0.1 M, about 0.5 M, about 1 M, about 1.5 M or about 2 M, at a pH of from about 12 to about 14, about 13 to about 14, or about 14, at a temperature of about 10° C., about 15° C., about 20° C., about 25° C., about 30° C., about 35° C., or about 40° C., for a time suitable to achieve essentially complete hydrolysis, such as about 0.5 hours, about 1 hour, about 1.5 hours, about 2 hours, or longer. Such hydrolyzed amine-HA has a number average molecular weight essentially the same as the native HA starting material, is soluble in aqueous systems, and is sterile filterable. Following hydrolysis, the pH may be adjusted to from about 6 to about 8.5, from about 6.5 to about 8, or to about 7.5 with a mineral acid or an organic acid. In some aspects, the acid is acetic acid.

wherein $Ra^1$, $Ra^2$ and $L^A$ are as described elsewhere herein. In some particular aspects, the maleimide spacer is $L^B$. In other aspects, the maleimide spacer is $L^C$. The degree of functionalization of HA II and IV with amine reagent $H_2N$-$L^A$-$NH_2$ and $L^B$-maleimide or $L^C$-maleimide respectively, as shown in Reaction Scheme 2 is arbitrary, and it should be understood that the degree of functionalization may be varied as desired for different embodiments of the invention, and the degree of maleimide fuctionalization may be as described elsewhere herein. In many embodiments most or all of the amine functional groups on HA II are reacted with LB-maleimide or $L^C$-maeleimide, but in certain embodiments residual amine functional groups may be present.

In some aspects, $L^B$ is a spacer moiety as described herein. In some aspects, $L^B$ is an optionally substituted and/or optionally interrupted $C_{1-10}$ alkylene. In some aspects, $L^B$ is —C(O)—$C_{1-5}$ alkylene. In some such aspects, $L_B$ is linear —(O)—$C_{2-3}$ alkylene, or is —C(O)-ethylene.

In some aspects, $L^C$ is a biodegradable spacer moiety as described herein. In some aspects, $L^C$ may comprises at least one ester moiety, at least one carbonate linkage or combinations thereof.

In some aspects, $L^C$ is of the structure:

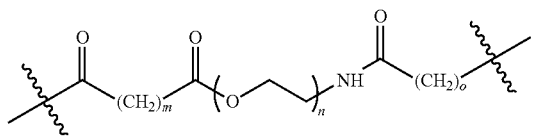

wherein m is selected from 1, 2, 3, 4, 5, 6, 7, 8, 9, and 10, and ranges constructed therefrom, such as from 1 to 10, from 2 to 8, or from 5 to 8. n is selected from 1, 2, 3 and 4, and ranges constructed therefrom, such as from 1 to 4, or from 1 to 3. o is selected from 1, 2, 3 and 4, and ranges constructed therefrom, such as from 1 to 4, or from 1 to 3. In such embodiments $L_C$-maleimide reagent has the structure

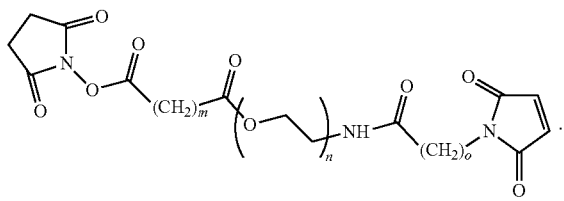

In some aspects, wherein m is 7, $L^C$ comprises a moiety derived from azelaic acid, such as an azelaic acid ester moiety. In one such aspect, $L_C$ is of the structure:

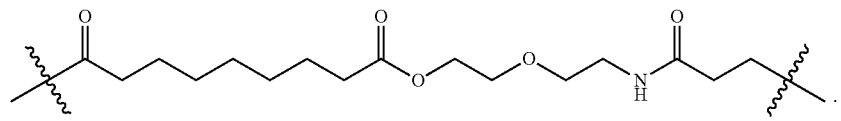 [SMILES: *CCC(=O)NCCOCCOC(=O)CCCCCCCC(*)=O]

In such embodiments $L_C$-maleimide reagent has the structure

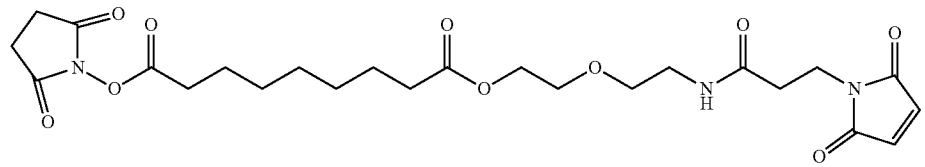 [SMILES: O=C(CCN1C(=O)C=CC1=O)NCCOCCOC(=O)CCCCCCCC(=O)ON1C(=O)CCC1=O]

The reaction pH for the events of Reaction Scheme 2 is suitably from about 6.5 to about 9, from about 7 to about 8, or about 7,4. A buffer concentration of from about 50 mM to about 150 mM is generally suitable for the reaction mixture for forming maleimide-functionalized hyaluronic acid. In some such aspects, the buffer is selected from (4-(2-hydroxyethyl)-1-piperazineethanesulfonic acid) (HEPES), maleate, citrate, BIS-Tris, phosphate, N-(2-Acetamido)iminodiacetic acid (ADA), carbonate, piperazine-N,N'-bis(2-ethanesulfonic acid) (PIPES), 3-Morpholino-2-hydroxypropanesulfonic acid (MOPSO), imidazole, BIS-Tris-Propane, N,N-bis(2-hydroxyethyl)-2-aminoethanesulfonic acid (BES), (3-(N-morpholino)propane sulfonic acid) (MOPS), 2-[(2-Hydroxy-1,1-bis(hydroxymethypethypaminol ethane sulfonic acid (TES), 3-(B is (2-hydroxyethyl)amino]-2-hydroxypropane-1-sulfonic acid (DIPSO), 2-Hydroxy-3-[tris (hydroxymethypmethylamino]-1-propane sulfonic acid (TAPSO), 4-(2-Hydroxyethyl)piperazine-1-(2-hydroxypropanesulfonic acid) (HEPPSO), Piperazine-1,4-bis(2-hydroxypropanesulfonic acid) dehydrate (POPSO), tricene, glycylglycine, and Tris. In some particular aspects, the buffer is HEPES. The reaction mixture may further comprise a polar aprotic solvent to improve the solubility of the reactants. In such aspects, suitable ratios of buffer to polar aprotic solvent are about 1:3 v/v, about 1:2 v/v, about 1:1.5 v/v, about 1:1 v/v, about 1.5:1 v/v, about 2:1 v/v, about 3:1 v/v, about 5:1 v/v or about 10:1 v/v. In some such aspects, the polar aprotic solvent may be selected from acetone, DMF, ACN, DMSO, and combinations thereof. In one aspect, the solvent is ACN. The reaction temperature is about 10° C., about 15° C., about 20° C., about 25° C., about 30° C., about 35° C., or about 40° C., and the reaction time is about 0.5 hours, about 1 hour, about 1.5 hours, about 2 hours, or longer.

In some reaction scheme 2 aspects, maleimide-functionalized HA is obtained by reacting the primary amine of the amine-functionalized HA with a NHS-$L_B$-maleimide reagent according to reaction scheme 3 below.

Reaction Scheme 3

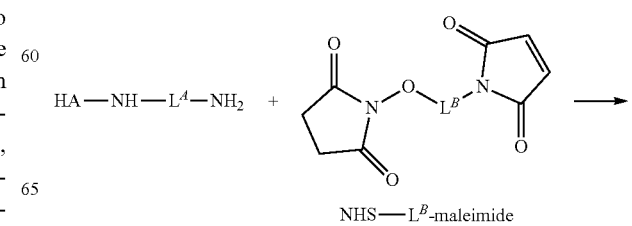

NHS—$L^B$-maleimide

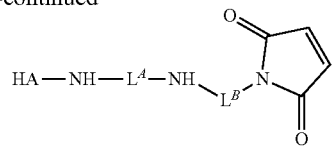

In some particular aspects, $L^A$ is n-propylene and $L^B$ is —C(O)—(CH$_2$)$_2$—. In some aspects, the buffer is HEPES, the reaction pH is from about 7 to about 8, or about 7.4, the buffer comprises ACN at a volume ratio of buffer to ACN of about 2:1, the reaction temperature is from about 20° C. to about 30° C., and the reaction time is from about 0.5 hours to about 2 hours.

In some other reaction scheme 2 aspects, maleimido-functionalized HA is obtained by reacting the primary amine of the amine-functionalized HA with a NHS-L$_C$-maleimide reagent according to reaction scheme 4 below.

Reaction Scheme 4

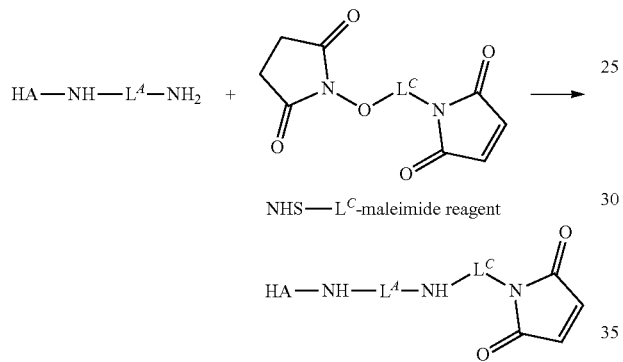

In some particular aspects, $L^A$ is n-propylene and $L^C$ is of the structure

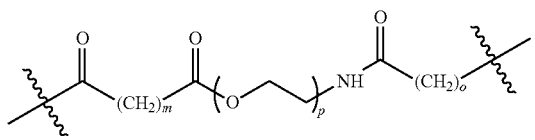

where m is 7, p is 2, and o is 2. In some aspects, the buffer is HEPES, the reaction pH is from about 8 to about 9, or about 7.4, the buffer comprises ACN at a volume ratio of buffer to ACN of about 2:1, the reaction temperature is from about 20° C. to about 30° C., and the reaction time is from about 1 hours to about 3 hours.

Direct Preparation of Maleimido-Functionalized HA

In some aspects, as depicted in FIG. 2, maleimide groups may be directly conjugated to HA by reacting a reaction mixture comprising HA (or a derivative or salt thereof), maleimide compound 2 of the structure and a carboxyl-activating coupling reagent to form compound 4 having conjugated maleimide groups.

$L^1$ is a spacer moiety as described herein. In some aspects, $L_1$ is $C_{1-12}$ alkyl, $C_{2-10}$ alkyl or $C_{3-8}$ alkyl. $L_1$ may be optionally substituted and/or optionally interrupted as described elsewhere herein. For instance, $L^1$ may optionally be interrupted by one or more of an amide or an amine.

Preparation of Thiol-Functionalized HA

In some aspects of the disclosure, amine-functionalized HA described elsewhere herein is reacted with NHS-$L^B$-S-protecting group or NHS-$L^C$-S-protecting group followed by deprotection to form thiol-functionalized HA. In some such aspects, formula II or formula IIa is reacted with NHS-$L^B$-S-protecting group or NHS-$L^C$-S-protecting group to form formula V followed by deprotection to form thiol-functionalized HA of formula VI according to Reaction Scheme 5 below.

Reaction Scheme 5

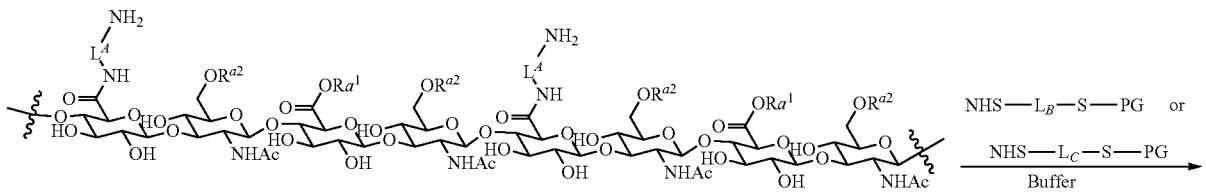

II

-continued

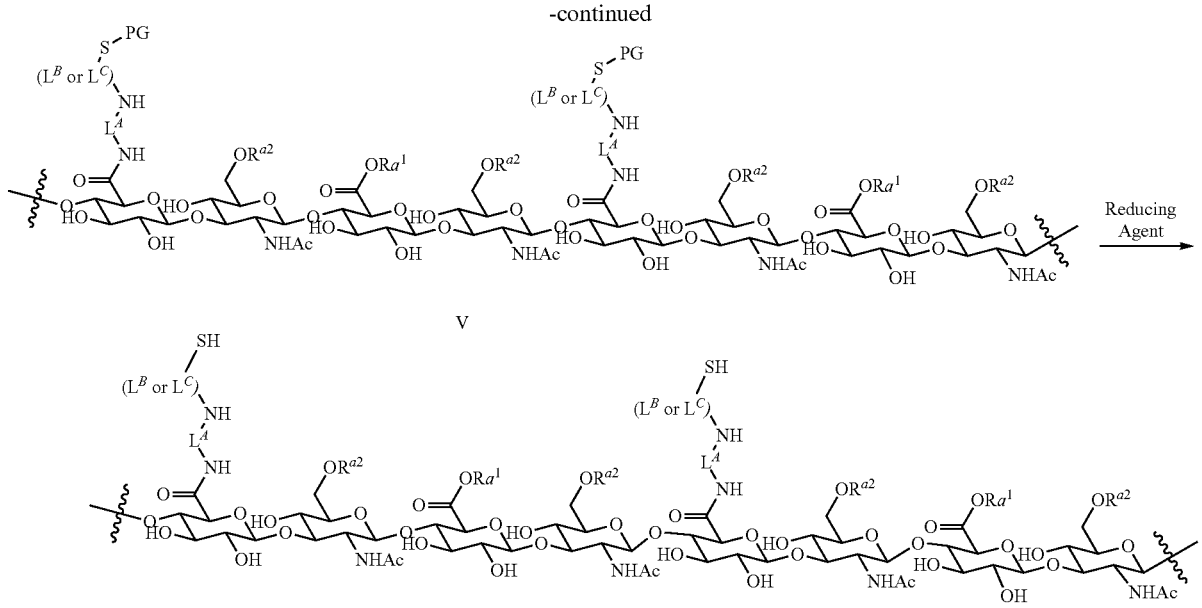

V

VI wherein $Ra^1$, $Ra^2$, $L^A$, $L^B$ and $L^C$ are as described elsewhere herein. In some particular aspects, the spacer connecting to —S-PG in compound V of and to —SH in compound VI of Scheme 5 is $L^C$.

As with Reaction Scheme 5 above, the degree of functionalization of HA V and VI with NHS-$L^B$-S-protecting group or NHS-$L^C$-S-protecting group shown in Reaction Scheme 5 is arbitrary, and it should be understood that the degree of functionalization may be varied as desired for different embodiments of the invention. The degree of protected thiol (and ultimately thiol) fuctionalization is as described elsewhere herein. In many embodiments most or all of the amine functional groups on HA II are reacted with NHS-$L^B$-S-protecting group or NHS-$L^C$-S-protecting group, but in certain embodiments residual amine functional groups may be present.

The conjugation reaction pH for Reaction Scheme 5 is suitably from about 7.5 to about 9.5, or from about 8 to about 9, such as about 8.5. Suitable buffers at a concentration of from about 50 mM to about 150 mM are described elsewhere herein. In some aspects, the buffer is HEPES. The reaction mixture may further comprise a polar aprotic solvent as described elsewhere herein to improve the solubility of the reactants. In some aspects, the solvent is ACN. The ratio of buffer to polar aprotic solvent is suitably about 1:2 v/v to about 4:1, or from about 3:1 to about 1:1, such as about 2:1. The reaction temperature is about 10° C., about 15° C., about 20° C., about 25° C., about 30° C., about 35° C., or about 40° C., and the reaction time is about 1 hour, about 2 hours, about 3 hours, about 4 hours, or longer.

The HA derivative of Formula V is contacted with a reducing agent to cleave the protecting group at the disulfide bond thereby generating $L_B$ or $L_C$ terminated with a thiol (Formula VI). Cleavable protecting groups are known in the art and non-limiting examples include pyridyl-thiol and phenyl-thiol which may be optionally substituted with at least one substituent independently selected from $NO_2$, Cl, F, CN, $CO_2H$, and Br. In one such aspect, the leaving group is 2-mercaptopyridyl. Reducing agents are known in the art and include (tris(2-carboxyethyl)phosphine) HCl salt (TCEP), 2-mercaptoethanol, and dithiothreitol.

Direct Preparation of Thiol-Functionalized HA

In some aspects, as depicted in FIG. 3, protected disulfide groups may be directly conjugated to HA by reacting a reaction mixture comprising HA (or a derivative or salt thereof), protected disulfide compound 6 of the structure $H_2N$-$L_3$-S-PG, and a carboxyl-activating coupling reagent to form compound 8 having conjugated protected disulfide groups. The protecting group may be cleaved as described elsewhere herein to generate thiol-functionalized HA.

Drug-Linker Conjugates

Drug-linker conjugates such as reagent 5 in FIG. 2, reagent 14 in FIG. 5 and reagent 5 in FIG. 7 are used in preparation of cross-linked HA drug conjugates in accordance with the invention. In many embodiments, the drug linker conjugate may utilize a reversible prodrug linker $L_2$ of formula II as described above. In some other aspects, the reversible prodrug linker moiety $L_2$ used in such drug monoconjugates may be represented by formula XIIa:

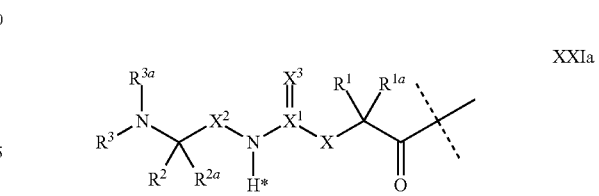

XXIa wherein:

the dashed line indicates the attachment to a nitrogen of a drug compound (not shown) by forming an amide bond; and X, $X^1$, $X^2$, $X^3$, $R^1$, $R^{1a}$, $R^2$, $R^{2a}$, $R^3$ and $R^{3a}$ are defined as above;

In many embodiments the reversible prodrug linker $L_2$ may, for synthetic convenience, be prepared together with a spacer $L_4$ or a portion of a spacer $L_4$.

In some embodiments the reversible prodrug linker moiety $L_2$ together with a portion of a spacer $L_4$ may be represented by a spacer-linker compound comprising formula XIIc

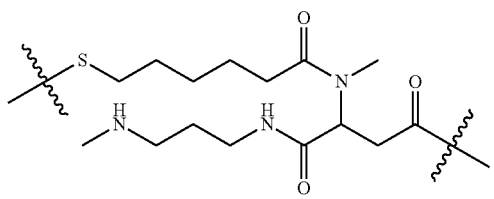

XIIc wherein the right-most wavy line represents the point of attachment to the nitrogen atom of a drug via an amide bond, and the left-most wavy line represents the point of attachment to the cross-linked HA hydrogel or precursor thereof as disclosed in the present specification via a sulfide bond (not shown). The linker spacer moiety XIIc represents a particular combination of a reversible prodrug linker moiety $L_2$ with a portion of a spacer $L_4$ that can conveniently be synthesized together as described below for use in particular embodiments of the invention.

In some aspects, the reversible prodrug linker moiety $L^2$ moiety may be selected from the following, where the wavy line indicates the site of attachment of to the nitrogen of the drug and wherein the the each $L^2$ is substituted with one moiety $L^4$ provided that the hydrogen marked with the asterisk is not replaced:

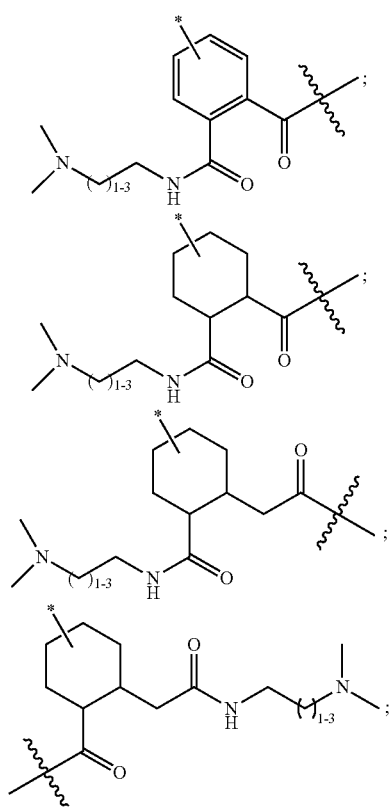

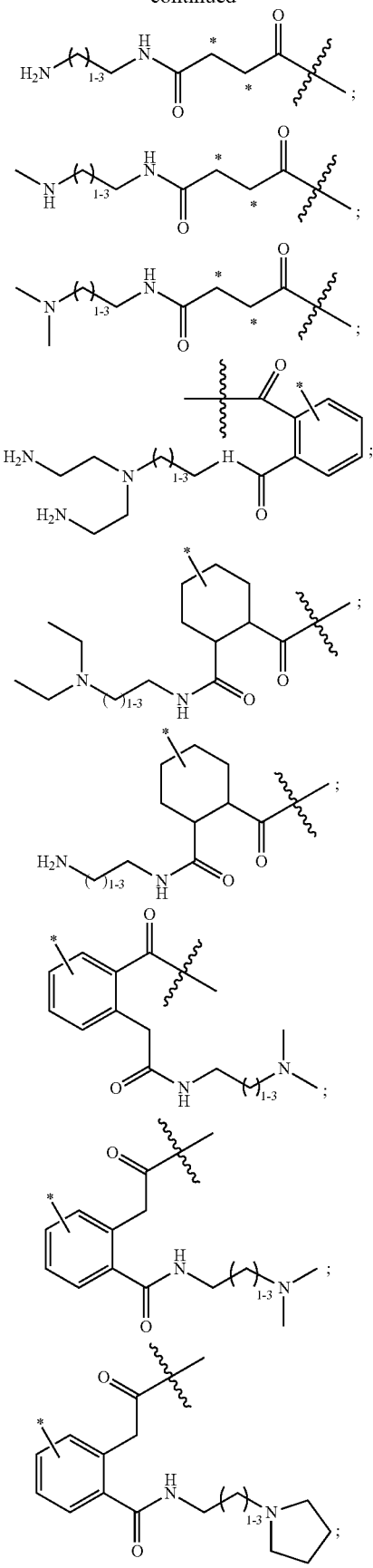

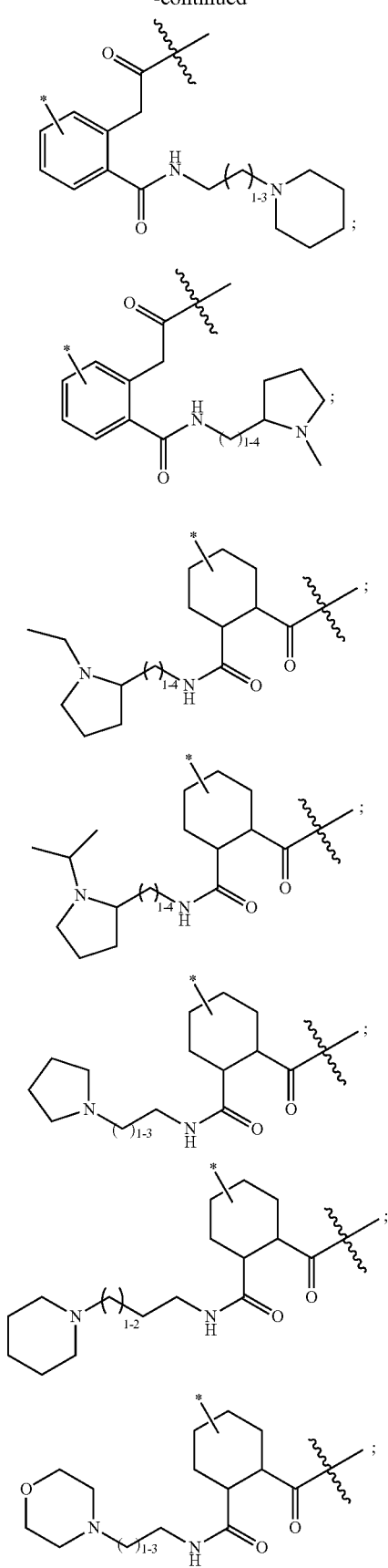
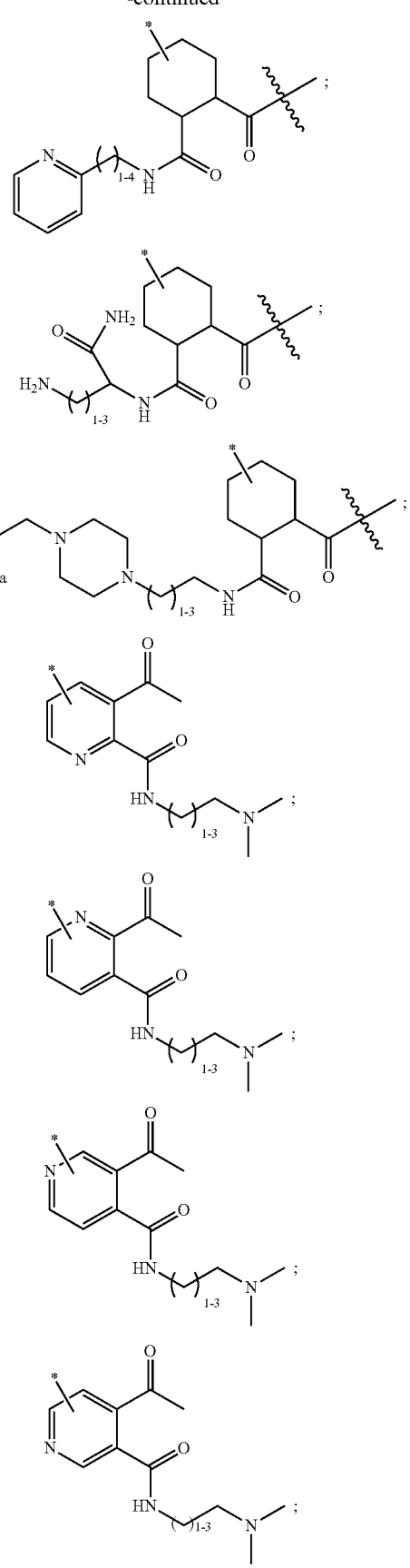

-continued

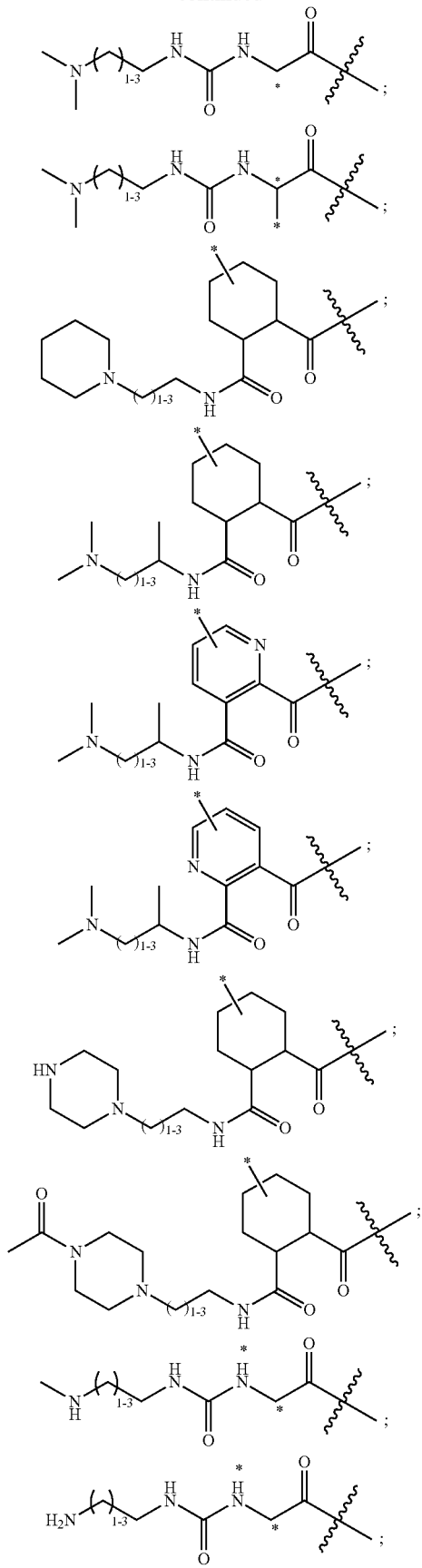

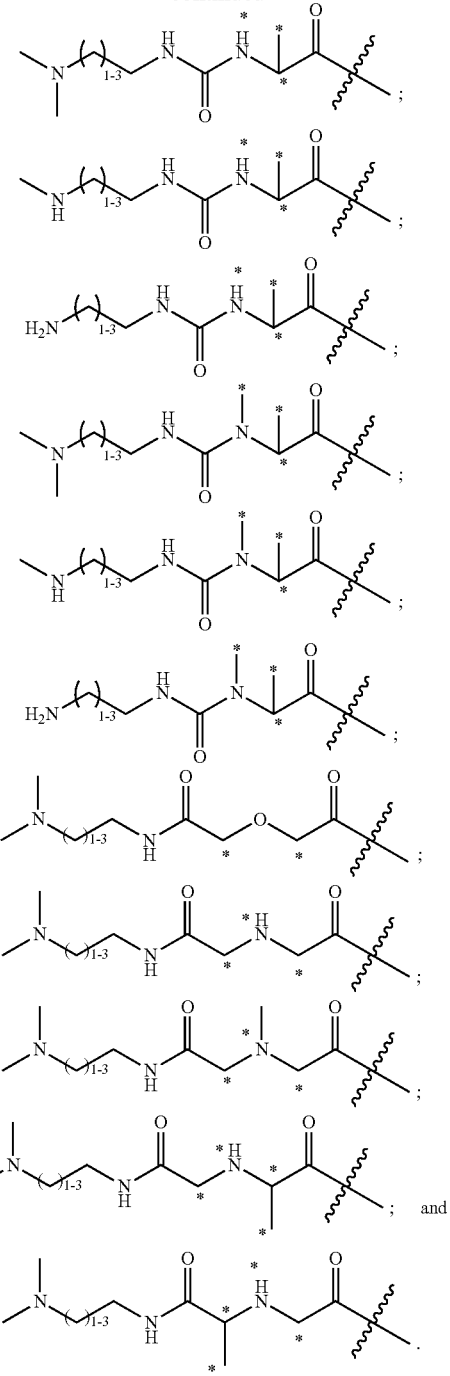

Preparation and Purification of Drug-Spacer-Linker conjugates

In any of the various aspects of the disclosure, a drug-linker conjugate using a reversible prodrug linker $L_2$ may be prepared as follows. As noted above, in many embodiments the reversible prodrug linker $L_2$ may for synthetic convenience be prepared together with a spacer $L_4$ or a portion of a spacer $L_4$. The moiety of formula XIIb is used for exemplary purposes, but those skilled in the art will recognize that variations of the procedure below may be used for other embodiments of linker $L_2$ and spacer $L_4$ in accordance with the invention.

The compound of formula VIIIa

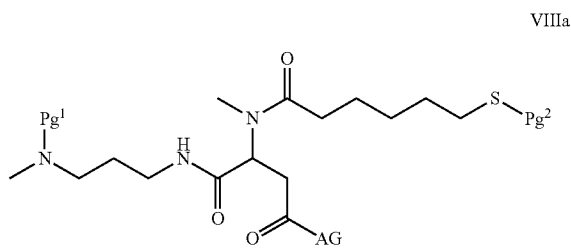

represents a moiety comprising reversible prodrug linker $L^2$ with an amine protecting group $Pg^1$, a portion of a spacer $L^4$ with a thiol protecting group $Pg^2$ thereon, and an activating group AG. The thiol protecting group represents the point of attachment to the cross-linked HA conjugates 10, 16 and 26, or the corresponding precursor HA portions 5, 14 and 19 as shown in FIGS. 2 through 9. The activating group AG is a group that is displaced during reaction with a drug group such as ranibizumab or other peptidic therapeutic having a free amino group thereon, to form an amide bond. The amine group protected by group $Pg^1$ is a catalytic group that participates in cleavage of the amide bond connecting the drug to linker $L_2$.

The combined linker $L^2$ and portion of spacer $L^4$ compound of formula VIIIa may be used to prepare a compound of formula VIIIb

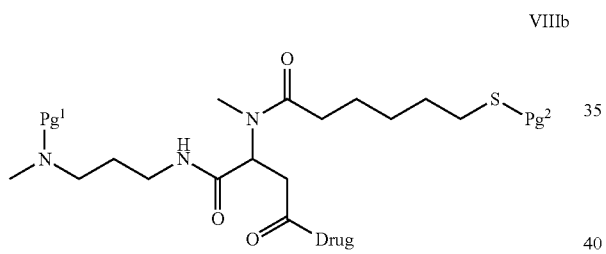

by displacement of the activation group AG to form an amide bond with the drug. The drug may be, for example, a therapeutic protein, antibody or antibody fragment as described herein having one or more available free amino groups that are available to react with the linker to form the linker drug conjugate via amide bond.

Protecting groups (PG) are known in the art. For instance, some protecting groups within the scope of the present disclosure are described in International Publication No. WO 2015/052155, the contents of which are incorporated by reference herein in its entirety. Those skilled in the art will recognize that various different protection and deprotection schemes, such as those described in "Greene's Protective Groups in Organic Synthesis," Fifth Edition, 2014 by John Wiley & Sons, Inc., also incorporated by reference, may be used with the invention as alternatives to the specific examples shown herein.

In some aspects, the amine protecting group $Pg^1$ is a self immolative protecting group which may comprise one of the moieties

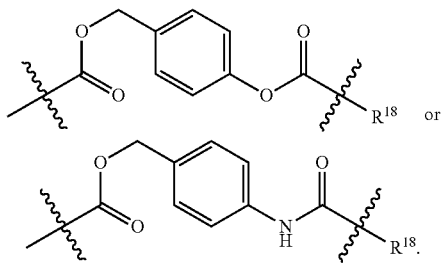

wherein $R^{18}$ is optionally substituted and/or optionally interrupted $C_{1-10}$ alkyl. In some aspects, $R^{18}$ is a $C_{1-6}$ amine. In other aspects, V is a $C_{1-6}$ diamine One example of an amine protecting group $Pg^1$ group is as follows:

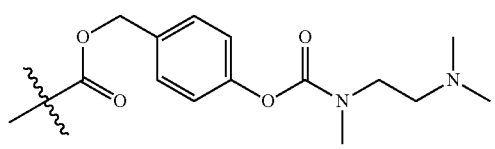 [SMILES: *C(=O)OCc1ccc(OC(=O)N(C)CCN(C)C)cc1]

where the wavy line indicates the point of attachment to an amine group on the linker $L^2$.

One example of a thiol protecting group is methanesulfonyl of the formula $—SO_2CH_3$ such that a methane thiosulfonate MTS is formed.

Activating groups are also well known in the art. In certain embodiments the activating group AG may be N-hydroxysuccinimide (NHS) in the form of an ester. Other such activated ester groups include 4-nitrophenol and pentafluorophenol esters.

In one particular aspect, the moiety of formula VIIIa above may be an N-Hydroxysuccinimide (NHS) ester methane thiosulfonate compound of the structure VIIIc:

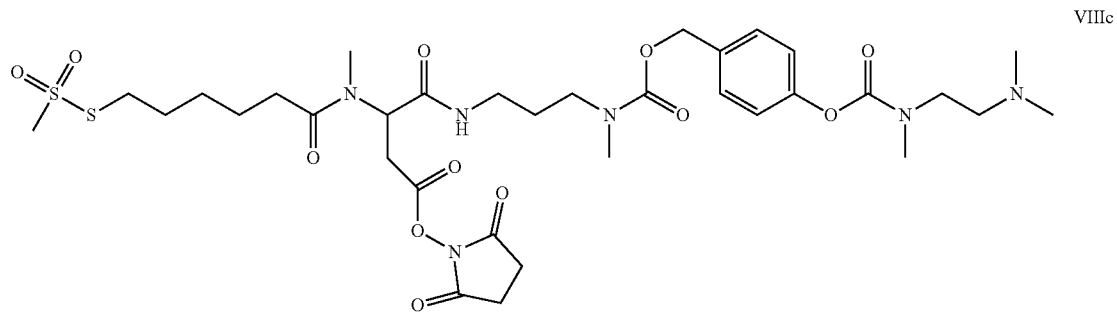 [SMILES: CN(C)CCN(C)C(=O)Oc1ccc(COC(=O)N(C)CCCNC(=O)C(CC(=O)ON2C(=O)CCC2=O)N(C)C(=O)CCCCCSS(C)(=O)=O)cc1]

Compound VIIIc represents compound VIIIb more particularly with a methanesulfonyl group as as Pg², an N-Hydroxysuccinimide (NHS) ester as AG, and the above amine protecting group as Pg¹. Reaction of the compound VIIIc with drug then provides a spacer-linker-drug conjugate compound of formula VIIId The pH of the solution of the drug conjugate may be adjusted as required for use of particular protecting groups. For use with the N-hydroxysuccinimide (NHS) ester methane thiosulfonate compound shown above, pH may be adjusted to about 4. In some aspects, the pH is adjusted with a buffer having a pH of from about 2 to about 3.5. In some

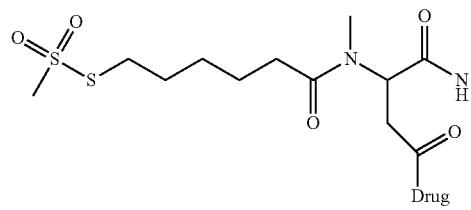
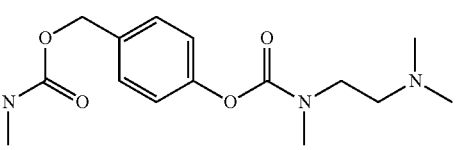

VIIId

Drug spacer linker bisconjugate and trisconjugate (not shown) may also form in some embodiments together with monoconjugate VIIId and the monoconjugate may be isolated from the higher conjugates by column separation as described in the experimental examples below. The unprotected thiol group of mono conjugate VIIId is reacted with a maleimide group on an HA moiety as described above, and the unprotected amino group participates in catalytic cleavage of the Drug-amide bond to provide time-controlled release of the Drug.

The Drug (e.g., ranibizumab or other therapeutic) which displaces the NHS group may be suitably solubilized in a buffer at a pH of from about 6 to about 9, or from about 7 to about 8, such as about 7.4, at a concentration of from about 20 mg/mL to about 100 mg/mL, from about 30 mg/mL to about 50 mg/mL, or about 40 mg/mL. In some aspects, the buffer comprises about 30 mM sodium phosphate. The linker N-Hydroxysuccinimide ester may suitably be solubilized in a polar aprotic solvent, such as DMSO.

The solutions of the linker N-Hydroxysuccinimide ester and the drug are combined at about 5° C. at a pH of from about 7 to about 8, such as about 7.4, and reacted for up to about 10 minutes, such as about 5 minutes, to form a solution of the linker-drug conjugate. The ratio of equivalents of linker N-Hydroxysuccinimide ester to drug is about 1:1, about 5:1, about 10:1, about 15:1 or about 20:1, such as about 5:1, about 10:1 or about 15:1. The linker-drug conjugate typically comprises a mixture of unconjugated drug, drug monoconjugates, drug bisconjugates, drug trisconjugates, and higher conjugates. Longer reaction times and larger amounts of equivalents are used as required as well as higher reaction temperatures.

such aspects, the buffer is pH 3 succinic acid (e.g., about 3 M succinic acid). In some aspects, following pH adjustment, buffer exchange of the solution of the linker-drug conjugate with a buffer having a pH of about 4 may be done. In some such aspects, the buffer exchange may be done with about 5 mM, pH 4.0, succinic acid.

A purification TAG moiety may be used in preparation and purification of drug linker monoconjugates in accordance with the invention. In a TAGylation step, a purification TAG is introduced by displacing the methanesulfonyl group so that the purification TAG is joined to the conjugate via a disulfide bond. Purification tags within the scope of the present disclosure are described in International Publication No. WO 2015/052155. In some aspects, the purification TAG comprises a moiety of formula IX below:

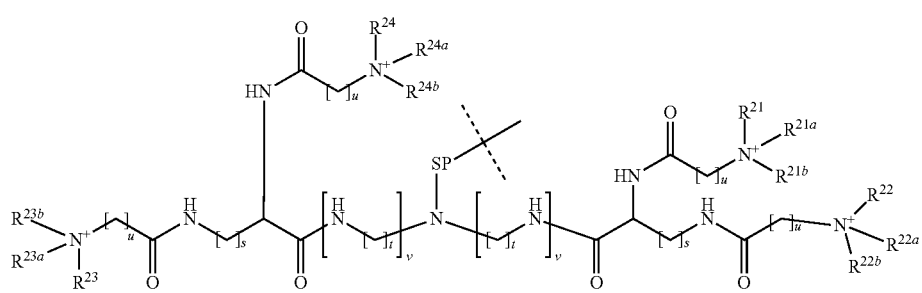

IX wherein:
SP is a spacer moiety;
The dashed line indicates attachment to the remainder of the TAG or alternatively the point of attachment of the TAG to to the Drug linker conjugate (via, for example, by formation of a disulfide bond where 4-mercapto-3-nicotinic acid is the spacer;
$R^{21}$, $R^{21a}$, $R^{21b}$, $R^{22}$, $R^{22a}$, $R^{22b}$, $R^{23}$, $R^{23a}$, $R^{23b}$, $R^{24}$, $R^{24a}$ and $R^{24b}$ are each independently H or methyl;
Each s is independently of each other 1, 2, 3, 4, 5, 6, 7, or 8;
Each t is independently of each other 1, 2, 3, 4, 5, 6, 7, or 8;
Each u is independently of each other 1, 2, 3, 4, 5, 6, 7, or 8; and
Each v is independently of each other 1, 2, 3, 4, 5, 6, 7, or 8.

In some aspects, $R^{21}$, $R^{21a}$ and $R^{21b}$, are each methyl. In some other aspects, $R^{21}$ is H and $R^{21a}$ and $R^{21b}$ are methyl. In some aspects, $R^{22}$, $R^{22a}$ and $R^{22b}$, are each methyl. In some other aspects, $R^{22}$ is H and $R^{22a}$ and $R^{22b}$ are methyl. In some aspects, $R^{23}$, $R^{23a}$ and $R^{23b}$, are each methyl. In some other aspects, $R^{23}$ is H and $R^{23a}$ and $R^{23b}$ are methyl. In some aspects, $R^{24}$, $R^{24a}$ and $R^{24b}$, are each methyl. In some other aspects, $R^{24}$ is H and $R^{24a}$ and $R^{24b}$ are methyl.

In some aspects, s is 1, 2, 3, 4, 5, or 6; 2, 3, 4 or 5; 3, 4 or 5; or 4. In some aspects, t is 1, 2, 3, 4, 5, or 6; 2, 3, 4 or 5; 2, 3 or 4; or 3. In some aspects, u is 1, 2, 3, 4, 5, or 6; 1, 2, 3 or 4; 1, 2 or 3; or 1. In some aspects, v is 1, 2, 3, 4, 5, or 6; 1, 2, 3 or 4; 1, 2 or 3; or 1.

In some aspects, $R^{21}$, $R^{21a}$, $R^{21b}$, $R^{22}$, $R^{22a}$, $R^{22b}$, $R^{23}$, $R^{23a}$, $R^{23b}$, $R^{24}$, $R^{24a}$ and $R^{24b}$ are each methyl; s is 4, t is 3, u is 1, and v is 1. In some other aspects, $R^{21}$, $R^{22}$, $R^{23}$ and $R^{24}$, are each H; $R^{21a}$, $R^{21b}$, $R^{22a}$, $R^{22b}$, $R^{23a}$, $R^{23b}$, $R^{24a}$ and $R^{24b}$ are each methyl; s is 4, t is 3, u is 1, and v is 1.

Counterions for formula IX within the scope of the present disclosure include Cl$^-$, TFA$^-$, HSO4$^-$ and SO4$^{2-}$.

It is understood that the dashed line in formula IX indicates attachment to the rest of the tag if the compound of formula IX is a reagent and is preferably a hydrogen and alternatively indicates attachment to the drug linker conjugate after conjugation to said drug linker conjugate.

In some particular aspects, the purification tag is of the formula X:

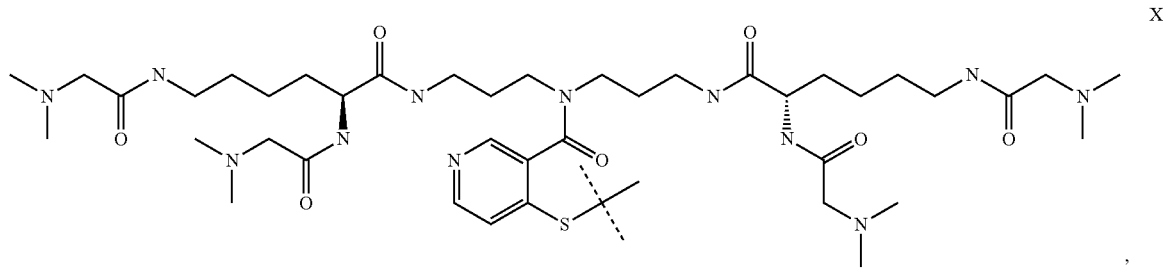

wherein the dashed line indicates attachment to the moiety of thiol of formula X.

In some particular aspects, the purification tag reagent is of the formula Xa:

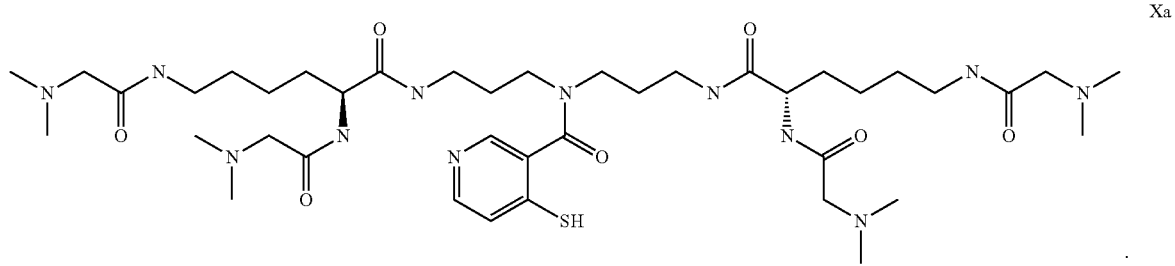

In some particular aspects, the TAG-spacer-linker-drug deprotected monoconjugate is of the formula VIIIe:

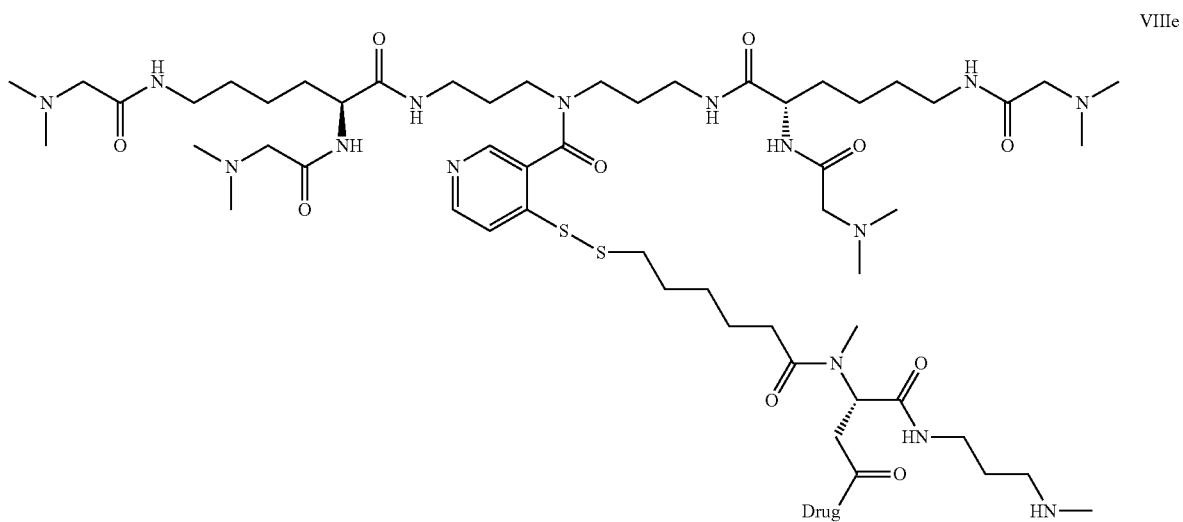

The TAG-spacer-linker-drug deprotected monoconjugate VIIIe represents conjugate VIIId together with purification TAG Xa in place of the methanesulfonyl protecting group. TAG-spacer-linker-drug deprotected monoconjugate VIIIe may be present with higher conjugates (not shown) as described above.

It is understood that moiety VIIIe and other compounds mentioned in the following sections also comprises parts of $L_4$. For convenience and easier naming, the spacer portions are omitted from the names of compounds described below.

TAGylation and amine deprotection may be carried out as follows. Introduction of the purification tag is done by combining a solution containing a stoichiometric excess of a purification tag, such as about 1.5, 2, 2.5 or 3 or even more equivalents of purification tag to linker-drug conjugate, to a solution of linker-drug conjugate. The concentration of linker-drug conjugate in the solution thereof is suitably about 5 mg/mL, about 10 mg/mL, about 15 mg/mL, about 20 mg/mL, about 25 mg/mL, about 30 mg/mL, about 35 mg/mL or about 40 mg/mL, such as about 10 mg/mL to about 20 mg/mL or about 10 mg/mL to about 40 mg/mL. The concentration of the TAG in the solution used for reaction with the drug linker conjugate is suitably from about about 0.1 mM to about 1 mM, from about 0.2 mM to about 0.8 mM, from about 0.3 mM to about 0.7 mM, from about 0.4 mM to about 0.6 mM. In certain embodiments the TAG concentration is about 0.5 mM. In some aspects, the tag solution is an aqueous solution. The pH for the reaction is suitably from about 3 to about 5, from about 3.5 to about 4.5, or about 4. The reaction temperature is suitably from about 10° C. to about 40° C., such as about 25° C. The reaction time is suitably at least 5 minutes, or at least 10 minutes, or at least 30 minutes, such as about 15 minutes or about 35 minutes.

Deprotection may be done by incubation at a pH of from about 7 to about 8, such as about 7.4. In some aspects, the pH is adjusted to from about 7 to about 8 with phosphate buffer containing N,N,N'-Trimethylethylene-1,3-diamine (TriMED). The incubation may suitably be done at a temperature of from about 10° C. to about 40° C., such as about 25° C., and for a time of at least 8 hours, such as about 16 hours.

After deprotection, the pH of the solution of the TAG-linker-drug deprotected conjugate is adjusted to from about 3.5 to about 4.5, or about 4.0 for subsequent purification. In some aspects, pH adjustment may be done with a buffer having a pH of from about 2.5 to about 3.5, such as pH 3.0 succinic acid buffer. The pH adjusted solution may be optionally diluted with buffer prior to subsequent purification. In some aspects, dilution may be done with pH 4.0 succinic acid buffer, e.g., 20 mM succinic acid buffer.

Following deprotection, the monoconjugate species of the TAG-linker-drug deprotected conjugate is isolated. In some aspects, the monoconjugate may be isolated by cation exchange chromatography (CIEC). In some other aspects, the monoconjugate may be isolated by size exclusion chromatography. In some other aspects, the monoconjugate may be isolated by affinity chromatography. In CIEC aspects, suitable resins are known in the art and are commercially available from, for instance, Bio-Rad Laboratories and GE Healthcare and include, for instance and without limitation, AG® 50W, AG® MP-50, Bio-Rex 70, Chelex® 100, AG® 50W, Macro-Prep® series, UNOsphere™ series, Source 15S, Source 30S and Nuvia™ S. The same buffer used for dilution in the second step may be used for the CIEC buffers. For instance, buffer A may be 20 mM succinic acid (pH 4.0) and buffer B (for elution) may be 20 mM succinic acid, 1 M NaCl (pH 4.0). Unconjugated drug elutes first in CIEC separation, followed by the drug monoconjugate, and thereafter followed by higher conjugates (bis- and tris-), etc.

After isolation of the TAG-linker-drug deprotected monoconjugate, the monoconjugate may be concentrated by methods known in the art, such as by tangential flow filtration (TFF) or by centrifugation through a membrane. The concentrated monoconjugate may be optionally filtered. After concentration, the final concentration may suitably be from about 0.2 mg/mL to about 20 mg/mL, from about 0.2 mg/mL to about 10 mg/mL, or about 5 mg/mL.

Next, the purification tag is cleaved from the isolated and potentially concentrated TAG-linker-drug deprotected monoconjugate by cleavage of the disulfide bond in the presence of reducing agent to form an admixture comprising cleaved TAG and a linker-drug monoconjugate.

The reducing agent is typically a small molecule and may be selected from, for instance, 13-mercaptoethanol, glutathione, dithiothreitol (DTT) and TCEP. In some aspects, the reducing agent is DTT. TAG cleavage may suitably be done at a pH of from about 3.5 to about 5.5, such as about 4 or about 4.5. In some aspects, DTT is added to the solution of the TAG-linker-drug deprotected monoconjugate to a concentration of from about 0.1 mM to about 20 mM, such as about 1 mM at a temperature of less than about 15° C., such as from about 2° C. to about 8° C. Incubation may be suitably be done for at least 2 hours, at least 4 hours, at least 8 hours.

In some aspects, the linker-drug monoconjugate following deprotection and removal of the purification TAG is of the formula VIIIf:

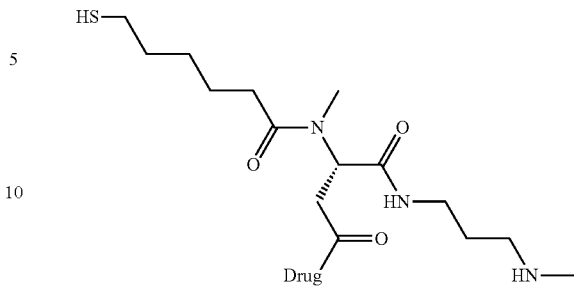

VIIIf

The linker-drug monoconjugate may be isolated from the mixture containing cleaved TAG via chromatography as described elsewhere herein. In CIEC aspects, suitable resins are described elsewhere herein. Generally CIEC for isolation of the linker-drug monoconjugate is done with a buffer system having a pH of from about 4 to about 7, such as about 5.5. For instance, buffer A may be 10 mM histidine (pH 5.5) and buffer B (for elution) may be 10 mM histidine, 500 mM NaCl (pH 5.5). The linker-drug monoconjugate elutes first in CIEC separation, followed by potential disulfide-linked dimer and the cleaved TAG.

Additional buffer B might optionally be added to adjust the osmolality of the protein solution. The isolated linker-drug monoconjugate may be optionally concentrated to a concentration in excess of 50 mg/mL or in excess of 60 mg/mL for subsequent use in the preparation of the prodrug compositions comprising cross-linked HA of the present disclosure. Concentration may be done by TFF or by centrifugation through a membrane.

Conjugation of the drug-linker monoconjugate with maleimido-functionalized HA

Referring again to FIGS. 2 and 3 and FIG. 6 through FIG. 9, the linker-drug monoconjugate VIIIf may be used as the linker drug conjugate reagent 5. The maleimido groups are in equivalent excess over the reagent 5 such that some proportion of the maleimido groups are not conjugated with the drug-linker monoconjugate and are therefore available for cross-linkage with thiol-functionalized HA as described elsewhere herein. In some aspects, the equivalent ratio of maleimido-functionalized HA to drug-linker monoconjugate is from 1.1:1 to about 2:1, such as about 1.2:1, about 1.3:1, about 1.4:1, about 1.5:1, about 1.6:1, about 1.7:1, or about 1.8:1. In some aspects, the reaction mixture comprises a drug-linker monoconjugate concentration of from about 25 mg/mL to about 100 mg/mL (on a protein basis), from about 35 mg/mL to about 55 mg/mL, or about 55 mg/mL. The conjugation is done in a buffer system having a pH of from about 4.5 to about 6.5 or from about 5 to about 6, such as about 5.5. In some aspects, the buffer is 10 mM histidine, 150 mM NaCl and 0.01% Tween 20. The reaction temperature is about 0° C., about 5° C., 10° C., about 15° C., about 20° C., about 25° C., about 30° C., about 35° C., or about 40° C., and the reaction mixture is incubated for a time suitable to achieve substantially complete conjugation, such as from about 1 hour to about 12 hours, or longer, such as about 2 hours, about 4 hours, or about 6 hours.

In some aspects, the drug-linker-maleimido-functionalized HA is of the structure XII:

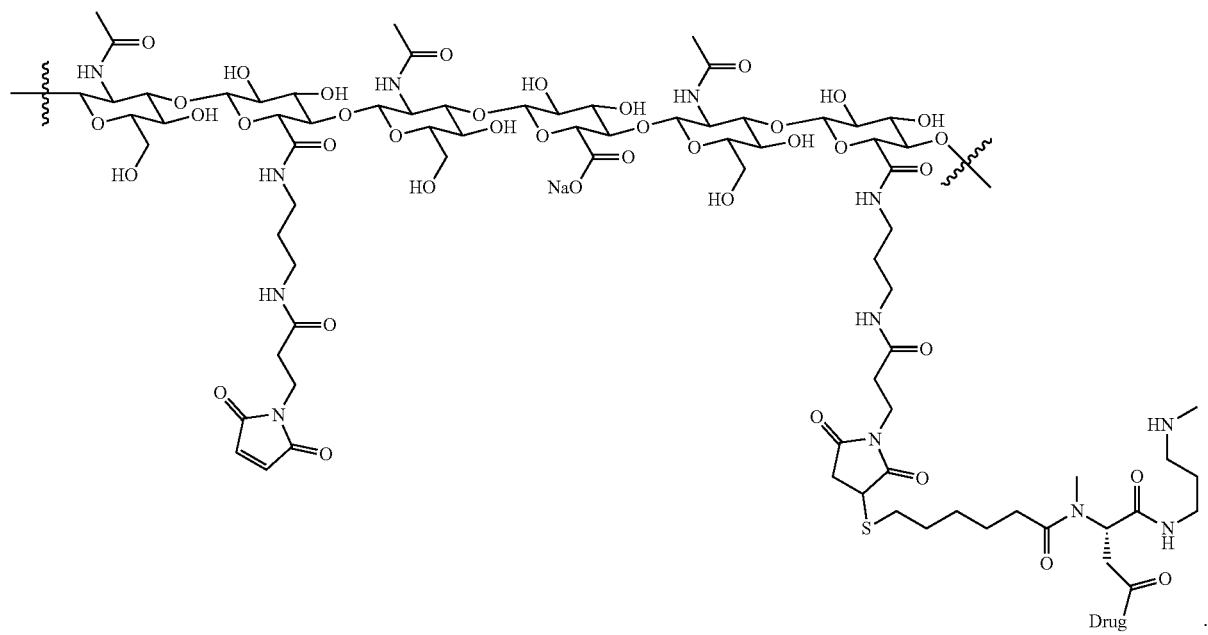

XII

The degree of functionalization of HA compound XII may be varied as described above, and the relative degree of fuctionalization in structure XII is only illustrative. In some embodiments, about 0.5% to about 6%, about 1% to about 5%, about 1.5% to about 4%, about 2% to 3%, or about 2% to about 2.5% of the carboxylate sites on the HA chain of XII are occupied by unreacted maleimide (and thus available for subsequent cross-linking reaction), while about 3% to about 10%, about 5% to about 9%, about 6% to about 8%, or about 7% to about 8% of the carboxylate sites are occupied by linker drug conjugate. In certain embodiments about 4% of the carboxylate sites on the HA chain of XII are occupied by unreacted maleimide and about 6% of the carboxylate sites are occupied by linker drug conjugate. In certain embodiments about 2.3% of the carboxylate sites on the HA chain of XII are occupied by unreacted maleimide and about 7.7% of the carboxylate sites are occupied by linker drug conjugate. The drug linker conjugate binds to the HA chain via reaction of the thiol group of the drug linker conjugate reacting with maleimide groups on the HA chain as described herein. The percentage of sites occupied by unreacted maleimide and by linker drug conjugate may be varied to control the degree of cross-linking and drug loading of the final hydrogel conjugate.

Preparation of Prodrug Compositions Comprising Cross-Linked HA

In some aspects, the prodrug compositions of the present disclosure may be prepared by forming a reaction mixture comprising a solution of drug-linker-maleimido-functionalized HA as described elsewhere herein and a solution of thiol-functionalized HA as described elsewhere herein, and incubating the reaction mixture at a pH and for a time and temperature sufficient to achieve HA cross-linking. The reaction generally proceeds according to step 7 of the reaction scheme depicted in FIG. 9 where $L^A$, $L^B$, $L^C$, $L^2$ and the drug are as described elsewhere herein. In some aspects, the pH is from about from about 4.5 to about 6.5 or from about 5 to about 6, such as about 5.5. The reaction temperature is about 0° C., about 5° C., about 10° C., about 15° C., about 20° C., about 25° C., about 30° C., about 35° C., or about 40° C.

In some aspects, the reaction mixture is thoroughly mixed and filled into syringes shortly thereafter. The pre-filled syringes may then be incubated at ambient temperature for from about 8 hours to about 4 weeks, to complete cross-linking and formation of the cross-linked HA prodrug compositions of the present disclosure. The pre-filled syringes can also be directly stored at 2-8° C. without further storage at ambient temperature. In one embodiment, separate solutions of drug-linker-maleimido-functionalized HA and thiol-functionalized HA are each directly introduced into a pre-fill syringe device and mixed therein, and the cross-linking is allowed to take place in the pre-fill syringe device and allowed undergo cross-linking reaction therein to form the cross-linked HA prodrug composition in situ within the pre-fill syringe device. After a suitable time (which may vary depending upon temperature and other conditions) is allowed for the cross-linking reaction, the cross-linked HA prodrug composition is ready for injection into a patient without further mixing or transfer.

In other embodiments, a batch polymerization can be performed to carry out the cross-linking reaction. The resulting gel is then shredded by passing it through a mesh to make it syringeable, and is subsequently transferred into a syringe device.

In some aspects, the prodrug compositions of the present disclosure are of formula 10:

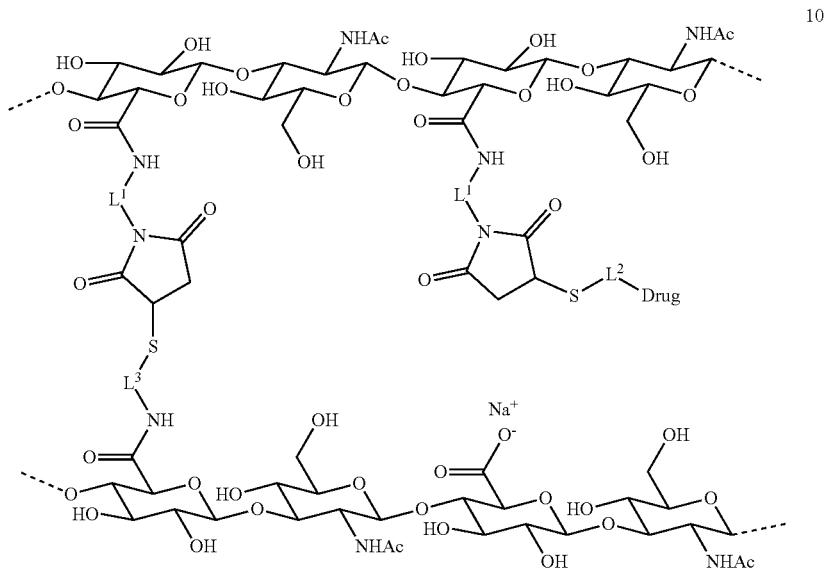

wherein $L^1$, $L^2$, $L^3$, the degree of functionalization and the drug are as defined elsewhere herein. In some other aspects, the HA may be substituted with $Ra^1$ and/or $Ra^2$ as described elsewhere herein.

In some other aspects, the prodrug compositions of the present disclosure are of formula 16:

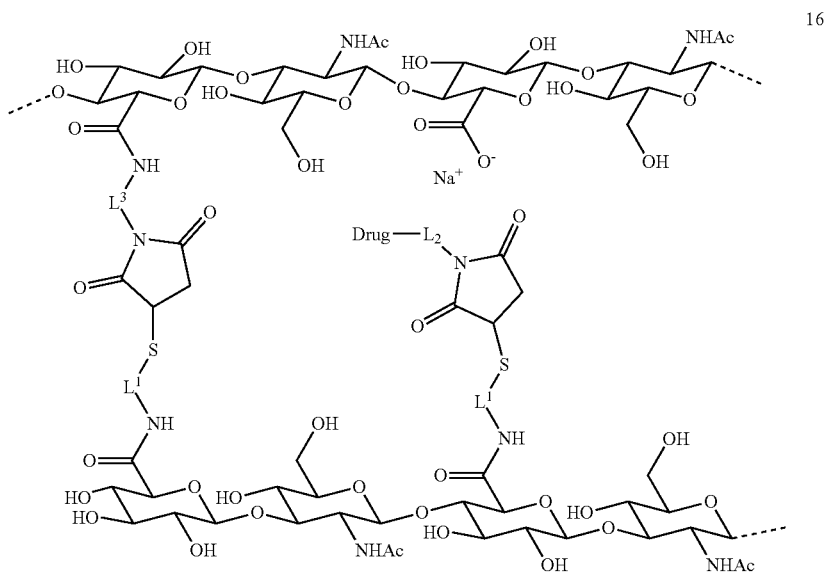

wherein $L^1$, $L^2$, $L^3$, the degree of functionalization and the drug are as defined elsewhere herein. In some other aspects, the HA may be substituted with $Ra^1$ and/or $Ra^2$ as described elsewhere herein.

In some other aspects, the prodrug compositions of the present disclosure are of formula 26:

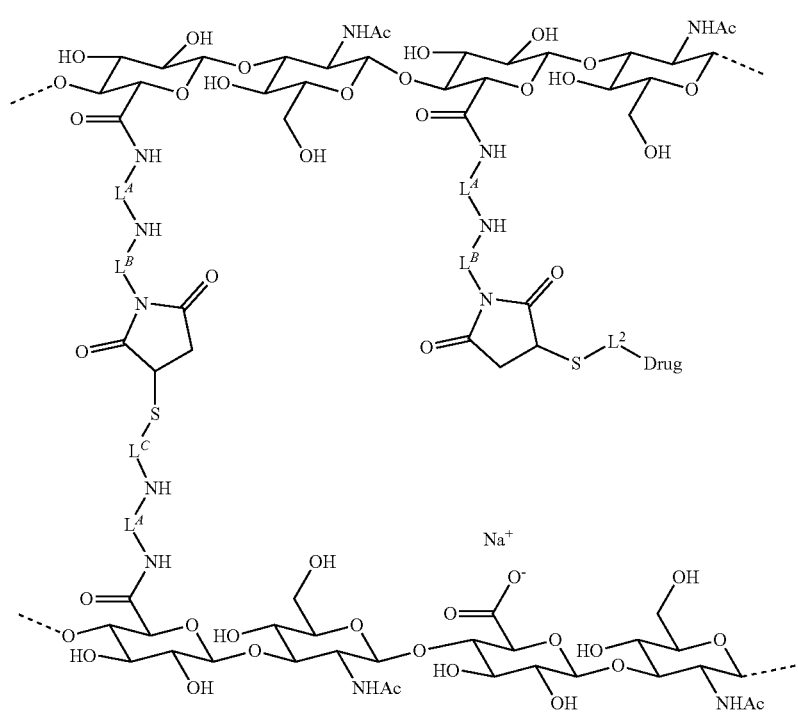

26 wherein $L^A$, $L^B$, $L^C$, $L^2$, the degree of functionalization and the drug are as defined elsewhere herein. In some other aspects, the HA may be substituted with $Ra^1$ and/or a as described elsewhere herein.

Figure 10:
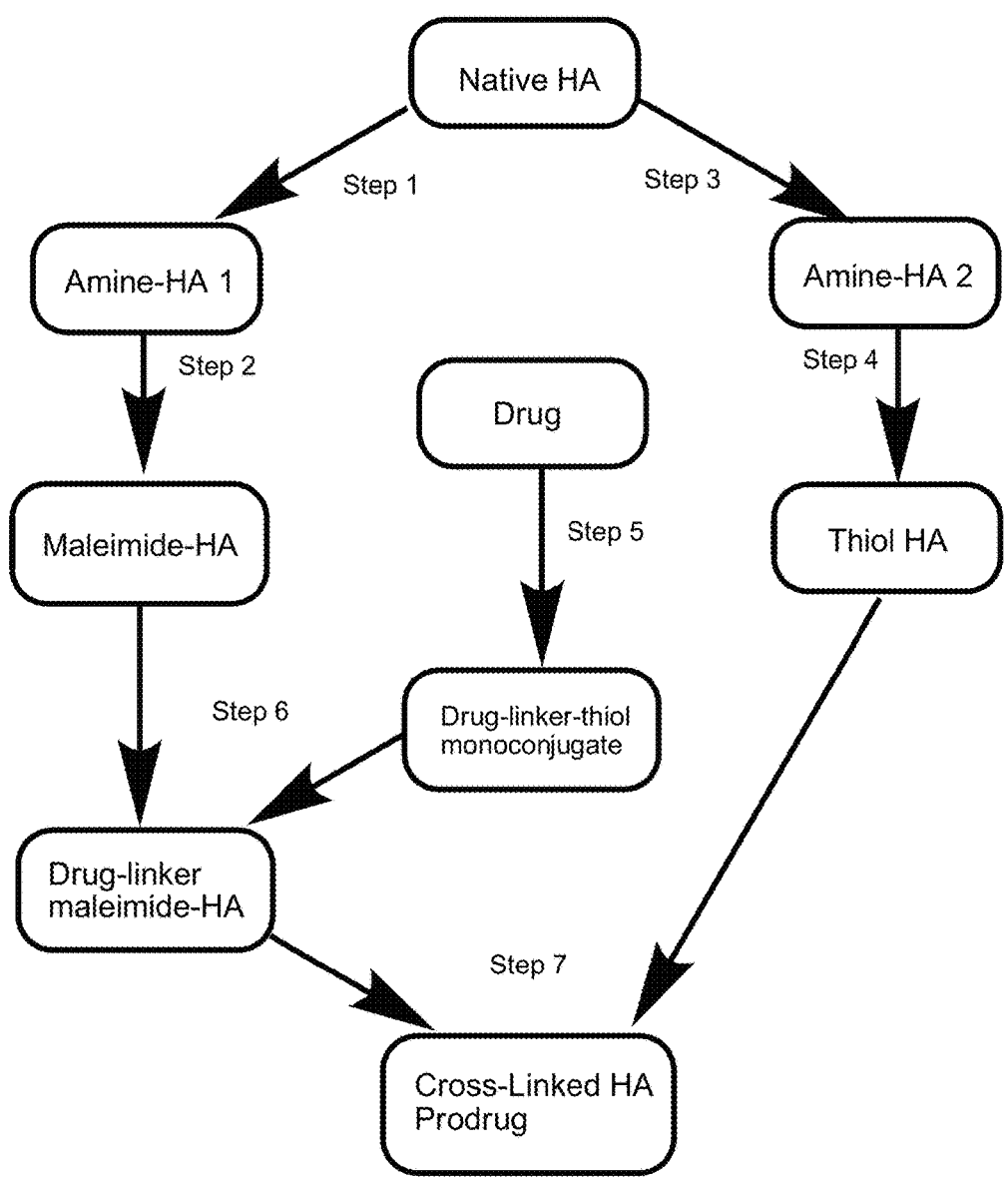
FIG. 10 is a reaction scheme according to one aspect of the present disclosure for the preparation of a cross-linked hyaluronic acid prodrug composition.
Figure 11:
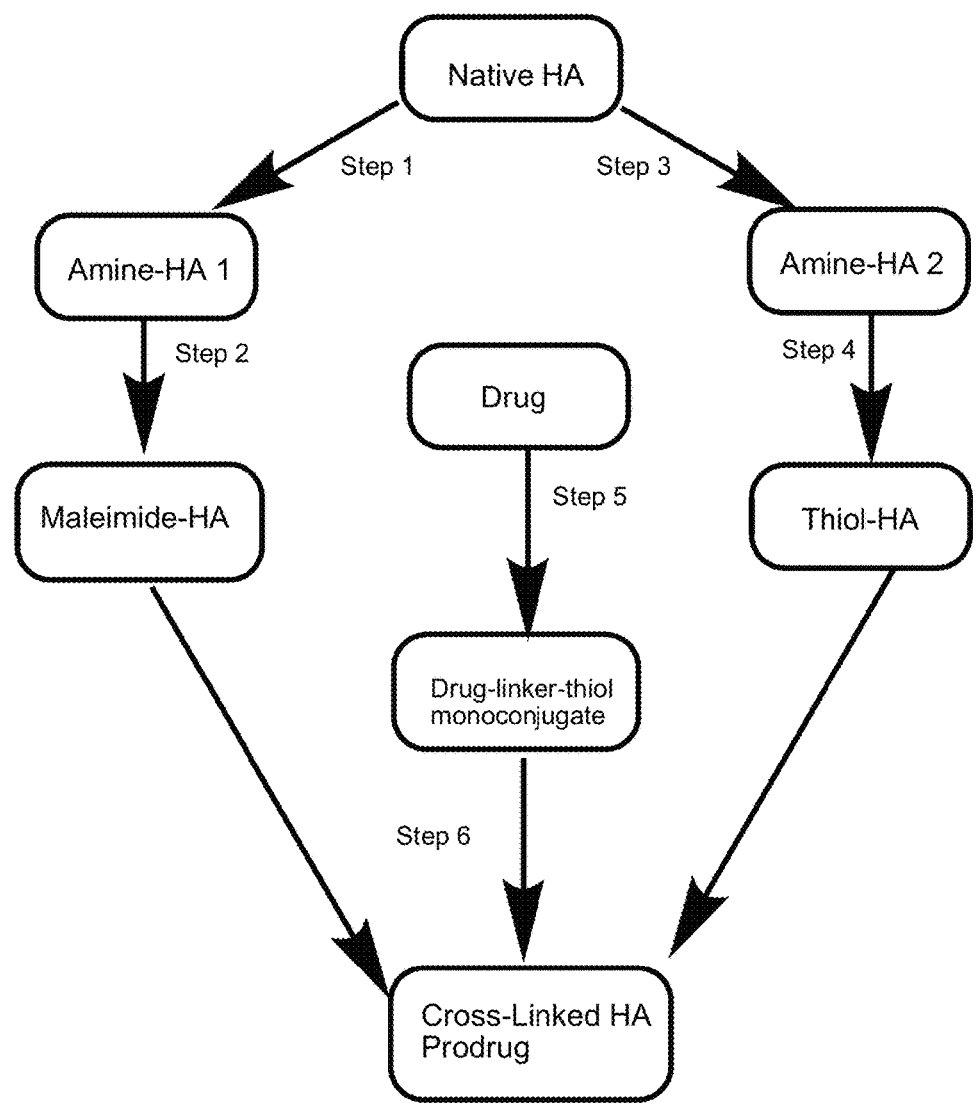
FIG. 11 is a reaction scheme according to one aspect of the present disclosure for the preparation of a cross-linked hyaluronic acid prodrug composition

Overall Processes for the Preparation of Prodrug Compositions Comprising Cross-Linked HA Overall processes for the preparation of prodrug compositions comprising cross-linked HA are depicted in FIGS. 10 and 11.

One process for preparing prodrug compositions comprising cross-linked HA is depicted in FIG. 10. In step 1, Amine-HA 1 is prepared according to methods for preparing amine-functionalized HA as described elsewhere herein. In step 2, maleimide-HA having a permanent spacer is prepared from Amine-HA 1 according to methods for preparing maleimido-functionalized HA as described elsewhere herein. In step 3, Amine-HA 2 is prepared according to methods for preparing amine-functionalized HA as described elsewhere herein. In step 4, Thiol-HA 2 comprising a degradably-linked thiol group is prepared according to a method for preparing thiol-functionalized HA as described elsewhere herein. In step 5, a drug-linker-thiol monoconjugate is prepared according to methods described elsewhere herein. In step 6, the drug-linker-thiol monoconjugate is conjugated to the maleimide-HA having a spacer as described elsewhere herein. In step 7, prodrug compositions comprising cross-linked HA are prepared from Drug-linker-maleimide-HA and Degradable thiol-HA as described elsewhere herein. Step 7 may comprising sterile filtration of the drug-maleimide-HA of step 6 and the degradable thiol HA of step 4 directly into a pre-fill syringe device in which the cross-linking is carried out.

Another process for preparing prodrug compositions comprising cross-linked HA is depicted in FIG. 11. In step 1, Amine-HA 1 is prepared according to methods for preparing amine-functionalized HA as described elsewhere herein. In step 2, maleimide-HA having a spacer is prepared from Amine-HA 1 according to methods for preparing maleimido-functionalized HA as described elsewhere herein. In step 3, Amine-HA 2 is prepared according to methods for preparing amine-functionalized HA as described elsewhere herein. In step 4, Thiol-HA 2 comprising a degradably-linked thiol group is prepared according to method for preparing thiol-functionalized HA as described elsewhere herein. In step 5, a drug-linker-thiol monoconjugate is prepared according to methods described elsewhere herein. In step 6, the drug-linker-thiol monoconjugate, the maleimide-HA having a permanent linker, and thiol-HA having a degradable linker are combined and conjugated to form prodrug compositions comprising cross-linked HA. The maleimide HA, drug linker thiol monoconjugate and thiol HA may each be sterile filtered and transferred into a prefill syringe device wherein they undergo reaction to form the final cross-linked HA prodrug. The reaction conditions for FIG. 11, step 6, are generally consistent with the reaction conditions for the conditions for preparing prodrug compositions comprising cross-linked HA a from Drug-linker-maleimide-HA and Degradable thiol-HA as described elsewhere herein.

Pharmaceutical Compositions

Pharmaceutical composition of the present invention comprises one or more pharmaceutically acceptable excipient(s) including buffering agents, isotonicity modifiers, preservatives/antimicrobials, stabilizers, anti-adsorption agents, anti-oxidants, viscosifiers/viscosity enhancing agents, and/or other auxiliary agents.

Buffering agents may be used to maintain composition pH in a desired range. Non-limiting examples of buffering agents include sodium phosphate, bicarbonate, succinate, histidine, citrate and acetate, sulphate, nitrate, chloride, and pyruvate.

Isotonicity modifiers may be used to minimize pain that can result from cell damage due to osmotic pressure differences at the injection side. Non-limiting examples of isotonicity agents include glycerin and sodium chloride.

Preservatives/antimicrobials may be used to minimize infection risk. Non-limiting examples of preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

Stabilizers may be used to inhibit degradation of the hydrogel and of the drug. Non-limiting examples of stabilizers include: amino acids such as alanine, arginine, aspartic acid, glycine, histidine, lysine, proline; sugars such as glucose, sucrose, trehalose; polyols such as glycerol, mannitol, sorbitol; salts such as potassium phosphate, sodium sulphate; chelating agents such as EDTA, hexaphosphate; ligands such as divalent metal ions (zinc, calcium, etc.); oligomers or polymers such as cyclodextrins, dextran, dendrimers, PEG or PVP or protamine or HAS; and/or other salts or organic molecules such as phenolic derivatives.

Anti-adsorption agents may be used to coat or adsorb competitively to, for example, the surface of the container, such as a syringe, in which the pharmaceutical composition is contained. Anti-absorption agents may be ionic or non-ionic surfactants, proteins or soluble polymers. Non-limiting examples of surfactants include: alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutane-sulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5-nitor-1,3-dioxane, dimethyldioctadecylammonium chloride, dioctadecyldimethylammonium bromide; zwitterionic s, such as 3-[(3-cholamidopropyl)dimethylammonio]-1-propanesulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octa-ethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatins.

Non-limiting examples of anti-oxidants include ascorbic acid, ectoine, methionine, glutathione, monothioglycerol, morin, polyethylenimine (PEI), propyl gallate, vitamin E, chelating agents such as citric acid, EDTA, hexaphosphate, and thioglycolic acid.

The cross-linked HA hydrogel prodrug pharmaceutical compositions may be provided in a container comprising multiple doses of the pharmaceutical composition. Such multiple dose pharmaceutical composition can either be used for different patients in need thereof or can be used for one patient, wherein the remaining doses are stored after the application of the first dose until needed. In some such aspects, the container is a pre-filled syringe.

The cross-linked HA hydrogel prodrug pharmaceutical compositions may be provided as a single or multiple dose pharmaceutical composition in a pre-filled syringe.

The cross-linked HA hydrogel prodrug pharmaceutical compositions of the present disclosure may be suitably stored in syringes at a temperature of less than about 10° C.

Therapeutic amounts of the cross-linked HA hydrogel prodrug pharmaceutical compositions may be administered by intraocular injection. For instance the composition may be injected into the vitreum of a subject in need thereof using a needle having a gauge of 22, 23, 24, 25, 26, 27, 28, 29, 30, 31, or 32.

In some aspects, the cross-linked HA hydrogel prodrug pharmaceutical compositions may be provided in a kit. In such aspects the kit may comprise a syringe prefilled with the cross-linked HA hydrogel prodrug pharmaceutical composition, a hypodermic needle, and instructions for use.

The invention provides antibody conjugates that include antibodies (e.g., anti-VEGF antibodies) covalently linked to cross-linked HA hydrogel compositions as described herein. Exemplary Antibodies for use in Cross-Linked HA Hydroget Conjugate Compositions) of the Invention Any suitable antibody (e.g., anti-VEGF antibody) may be used. For example, the antibody may specifically bind to an antigen selected from the group consisting of VEGF; interleukin-1 beta (IL-1β); interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, membrane-bound VEGF-receptor (mbVEGFR), or soluble VEGF receptor (5VEGFR)); ST-2 receptor; and a protein genetically linked to age-related macular degeneration (AMD) risk (e.g., complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A). Such antibodies can be useful, for example, for reducing angiogenesis and/or for treating or delaying the progression of a disorder associated with pathological angiogenesis (e.g., ocular disorders or cell proliferative disorders). Exemplary, non-limiting anti-VEGF antibodies that can be used in the antibody conjugates of the invention are described further below.

In some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of $GX_1TPX_2GGX_3X_4X_5YX_6DSVX_7X_8$ (SEQ ID NO: 2), wherein $X_1$ is Ile or His, $X_2$ is Ala or Arg, $X_3$ is Tyr or Lys, $X_4$ is Thr or Glu, $X_5$ is Arg, Tyr, Gln, or Glu, $X_6$ is Ala or Glu, $X_7$ is Lys or Glu, and $X_8$ is Gly or Glu; (c) an HVR-H3 comprising the amino acid sequence of FVFFLPYAMDY (SEQ ID NO: 3); (d) an HVR-L1 comprising the amino acid sequence of RASQX$_1$VSTAVA (SEQ ID NO: 4), wherein $X_1$ is Asp or Arg; (e) an HVR-L2 comprising the amino acid sequence of X$_1$ASFLYS (SEQ ID NO: 5), wherein $X_1$ is Ser or Met; and (f) an HVR-L3 comprising the amino acid sequence of X$_1$QGYGX$_2$PFT (SEQ ID NO: 6), wherein $X_1$ is Gln, Asn, or Thr and $X_2$ is Ala, Asn, Gln, or Arg, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

For instance, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7), GITPAGGYEYYADSVKG (SEQ ID NO: 21), or GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10) or QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 7-10, or 21-23.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, or 7-10. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 11 and (b) a VL domain comprising an amino acid sequence of SEQ ID NO: 12.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8, 9, 22, or 23. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 38.

In some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 38.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8-10, or 22. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQP GE SLEL SCAAS GFEI S (SEQ ID NO: 29) or EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19) or GVPSRFSGSGSGTDFTLTIESLQPEDAATYYC (SEQ ID NO: 28); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 34.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 35.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 35.

For example, in yet other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF- FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 36.

For example, in still further instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 37.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 37.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 12.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASG-FEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPED-AATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 12.

In some instances, the anti-VEGF antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 11, 40, or 42; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 41, or 46; or (c) a VH domain as in (a) and a VL domain as in (b). For example, in some instances, the antibody comprises a VH domain comprising the amino acid sequence of SEQ ID NO: 11 and a VL domain comprising the amino acid sequence of SEQ ID NO: 12. In some instances, the antibody comprises a VH domain comprising the amino acid sequence of SEQ ID NO: 40 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 41. In some instances, the antibody comprises a VH domain comprising the amino acid sequence of SEQ ID NO: 11 and a VL domain comprising the amino acid sequence of SEQ ID NO: 46.

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14) or WVRQEPGKGLEWVA (SEQ ID NO: 39); (c) an FR-H3 comprising the amino acid sequence of RFTISADTSKN-TAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17) or DIQMTQSPSSL-SASVGDRVTIDC (SEQ ID NO: 45); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPED-AATYYC (SEQ ID NO: 19), GVPSRFSGSGSGTDFTLTISSLQPEDSATYYC (SEQ ID NO: 44), or GVPSRFSGSGSGTDFTLTISSLQPED-VATYYC (SEQ ID NO: 54); and (d) an FR-L4 comprising the amino acid sequence of FGQGTKVEIK (SEQ ID NO: 20) or FGQGTKVEVK (SEQ ID NO: 55).

In some instances, the antibody comprises a VH domain comprising the amino acid sequence of SEQ ID NO: 11 and a VL domain comprising the amino acid sequence of

```
                                              (SEQ ID NO: 59)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGNPFTFGQGT

KVEIK.
```

In some instances, the antibody comprises a VH domain comprising the amino acid sequence of SEQ ID NO: 33 and a VL domain comprising the amino acid sequence of

```
                                              (SEQ ID NO: 59)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGNPFTFGQGT

KVEIK.
```

In some instances, the antibody comprises a VH domain comprising the amino acid sequence of SEQ ID NO: 40 and a VL domain comprising the amino acid sequence of

```
                                              (SEQ ID NO: 59)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGNPFTFGQGT

KVEIK.
```

In some instances, the antibody comprises a VH domain comprising the amino acid sequence of SEQ ID NO: 42 and a VL domain comprising the amino acid sequence of

```
                                              (SEQ ID NO: 59)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGNPFTFGQGT

KVEIK.
```

In some instances, the antibody comprises a VH domain comprising the amino acid sequence of SEQ ID NO: 51 and a VL domain comprising the amino acid sequence of

```
                                              (SEQ ID NO: 59)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGNPFTFGQGT

KVEIK.
```

In some instances, the antibody comprises a VH domain comprising the amino acid sequence of SEQ ID NO: 11 and a VL domain comprising the amino acid sequence of (SEQ ID NO: 60)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGAPFTFGQGT

KVEIK.

In some instances, the antibody comprises a VH domain comprising the amino acid sequence of SEQ ID NO: 33 and a VL domain comprising the amino acid sequence of (SEQ ID NO: 60)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGAPFTFGQGT

KVEIK.

In some instances, the antibody comprises a VH domain comprising the amino acid sequence of SEQ ID NO: 40 and a VL domain comprising the amino acid sequence of (SEQ ID NO: 60)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGAPFTFGQGT

KVEIK.

In some instances, the antibody comprises a VH domain comprising the amino acid sequence of SEQ ID NO: 42 and a VL domain comprising the amino acid sequence of (SEQ ID NO: 60)
DIQMTQSPSSLSASVGDRVTITCRASQDVSTAVAWYQQKPGKAPKLLIYSA

SFLYSGVPSRFSGSGSGTDFTLTISSLQPEDVATYYCQQGYGAPFTFGQGT

KVEIK.

In some instances, the antibody comprises a VH domain comprising the amino acid sequence of SEQ ID NO: 51 and a VL domain comprising the amino acid sequence of DIQMTQ SP S SL SASVGDRVTITCRA SQDV STAVAWYQQKP GKAPKLLIY SA SFLY S GV PSRFSGSGSGTDFTLTIS SLQPEDVATYYCQQGYGAPFTFGQGTKVEIK (SEQ ID NO: 60). For example, in some instances, the anti-VEGF antibody comprises (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 11; (b) a VL domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 11; or (c) a VH domain as in (a) and a VL domain as in (b). In some instances, the anti-VEGF antibody may include (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following heavy chain framework regions: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In some instances, the anti-VEGF antibody includes the following light chain framework regions: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes a binding domain comprising (a) a VH domain comprising an amino acid sequence of SEQ ID NO: 11 and (b) a VL domain comprising an amino acid sequence of SEQ ID NO: 12. In some instances, the exemplary anti-VEGF is N94A.F83A.N82aR.Y58R (also referred to as G6.31.AARR).

In some instances, the anti-VEGF antibody comprises (a) VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33 or 51; (b) a VL domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 34, 35, 36, 37, or 38; or (c) a VH domain as in (a) and a VL domain as in (b). For example, in some instances, the antibody comprises a VH domain comprising the amino acid sequence of SEQ ID NO: 33 and a VL domain comprising the amino acid sequence of SEQ ID NO: 12. In some instances, the antibody comprises a VH domain comprising the amino acid sequence of SEQ ID NO: 33 and a VL domain comprising the amino acid sequence of SEQ ID NO: 34. In some instances, the antibody comprises a VH domain comprising the amino acid sequence of SEQ ID NO: 33 and a VL domain comprising the amino acid sequence of SEQ ID NO: 35. In some instances, the antibody comprises a VH domain comprising the amino acid sequence of SEQ ID NO: 33 and a VL domain comprising the amino acid sequence of SEQ ID NO: 36. In some instances, the antibody comprises a VH domain comprising the amino acid sequence of SEQ ID NO: 33 and a VL domain comprising the amino acid sequence of SEQ ID NO: 37. In some instances, the antibody comprises a VH domain comprising the amino acid sequence of SEQ ID NO: 33 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 35. In some instances, the antibody comprises a VH domain comprising the amino acid sequence of SEQ ID NO: 51 and a VL domain comprising the amino acid sequence of SEQ ID NO: 37. In some instances, the antibody comprises a VH domain comprising the amino acid sequence of SEQ ID NO: 51 and a VL domain comprising the amino acid sequence of SEQ ID NO: 12.

In some instances, the anti-VEGF antibody comprises (a) VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33 or 51; (b) a VL domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 34, 35, 36, 37, or 38; or (c) a VH domain as in (a) and a VL domain as in (b). For example, in some instances, the antibody comprises a VH domain comprising the amino acid sequence of SEQ ID NO: 33 and a VL domain comprising the amino acid sequence of SEQ ID NO: 12. In some instances, the antibody comprises a VH domain comprising the amino acid sequence of SEQ ID NO: 33 and a VL domain comprising the amino acid sequence of SEQ ID NO: 34. In some instances, the antibody comprises a VH domain comprising the amino acid sequence of SEQ ID NO: 33 and a VL domain comprising the amino acid sequence of SEQ ID NO: 35. In some instances, the antibody comprises a VH domain comprising the amino acid sequence of SEQ ID NO: 33 and a VL domain comprising the amino acid sequence of SEQ ID NO: 36. In some instances, the antibody comprises a VH domain comprising the amino acid sequence of SEQ ID NO: 33 and a VL domain comprising the amino acid sequence of SEQ ID NO: 37. In some instances, the antibody comprises a VH domain comprising the amino acid sequence of SEQ ID NO: 33 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 35. In some instances, the antibody comprises a VH domain comprising the amino acid sequence of SEQ ID NO: 51 and a VL domain comprising the amino acid sequence of SEQ ID NO: 37. In some instances, the antibody comprises a VH domain comprising the amino acid sequence of SEQ ID NO: 51 and a VL domain comprising the amino acid sequence of SEQ ID NO: 12.

In some instances, any of the preceding anti-VEGF antibodies may include one, two, three, or four of the following heavy chain variable domain framework regions (FRs): an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30) or WVRQEPGKGLEWVA (SEQ ID NO: 39); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVP SRF S GS GS GTD FTLTIS SLQPEDAATYYC (SEQ ID NO: 19), GVPSRFSGSGSGTDFTLTISSLQPEDFATYYC (SEQ ID NO: 24), or GVPSRFSGSGSGTDFTLTIESLQPEDAATYYC (SEQ ID NO: 28); and (d) an FR-L4 comprising the amino acid sequence of FGQGTKVEIK (SEQ ID NO: 20).

In some instances, the invention provides an antibody comprising (a) a heavy chain comprising the amino acid sequence of SEQ ID NO: 48 and/or (b) a light chain comprising the amino acid sequence of SEQ ID NO: 50. In certain embodiments, the antibody is G6.31 AARR expressed in Fab format.

In some instances, the invention provides an antibody comprising (a) a heavy chain comprising the amino acid sequence of SEQ ID NO: 49 and/or (b) a light chain comprising the amino acid sequence of SEQ ID NO: 50. In certain embodiments, the antibody is a variant version of G6.31 AARR that lacks reactivity to anti-human IgG.

In a further aspect, an antibody (e.g., an anti-VEGF antibody) according to any of the above embodiments may incorporate any of the features, singly or in combination, as described in Sections 1-7 below:

Section 1: Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., 10-8 M or less, e.g., from 10-8 M to 10-13 M, e.g., from 10-9 M to 10-13 M). For example, in some instances, an antibody provided herein binds an antigen (e.g., human VEGF (hVEGF)) with a Kd of about 10 nM or lower. In some instances, an antibody provided herein binds an antigen (e.g., hVEGF) with a Kd of about 5 nM or lower. In some instances, an antibody provided herein binds hVEGF with a Kd of about 2 nM or lower. For example, in some instances, the antibody binds an antigen (e.g., hVEGF) with a Kd between about 25 pM and about 2 nM (e.g., about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM). In some instances, the antibody binds an antigen (e.g., hVEGF) with a Kd between about 75 pM and about 600 pM (e.g., about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM). In some instances, the antibody binds an antigen (e.g., hVEGF) with a Kd between about 75 pM and about 500 pM. In some instances, the antibody binds an antigen (e.g., hVEGF) with a Kd between about 75 pM and about 400 pM. In some instances, the antibody binds an antigen (e.g., hVEGF) with a Kd between about 75 pM and about 300 pM. In some instances, the antibody binds an antigen (e.g., hVEGF) with a Kd between about 75 pM and about 200 pM. In some instances, the antibody binds an antigen (e.g., hVEGF) with a Kd between about 75 pM and about 150 pM. In some instances, the antibody binds an antigen (e.g., hVEGF) with a Kd between about 75 pM and about 125 pM. In some instances, the antibody binds an antigen (e.g., hVEGF) with a Kd between about 75 pM and about 100 pM. In some instances, the antibody binds an antigen (e.g., hVEGF) with a Kd of about 80 pM. In some instances, the antibody binds an antigen (e.g., hVEGF) with a Kd of about 60 pM. In some instances, the antibody binds an antigen (e.g., hVEGF) with a Kd of about 40 pM.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin (BSA) in phosphate buffered saline (PBS) for two to five hours at room temperature (approximately 23° C.). In a non-adsorbent plate (Nunc #269620), 100 pM or 26 pM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20Tm) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, for example, Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCOTm spectrophotometer (ThermoSpectronic) with a stirred cuvette.

Section 2: Antibody Stability

In some instances, the antibody used in the antibody conjugates of the invention or compositions thereof have enhanced stability, for example, as compared to an anti-VEGF antibody, for instance, G6.31 (see, e.g., U.S. Pat. No. 7,758,859 and International Application Pub. No. WO 2005/012359, which are incorporated herein by reference in their entirety). The stability of an antibody may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The anti-VEGF antibody may have, for example, an enhanced melting temperature (Tm), temperature of aggregation (Tagg), or other metrics of stability compared to an anti-VEGF antibody, for example, G6.31.

In certain embodiments, an antibody provided herein has a Tm that is greater than or equal to about 80° C. (e.g., about 81° C., about 82° C., about 83° C., about 84° C., about 85° C., about 86° C., about 87° C., about 88° C., about 89° C., about 90° C., about 91° C., about 92° C., or about 93° C.). For example, in some instances, the anti-VEGF antibody has a Tm that is greater than or equal to about 83.5° C. (e.g., about 83.5° C., about 84° C., about 85° C., about 86° C., about 87° C., about 88° C., about 89° C., about 90° C., about 91° C., about 92° C., or about 93° C.). In some instances, the anti-VEGF antibody has a Tm of about 82° C. to about 92° C. (e.g., about 82° C., about 83° C., about 84° C., about 85° C., about 86° C., about 87° C., about 88° C., about 89° C., about 90° C., about 91° C., or about 92° C.). In some about instances, the anti-VEGF antibody has a Tm of about 82° C. In some instances, any of the preceding Tm values of an anti-VEGF antibody is determined using DSF. In some embodiments, the Tm value of an anti-VEGF antibody is determined as described, for example, in Example 1 of International Patent Application No. PCT/US2016/053454, which is incorporated herein by reference in its entirety.

Section 3: Antibody Fragments

In certain embodiments, an antibody provided herein is an antibody fragment. Antibody fragments include, but are not limited to, Fab, Fab', Fab-C, Fab'-SH, F(ab')2, Fv, and scFv fragments, and other fragments described below. For a review of certain antibody fragments, see Hudson et al., Nat. Med. 9:129-134 (2003). For a review of scFv fragments, see, e.g., Pluckthiln, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

Section 4: Chimeric and Humanized Antibodies

In certain embodiments, an antibody provided herein is a chimeric antibody. Certain chimeric antibodies are described, for example, in U.S. Pat. No. 4,816,567; and Morrison et al., Proc. Natl. Acad. Sci. USA, 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, for example, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, for example, in Almagro and Fransson, Front. Biosci. 13:1619-1633 (2008), and are further described, for example, in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al., J. Immunol. 151:2296 (1993)); framework regions derived from the consensus sequence of human antibodies of a particular subgroup of light or heavy chain variable regions (see, e.g., Carter et al., Proc. Natl. Acad. Sci. USA, 89:4285 (1992); and Presta et al., J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Section 5: Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments can be derived from phage libraries as described in International Patent Application No. PCT/US2016/053454.

Antibodies or antibody fragments isolated from human antibody libraries are considered human antibodies or human antibody fragments herein.

Section 6: Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, one of the binding specificities is for VEGF and the other is for any other antigen (e.g., a second biological molecule, e.g., interleukin-1 beta (IL-1β; interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, membrane-bound VEGF-receptor (mbVEGFR), or soluble VEGF receptor (5VEGFR)); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; C OL10A 1; and TNFRSF10A. Accordingly, the bispecific antibody may have binding specificity for VEGF and IL-1β; VEGF and IL-6; VEGF and IL-6R; VEGF and IL-13; VEGF and IL-13R; VEGF and PDGF (e.g., PDGF-BB); VEGF and angiopoietin; VEGF and Ang2; VEGF and Tie2; VEGF and S1P; VEGF and integrin αvβ3; VEGF and integrin αvβ5; VEGF and integrin α5β1; VEGF and betacellulin; VEGF and apelin/APJ; VEGF and erythropoietin; VEGF and complement factor D; VEGF and TNFα; VEGF and HtrA1; VEGF and a VEGF receptor (e.g., VEGFR1, VEGFR2, VEGFR3, mbVEGFR, or 5VEGFR); VEGF and ST-2 receptor; VEGF and C2; VEGF and factor B; VEGF and factor H; VEGF and CFHR3; VEGF and C3b; VEGF and C5; VEGF and C5a; VEGF and C3a; VEGF and ARMS2; VEGF and TIMP3; VEGF and HLA; VEGF and IL-8; VEGF and CX3CR1; VEGF and TLR3; VEGF and TLR4; VEGF and CETP; VEGF and LIPC; VEGF and COL10A1; or VEGF and TNFRSF10A. In certain embodiments, bispecific antibodies may bind to two different epitopes of VEGF. Bispecific antibodies may also be used to localize cytotoxic agents to cells which express VEGF. Bispecific antibodies can be prepared as full length antibodies or antibody fragments (e.g., Fab, Fab', or Fab-C fragments).

In some instances, the bispecific antibody is a bispecific anti-VEGF/anti-angiopoeitin 2 (Ang2) antibody disclosed in U.S. Patent Application No. US 2014/0017244, which is incorporated herein by reference in its entirety. For example, the anti-VEGF/anti-Ang2 bispecific antibody may include a first binding domain that binds VEGF (such as any of the anti-VEGF antibodies described herein) and a second binding domain that binds Ang2 that includes (a) an HVR-H 1 comprising the amino acid sequence of GYYMH (SEQ ID NO: 61); (b) an HVR-H2 comprising the amino acid sequence of WINPNSGGTNYAQKFQG (SEQ ID NO: 62); (c) an HVR-H3 comprising the amino acid sequence of SPNPYYYDSSGYYYPGAFDI (SEQ ID NO: 63); (d) an HVR-L1 comprising the amino acid sequence of GGNNIG-SKSVH (SEQ ID NO: 64); (e) an HVR-L2 comprising the amino acid sequence of DDSDRPS (SEQ ID NO: 65 and (f) an HVR-L3 comprising the amino acid sequence of QVWDSSSDHWV (SEQ ID NO: 66), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 61-66.

In some instances, the anti-VEGF/anti-Ang2 bispecific antibody may include a first binding domain that binds VEGF (such as any of the anti-VEGF antibodies described herein) and a second binding domain that binds to Ang2. In some instances, the anti-VEGF/anti-Ang2 bispecific antibody may include a first binding domain that binds VEGF (such as any of the anti-VEGF antibodies described herein) and a second binding domain that specifically bind to Ang2, wherein the second binding domain is any antibody binding domain described in International Patent Application Publication No. WO 2010/069532, which is incorporated herein by reference in its entirety, or a variant thereof.

In other instances, the anti-VEGF/anti-Ang2 bispecific antibody is any anti-VEGF/anti-Ang2 bispecific antibody described in International Patent Application Publication No. WO 2016/073157.

In some instances, the bispecific antibody is a bispecific anti-VEGF/anti-IL-6 antibody. In some instances, an anti-VEGF/anti-IL-6 bispecific antibody may include a first binding domain that binds VEGF (such as any of the anti-VEGF antibodies described herein) and a second binding domain that binds IL-6. The second binding domain may be a binding domain of any anti-IL-6 antibody known in the art, for example, EBI-031 (Eleven Biotherapeutics; see, e.g., WO 2016/073890, which is incorporated herein by reference in its entirety), siltuximab (SYLVANT®), olokizumab, clazakizumab, sirukumab, elsilimomab, gerilimzumab, OPR-003, MEDI-5117, PF-04236921, or a variant thereof.

In some instances, the bispecific antibody is a bispecific anti-VEGF/anti-IL-6R antibody. In some instances, an anti-VEGF/anti-IL-6R bispecific antibody may include a first binding domain that binds VEGF (such as any of the anti-VEGF antibodies described herein) and a second binding domain that binds IL-6R. The second binding domain may be a binding domain any anti-IL-6R antibody known in the art, for example, tocilizumab (ACTEMRA®) (see, e.g., WO 1992/019579, which is incorporated herein by reference in its entirety), sarilumab, vobarilizumab (ALX-0061), SA-237, or a variant thereof.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, for example, in Tuft et al., J. Immunol. 147:60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to VEGF as well as another, different antigen (see, e.g., US 2008/0069820).

Section 7: Antibody Variants

In certain embodiments, amino acid sequence variants (e.g., antibody variants including one or more amino acid residue alterations) of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen binding.

(a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or other functional features, e.g., stability or effector function.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe; Non-conservative substitutions will entail exchanging a member of one of these classes for another class.

One type of substitutional variant involves substituting one or more hypervariable region residues and/or FR residues of a parent antibody (e.g., a humanized antibody). Generally, the resulting variant(s) selected for further study will have modifications (e.g., improvements) in certain biological properties (e.g., increased affinity, increased stability, increased expression, altered pI, and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, for example, in Hoogenboom et al., in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

In certain embodiments, substitutions, insertions, or deletions may occur within one or more FRs so long as such alterations do not substantially reduce the ability of the antibody to bind antigen. Such alterations may, for example, improve antibody affinity and/or stability (e.g., as assessed by an increased melting temperature).

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

(b) Isoelectric Point Variants

The invention provides antibodies variants with altered isoelectric points. For example, the invention provides antibodies variants with a reduced isoelectric point (pI), for example, as compared to an anti-VEGF antibody, for instance, G6.31. In some instances, the surface charge is reduced at physiological pH. In some instances, the anti-VEGF antibody has a pI equal to or lower than about 8 (e.g., about 8, about 7, about 6, about 5, or about 4). In some instances, the antibody has a pI from about 4 to about 8 (e.g., about 4, about 5, about 6, about 7, or about 8). In some instances, the anti-VEGF antibody has a pI from about 5 to about 7 (e.g., about 5, about 6, or about 7). In some instances, the anti-VEGF antibody has a pI from about 5 to about 6 (e.g., about 5.1, about 5.2, about 5.3, about 5.4, about 5.5, about 5.6, about 5.7, about 5.8, about 5.9, or about 6).

Antibodies of the invention may be engineered to have a reduced pI, for example, by substituting wild-type amino acid residues at a given position with an amino acid having a lower pI. The pI of an amino acid can be determined based on the pKa values of the amine (~NH2), carboxylic acid (—COOH), and side-chain of the amino acid, which are known in the art. In some embodiments, surface-exposed amino acid residues may be substituted to reduce the pI of an antibody. In one embodiment, surface-exposed amino acid residues may be substituted with glutamate (E). In one embodiment, surface-exposed amino acid residues may be substituted with aspartate (D).

Recombinant Methods and Compositions

Any of the antibodies (e.g., anti-VEGF antibodies) described herein may be produced using recombinant methods and compositions, for example, as described in U.S. Pat. No. 4,816,567. In one embodiment, an isolated nucleic acid encoding an anti-VEGF antibody described herein is provided. Such a nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such a nucleic acid are provided. In a further embodiment, a host cell comprising such a nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell or lymphoid cell (e.g., Y0, NS0, Sp20 cell). In one embodiment, a method of making an anti-VEGF antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody (e.g., an anti-VEGF antibody), nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, Methods in Molecular Biology, Vol. 248 (B.K.C. Lo, ed., Humana Press, Totowa, NJ, 2003), pp. 245-254, describing expression of antibody fragments in E. coli. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR- CHO cells (Urlaub et al., Proc. Natl. Acad. Sci. USA 77:4216 (1980)); and myeloma cell lines such as YO, NS0 and Sp2/0. For a review of certain mammalian host cell lines suitable for antibody production, see, for example, Yazaki and Wu, Methods in Molecular Biology, Vol. 248 (B.K.C. Lo, ed., Humana Press, Totowa, N.J.), pp. 255-268 (2003).

Assays

Antibodies (e.g., anti-VEGF antibodies described herein), as well as antibody conjugates (e.g., antibody conjugates that include anti-VEGF antibodies (e.g., any anti-VEGF antibody provided herein)), may be identified, screened for, or characterized for their physical/chemical properties and/or biological activities by various assays known in the art.

(a) Binding Assays and Other Assays

In one aspect, an antibody (e.g., an anti-VEGF antibody), or an antibody conjugate thereof, is tested for its antigen binding activity, e.g., by known methods such as ELISA, Western blot, etc.

In another aspect, competition assays may be used to identify an antibody that competes with an antibody as described herein, or an antibody conjugate thereof, for binding to an antigen (e.g., VEGF). In certain embodiments, such a competing antibody binds to the same epitope (e.g., a linear or a conformational epitope) that is bound by an antibody as described herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized VEGF is incubated in a solution comprising a first labeled antibody that binds to VEGF and a second unlabeled antibody that is being tested for its ability to compete with the first antibody for binding to VEGF. The second antibody may be present in a hybridoma supernatant. As a control, immobilized VEGF is incubated in a solution comprising the first labeled antibody but not the second unlabeled antibody. After incubation under conditions permissive for binding of the first antibody to VEGF, excess unbound antibody is removed, and the amount of label associated with immobilized VEGF is measured. If the amount of label associated with immobilized VEGF is substantially reduced in the test sample relative to the control sample, then that indicates that the second antibody is competing with the first antibody for binding to VEGF. Similar assays may be performed for other antigens. See Harlow and Lane (1988) Antibodies: A Laboratory Manual ch.14 (Cold Spring Harbor Laboratory, Cold Spring Harbor, N.Y.).

(b) Activity Assays

In one aspect, assays are provided for identifying antibodies (e.g., anti-VEGF antibodies), or antibody conjugates thereof, having biological activity. Biological activity may include, for example, binding to an antigen (e.g., VEGF (e.g., VEGF in the blood stream)), or a peptide fragment thereof, either in vivo, in vitro, or ex vivo. In certain embodiments, biological activity may include blocking or neutralizing an antigen. For example, in certain embodiments, biological activity may include blocking or neutralizing VEGF, or preventing VEGF from binding to a ligand, for example, a receptor such as KDR or Flt-1. Antibodies, or antibody conjugates thereof, having such biological activity in vivo and/or in vitro are also provided. In certain embodiments, an antibody of the invention, or an antibody conjugate thereof, is tested for such biological activity.

(c) Stability Assays

In one aspect, assays are provided for determining the stability (e.g., thermostability) of an antibody (e.g., an anti-VEGF antibody), or an antibody conjugate thereof. For example, the stability of an antibody, or an antibody conjugate thereof, may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The stability of an antibody, or an antibody conjugate thereof, may be determined as described herein, for example, using DSF as described, for example, in Examples 1 and 2 of International Patent Application No. PCT/US2016/053454. In some instances, the stability of an antibody conjugate can be determined by size exclusion chromatography in-line with refractive index and multi-angle light scattering detectors (SEC-RI-MALS).

Therapeutic Methods and Compositions

Any of the antibodies (e.g., anti-VEGF antibodies) or antibody conjugates thereof (e.g., cross-linked HA hydrogel conjugates) provided herein may be used in therapeutic methods.

In one aspect, an anti-VEGF antibody for use as a medicament is provided. In another aspect, an antibody conjugate (e.g., a cross-linked HA hydrogel conjugate) for use as a medicament is provided. In further aspects, the invention provides an anti-VEGF antibody for use in treating a disorder associated with pathological angiogenesis. In another aspect, the invention provides an antibody conjugate (e.g., a cross-linked HA hydrogel conjugate) for use in treating a disorder associated with pathological angiogenesis. In some embodiments, the disorder associated with pathological angiogenesis is an ocular disorder or a cell proliferative disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In another aspect, an anti-VEGF antibody for use in treating a disorder associated with undesirable vascular permeability is provided. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases.

In another aspect, an anti-VEGF antibody for use in a method of treatment is provided. In another aspect, an antibody conjugate (e.g., a cross-linked HA hydrogel conjugate) for use in a method of treatment is provided. In certain instances, the invention provides an anti-VEGF antibody (e.g., an anti-VEGF antibody) for use in a method of treating a subject having a disorder associated with pathological angiogenesis comprising administering to the individual an effective amount of the anti-VEGF antibody. The invention also provides an antibody conjugate (e.g., a cross-linked HA hydrogel conjugate) for use in a method of treating a subject having a disorder associated with pathological angiogenesis comprising administering to the individual an effective amount of the antibody conjugate. In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g, allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma.

In other instances, the invention provides an anti-VEGF antibody for use in a method of treating an individual having a disorder associated with undesirable vascular permeability. In other instances, the invention provides an antibody conjugate (e.g., a cross-linked HA hydrogel conjugate) for use in a method of treating an individual having a disorder associated with undesirable vascular permeability. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. Any of the preceding uses may further include administering to the individual an effective amount of at least one additional therapeutic agent, for example, as described below.

In some instances, the invention provides an anti-VEGF for use in reducing or inhibiting angiogenesis in a subject. In another aspect, an antibody conjugate (e.g., a cross-linked HA hydrogel conjugate) for use in reducing or inhibiting angiogenesis in a subject is provided. In certain embodiments, the invention provides an anti-VEGF antibody for use in a method of reducing or inhibiting angiogenesis in a subject comprising administering to the individual an effective of the anti-VEGF antibody to reduce or inhibit angiogenesis. The invention also provides an antibody conjugate (e.g., a cross-linked HA hydrogel conjugate) for use in a method of reducing or inhibiting angiogenesis in a subject comprising administering to the individual an effective amount of the antibody conjugate. In other instances, the invention provides an anti-VEGF antibody or an antibody conjugate (e.g., a cross-linked HA hydrogel conjugate) thereof for use in reducing or inhibiting vascular permeability in a subject. In certain embodiments, the invention provides an anti-VEGF antibody or an antibody conjugate (e.g., a cross-linked HA hydrogel conjugate) thereof for use in a reducing or inhibiting vascular permeability in a subject comprising administering to the individual an effective of the anti-VEGF antibody or antibody conjugate to reduce or inhibit vascular permeability. A "subject" according to any of the above uses may be a human.

The invention provides for the use of an anti-VEGF antibody in the manufacture or preparation of a medicament. The invention also provides for the use of an antibody conjugate (e.g., a cross-linked HA hydrogel conjugate) in the manufacture or preparation of a medicament. For example, in one instance, the medicament is for treatment of a disorder associated with pathological angiogenesis. In a further instance, the medicament is for use in a method of treating a disorder associated with pathological angiogenesis comprising administering to a subject having a disorder associated with pathological angiogenesis an effective amount of the medicament. In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g, allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In a further instance, the medicament is for reducing or inhibiting angiogenesis in a subject. In a further instance, the medicament is for use in a method of reducing or inhibiting angiogenesis in a subject comprising administering to the subject an amount effective of the medicament to reduce or inhibit angiogenesis. In any of the preceding uses of medicaments, the method may include administering to the individual an effective amount of at least one additional therapeutic agent, e.g., as described below.

In another instance, the medicament is for treatment of a disorder associated with undesirable vascular permeability. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. In a further instance, the medicament is for use in a method of treating a disorder associated with undesirable vascular permeability comprising administering to a subject having a associated with undesirable vascular permeability an effective amount of the medicament. In another instance, the medicament is for reducing or inhibiting vascular permeability in a subject. In a further instance, the medicament is for use in a method of reducing or inhibiting vascular permeability in a subject comprising administering to the subject an amount effective of the medicament to reduce or inhibit angiogenesis. In any of the preceding uses of medicaments, the method may include administering to the subject an effective amount of at least one additional therapeutic agent, e.g., as described below. A "subject" according to any of the above uses may be a human.

The invention provides a method for treating a disorder associated with pathological angiogenesis. In one embodiment, the method comprises administering to an individual having a disorder associated with pathological angiogenesis an effective amount of an anti-VEGF antibody In another example, the method comprises administering to an individual having a disorder associated with pathological angiogenesis an effective amount of an antibody conjugate (e.g., a cross-linked HA hydrogel conjugate). In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g, allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In further instances, the method further comprises administering to the individual an effective amount of at least one additional therapeutic agent, as described below. A "subject" according to any of the above methods may be a human.

The invention provides a method for treating a disorder associated with undesirable vascular permeability. In one embodiment, the method comprises administering to an individual having a disorder associated with undesirable vascular permeability an effective amount of an anti-VEGF antibody. In another embodiment, the method comprises administering to an individual having a disorder associated with undesirable vascular permeability an effective amount of an antibody conjugate (e.g., a cross-linked HA hydrogel conjugate). In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. In further instances, the method further comprises administering to the individual an effective amount of at least one additional therapeutic agent, as described below. A "subject" according to any of the above methods may be a human.

It is contemplated that the antibody or antibody conjugate (e.g., cross-linked HA hydrogel conjugate) of the present invention may be used to treat a mammal. In one embodiment, the antibody or antibody conjugate (e.g., cross-linked HA hydrogel conjugate) is administered to a nonhuman mammal for the purposes of obtaining preclinical data, for example Exemplary nonhuman mammals to be treated include nonhuman primates, dogs, cats, rodents (e.g., mice and rats) and other mammals in which preclinical studies are performed. Such mammals may be established animal models for a disease to be treated with the antibody or may be used to study toxicity or pharmacokinetics of the antibody of interest. In each of these embodiments, dose escalation studies may be performed in the mammal. The antibody or antibody conjugate (e.g., cross-linked HA hydrogel conjugate) may be administered to a host rodent in a solid tumor model, for example The antibody or antibody conjugate may be administered to a host (e.g., a rodent, e.g., a rabbit) for ocular pharmacokinetic studies, for example, by intravitreal administration (e.g., intravitreal injection).

In a further aspect, the invention provides pharmaceutical formulations comprising any of the antibodies (e.g., anti-VEGF antibodies) or antibody conjugates (e.g., cross-linked HA hydrogel conjugates) provided herein, for example, for use in any of the above therapeutic methods. In one embodiment, a pharmaceutical formulation comprises any of the antibodies (e.g., anti-VEGF antibodies) or antibody conjugates (e.g., cross-linked HA hydrogel conjugates) provided herein and a pharmaceutically acceptable carrier. In another embodiment, a pharmaceutical formulation comprises any of the antibodies (e.g., anti-VEGF antibodies) or antibody conjugates (e.g., cross-linked HA hydrogel conjugates) provided herein and at least one additional therapeutic agent, for example, as described below. In certain embodiments, the pharmaceutical formulation comprises one or more additional compounds. In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC, COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

Antibodies (e.g., anti-VEGF antibodies) or antibody conjugates (e.g., cross-linked HA hydrogel conjugates) can be used either alone or in combination with other agents in a therapy. For instance, an antibody (e.g., anti-VEGF antibody) or antibody conjugate (e.g., cross-linked HA hydrogel conjugate) may be co-administered with at least one additional therapeutic agent. In certain embodiments, an additional therapeutic agent is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, a growth-inhibitory agent, or combinations thereof.

For example, in certain embodiments, any of the preceding methods further comprises administering one or more additional compounds. In certain embodiments, the antibody (e.g., anti-VEGF antibody) or antibody conjugate (e.g., a cross-linked HA hydrogel conjugate) is administered simultaneously with the additional compound(s). In certain embodiments, the antibody or antibody conjugate is administered before or after the additional compound(s). In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A 1; and TNFRSF10A. In certain embodiments, the additional compound is an antibody or antigen-binding fragment thereof. In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP). For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

In some instances, an antibody (e.g., a anti-VEGF antibody) or antibody conjugate (e.g., a cross-linked HA hydrogel conjugate) of the invention may be administered in combination with at least one additional therapeutic agent for treatment of an ocular disorder, for example, an ocular disorder described herein (e.g., AMD (e.g., wet AMD), DME, DR, or RVO). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-ylmethoxy)quinazoline (ZD 6474), 4-(4-fluoro-2-methylindo1-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P); MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin β3 function; angiostatin, and combinations thereof. These and other therapeutic agents that can be administered in combination with an antibody conjugate of the invention are described, for example, in U.S. Patent Application No. US 2014/0017244, which is incorporated herein by reference in its entirety.

Further examples of additional therapeutic agents that can be used in combination with an antibody (e.g., anti-VEGF antibody) or an antibody conjugate (e.g., a cross-linked HA hydrogel conjugate) of the invention for treatment of an ocular disorder (e.g., AMD, DME, DR, or RVO), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), Candy (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, Isis Pharmaceuticals), and combinations thereof.

An antibody (e.g., anti-VEGF antibody) or antibody conjugate (e.g., a cross-linked HA hydrogel onjugate) of the invention may be administered in combination with a therapy or surgical procedure for treatment of an ocular disorder (e.g., AMD, DME, DR, or RVO), including, for example, laser photocoagulation (e.g., panretinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, Cell Genesys, Inc.), acupuncture, and combinations thereof.

In some instances, an antibody (e.g., anti-VEGF antibody) or antibody conjugate (e.g., a cross-linked HA hydrogel conjugate) of the invention can be administered in combination with an anti-angiogenic agent for treatment of an ocular disorder (e.g., AMD, DME, DR, or RVO). Any suitable anti-angiogenic agent can be used in combination with an antibody (e.g., an anti-VEGF antibody) or an antibody conjugate of the invention, including, but not limited to, those listed by Carmeliet et al. Nature 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol), a small interfering RNAs which inhibits expression of VEGF or VEGFR, a VEGFR tyrosine kinase inhibitor (e. g., 4-(4-bromo-2-fluor° anilino)-6-methoxy-7-(1-methylp iperidin-4-ylmethoxy) quinazoline (ZD 6474), 4-(4-fluoro-2-methylindo1-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)), and combinations thereof. In some instances, the bispecific anti-VEGF antibody binds to a second biological molecule, including but not limited to IL-1β; IL-6; IL-6R; PDGF (e.g., PDGF-BB); angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or 5VEGFR); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof.

Other suitable anti-angiogenic agents that may be administered in combination with an antibody (e.g., anti-VEGF antibody) or an antibody conjugate (e.g., cross-linked HA hydrogel conjugate) of the invention for treatment of an ocular disorder (e.g., AMD, DME, DR, or RVO) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-la antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, an antibody (e.g., an anti-VEGF antibody) or an antibody conjugate (e.g., cross-linked HA hydrogel conjugate) of the invention can be administered in combination with an agent that has activity against neovascularization for treatment of an ocular disorder (e.g., AMD, DME, DR, or RVO), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFa antibody or antigen-binding fragment thereof (e.g., infliximab, adalimumab, certolizumab pegol, and golimumab) or a soluble receptor fusion protein (e.g., etanercept)), an anti-complement agent, a nonsteroidal antiinflammatory agent (NSAID), or combinations thereof.

In a still further example, in some instances, an antibody (e.g., anti-VEGF antibody) or an antibody conjugate (e.g., cross-linked HA hydrogel conjugate) of the invention can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with an antibody (e.g., an anti-VEGF antibody) or an antibody conjugate (e.g., a cross-linked HA hydrogel conjugate) of the invention for treatment of an ocular disorder (e.g., AMD, DME, DR, or RVO), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhibitor (e.g., ARC-1905; Opthotech) or an anti-05 antibody (e.g., LFG-316; Novartis), a properdin antagonist (e.g., an anti-properdin antibody, e.g., CLG-561; Alcon), or a complement factor D antagonist (e.g., an anti-complement factor D antibody, e g, lampalizumab; Roche)); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (Janssen), OpRegen (Cell Cure Neurosciences), or MA09-hRPE cell transplantation (Ocata Therapeutics); a tissue factor antagonist (e.g., hI-coni; Iconic Therapeutics); an alpha-adrenergic receptor agonist (e.g, brimonidine tartrate); a peptide vaccine (e.g., S-646240; Shionogi); an amyloid beta antagonist (e.g., an anti-beta amyloid monoclonal antibody, e.g., GSK-933776); an S1P antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody of the invention. In some instances, the ocular disorder is AMD (e.g., wet AMD).

Such combination therapies noted above encompass combined administration (where two or more therapeutic agents are included in the same or separate formulations), and separate administration, in which case, administration of the antibody or antibody conjugate of the invention can occur prior to, simultaneously, and/or following, administration of the additional therapeutic agent or agents. In one embodiment, administration of the antibody or antibody conjugate and administration of an additional therapeutic agent occur within about one, two, three, four, or five months, or within about one, two or three weeks, or within about one, two, three, four, five, or six days, of each other.

EXAMPLES

The following abbreviations may be used in the examples below and elsewhere herein.

| Abbreviation | Full expression and/or definition |
|---|---|
| CIEC | Cation-exchange chromatography |
| CV | Column volumes |
| BHT | 3,5-Di-tert-butyl-4-hydroxytoluol |

-continued

| Abbreviation | Full expression and/or definition |
|---|---|
| DBU | 1,8-Diazabicyclo[5.4.0]undec-7-ene |
| DCC | Dicyclohexylcarbodiimide |
| DCM | Dichloromethane |
| DIPEA | N,N-Diisopropylethylamine |
| DMAP | 4-(Dimethylamino)-pyridine |
| DTT | Dithiothreitol |
| EDC | 1-Ethyl-3-(3-dimethylaminopropyl)carbodiimide |
| Fab | Fragment antigen-binding |
| Fmoc-Ado-OH | Fmoc-8-amino-3,6-dioxaoctanoic acid |
| HA | Hyaluronic acid |
| HEPES | 4-(2-Hydroxyethyl)-1-piperazineethanesulfonic acid |
| HOBt | Hydroxybenzotriazole |
| HOSu | Hydroxysuccinimide |
| HPLC | High-performance liquid chromatography |
| IPC | In-process control |
| LCMS | Mass spectrometer coupled liquid chromatography |
| LPLC | Low pressure liquid chromatography |
| MES | 2-(N-Morpholino)ethanesulfonic acid |
| MS | Mass spectrometry |
| MTBE | Methyl tert-butyl ether |
| MTS | Methanethiosulfonyl |
| NHS | N-Hydroxysuccinimide |
| PFP | Pentafluorophenol |
| PTSA | para-toluene sulfonic acid |
| PyBOP | Benzotriazol-1-yl-oxytripyrrolidinophosphonium hexafluorophosphat |
| QC | Quality control |
| Rbz | Ranibizumab |
| RP-HPLC | Reverse phase high-performance liquid chromatography |
| RP-LPLC | Reverse phase low pressure liquid chromatography |
| SEC | Size exclusion chromatography |
| Su | Succinimide |
| TCEP | tris(2-Carboxyethyl)phosphine hydrochloride |
| TFA | Trifluoroacetic acid |
| TFF | Tangential flow filtration |
| TLC | Thin layer chromatography |
| $t_R$ | Retention time |
| TransCon | Transiently conjugated |
| TriMED | N,N,N'-trimethyl ethylenediamine |
| UPLC | Ultra-performance liquid chromatography |
| wt % | Weight percent |

Example 1A

Synthesis of Self-Immolative Protecting Group 4-(((perfluorophenoxy)carbonyloxy)methyliphenyl2-(dimethylamino)ethyhmethylicarbamate a3

Scheme 1A

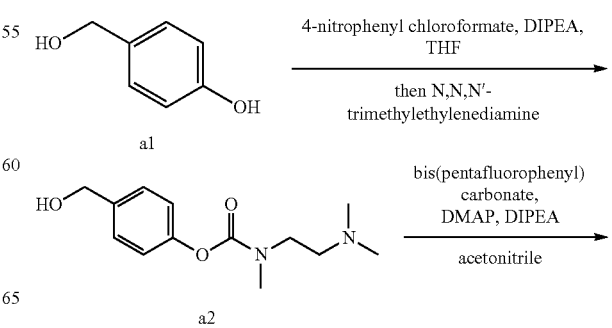

119

-continued

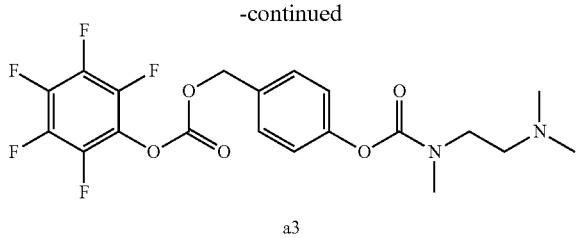

a3

The synthesis of 4-(((perfluorophenoxy)carbonyloxy)methyl)phenyl 2-(dimethylamino)ethyl(methyl)carbamate a3 is illustrated in Scheme 1A Step 1 Preparation of 4-(hydroxymethyl)phenyl 2-(dimethylamino)ethyl (methyl)carbamate a2

4-Hydroxybenzyl alcohol a1 (1.70 g; 13.69 mmol; 1.00 eq.) was dissolved in THF (20.5 ml) and DIPEA (4.8 ml; 27.39 mmol; 2.00 eq.) was added with stirring. 4-Nitrophenyl chloroformate (2.90 g; 14.38 mmol; 1.05 eq.) in THF (5 ml) was added dropwise over 25 min. The reaction was stirred for additional 20 minutes at room temperature. An IPC by LCMS confirmed formation of the desired intermediate. N,N,N'-trimethylethylenediamine (2.21 ml; 17.12 mmol; 1.25 eq.) was slowly added to the solution and the reaction mixture was stirred for additional 20 min. An IPC by LCMS confirmed full conversion of the carbonate. The reaction was cooled in an ice-bath, quenched with TFA (3.17 ml; 41.08 mmol; 3.00 eq.) and diluted with water. The pH should be below 2 as indicated by pH paper. The aqueous phase was washed with ethyl acetate (3×100 ml), after which the pH of the aqueous phase rose to ca. pH 4.5. The aqueous phase was lyophilized to yield an oily residue. The residue was co-evaporated with ethyl acetate (3×), dissolved in DCM and dried ($Na_2SO_4$). After filtration the solvent was evaporated and the oily residue was dried under high vacuum (2 h). A QC by LCMS revealed a purity of 93%. The resulting crude 4-(hydroxymethyl)phenyl 2-(dimethylamino) ethyl(methyl)carbamate a2 was used in the next step without purification.

Step 2 Preparation of 4-(((perfluorophenoxy)carbonyloxy)methyl)phenyl 2-(dimethylamino) ethyl(methyl)carbamate a3

The crude 4-(hydroxymethyl)phenyl 2-(dimethylamino) ethyl(methyl)carbamate a2 from step 1 (11.76 g; max. 13.69 mmol; 1.00 eq.; max. purity of 40 wt %) was dissolved in acetonitrile (24 ml) and the solution was cooled in an ice-bath. Bis(pentafluorophenyl) carbonate (10.15 g; 25.75 mmol; 1.88 eq.), DMAP (315 mg; 2.58 mmol; 0.19 eq.) and DIPEA (9.0 ml; 51.53 mmol; 3.76 eq.) were added with stirring. The solution turned from orange to green, then grey. The reaction mixture was stirred for 15 minutes. Formation of product was confirmed by LCMS. The reaction mixture was cooled to −15° C. and quenched with a mixture of water with 0.1% TFA (12.38 ml) and neat TFA (3.9 ml; 51.48 mmol; 3.76 eq.). The yellow solution was purified by RP-LPLC in 4 runs. The pure fractions were combined, frozen and lyophilized to yield 4-(((perfluorophenoxy)carbonyloxy)methyl)phenyl 2-(dimethylamino) ethyl(methyl) carbamate a3 as yellow oil, 4.73 g TFA salt (8.21 mmol, 60% over 2 steps).

120

Example 1B

Synthesis of Protected Linker b5

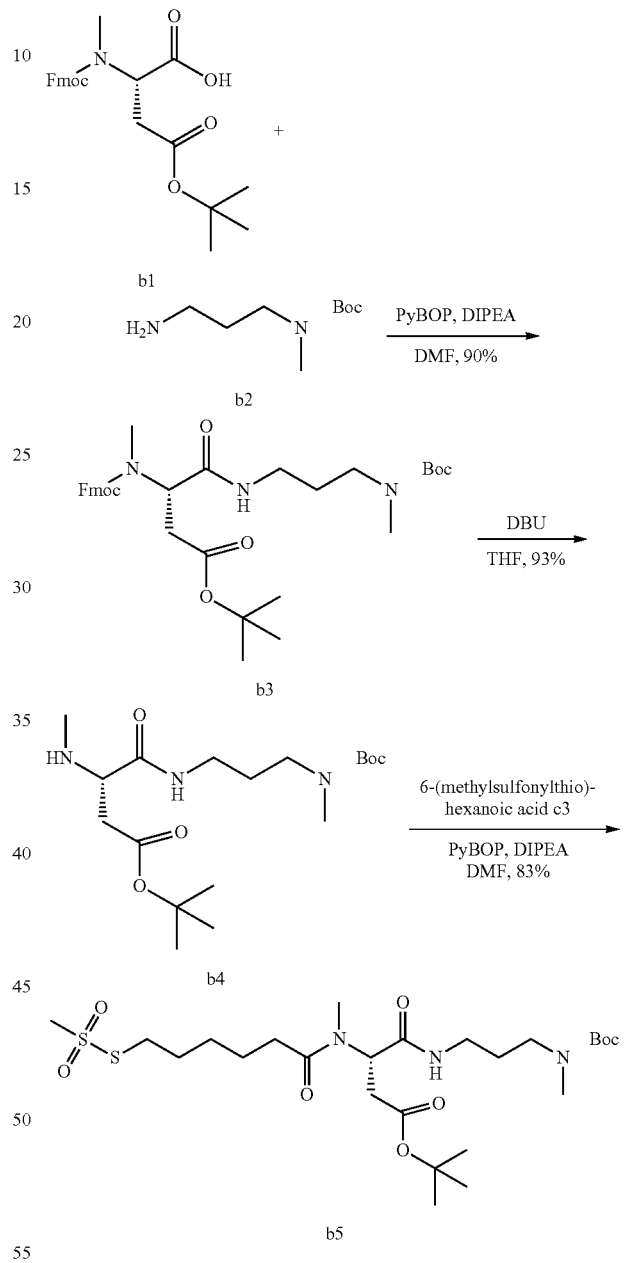

The synthesis of linker b5 is shown in scheme 1B

Step 1 Preparation of Amide Compound b3

Fmoc-N-Me-Asp(tBu)-OH b1 (6.96 g; 16.36 mmol; 1.00 eq.) was dissolved in DMF (139 ml). PyBOP (12.77 g; 24.54 mmol; 1.50 eq.) and DIPEA (14.25 ml; 81.79 mmol; 5.00 eq.) were added and stirred until dissolved completely. N-Boc-N-methyl-1,3-diaminopropane hydrochloride b2 (4.04 g; 17.99 mmol; 1.10 eq.) was added and the reaction mixture was stirred at room temperature for 15 min. Complete conversion to the product was observed by LCMS. The reaction mixture was diluted with 400 ml of dichloromethane and was washed three times with 400 ml of 0.1 N HCl. The organic layer was washed three times with 400 ml of saturated NaHCO$_3$ solution and once with 200 ml of brine. The organic layer was dried over MgSO$_4$, filtered and concentrated. The crude material was dissolved in 14 ml of dichloromethane and purified by normal phase flash chromatography. The product containing fractions were pooled and the solvent was evaporated. The final material was dried under high vacuum to yield amide compound b3 as a white foam. Yield: 8.81 g (14.79 mmol, 90%).

Step 2 Preparation of Amide Compound b4

Amide compound b3 (8.81 g; 14.79 mmol; 1.00 eq.) was dissolved in THF (130 ml). DBU (2.56 ml; 17.15 mmol; 1.16 eq.) was added and the mixture was stirred at room temperature for 5 minutes. An LCMS chromatogram showed complete conversion of the starting material Additionally, a TLC was prepared (ethyl acetate/methanol 9:1, KMnO$_4$ stain), R$_f$(Pdt)=0.48). The solvent of the crude reaction mixture was evaporated. The residue was dissolved in ethyl acetate to reach a final volume of 20 ml and the solution was purified by flash chromatography. The product containing fractions were pooled and the solvent was evaporated. The final material was dried under high vacuum overnight to yield amide compound b4 as yellowish oil. Yield: 5.13 g (13.74 mmol, 87% yield, 94% purity at 215 nm)

Step 3 Preparation of Linker Compound b5

DIPEA (7.19 ml; 41.21 mmol; 3.00 eq.) was added to a solution of carboxylic acid c3 from example 1E (3.42 g; 15.11 mmol; 1.10 eq.) and PyBOP (7.86 g; 15.11 mmol; 1.10 eq.) in dichloromethane (35 ml), whereupon the mixture warmed significantly and turned from yellowish to dark yellow. The mixture was stirred at room temperature for 5 minutes to pre-activate the acid. To the activated acid solution a freshly prepared solution of amide compound b4 (5.13 g; 13.74 mmol; 1.00 eq.) in dichloromethane (35 ml) was added all at once, whereupon the mixture turned light brown. The coupling solution was stirred at room temperature for 100 min. An IPC by LCMS showed almost complete conversion of the starting material. The reaction mixture was diluted with 500 ml of ethyl acetate and was washed with 0.2 N HCl (4×300 ml), brine (1×100 ml), sat. NaHCO$_3$ (50, 25, 160 ml), 5% citric acid (1×100 ml) and brine (1×100 ml). The organic layer was dried over Na$_2$SO$_4$, filtered and concentrated. The residue was dried under high vacuum over the weekend (13.59 g crude material). The residue was dissolved in ethyl acetate to reach a final volume of about 22 ml. The crude material was purified by flash chromatography. The product containing fractions (TLC: ethyl acetate, KMnO$_4$ stain, R$_f$(Pdt)=0.54) were pooled and the solvent was evaporated to yield a sticky, brown, gum-like residue. The final material was dried under high vacuum overnight to yield linker compound b5 as a foam. Yield: 6.61 g (11.36 mmol, 83% yield, 96% purity).

Example 1C

Synthesis of linker (S)-4-(3-(((44(2-fdimethyl-amino)ethyl)(methyl)carbamoyloxy) benzyloxy) carbonyl)(methypamino)propylamino)-3-(N-methyl-6-(methylsulfonylthio)hexanamido)-4-oxobutanoic acid b7

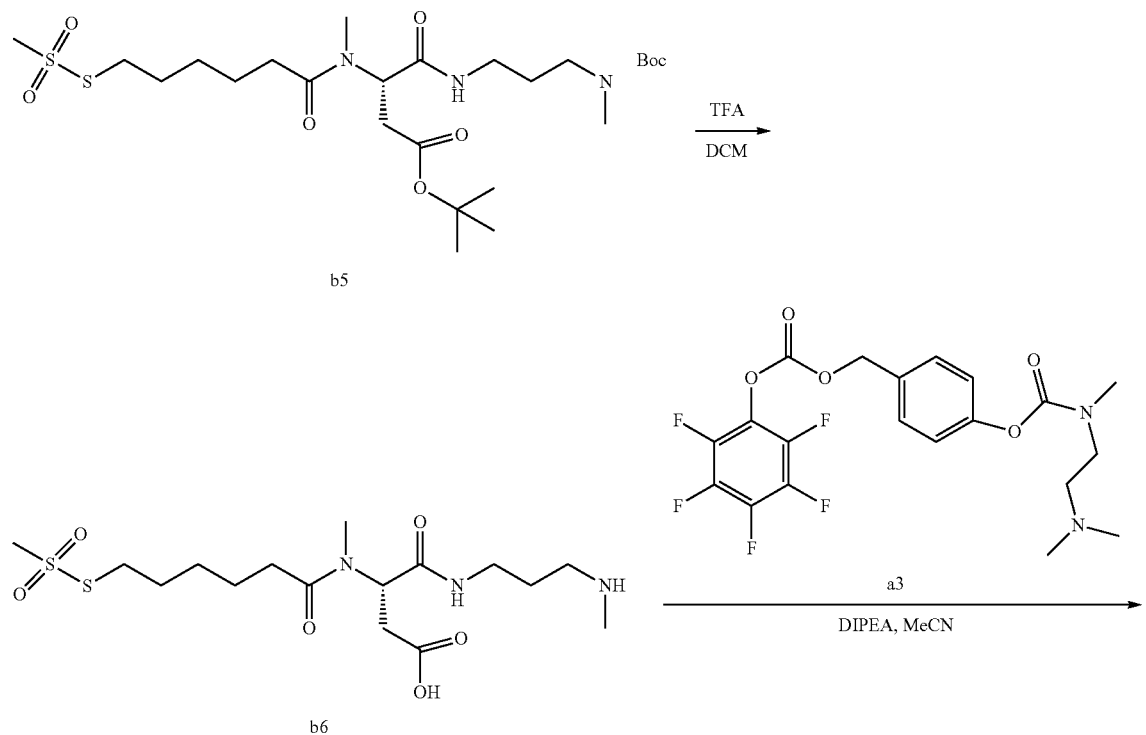

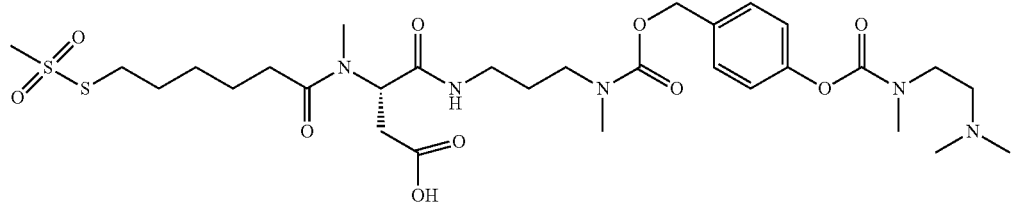

b7

The synthesis of (S)-4-(3-(((4-((2-(dimethylamino)ethyl)(methyl)carbamoyloxy)benzyloxy)carbonyl) (methyl)amino)propylamino)-3-(N-methyl-6-(methylsulfonylthio)hexanamido)-4-oxobutanoic acid b7 is illustrated in Scheme 1C.

Step 1 Preparation of (S)-3-(N-methyl-6-(methylsulfonylthio)hexanamido)-4-(3-(methylamino)propylamino)-4-oxobutanoic acid b6

Amide compound b5 (3.40 g; 5.84 mmol; 1.00 eq.) was dissolved in dichloromethane (19 ml) and TFA (19 ml) was added. The reaction mixture was stirred for 75 minutes at room temperature in an open flask. An IPC by LCMS showed good conversion to the product. Removal of volatiles was performed in a controlled manner (rotary evaporator at 25° C. and 12 mbar, then high vacuum at room temperature for 60 min). The resulting crude (S)-4-(3-(((4-((2-(dimethylamino)ethyl)(methyl)carbamoyloxy) benzyloxy)carbonyl)(methypamino)propylamino)-3-(N-methyl-6-(methylsulfonylthio)hexanamido-4-oxobutanoic acid b6 was immediately used in the next step without further purification.

Step 2 Preparation of (S)-4-(3-(((4((2-(dimethylamino)ethyl)(methypcarbamoyloxy) benzyloxy)carbonyl)(methybamino)propylamino)-3-(N-methyl-6-(methylsulfonylthio)hexanamido)-4-oxobutanoic acid b7

A solution of 4-(((perfluorophenoxy)carbonyloxy)methyl)phenyl 2-(dimethylamino) ethyl(methyl)carbamate a3 from Example 1 (4.38 g; 7.60 mmol; 1.30 eq.) in acetonitrile (35.00 ml) was cooled to 0° C. in an ice-bath. DIPEA (10.19 ml; 58.44 mmol; 10.00 eq.) was added and the mixture was stirred at this temperature for 1 minute before a solution of crude compound b6 in acetonitrile (35.00 ml) was added dropwise within 10 min. After complete addition, the mixture was stirred at 0° C. for additional 5 minutes, then the reaction mixture was analyzed by. Full conversion of the zwitterion b6 was observed. The reaction was quenched by addition of TFA (4.00 ml; 51.92 mmol; 8.88 eq.) at 0° C. All volatiles were removed and the residue was dried at <10 mbar and 40° C. for 10 minutes on the rotary evaporator. The crude residue was dissolved in a mixture of 6 ml H₂O/MeCN/TFA 1:1:0.002 and 12 ml 0.1% TFA. The light brown solution was purified by RP-flash chromatography. The solution was kept on ice until injection. Product containing fractions were combined, frozen and lyophilized to give (S)-4-(3-(((4-((2-(dimethylamino)ethyl)(methypcarbamoyloxy)benzyloxy)carbonyl)(methyl)amino)propylamino)-3-(N-methyl-6-(methylsulfonylthio)hexanamido)-4-oxobutanoic acid b7. Yield: 3.25 g as TFA salt (68% yield).

Example 1D

Synthesis of NHS-activated linker (S)-2,5-dioxopyrrolidin-1-yl 4-(3-(((4-((2-(dimethylamino)ethyl)(methyl)carbamoyloxy)benzyloxy)carbonyl) (methypamino)propylamino)-3-(N-methyl-6-(methylsulfonylthio)hexanamido)-4-oxobutanoate b8

Scheme 1D

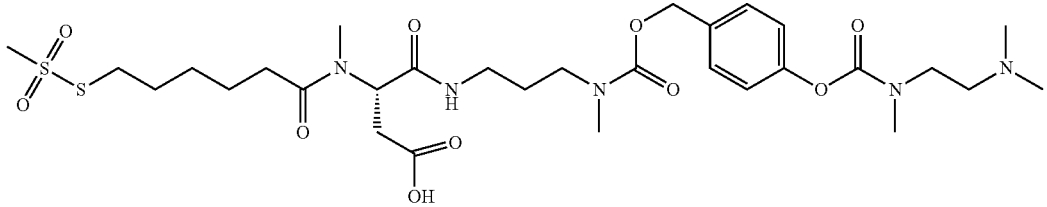

b7

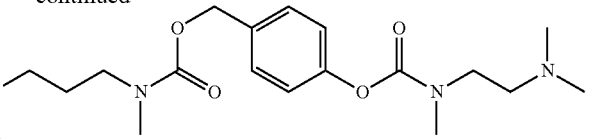
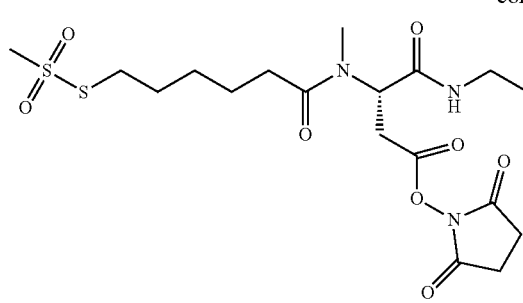

b8

Preparation of (S)-2,5-dioxopyrrolidin-1-yl 4-(3-(((4-((2-(dimethylamino)ethyl)(methyl) carbamoyloxy)benzyloxy) carbonyl)(methypamino)propylamino)-3-(N-methyl-6-(methylsulfonylthio)hexanamido)-4-oxobutanoate b8 is shown in Scheme 1D Linker b7 from Example 1C (2.02 g; 2.47 mmol; 1.00 eq.) was dissolved in dichloromethane (20 ml). HOSu (852.72 mg; 7.41 mmol; 3.00 eq.) and EDC (1.42 g; 7.41 mmol; 3.00 eq.) were added and the mixture was stirred at room temperature under a nitrogen atmosphere. Upon dissolution of the added reagents, the mixture turned slightly yellow. After 1 h an IPC by LCMS showed good conversion to the product. After 75 min the reaction mixture was diluted with DCM (75 ml) and washed once with 75 ml of acidic brine (250 ml brine were mixed with 2.5 ml 1 M HCl and the resulting solution was saturated with additional NaCl). The aqueous layer (pH ca. 6.5) was extracted with 50 ml of DCM. The combined organic phases were dried over $Na_2SO_4$ and filtrated. After addition of TFA (190 µL; 2.47 mmol; 1.00 eq.) the volatiles were evaporated. The oily residue was dried under high vacuum for 30 minutes to yield crude (S)-2,5-dioxopyrrolidin-1-yl 4-(3-(((4-((2-(dimethylamino)ethyl)(methyl) carbamoyloxy)benzyloxy)carbonyl) (methypamino)propylamino)-3-(N-methyl-6-(methylsulfonylthio)hexanamido)-4-oxobutanoate b8 (about 2.4 g) as a white foam. The crude product was dissolved in 5 ml of anhydrous acetonitrile (total volume ~6 ml) and purified by RP-LPLC. Eluents for the chromatography were cooled, then frozen and lyophylized. The lyophilized, dry material was combined with anhydrous acetonitrile (circa 20 ml in total). The solvent was removed (rotary evaporator, 40° C.) and dried under high vacuum to yield 2.05 g (91% yield) of (S)-2,5-dioxopyrrolidin-1-yl 4-(3-(((4-((2-(dimethylamino) ethyl)(methyl) carbamoyloxy)benzyloxy)carbonyl)(methyl) amino)propylamino)-3-(N-methyl-6-(methylsulfonylthio) hexanamido)-4-oxobutanoate b8 as colorless foam. The material was dissolved in 22.37 ml of anhydrous DMSO. The clear, colorless solution was sterile filtered (sterile PTFE syringe filters, Millipore Millex-LG, 25 mm, 0.2 µm) to yield about 23.5 ml of a clear, colorless solution. The material was stored in aliquots under argon at −80° C. By LCMS analysis a NHS activity of 79% was determined.

Example 1E

Synthesis of 6-(methylsulfonylthio)hexanoic acid c3

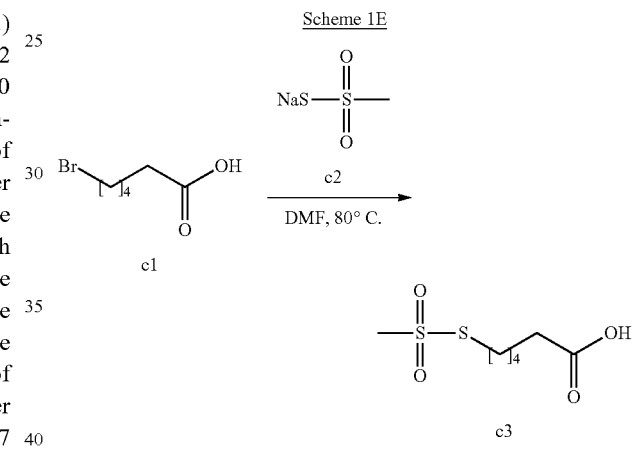

Preparation of 6-(methylsulfonylthio)hexanoic acid c3 is shown in Scheme 1E.

6-bromohexanoic acid (5.89 g; 30.19 mmol; 1.00 eq.) and sodium methanethiosulfonate (4.05 g; 30.19 mmol; 1.00 eq.) were dissolved in N,N-dimethylformamide, anhydrous (47.10 ml). The reaction mixture was stirred at 80° C. for 3 hours and then left to cool down to room temperature. LCMS analysis confirmed formation of the product c3. The reaction mixture was diluted with 116 ml of water and was washed three times with 233 ml of diethyl ether. The organic phase was washed with brine (350 ml), dried over $MgSO_4$, filtered and concentrated under reduced pressure to a volume of 40 ml. The resulting solution was precipitated in 2×1000 ml of cold n-heptane at −18° C. overnight. The supernatant was decanted and the precipitate was dissolved in 80 ml of diethylether (40° C.). The resulting solution was precipitated in 2×1000 ml of cold n-heptane at −18° C. for 3 hours. The precipitate was filtered off and the white solid was dried under high vacuum overnight to give 6-(methylsulfonylthio) hexanoic acid c3. Yield: 5.72 g; 84%.

Example 1F

Synthesis of 1-(2,5-dioxopyrrolidin-1-yl) 9-(2-(2-(3-(pyridin-2-yldisulfanyl)propanamido)ethoxy)ethyl) nonanedioate d9

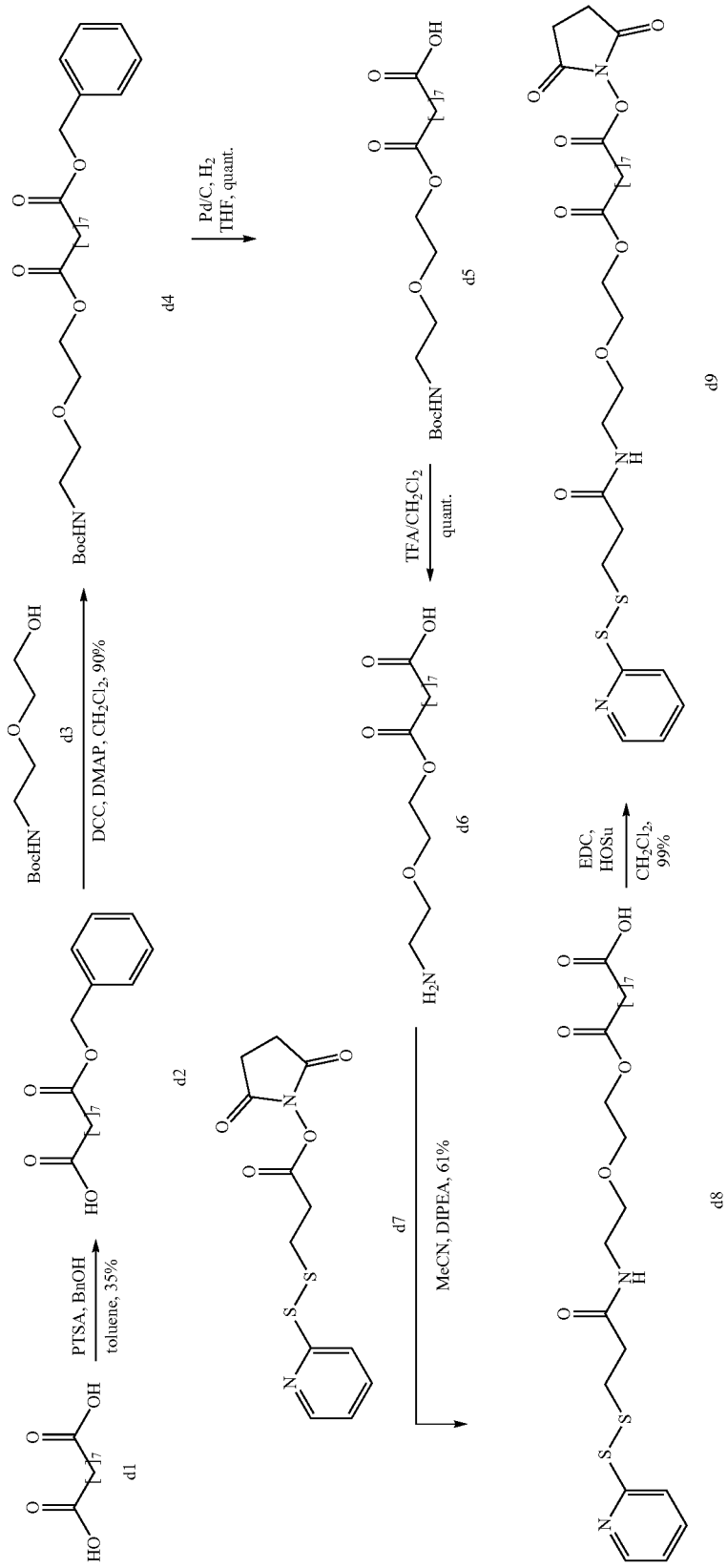

Scheme 1F

Preparation of 1-(2,5-dioxopyrrolidin-1-yl) 9-(2-(2-(3-(pyridin-2-yldisulfanyl)propanamido)ethoxy)ethyl) nonanedioate d9 is shown in Scheme 1F.

Step 1 Synthesis of 9-(benzyloxy)-9-oxononanoic acid d2

A mixture of azelaic acid dl (103.00 g; 547.23 mmol; 1.10 eq.), benzyl alcohol (51.73 ml; 497.48 mmol; 1.00 eq.) and p-toluenesulfonic acid monohydrate (1.99 g; 10.45 mmol; 0.02 eq.) in toluene (561.82 ml) was refluxed for 5 h in a Dean-Stark apparatus. The reaction mixture was then left to cool down to room temperature and stored for 1 h at this temperature. Then, the solid was filtered off and washed with 50 ml of toluene. The residue was treated with approx. 800 ml of a 0.4 M NaOH solution and the pH was adjusted to pH=9 using approx. 30 ml of 4 M NaOH. The aqueous phase was separated, to the organic phase 100 ml of water, and 80 ml 0.4 M NaOH were added, adjusting the pH to 9. The combined aqueous phases were acidified with 50 ml of 1 M sulfuric acid to pH=5 and extracted twice with 200 ml of MTBE. The combined organic phases were washed with 200 ml of brine, dried over $MgSO_4$ and the solvent was evaporated in vacuo. The crude product (62 g) was dissolved in 40 ml of heptane and 20 ml of THF (total volume 120 ml) and purified in two runs by automated flash chromatography. The eluent was evaporated and the residue was obtained as an oil (55.00 g; 39.72%). The residue was dissolved in 80 ml of MTBE and 2000 ml of heptane heated to 30° C. were added. For crystallization, the solution was stored at −20° C. overnight. The product was collected by filtration through a glass filter (Por. 3) and washed with 500 ml of heptane. The white crystals were dried for 4 h at <1 mbar to give 9-(benzyloxy)-9-oxononanoic acid d2. Yield:48.02 g; 35%.

Step 2 Synthesis of Boc-protected 1-(2-(2-aminoethoxy)ethyl) 9-benzyl nonanedioate d4

DCC (3.32 g; 16.08 mmol; 1.10 eq.) was added to a solution of Boc-2-(2-aminoethoxy)ethanol d3 (3.00 g; 14.62 mmol; 1.00 eq.), compound d2 (4.07 g; 14.62 mmol; 1.00 eq.) and DMAP (446.41 mg; 3.65 mmol; 0.25 eq.) in DCM (50.00 ml). The forming suspension was stirred at room temperature overnight. The white suspension was filtrated through a 20 ml-syringe frit and the filter cake was washed with about 50 ml of DCM. Product was detected by LCMS. All volatiles were removed. And the residue was dissolved in DCM (total volume 20 ml). The resulting slightly turbid suspension was purified by flash chromatography. Product containing fractions were combined and all volatiles were evaporated to yield Boc-protected 1-(2-(2-aminoethoxy)ethyl) 9-benzyl nonanedioate d4 as colorless oil. Yield: 6.11 g; 90%.

Step 3 Synthesis of Boc protected 9-(2-(2-aminoethoxy)ethoxy)-9-oxononanoic acid d5

10% Pd/C (348.58 mg; 0.33 mmol; 0.03 eq.) was added to a solution of Boc-protected 1-(2-(2-aminoethoxy)ethyl) 9-benzyl nonanedioate d4 (6.10 g; 13.10 mmol; 1.00 eq.) in THF (75.00 ml) and the air layer in the flask was exchanged against nitrogen. Then, the flask was placed in a 50° C. water-bath and a stream of hydrogen was passed through the black suspension using a balloon and a 20G cannula. After 5 minutes, the hydrogen stream was stopped and the mixture was vigorously stirred under hydrogen atmosphere at 50° C. until completion of the deprotection reaction. The resulting suspension was filtrated through a pad of Celite. The filter cake was washed with additional EtOAc (25 ml). The volatiles of the combined filtrates were evaporated and the crude material was dissolved in EtOAc (30 ml). The solution was filtrated through a 0.22 μm-RC syringe filter and volatiles were removed to yield Boc protected 9-(2-(2-aminoethoxy)ethoxy)-9-oxononanoic acid d5 as a slightly yellow oil. Yield: 5.09 g, quantitative.

Step 4 Synthesis of 9-(2-(2-aminoethoxy)ethoxy)-9-oxononanoic acid d6

TFA (5.00 ml; 64.90 mmol; 4.79 eq.) was added to a solution of Boc protected 9-(2-(2-aminoethoxy)ethoxy)-9-oxononanoic acid d5 (5.09 g; 13.55 mmol; 1.00 eq.) in dichloromethane (10.00 ml). After 40 minutes, an additional aliquot of TFA (5.00 ml; 64.90 mmol; 4.79 eq.) was added to the mixture and a stream of nitrogen was passed through the reaction mixture. An LCMS after 70 min revealed complete conversion of the starting material. Volatiles were removed and the brown, oily residue was diluted with diethylether (50 ml), whereupon a two-phase system was formed. The emulsion was again freed from all volatiles on the rotavap and the brown, oily residue was dried in high vacuum overnight. Toluene (30 ml) was added to the residue and the mixture was again freed from all volatiles on the rotavap (60° C. water bath). The material was dried on the rotavap at <9 mbar and 60° C. water bath temperature to yield 9-(2-(2-aminoethoxy)ethoxy)-9-oxononanoic acid d6 as a brown oil. Yield: 6.04 g; 97%.

Step 5 Synthesis of 9-oxo-9-(2-(2-(3-(pyridin-2-yldisulfanyl)propanamido)ethoxy)ethoxy)nonanoic acid d8

DIPEA (951.90 μL; 5.46 mmol; 5.00 eq.) was added to a solution of 9-(2-(2-aminoethoxy)ethoxy)-9-oxononanoic acid d6 (500.00 mg; 1.09 mmol; 1.00 eq.) and succinimidyl 3-[[(2-pyridyl)thio]thio]propionate d7 (375.05 mg; 1.20 mmol; 1.10 eq.) in acetonitrile (5.00 ml). The reaction mixture was stirred at room temperature for 45 min. The reaction was quenched by addition of acetic acid (1.00 ml; 17.48 mmol; 16.02 eq.). The mixture was diluted with 6.5 ml of acetonitrile and 14.5 ml of water and the resulting solution was purified by preparative HPLC. Product containing fractions were combined, frozen in liquid nitrogen and lyophilized overnight. The product batches were combined with DCM. Volatiles were removed and the oily residue was dried under high vacuum to yield 9-oxo-9-(2-(2-(3-(pyridin-2-yldisulfanyl)propanamido)ethoxy) ethoxy) nonanoic acid d8 as slightly yellow oil; 392.00 mg; 61%.

Step 6 synthesis of 1-(2,5-dioxopyrrolidin-1-yl) 9-(2-(2-(3-(pyridin-2-yldisulfanyl) propanamido) ethoxy)ethyl) nonanedioate d9

To a solution of 9-oxo-9-(2-(2-(3-(pyridin-2-yldisulfanyl) propanamido)ethoxy) ethoxy)nonanoic acid d8 (392.00 mg; 0.67 mmol; 1.00 eq.) in dichloromethane (5.00 ml) HOSu (153.81 mg; 1.34 mmol; 2.00 eq.) and EDC*HCl (256.19 mg; 1.34 mmol; 2.00 eq.) were added successively. The suspension was stirred at room temperature, whereupon the solid contents slowly dissolved over time and a light yellow clear solution was formed. After 80 min additional HOSu (50.00 mg; 0.43 mmol; 0.65 eq.) and EDC*HCl (50.00 mg; 0.26 mmol; 0.39 eq.) were added. After 120 min analysis by LCMS revealed completion of the reaction. Volatiles were removed and the residue was dissolved in acetonitrile (5 ml). Water (5 ml) and H$_2$O/MeCN/TFA 1:1:0.002 (4 ml) were added. Acetonitrile was added to the turbid emulsion until a clear solution was obtained. The resulting solution was purified by preparative HPLC. All product containing fractions were kept on ice until they were combined, frozen and lyophilized. The product batches were combined with dichloromethane and all volatiles were removed. The product was dried under high vacuum to yield 1-(2,5-dioxopyrrolidin-1-yl)9-(2-(2-(3-(pyridin-2-yldisulfanyl)propanamido)ethoxy)ethyl) nonanedioate d9 as a colorless oil; 455.00 mg; quantitative yield.

Example 1G

Synthesis of Purification TAG N,N'-((10S,22S)-10-(2-(dimethylamino)acetamido)-16-(4-mercaptonicotinoyl)-2-methyl-4,11,21-trioxo-2,5,12,16,20-pentaazahexacosane-22,26-diyl)bis(2-(dimethylamino)acetamide) e8

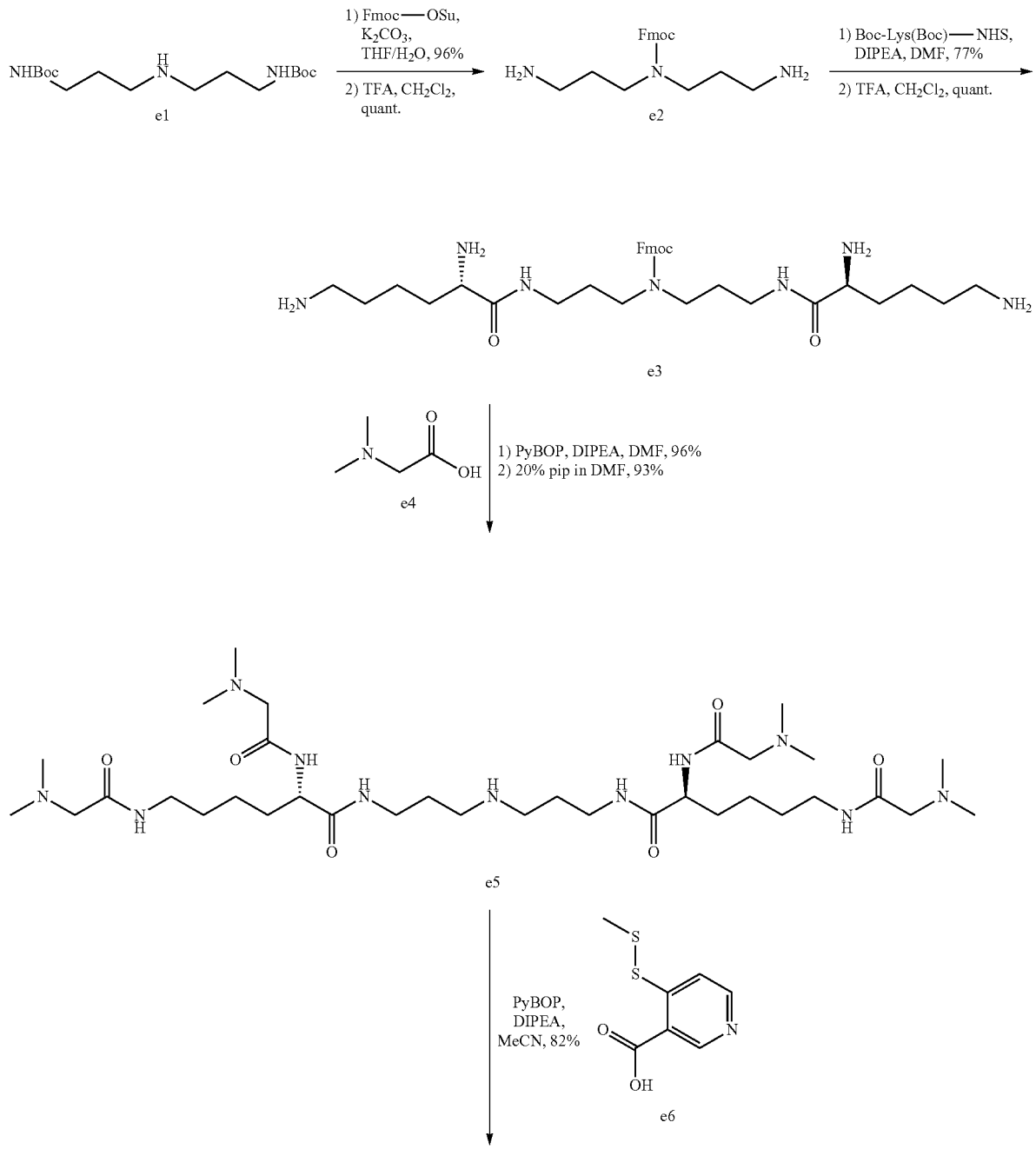

-continued

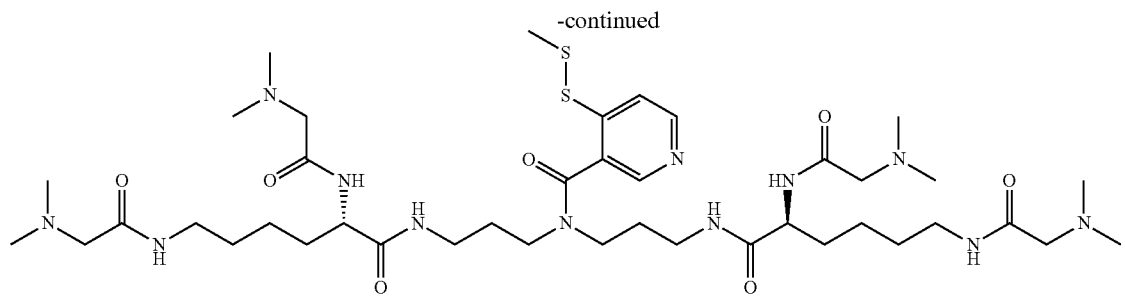

e7

↓ NaBH₄, H₂O, 79%

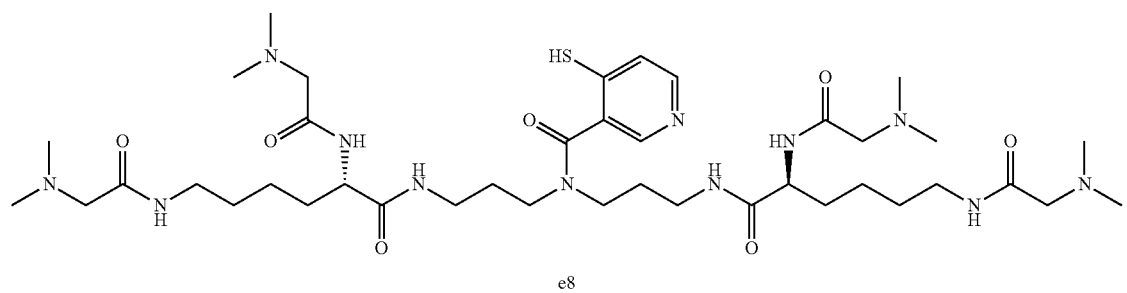

e8

Preparation of purification TAG N,N'-((10S,22S)-10-(2-(dimethylamino)acetamido)-16-(4-mercaptonicotinoyl)-2-methyl-4,11,21-trioxo-2,5,12,16,20-p entaazahe xaco sane-22,26-diyl)bis(2-(dimethylamino)acetamide) e8 is shown in Scheme 1G.

Step 1 Synthesis of (9H-fluoren-9-yl)methyl bis(3-aminopropyl)carbamate e2

Fmoc-OSu (9.77 g; 28.96 mmol; 1.20 eq.) was added to a solution of 1,9-bis-Boc-1,5,9-triazanonane e1 (8.00 g; 24.14 mmol; 1.00 eq.) in THF (80.00 ml). To this mixture a solution of K₂CO₃ (5.00 g; 36.20 mmol; 1.50 eq.) in water (80.00 ml) was added dropwise over 10 minutes at room temperature. A white emulsion formed during the addition. After 50 min stirring at room temperature the reaction mixture was diluted with ethyl acetate (600 ml). The organic layer was washed with hydrochloric acid (0.1 M, 3×200 ml), saturated NaHCO₃ solution (200 ml) and brine (100 ml). After drying over MgSO₄ and filtration all volatiles were removed. The crude residue was dried in high vacuum for 20 minutes to give a white foam. This foam was dissolved in dichloromethane and purified by flash chromatography. Product containing fractions were combined and concentrated to yield 9H-fluoren-9-ylmethyl N,N-bis[3-(tert-butoxycarbonylamino)propyl]carbamate intermediate (not shown in Scheme 1G) as colorless, glassy solid; 12.81 g; 96%.

This intermediate product (12.78 g; 23.08 mmol; 1.00 eq.) was dissolved in TFA (30.00 ml; 389.39 mmol; 16.87 eq.) at room temperature. After complete dissolution, the yellow solution was stirred at room temperature for 35 min. The product was precipitated by dropwise addition of the reaction mixture into diethyl ether (2 ml reaction solution in 40 ml diethylether) in 50 ml Falcon tubes. The Falcon tubes were centrifuged at 7000× G and 0° C. for 3 minutes. The ether supernatant was discarded and the residues were dissolved in methanol (1 ml each tube). The combined methanolic solutions were added dropwise to diethyl ether (200 ml) in a 500 ml round-bottom flask. All tubes were washed with methanol (total ~150 ml) and the washing solutions were added to the ether/precipitate mixture, whereupon a colorless, clear solution formed. This solution was concentrated and the oily residue was dried in high vacuum overnight to give (9H-fluoren-9-yl)methyl bis(3-aminopropyl)carbamate e2 as a white foam: 13.68 g; quantitative yield.

Step 2 Synthesis of (9H-fluoren-9-yl)methyl bis (3-((S)-2,6-diaminohexanamido)propyl)carbamate e3

DIPEA (20.44 ml; 117.20 mmol; 5.00 eq.) was added to a solution of compound e2 (13.63 g; 23.44 mmol; 1.00 eq.) and Boc-Lys(Boc)-OSu (24.95 g; 56.25 mmol; 2.40 eq.) in DMF (250.00 ml) and the light yellow mixture was stirred at room temperature for 45 min. The reaction mixture was diluted with ethyl acetate (1200 ml) and the organic layer was washed with hydrochloric acid (0.1 M, 4×500 ml), saturated NaHCO$_3$ solution (3×250 ml) and brine (200 ml). After drying over MgSO$_4$ and filtration all volatiles were removed to yield the Boc-protected intermediate (not shown in Scheme 1G) as white foam. The crude residue was dissolved in dichloromethane (30 ml) and purified by flash column chromatography. Product containing fractions were combined and all volatiles were removed in vacuo. The pure product precipitated from cold ethyl acetate solutions. Methanol was added to dissolve the product completely. Evaporation of the combined fractions led to a colorless oil, which was dried in high vacuum overnight to give the Boc protected intermediate: 18.27 g; 77%.

This intermediate (18.12 g; 17.94 mmol; 1.00 eq.) was dissolved in TFA (40.00 ml; 519.19 mmol; 28.95 eq.). During dissolution a lot of gas evolved and the mixture warmed to about 45° C. and turned yellow. The clear, viscous solution was stirred at room temperature for 2 h. The reaction mixture was added to diethyl ether (2 ml reaction solution in 40 ml ether in a 50 ml Falcon tube). After vigorous shaking the biphasic system transformed into a suspension of a white, powdery precipitate in acidic diethyl ether. The mixture was transferred to Falcon tubes and all Falcons were centrifuged at 0° C. and 7000× G for 3 min and the supernatant was discarded. All precipitates were washed with 40 ml diethyl ether each and centrifugation was repeated. After discarding the supernatants again, all precipitates were pre-dried on the rotavap to form dry powders. All aliquots were combined and dried in high vacuum overnight to give (9H-fluoren-9-yl)methyl bis(3-((S)-2,6-diaminohexanamido)propyl)carbamate e3: 19.52 g; quantitative yield.

Step 3 Synthesis of Compound e5

DIPEA (18.02 ml; 103.29 mmol; 6.00 eq.) was added to a suspension of N,N-dimethylglycine e4 (8.88 g; 86.08 mmol; 5.00 eq.) and PyBOP (44.79 g; 86.08 mmol; 5.00 eq.) in DMF (180.00 ml). The mixture was stirred for 15 minutes at room temperature, whereupon a clear solution formed. This solution was added in one portion to a solution of (9H-fluoren-9-yl)methyl bis(3-((S)-2,6-diaminohexanamido)propyl)carbamate e3 (18.35 g; 17.22 mmol; 1.00 eq.) and DIPEA (15.01 ml; 86.08 mmol; 5.00 eq.) in DMF (180.00 ml). The yellow reaction mixture was stirred at room temperature. After 35 min, the reaction mixture was quenched by the addition of TFA (22.02 ml; 285.82 mmol; 16.60 eq.). The solution was concentrated to yield a yellow oil, which was subsequently dissolved in methanol (450 ml) to yield 600 ml of a dark yellow solution. This intermediate product (not shown in Scheme 1G) was precipitated twice from diethyl ether. After washing the precipitate with diethyl ether, the product slurry was concentrated and the product was dried in vacuo for 72 hours: 23.17 g; 96%. Piperidine (17.50 ml; 0.18 mol; 10.83 eq.) was added in one portion to a solution of the intermediate product (23.00 g; 0.02 mol; 1.00 eq.) in DMF (69.00 ml) and the orange colored solution was stirred at room temperature for 35 min. The reaction mixture was concentrated and TFA (200 ml) was added to the residue. The slurry was filtrated through a PE frit. The product was precipitated from diethyl ether and after the product was washed with diethyl ether, it was dried in vacuo to yield compound e5 as an off-white powder: 19.82 g; 93%.

Step 4 Synthesis of N,N'-((10S,22S)-10-(2-(dimethylamino)acetamido)-2-methyl-16-(4-(methyldisulfanyl)nicotinoyl)-4,11,21-trioxo-2,5,12,16,20-pentaazahexacosane-22,26-diylbis(2-(dimethylamino)acetamide) e7

PyBOP (528.17 mg; 1.01 mmol; 1.00 eq.) and 4-(methyldisulfanyl)nicotinic acid e6 (320.00 mg; 1.01 mmol; 1.00 eq., prepared by reacting 4-mercaptonicotinic acid with S-methyl methanethiolsulfonate were suspended in acetonitrile (10.00 ml). DIPEA (1.59 ml; 9.13 mmol; 9.00 eq.) was added, whereupon a clear, dark yellow solution formed. After 2 min at room temperature the mixture was added to a solution of compound e5 (1 317.49 mg; 1.01 mmol; 1.00 eq.) in acetonitrile (10.00 ml). The reaction mixture was stirred at room temperature for 1 h. TFA (1.59 ml; 20.64 mmol; 20.33 eq.) was added and the product was precipitated from diethylether (140 ml). The precipitate was washed with diethylether (100 ml). The precipitate was dissolved in methanol (8 ml) and precipitated from diethyl ether (140 ml) a second time. The product was dried in high vacuum overnight to yield N,N'-((10S,22S)-10-(2-(dimethylamino)acetamido)-2-methyl-16-(4-(methyldisulfanyl)nicotinoyl)-4,11,21-trioxo-2,5,12,16,20-pentaazahexacosane-22,26-diyl)bis(2-(dimethylamino)acetamide) e7 as a powder: 1. 231 g; 82%.

Step 5 Synthesis of N,N'-((10S,22S)-10-(2-(dimethylamino)acetamido)-16-(4-mercaptonicotinoyl)-2-methyl-4,11,21-trioxo-2,5,12,16,20-pentaazahexacosane-22,26-diyl)bis(2-(dimethylamino)acetamide) e8

NaBH$_4$ (220.07 mg; 5.82 mmol; 7.00 eq.) was added in four portions to a solution of N,N'-((10S,22S)-10-(2-(dimethylamino)acetamido)-2-methyl-16-(4-(methyldisulfanyl)nicotinoyl)-4,11,21-trioxo-2,5,12,16,20-pentaazahexacosane-22,26-diyl)bis(2-(dimethylamino)acetamide) e7 (1.231 g; 0.83 mmol; 1.00 eq.) in water (15.00 ml). After the last addition the mixture was stirred for 60 minutes at room temperature. TFA (1.00 ml; 12.98 mmol; 15.62 eq.) was added to the reaction mixture. The reaction mixture was diluted with water to a final volume of 25 ml. The solution was purified by preparative HPLC. Product containing fractions were combined, frozen and lyophilized to give the TFA salt of N,N'-((10S,22S)-10-(2-(dimethylamino)acetamido)-16-(4-mercaptonicotinoyl)-2-methyl-4,11,21-trioxo-2,5,12,16,20-pentaazahexacosane-22,26-diyl)bis (2-(dimethylamino)acetamide) e8; 942.00 mg; 79%.

Example 2A

Preparation of Amine Functionalized Hyaluronic Acid (HA)

Amine functionalities were introduced on HA. In some aspects, a degree of functionalization of up to about 11% was introduced for the subsequent maleimide functionalized HA and drug attachment to the maleimide, and up to about 5% for the subsequent thiol functionalized HA.

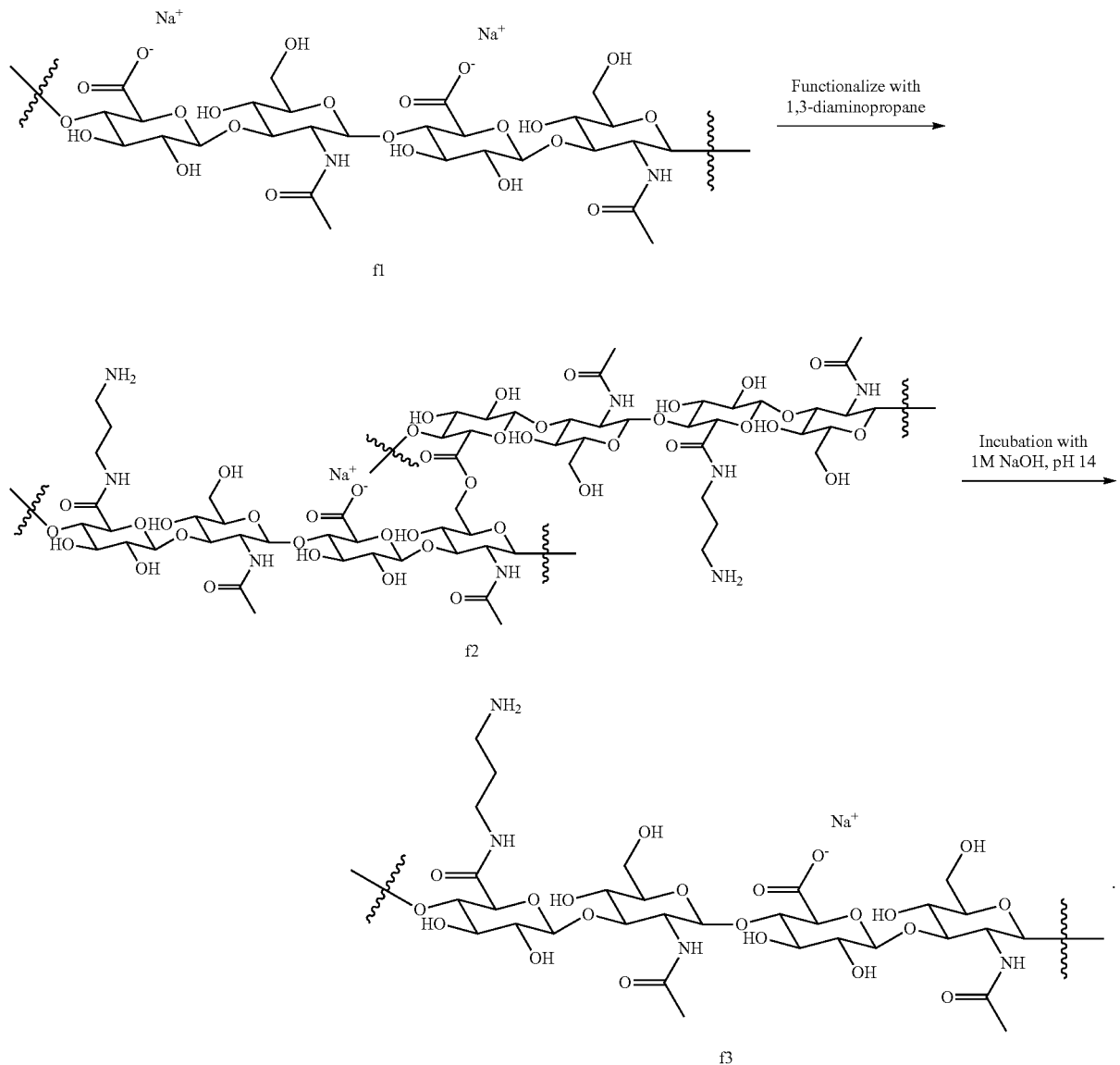

Scheme 2A

Amine functionalization of HA proceeds according to reaction scheme 2A:

200 mg of 116 kDa hyaluronic acid sodium salt f1 was dissolved in 25 mL of a buffered solution (100 mM MES, 0.4 M 1,3-diaminopropane, pH 5.5) under vigorous stirring. 3.00 eq. (229.14 mg; 1.50 mmol) HOBt with respect to carboxylic acid functionalities at the HA were added. 0.93 eq (88.92 mg; 0.46 mmol) EDC.HCl were added after which the suspension slowly turned into a solution. The solution was stirred at ambient temperature over night and subsequently formed a suspension. To the suspension, 50.00 eq. (3.39 g; 24.94 mmol) sodium acetate were added to form a solution. The modified HA f2 was precipitated by addition of absolute ethanol, washed with ethanol and dried under high vacuum overnight. The pellets were dissolved in 16 mL water to form a clear solution. 5.40 mL of 4 M NaOH were added and the solution was stirred at ambient temperature for two hours. 1.24 mL of acetic acid were added. The amino-functionalized HA f3 was precipitated by addition of absolute ethanol, washed with 80 v/v % ethanol and absolute ethanol and dried under high vacuum to give white pellets. The 0.93 equivalents of EDC resulted in amine functionalization of approximately 11% of the carboxylate groups on the HA. For the preparation of amine functionalized HA with approximately 5% amine functionalization, 0.40 eq (38.63 mg; 0.20 mmol) EDC.HCl were used.

Example 2B

Preparation of Maleimide Functionalized HA

Maleimide functionalized HA was obtained by reacting the amine functionalized HA f3 with maleimidopropionic acid NHS ester f4 according to the following reaction scheme:

Scheme 2B

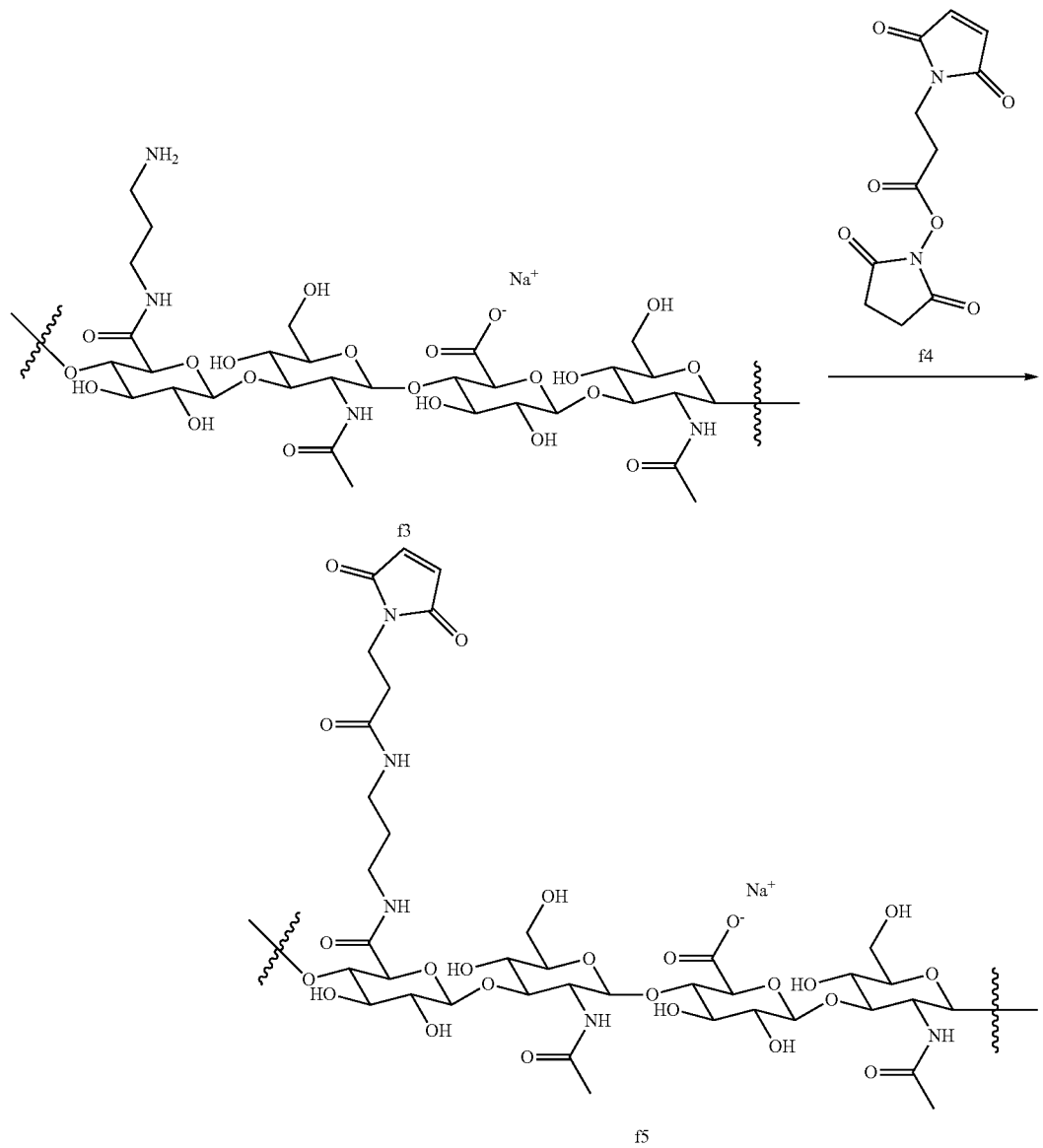

176.1 mg of amine functionalized HA f3 (0.252 mmol/g amine) was dissolved in 17.6 mL of 100 mM HEPES buffer pH 7.4. 150.48 mg (0.57 mmol; 10.00 eq.) of 3-Maleimidopropionic acid N-hydroxysuccinimide ester f4 in 9.50 mL acetonitrile were added. The reaction mixture was stirred at ambient temperature for exactly 60 minutes. 27.1 mL of 1 M sodium acetate solution pH 5.5 were added to the solution under stirring. Absolute ethanol was added to precipitate the HA. The obtained pellets were successively washed with 80 v/v % ethanol and absolute ethanol. The pellets were combined and the material was dried in high vacuum for three hours with subsequent storage at −20° C. The obtained pellets were dissolved in 17.6 mL of 1% acetic acid. 17.6 mL of 1 M sodium acetate solution pH 5.5 were added to the solution. The resulting mixture was filtered through a 33 mm diameter 0.22 μm PES syringe filter and the maleimide functionalized HA f5 was precipitated by addition of absolute EtOH. The pellets were successively washed with 80% v/v ethanol and absolute ethanol. The pellets were combined and dried under high vacuum for three hours to give 159.50 mg as white pellets. Maleimide content determination was done via inverse Ellman assay by addition of 2-mercaptoethanol and detection of unreacted, residual 2-mercaptoethanol. A degree of maleimide functionalization of approx. 10% with respect to the initially available carboxylate groups in the native HA was detected.

Example 2C

Preparation of Thiol Functionalized HA

The thiol functionalized HA was designed to enable the degradation of the HA gel after incubation of the crosslinked HA gel under physiological conditions. In this example, an ester bond using azelaic acid was introduced.

Scheme 2C

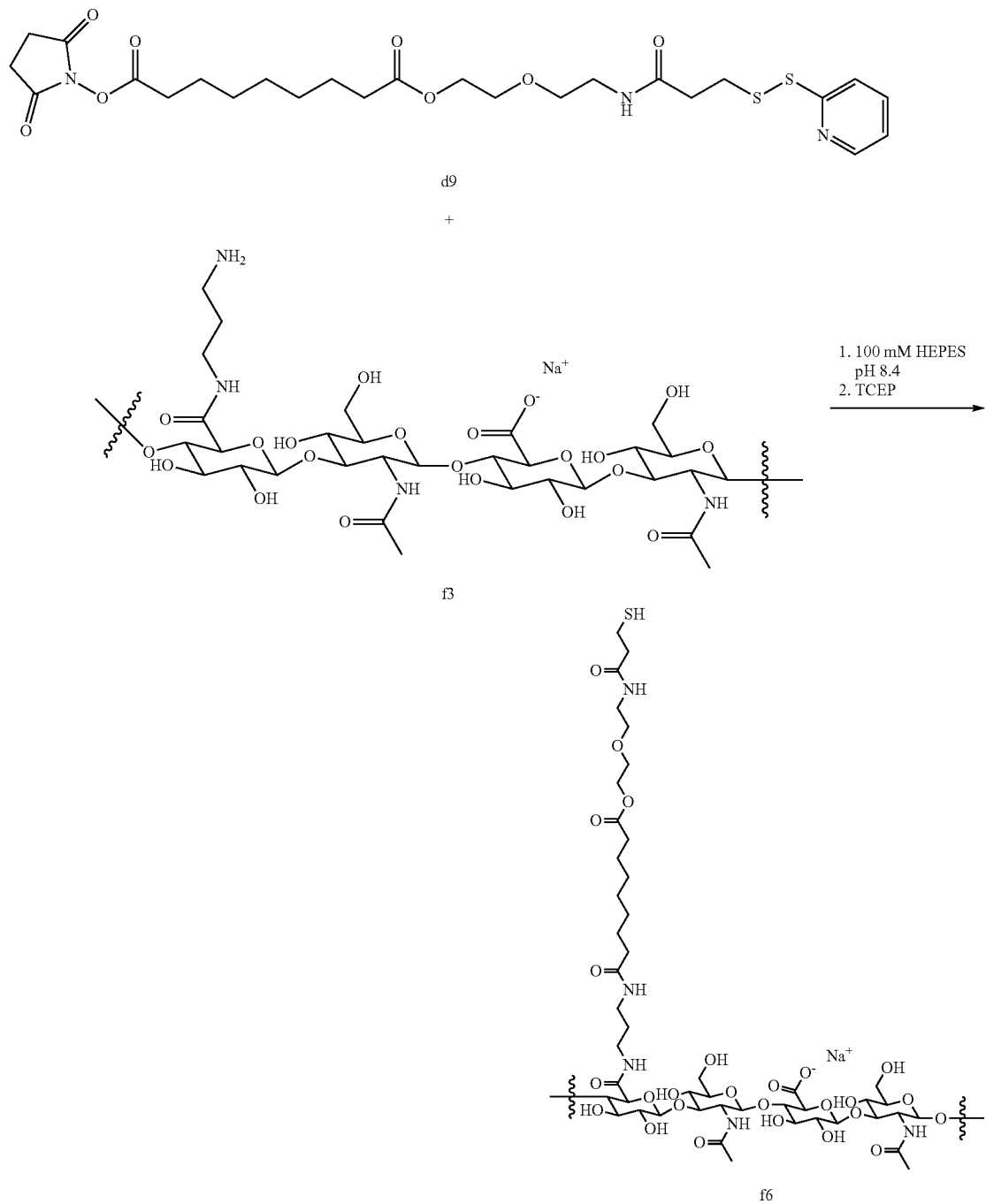

166.90 mg of the amine functionalized HA f3 (0.104 mmol/g amine functionality) was dissolved in 13.9 mL 100 mM HEPES buffer pH 8.40. A freshly prepared solution of 75.3 mg (0.11 mmol; 5.00 eq.) of NHS ester d9 (see Scheme 1F) in 7.5 mL acetonitrile was added to the mixture. The mixture was stirred at ambient temperature for 120 minutes to prepare disulfide functionalized HA (not shown). A freshly prepared solution of 63.2 mg tris(2-carboxyethyl) phosphine HCl-salt (TCEP) (0.22 mmol; 10.00 eq.) in 2.1 mL water was added to the reaction mixture. The solution was stirred for one hour at ambient temperature. 22.9 mL of 1 M sodium acetate solution pH 5.5 were added to the reaction mixture. The resulting solution was partitioned between Falcon tubes. To precipitate the HA content, absolute ethanol was added. The tubes were closed, shaken and centrifuged. The obtained pellets were successively washed with 80 v/v % ethanol and absolute ethanol. The pellets were combined and dried in high vacuum for three hours and subsequently stored at −20° C. under an argon atmosphere until further use. The pellets were dissolved in 16.7 mL of 1% acetic acid by vigorous stirring under an argon atmosphere. 16.7 mL of 1 M sodium acetate solution pH 5.5 were added to the solution. The resulting mixture was filtered through a 33 mm diameter 0.22 gm PES syringe filter into Falcon tubes and precipitated by addition of absolute ethanol. The tubes were closed, shaken and centrifuged. The pellets were successively washed with 80% v/v ethanol and absolute ethanol. The pellets were combined and dried under high vacuum for three hours to give 150.10 mg of thiol-functionalized HA f6 as white pellets. Thiol content determination was performed via Ellman assay. A degree of thiol functionalization of approx. 4% with respect to the initially available carboxylate groups in the native HA was detected.

Example 3A

Preparation of Linker-Ranibizumab Conjugate mg/mL by addition of phosphate buffer to give a final volume of 53.1493 g. 2118.5 mg (85%) of Rbz were recovered at a concentration of 39.8 mg/mL and a total volume of about 53 mL volume.

1990 mg Rbz (50 mL at 39.8 mg/mL) in 30 mM sodium phosphate, pH 7.4 was cooled on ice. 15 eq. (8.0 mL) of compound b8 (example 1D) (corrected with respect to NHS content, 100 mM stock solution in DMSO) were added, and the solution was shaken carefully (no stirrer was used).

The solution was incubated for 5 min on ice immediately followed by a pH shift and a buffer exchange was done to remove excess linker species from the Rbz linker conjugate solution. The buffer shift was done by adding 0.12 vol. eq. (6 mL) of 0.5 M succinic acid pH 3.0, and the solution was shaken carefully. The pH of the solution was shifted towards about pH 4.0. The buffer exchange was performed using an

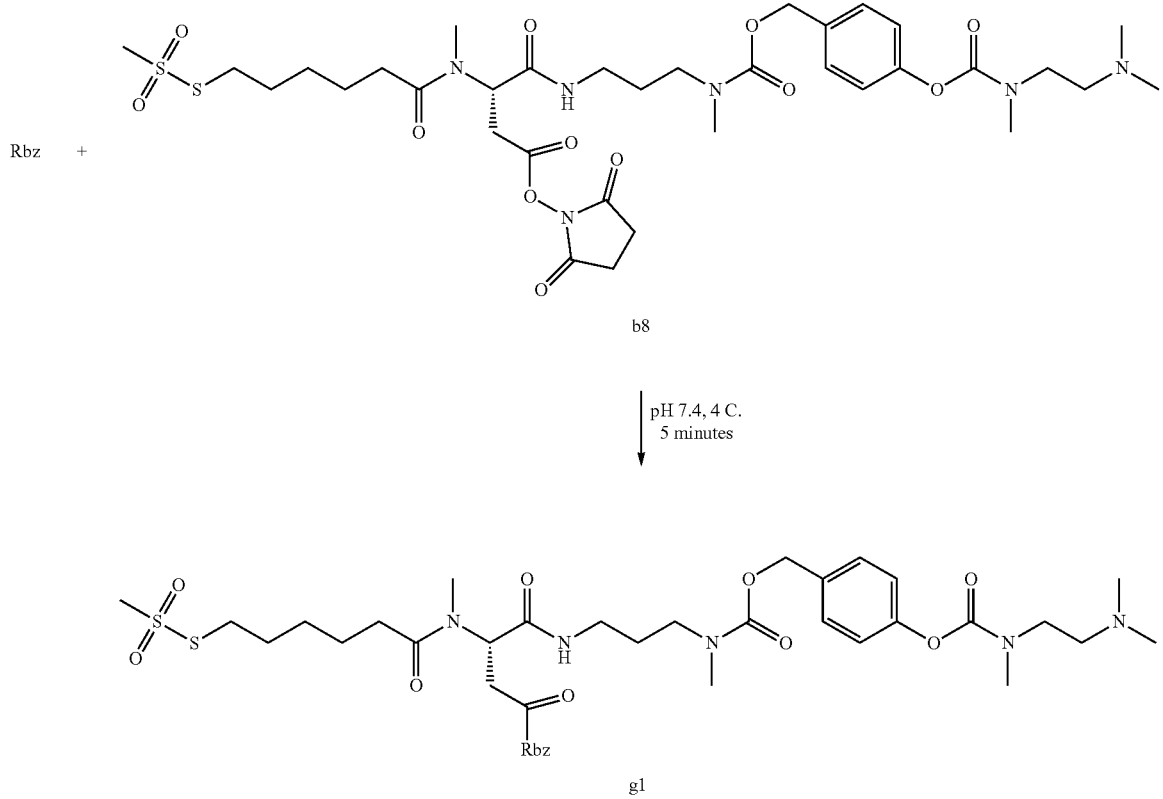

Conjugation of Rbz to linker b8 from example 1D was done according to the Scheme 3A Buffer exchange and concentration may be performed with either a HiPrep column followed by concentration via centrifugal filters (small scale) or by using a tangential flow filtration (TFF) system (larger scale).

62 mL Rbz at 40 mg/mL formulated in 10 mM histidine, 10 wt % α,α-D-trehalose, 0.01% Tween 20, pH 5.5 was used in this example After buffer exchange to 30 mM phosphate pH 7.4 and concentration, the Rbz solution was filtered using Millex GV 33 mm filters with a pore size of 0.22 μm. About 50 g of the protein solution was recovered. After concentration determination, the sample was diluted to 40

Äkta P-900 equipped with a GE HiPrep column. The buffer was 5 mM succinic acid pH 4.0 introduced at a flow rate of 8.0 mL/min with 13 runs with 5 mL injection volume per run. 134 mL product solution with a concentration of 14.5 mg/mL (calculation based on the extinction coefficient of the native drug) were collected.

Samples before and after conjugation were analyzed by mass spectrometry. The deconvoluted MS spectrum before conjugation indicated a Rbz single peak at 48381. The spectrum after conjugation indicated a Rbz peak at 48382, a monoconjugate g1 peak at 49066, a bisconjugate at 497543, and a trisconjugate at 50437. Only the majority product monoconjugate g1 is shown in Scheme 3A for clarity, and the monoconjugate was isolated from the higher conjugates as described below.
Example 3B
Introduction of Purification Tag to Rbz Linker Conjugate
Scheme 3B
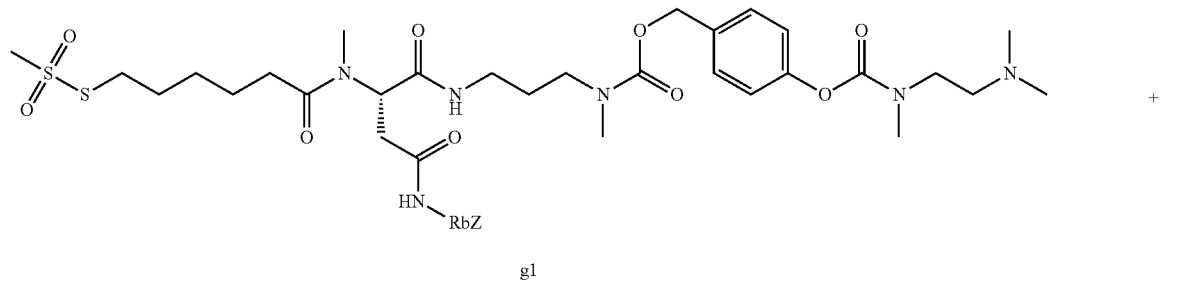
g1
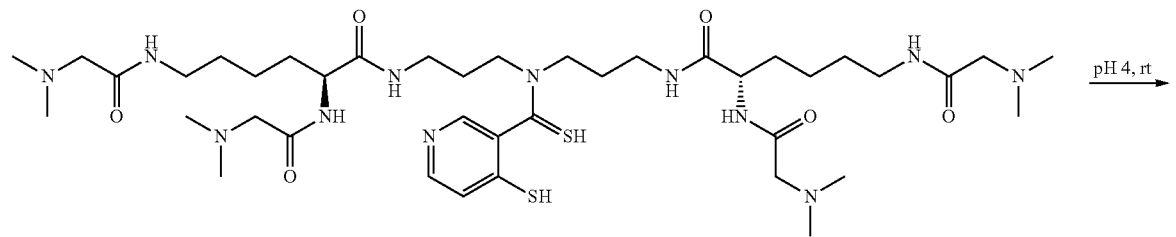
e8
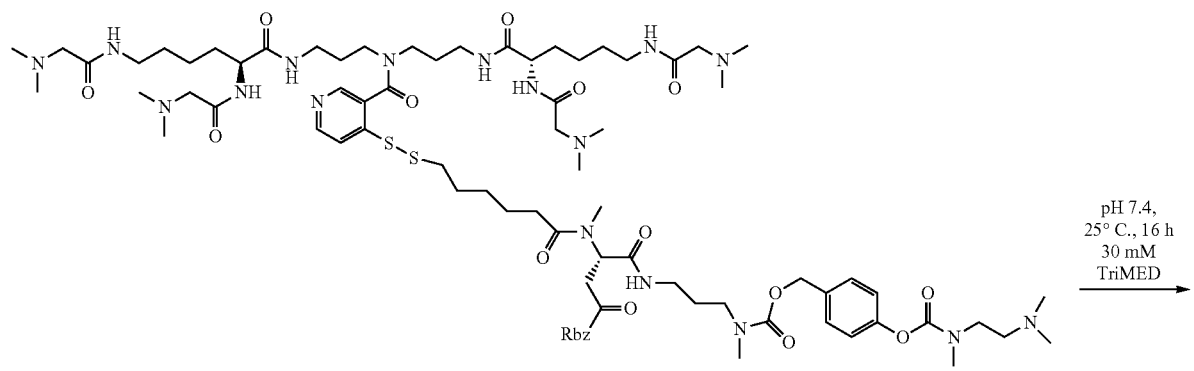
g2

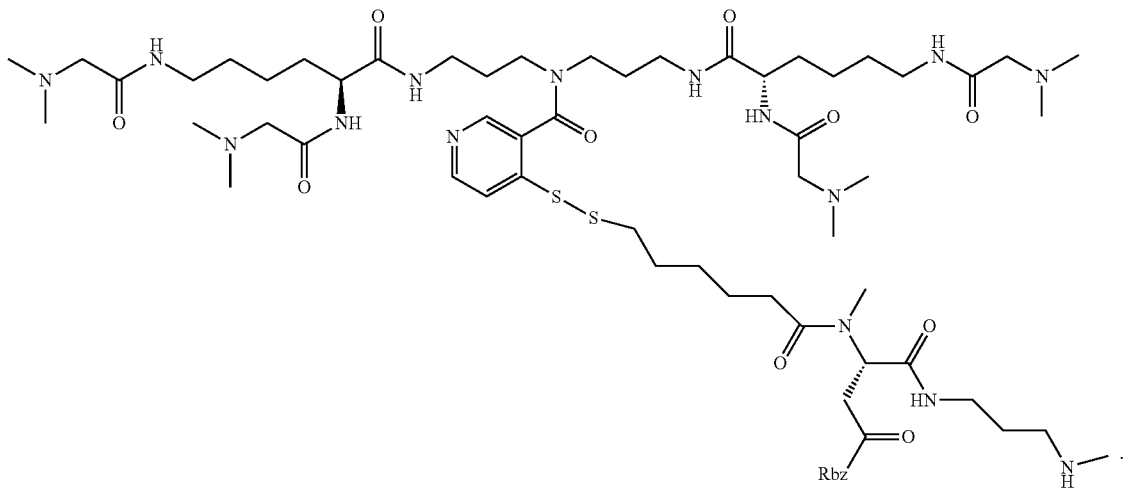

g3

Introduction of purification tag e8 to Rbz linkerconjugate g1 was done according to Scheme 3B To a solution of 125 mL linker conjugate mixture including monoconjugate g1 (and higher conjugates not shown) (14.53 mg/mL, 1824 mg protein, 37.7 ₁ tmol), 2.5 molar equivalents of purification-tag e8 (Scheme 1G) with respect to the protein content were added at ambient temperature (1886 μL of 50 mM e8, 94.3 ₁ tmol, in water) and the solution was shaken carefully to afford TAGylated Rbz linker monoconjugate g2 and higher conjugates (not shown). After 35 min, a pH shift to pH 7.4 and amine deprotection was carried out by addition of 0.170 vol. eq. (21.4 mL) of 0.5 M phosphate, 200 mM TriMED, pH 7.8 (the volume of the TAGylation solution was not taken into account) during which the protecting group was cleaved off to afford TAGylated Rbz linker monoconjugate g3 and higher conjugates (not shown). The solution was stored at a controlled temperature of 25° C. over night in an incubator.

About 148 mL of protein solution were removed from the 25° C. incubator and 0.419 vol. eq. (52.4 mL, based on the initial 125 mL protein volume, 52.7 mL actually added) of 0.5 M succinic acid, pH 3.0 was added to the solution of g3 and higher conjugates to obtain a pH of approx. pH 4.0.

Example 3C

Isolation of Rbz Linker Monoconjugate

For CIEC purification, the protein solution, containing a mixture of unconjugated Rbz and a mixture of TAGylated Rbz-linker monoconjugate g3 and higher conjugates, was diluted 3.3 fold with 20 mM succinic acid, pH 4.0, to a final volume of about 660 mL. A GE Healthcare Source column 15S (column XK26, 5.2 cm height) was used with the following buffers: 20 mM succinic acid, pH 4.0 (buffer A); and 20 mM succinic acid, 1 M NaCl, pH 4.0 (buffer B). The gradient was linear, 10%-50% B, 32 CV (20 mL/min flow rate). The load was approximately 300 mg. The conjugate mixture was analyzed by MS prior to CIEC and in the deconvoluted MS spectrum, a 48380 m/z peak (native Rbz), a 49573 peak (monoconjugate g3), a 50766 peak (bisconjugate), and a 51958 peak (triconjugate) were indicated. CIEC fraction 1 predominantly contained native Rbz (m/z peak of 48380), CIEC fraction 2 predominantly contained the monoconjugate g3 (m/z peak of 49573) and CIEC fraction 3 predominantly contained the bisconjugate (m/z peak of 50766).

After the isolation of the Rbz-linker monoconjugate g3, the protein solution was concentrated to about 5 mg/mL using tangential flow filtration. The starting material contained about 450 mL Rbz-linker monoconjugate g3 at about 0.85 mg/mL formulated in succinate buffer pH 4.0. The sample was filtered using one Millex GV 33 mm filter, with a pore size of 0.22 μm. 68 mL of the Rbz-linker monoconjugate solution at a concentration of 4.82 mg/mL was obtained.

Example 3D

Purification Tag Cleavage

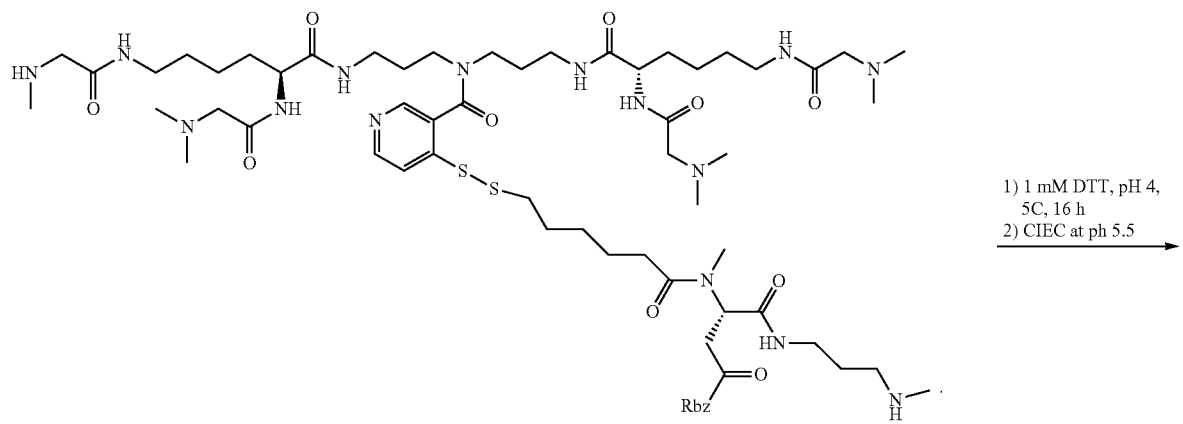

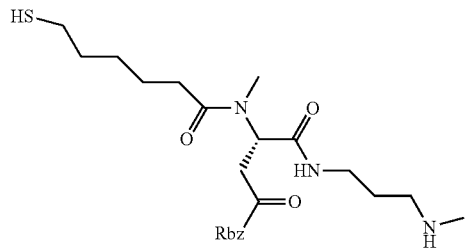

Purification tag e8 was removed by the procedure shown in Scheme 3C.

Cleavage of the purification tag e8 (detagylation) was obtained by incubation of Rbz-linker monoconjugate g3 (68 ml, 4.82 mg/ml) with DTT over night at 2-8° C. with a DTT concentration of 1 mM. A 25 mM DTT stock solution in 20 mM succinic acid, pH 4.0 was prepared by dissolving 0.0161 g of DTT in 4.175 mL succinate buffer. The solution was filtered through a Millex-GV 13 mm filter (pore size 0.22 µm). The Rbz-linker monoconjugate solution and the 25 mM DTT stock solution were cooled down to 4° C. on ice. 2.838 mL of the 25 mM DTT solution were added to the protein solution to give a final DTT concentration of 1 mM. Incubation was performed over night at 2-8° C. Purification tag removal was monitored by MS. The Rbz-spacer-linker-purification tag prior to cleavage had a peak at 49573 indicating the purification tag monoconjugate g3. The Rbz-linker conjugate g4 after cleavage had a peak at 48709 indicating the Rbz-linker monoconjugate after cleavage of the purification tag.

The Rbz-linker conjugate g4 was purified by CIEC. 70.9 mL of Rbz-linker monoconjugate after DTT mediated deprotection were diluted 12-fold with 10 mM histidine pH 5.5 to a final volume of about 850 mL. The column was a GE Healthcare Source 15S XK26 column (5.2 cm height). The buffer system was: 10 mM histidine, pH 5.5 (buffer A); and 10 mM histidine, 500 mM NaCl, pH 5.5 (buffer B). The Gradient was: linear, 0%-50% B, 25 CV (17.5 mL/min flow rate). The load was about 300 mg.

After the CIEC step, the osmolality of the protein solution was adjusted by further dilution using buffer B (10 mM histidine, 500 mM NaCl, pH 5.5) to give a NaCl concentration of about 150 mM. 63 mL of Rbz-linker monoconjugate were collected during the CIEC run. 15.6 mL of 10 mM histidine, 500 mM NaCl, pH 5.5 were added to the sample to give an overall volume of 78.6 mL of Rbz-spacer-linker monoconjugate g4.

Example 3E

Rbz-Linker Concentration

For preparation of HA-linker-Rbz h1 with a protein load of 40 mg/mL, the Rbz-linker monoconjugate g4 was concentrated to above 60 mg/mL. Two Amicon Ultra 15 PLCG Ultracel Membranes MWCO 10 kDa were used for concentration of the protein solution by centrifugation at 3000 g. About 4.5 g of solution of Rbz-linker monoconjugate g4 with a protein content of 64.6 mg/mL (293.8 mg) was obtained. The Rbz-linker monoconjugate g4 was analyzed by MS and a peak at 48710 was found indicating Rbz-linker monoconjugate.

Example 4A

Conjugation of Linker-Rbz Conjugate to Maleimide Functionalized HA

Scheme 4A

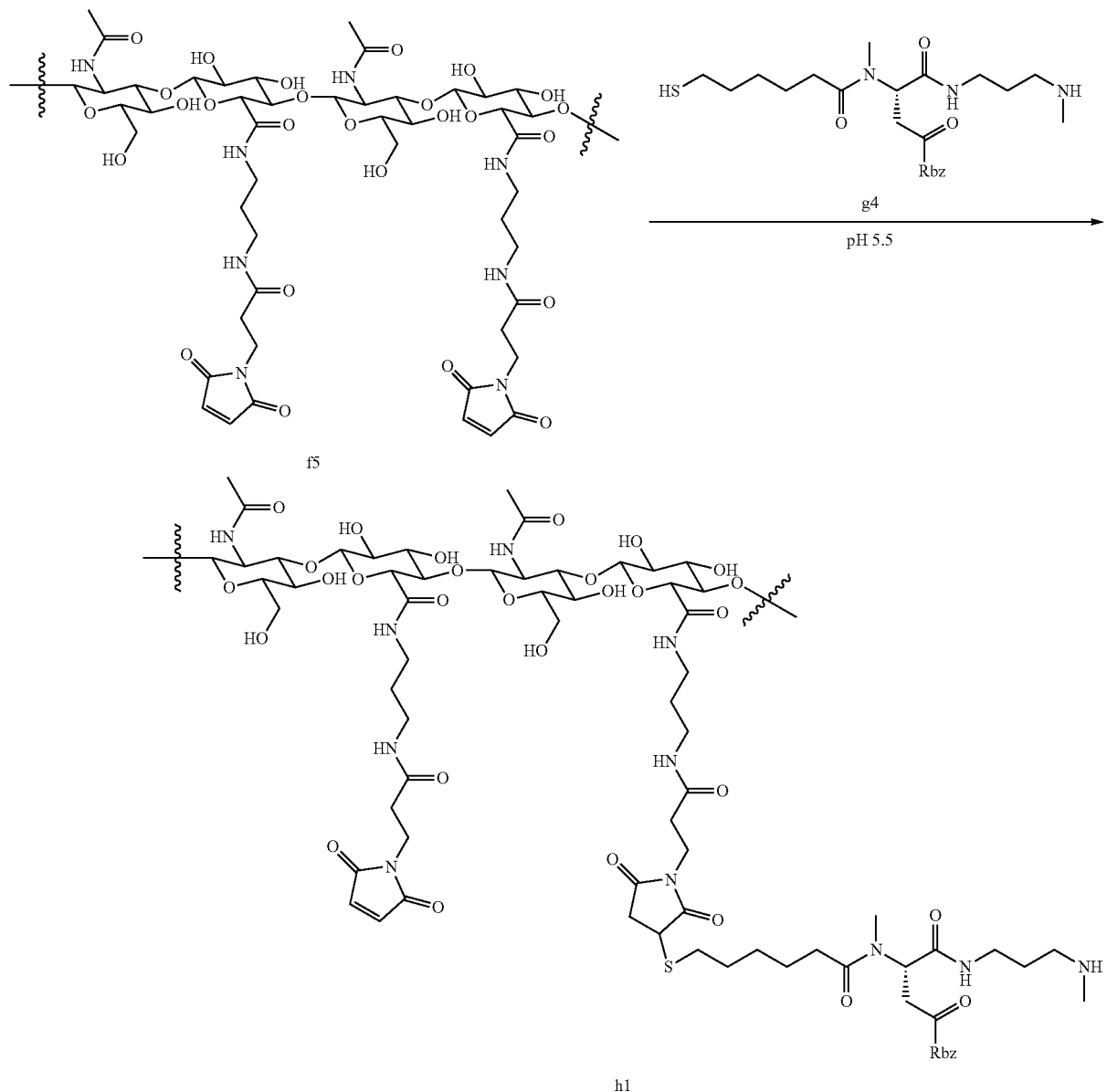

The conjugation of Rbz linker monoconjugate g4 to maleimide functionalized HA f5 was carried out as shown in Scheme 4A Conjugation of Rbz-linker monoconjugate g4 to maleimide functionalized HA f5 was performed by addition of concentrated solution of Rbz linker monoconjugate g4 to 1.3 eq. of maleimide functionalized HA f5 with respect to thiol content resulting in a protein (Rbz) concentration of 44 mg/mL (based on thiol content) and a HA content of about 0.49%. Rbz-linker monoconjugate samples (protein solution of 64.6 mg/mL formulated in 10 mM histidine, 150 mM NaCl, pH 5.5) prepared according to Example 3C were allowed to warm up to ambient temperature. The samples were filtered via a GV Millex filter 33 mm with a pore size of 0.22 gm. The thiol content of the Rbz linker monoconjugate g4 solution was determined to be 69.0 mg/mL. 1300 µL of the Rbz linker monoconjugate g4 solution were transferred into a 5 mL Eppendorf tube. 336 µL of 10 mM histidine, 150 mM NaCl, 0.01% Tween 20 pH 5.5 buffer were added. 68 µL of 10 mM histidine, 150 mM NaCl, 0.2% Tween 20 pH 5.5 were added. 335 gt of HA-maleimide f5 solution (30 mg/mL content of a 116 kDa HA with a maleimide content of 0.24 mmol/g) were added. The resulting solution was mixed well and allowed to incubate for 4 hours at ambient temperature. After 4 hours reaction time, a sample of 25 µL was withdrawn and analyzed via SEC. 92% of the Rbz linker monoconjugate had already bound to the maleimide functionalized HA.

Example 4B
Thiol-Maleimide Cross-Linking to Form
Linker-Drug Cross-Linked HA Gels
The cross-linking was done according to Scheme 4B:
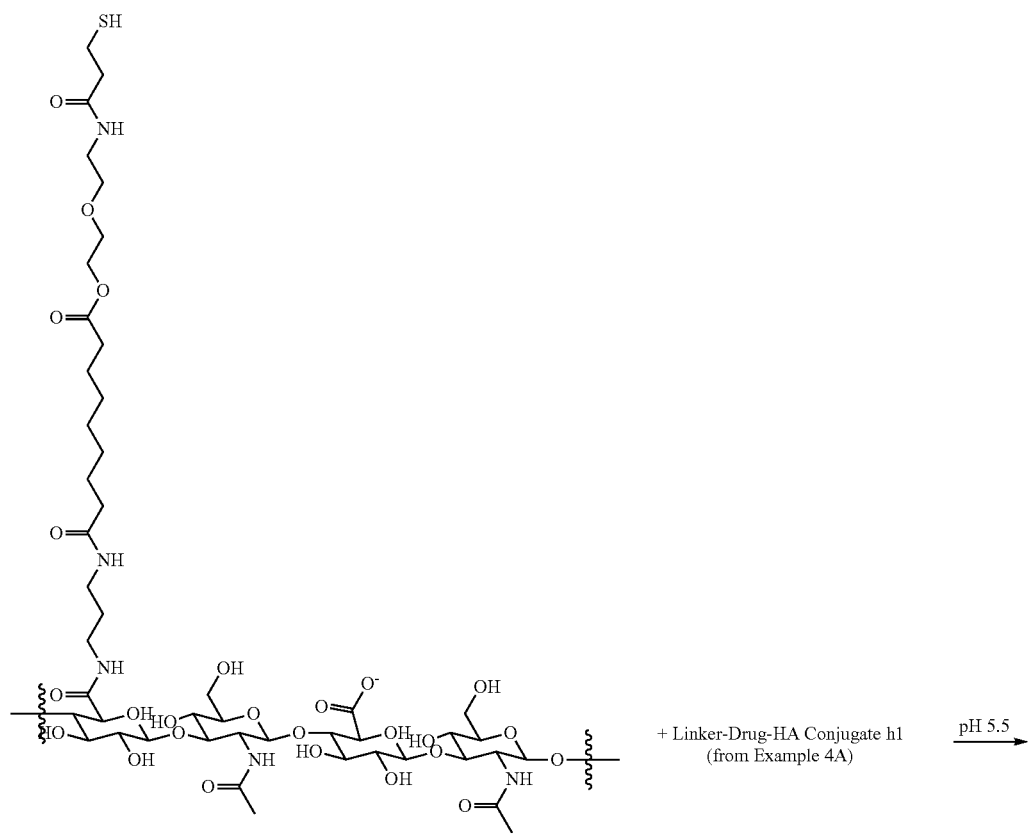
Scheme 4B

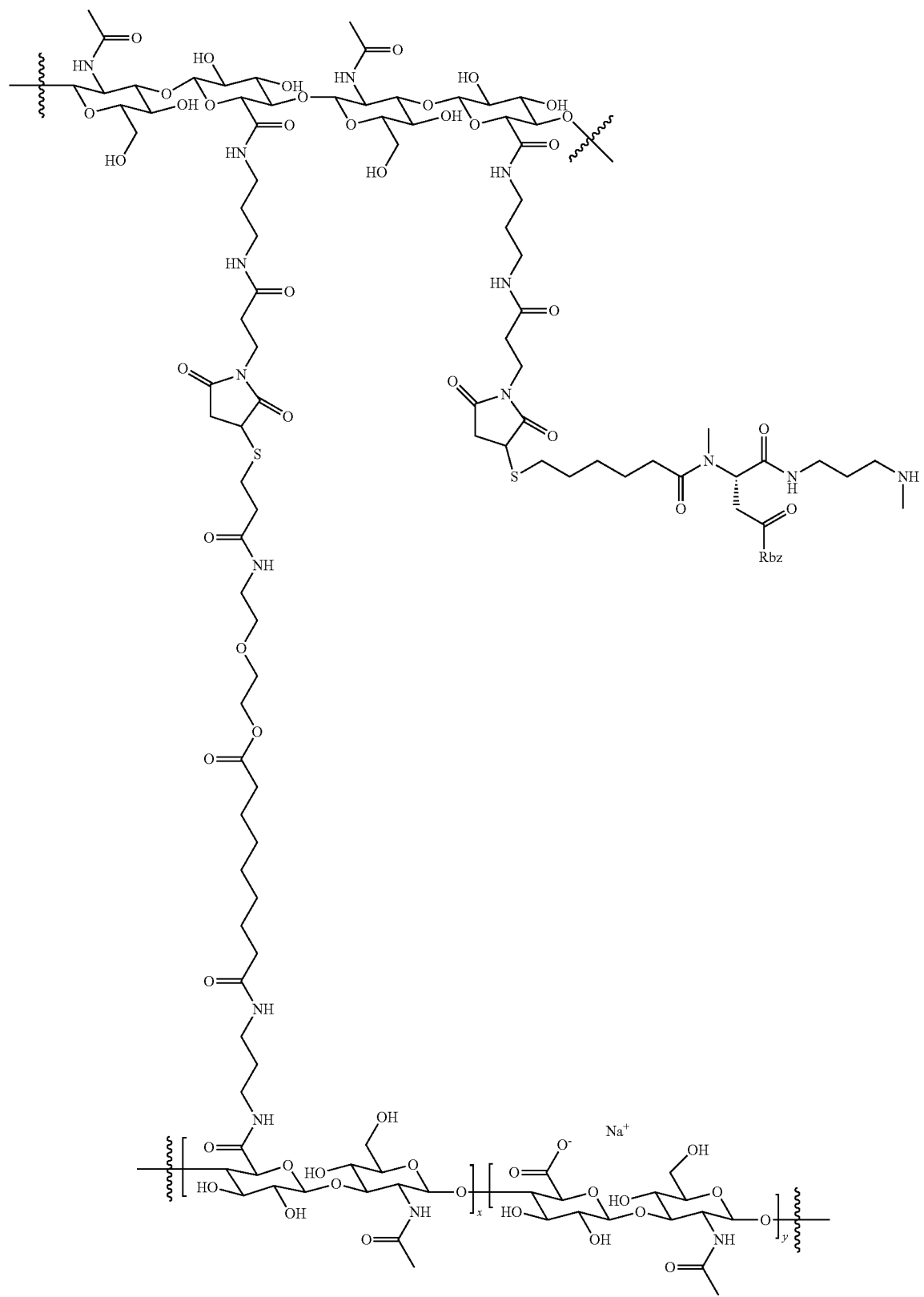

After 2014 μL of the linker-Rbz HA-conjugate h1 was incubated for 4 hours. 201 μL of HA-thiol f6 solution (27.8 mg/mL content of a 116 kDa HA with a thiol content of 0.098 mmol/g) was added, resulting in a final protein content of 40 mg/mL (based on thiol content) and a final HA content of 7.01 mg/mL in the resuting solution. The solution was mixed well and drawn into a 2 mL syringe equipped with a 18 G blunt cannula. The solution was quickly filled into eight 1 mL Luer Lock syringes using the syringe tip for filling. A screw cap was mounted on the syringes and they were allowed to incubate for about 24 h in an upright position at ambient temperature. The syringes were subsequently incubated at 5° C. for three weeks. The cross-linking reaction was completed in the syringes to yield cross-linked HA gel Rbz conjugate h2.

Example 4C

Release of Rbz from Cross-Linked HA Rbz Gel

The release of Rbz from cross-linked HA Rbz gel was analyzed in vitro using a material that was prepared according to example 4B with small adjustments. 13-17 mg of Rbz HA gel h2 were transferred into a sterile, pyrogen free Eppendorf tube. Release buffer (60 mM sodium phosphate, 3 mM EDTA, 0.01% Tween, pH 7.4) was added according to a ratio of 975 μL buffer for 25 mg of HA. Tubes were not inverted or shaken. All tubes were stored at a controlled temperature of 37° C. in an incubator. At different time points, a tube was removed from the incubator and centrifuged (9300 rcf, 3 min). The supernatant was transferred into a new Eppendorf tube and the protein concentration of the supernatant was determined by absorbance measurement at 280 nm with a reference wavelength of 338 nm using the extinction coefficient of Rbz of 1.9 mL/cm·mg. For each sample the release in % was calculated using the transferred mass and the protein content of the gel (Table 4c).

TABLE 4C

| | Ranibizumab Release |
| --- | --- |
| Time/d | Release % (Performed in duplicate) |
| 7 | 27.0; 27.0 |
| 21 | 41.0; 42.5 |
| 41 | 54.3; 57.7 |
| 63 | 68.7; 70.9 |

Example 5A

Preparation of Linker-G6.31 AARR Conjugate

Scheme 5A

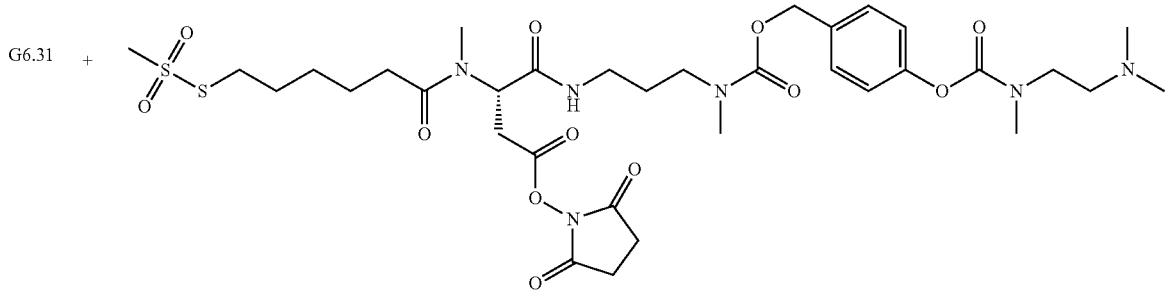

b8 pH 7.4, on ice
5 minutes

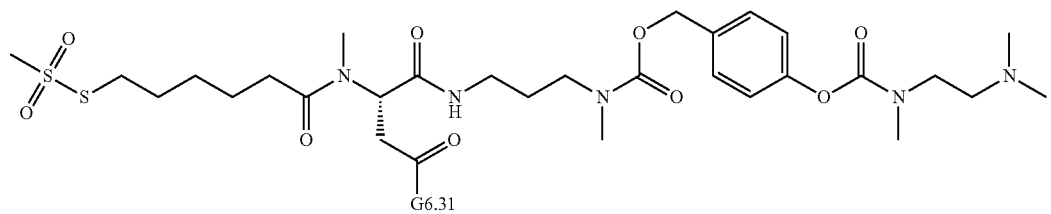

j1

Conjugation of G6.31 AARR to linker b8 from example 1D was done according to the Scheme:5A Buffer exchange and concentration may be performed with either a HiPrep column followed by concentration via centrifugal filters (small scale) or by using a tangential flow filtration (TFF) system (larger scale).

31 mL G6.31 AARR (shown as "G6.31" in Scheme 5A and the reaction Schemes below) at 40 mg/mL formulated in 20 mM histidine, 240 mM sucrose, 0.01% Tween 20, pH 5.5 was used in this example After buffer exchange to 30 mM phosphate pH 7.4 and concentration, about 23 g of the protein solution was recovered and the concentration determined. The sample was diluted to 40 mg/mL by addition of phosphate buffer. A total volume of 32.0 g of protein solution containing 1277 mg 66.31 at a concentration of 39.9 mg/mL was obtained.

1277 mg 66.31 AARR (32.0 mL at 39.9 mg/mL) in 30 mM sodium phosphate, pH 7.4 was cooled on ice. 15 eq. (4.6 mL) of compound b8 (example 1D) (corrected with respect to NHS content, 100 mM stock solution in DMSO) were added, and the solution was inverted several times.

The solution was immediately incubated on ice. After 5 min, the conjugation reaction was stopped by shifting the pH to about pH 4.0. Therefore, 0.12 vol. eq. (3.8 mL) of 0.5 M succinic acid pH 3.0 were added and the solution was inverted serveral times. Buffer exchange to 5 mM succinic acid pH 4.0 was performed in 10 runs at a flow rate of 8 mL/min using an Äkta Basic 10 equipped with a GE HiPrep column. 4 mL of the solution were injected per run. In total, 93.1 g of product solution with a concentration of 12.9 mg/mL were collected.

Samples before and after conjugation were analyzed by mass spectrometry. The deconvoluted MS spectrum before conjugation indicated a G6.31 single peak at 47390. The spectrum after conjugation indicated a G6.31 AARR peak at 47392, a monoconjugate j1 peak at 48077, a bisconjugate at 48766, a trisconjugate at 49452 and a tetraconjugate at 50147. Only the main product monoconjugate j1 is shown in Scheme 3A for clarity, and the monoconjugate was isolated from the higher conjugates as described below.

Example 5B

Introduction of Purification Tag to G6.31 AARR Linker Conjugate

Scheme 5B

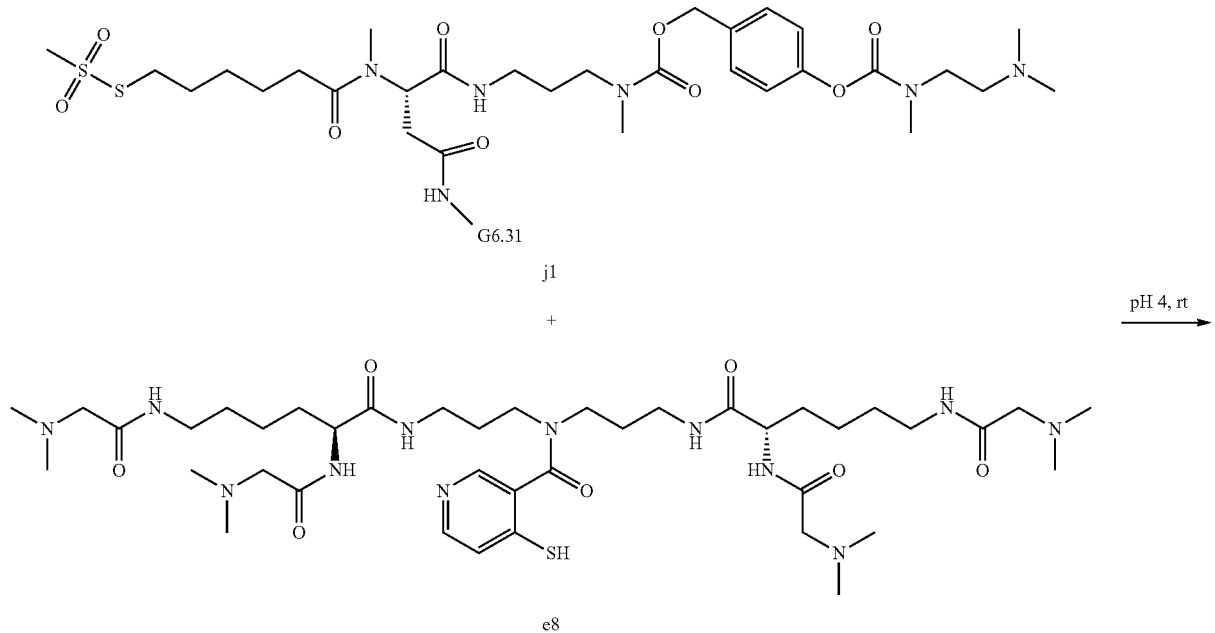

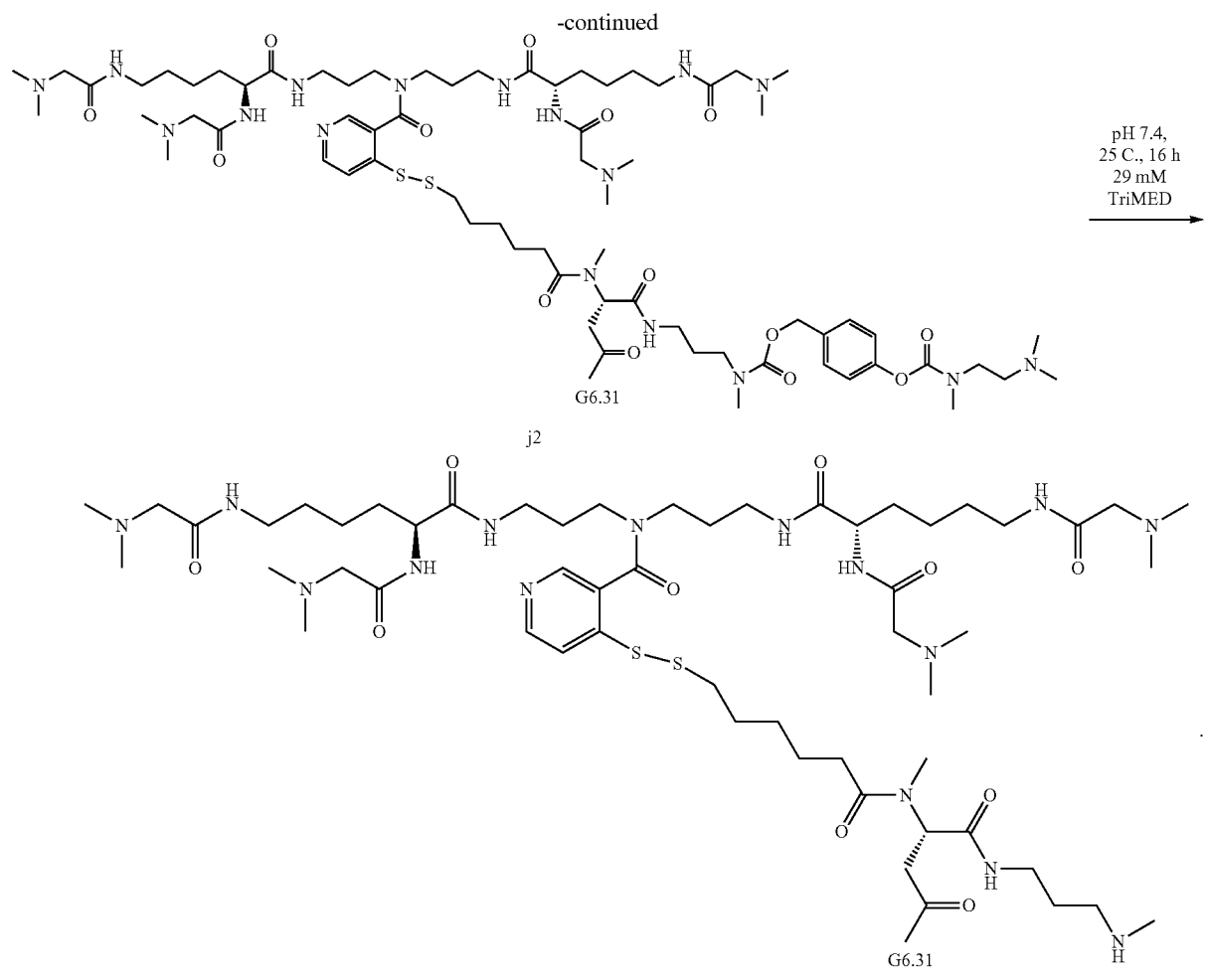

Introduction of purification tag e8 to 66.31 AARR linker conjugate j1 was done according to Scheme 5B.

To a solution of 93.1 mL linker conjugate mixture including monoconjugate j1 (native G6.31 AARR and higher conjugates not shown) (12.9 mg/mL, 1203 mg protein, 25.4 µmol (extinction coefficient and molecular weight of G6.31 AARR were used for simplicity's sake)), 2.5 mol equivalents of purification-tag e8 (Scheme 1G) with respect to the protein content were added at ambient temperature (1270 µL of 50 mM e8 in 20 mM succinic acid, pH 4.0, 63.5 tunol) and the solution was shaken carefully to afford TAGylated G6.31 linker monoconjugate j2 and higher conjugates (not shown). After 50 min, a pH shift to pH 7.4 and amine deprotection was carried out by addition of 0.170 vol. eq. (15.8 mL) of 0.5 M phosphate, 200 mM TriMED, pH 7.8 (the volume of the added purification-tag solution was not taken into account). As mono-tagylated bis-conjugate was still detected in the mixture after the pH shift, additional 0.2 eq. (100 µL of 50 mM e8 in 20 mM succinic acid, pH 4.0, 5 µmol) of purification-tag e8 (Scheme 1G) with respect to the protein content were added to the mixture. The solution was stored in an incubator at a controlled temperature of 25° C. overnight during which the protecting group of the linker of the TAGylated linker monoconjugate j2 (and the higher conjugates) was cleaved off generating j3.

About 110 mL of protein solution were removed from the 25° C. incubator and 0.419 vol. eq. (39.0 mL, based on the initial 93.1 mL protein volume) of 0.5 M succinic acid, pH 3.0 was added to the solution of j3 and higher conjugates to obtain a pH of approx. pH 4.0.

Example 5C

Isolation of G6.31 AARR Linker Monoconjugate

For CIEC (cation exchange chromatography) purification, the protein solution, containing a mixture of unconjugated G6.31 and a mixture of TAGylated G6.31 AARR-linker monoconjugate j3 and higher conjugates, was diluted 3.3 fold with 20 mM succinic acid, pH 4.0, to a final volume of about 500 mL. A GE Healthcare Source 15S column (column HiScale26, 9.8 cm height) was used with the following buffers: 20 mM succinic acid, pH 4.0 (buffer A); and 20 mM succinic acid, 1 M NaCl, pH 4.0 (buffer B). The gradient was linear, either 0%-50% B in 40 CV or 10%-50% B in 32 CV at 20 mL/min flow rate. The load was approximately 600 mg per run. The conjugate mixture was analyzed by MS prior to CIEC and in the deconvoluted MS spectrum, a peak at 47395 (native G6.31 AARR), a peak at 48584 (monoconjugate j3), a peak at 49782 (bisconjugate), a peak at 50986 (trisconjugate) and a peak at 52174 (tetraconjugate) were observed. All peaks of CIEC were collected. Fractions containing predominantly monoconjugate j3 were pooled (534.2 mL; 0.67 mg/mL) and used in the next step.

Example 5D

Purification Tag Cleavage

Scheme 5D

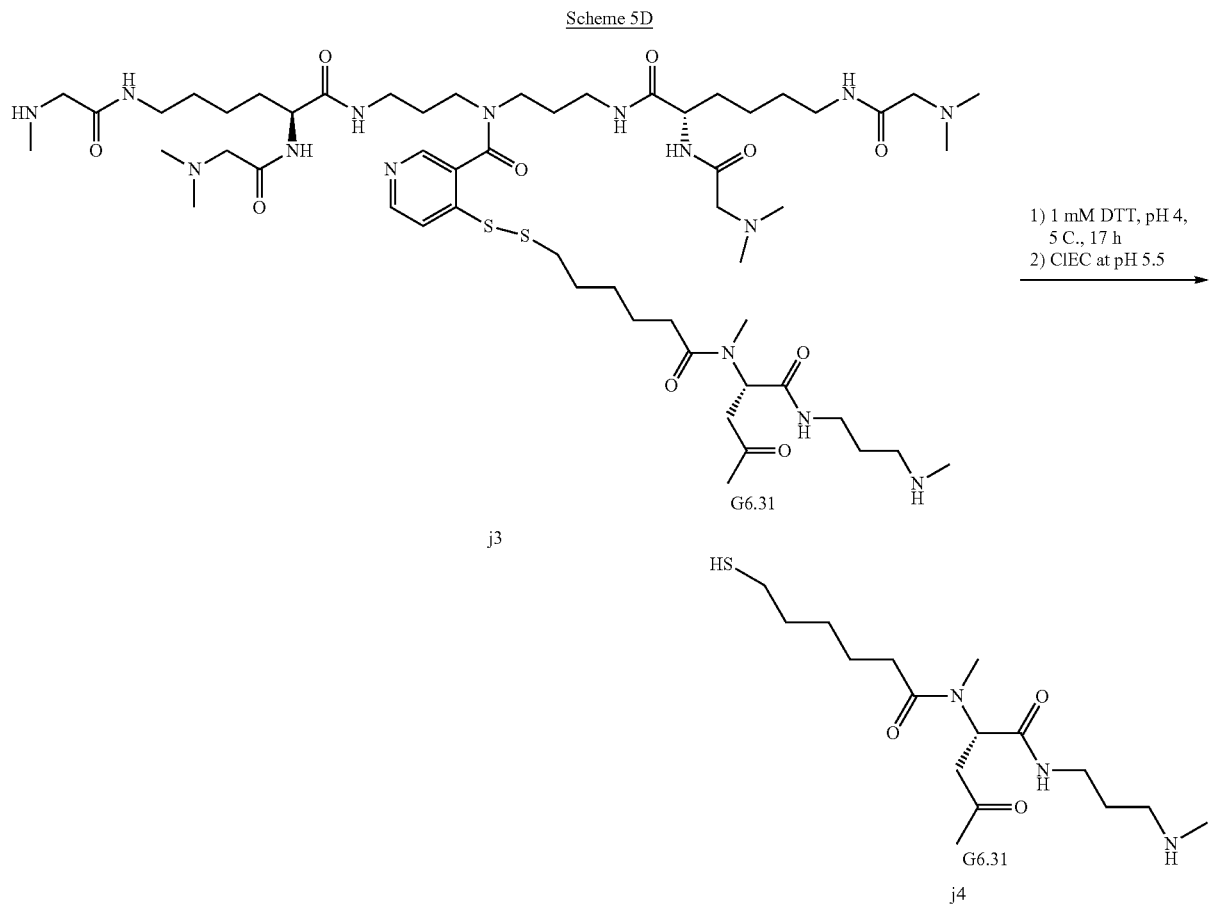

Purification tag e8 was removed by the procedure shown in Scheme 5D.

Cleavage of the purification tag e8 (detagylation) was obtained by incubation of isolated TAGylated G6.31AARR-linker monoconjugate j3 (534.2 ml, 0.67 mg/mL) in presence of DTT. A 25 mM DTT stock solution was prepared by dissolving 0.1364 g of DTT in 35.4 mL of 20 mM succinic acid pH 4.0. The G6.31-linker monoconjugate solution and the 25 mM DTT stock solution were cooled down to 4° C. 22.3 mL of the 25 mM DTT stock solution were added to the protein solution to give a final DTT concentration of 1 mM. The resulting solution was stored over night at a controlled temperature of 5° C. in an incubator. Purification tag removal was monitored by MS. Prior to cleavage a peak at 48585 was detected indicating TAGylated monoconjugate j3. After cleavage a peak at 47720 was detected confirming deTAGylation and generation of G6.31 AARR-linker monoconjugate j4.

The G6.31 AARR-linker monoconjugate j4 was purified by CIEC. 556.5 mL of G6.31-linker monoconjugate after DTT mediated deprotection were diluted 3-fold with 20 mM succinic acid pH 4.0 to a final volume of about 1660 mL. A GE Healthcare Source 15S HiScale26 column (9.8 cm height) was used. The buffer system was: 10 mM histidine, pH 5.5 (buffer A); 20 mM succinic acid, pH 4.0 (A2); and 10 mM histidine, 500 mM NaCl, pH 5.5 (buffer B). After column loading the column was washed with 2 CV of buffer A2 followed by a column wash with 2 CV A1. Subsequently, a linear gradient was applied: 0%-50% B, 25 CV (20 mL/min flow rate). The load was about 300 mg.

After the CIEC step, the osmolality of the protein solution was adjusted by further dilution using buffer B (10 mM histidine, 500 mM NaCl, pH 5.5) to give a NaCl concentration of about 150 mM. 130 mL of G6.31-linker monoconjugate were collected during the CIEC run. 28 mL of 10 mM histidine, 500 mM NaCl, pH 5.5 were added to the sample to give an overall volume of 158 mL of G6.31 AARR-linker monoconjugate j4.

Example 5E

G6.31 AARR-Linker Concentration

For preparation of HA-linker-G6.31 AARR k1 (Example 6A below) with a protein load of 40 mg/mL, the G6.31 AARR-linker monoconjugate j4 was concentrated to above 60 mg/mL. Four Amicon Ultra 15 PLCG Ultracel Membranes MWCO 10 kDa were used for concentration of the protein solution by centrifugation at 3000 g. About 3.9 g of solution of 66.31 AARR-linker monoconjugate j4 with a protein content of 76.5 mg/mL (298 mg) was obtained. The concentrated solution was analyzed by MS and a peak at 47723 was detected corresponding to G6.31-linker monoconjugate j4. The sample was diluted to 65 mg/mL by adding 689 μL of 10 mM histidine, 150 mM NaCl, pH 5.5.Example 6A: Conjugation of 66.31 AARR-linker monoconjugate j4 to maleimide functionalized HA The conjugation of G6.31 linker monoconjugate j4 to maleimide functionalized HA f5 to make linker-G6.31 AARR-HA conjugate k1 was carried out as shown in Scheme 6A.

Conjugation of G6.31-linker monoconjugate j4 to maleimide functionalized HA f5 (Example 2B) was performed by addition of concentrated solution of 66.31 linker monocon-

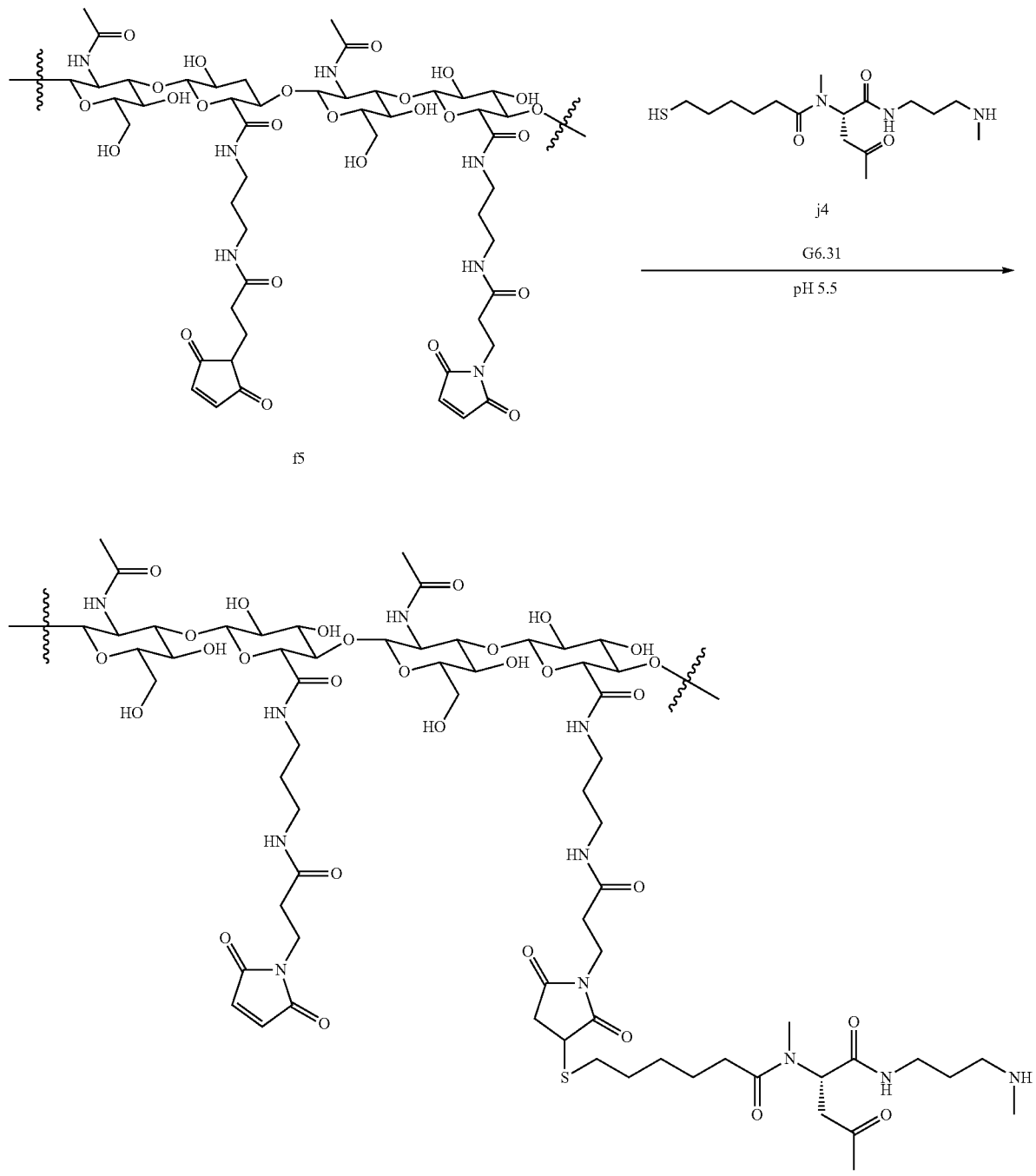

Scheme 6A jugate j4 to 1.3 eq. of maleimide functionalized HA f5 with respect to thiol content resulting in a protein (G6.31 AARR) concentration of 44 mg/mL (based on thiol content) and a HA content of about 0.49%. G6.31 AARR-linker monoconjugate j4 samples (protein solution of 64.7 mg/mL formulated in 10 mM histidine, 150 mM NaCl, pH 5.5) prepared according to Example 5D were allowed to warm up to ambient temperature. The samples were filtered via a GV Millex filter 33 mm with a pore size of 0.22 gm. The thiol content of the G6.31 linker monoconjugate j4 solution was determined to be 73.4 mg/mL. 2190 μL of the G6.31 linker monoconjugate j4 solution were transferred into a 50 mL Falcon tube. 735.5 p.L of 10 mM histidine, 150 mM NaCl, 0.01% Tween 20 pH 5.5 buffer were added. 115.3 μL of 10 mM histidine, 150 mM NaCl, 0.2% Tween 20 pH 5.5 were added. 612.5 μL of a sterile filtered (Millex GP, 25 mm diameter, 0.22 gm) HA-maleimide f5 solution (30 mg/mL content of a 116 kDa HA with a maleimide content of 0.24 mmol/g) were added. The resulting solution was mixed well and allowed to incubate for 4 hours at ambient temperature. After 4 hours reaction time, a sample of 25 μL was withdrawn and analyzed via SEC. 95% of the 66.31 AARR-linker monoconjugate j4 were conjugated to the maleimide functionalized HA f5 to provide linker-G6.31 AARR-HA conjugate k1.

Example 6B

Thiol-Maleimide Cross-Linking to Form Linker-G6.31 AARR Cross-Linked HA Gels The cross-linking of thiol HA f6 and linker-G6.31 AARR-HA conjugate k1 to afford linker-G6.31 AARR cross-linked HA hydrogel k2 was performed according to Scheme 6B:

Scheme 6B 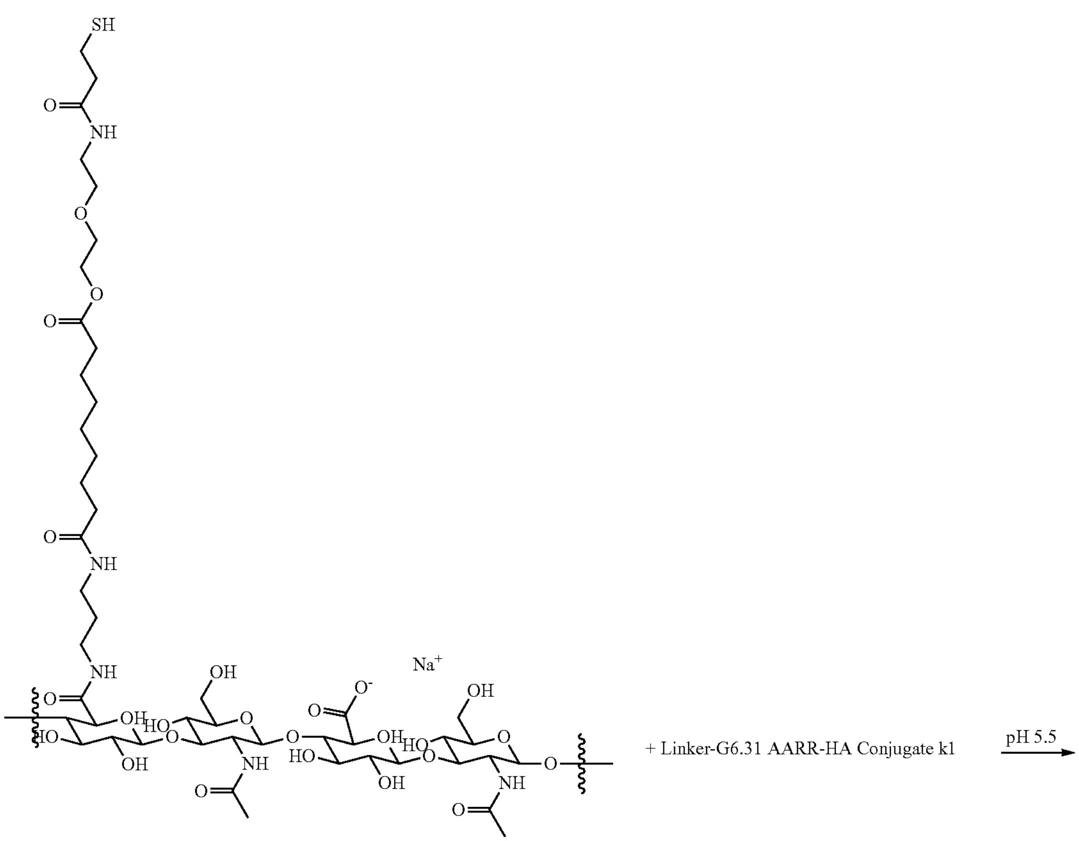 f6

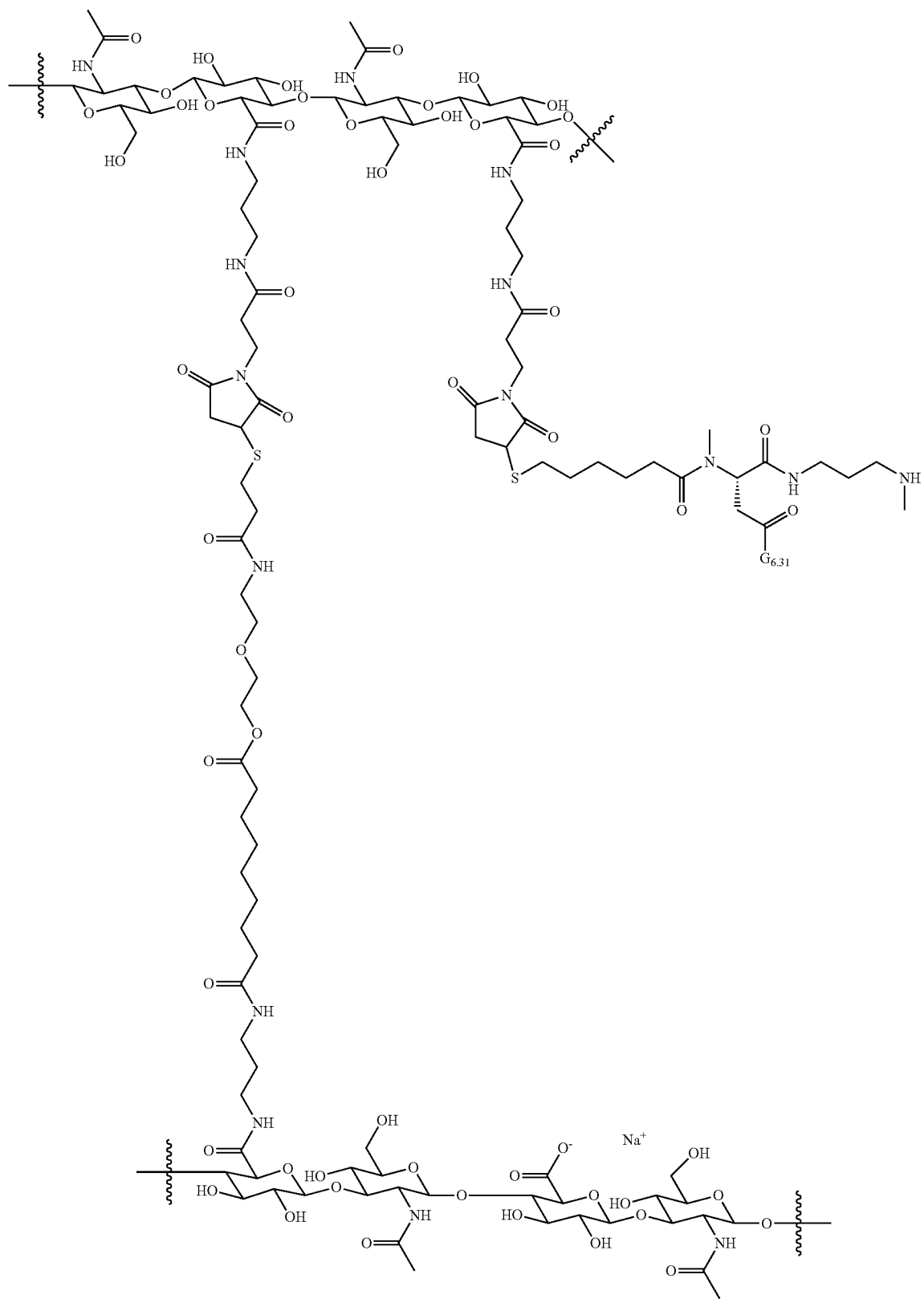

After 3628 µL of the linker-G6.31 HA- conjugate k1 were incubated for 4 hours. 363 µL of a sterile filtered (Millex GP, 25 mm diameter, 0.22 gm) HA-thiol f6 (Example 2C) solution (28.4 mg/mL content of a 116 kDa HA with a thiol content of 0.098 mmol/g) was added, resulting in a final protein content of 40 mg/mL (based on thiol content) and a final HA content of 7.16 mg/mL in the resulting solution. The solution was mixed well and drawn into a 5 mL syringe equipped with an 18 G blunt cannula. The solution was quickly filled into eighteen 1 mL Luer Lock syringes using the syringe tip for filling. A screw cap was mounted on the syringes and they were allowed to incubate for about 24 h in an upright position at ambient temperature. The syringes were subsequently incubated at 5° C. for three weeks. The cross-linking reaction was completed in the syringes to yield cross-linked HA gel G6.31 conjugate k2.

Example 6C

Release of G6.31 AARR from Cross-Linked HA G6.31 Gel

The release of G6.31 AARR from cross-linked HA G6.31 AARR gel k2was analyzed in vitro using the material from example 6B. 11-16 mg of G6.31 HA gel were transferred into a sterile, pyrogen free Eppendorf tube. Release buffer (60 mM sodium phosphate, 3 mM EDTA, 0.01% Tween, pH 7.4) was added according to a ratio of 975 μL buffer for 25 mg of HA. Tubes were not inverted or shaken. All tubes were stored at a controlled temperature of 37° C. in an incubator. At different time points, a tube was removed from the incubator and centrifuged (9300 rcf, 3 min). The supernatant was transferred into a new Eppendorf tube and the protein concentration of the supernatant was determined by absorbance measurement at 280 nm with a reference wavelength of 338 nm using the extinction coefficient of G6.31 of 1.38 mL/cm·mg. For each sample the release in % was calculated using the transferred mass and the protein content of the gel (Table 6C).

TABLE 6C

| G6.31 Release | |
|---|---|
| Time/d | Release/% |
| 7 | 14.67 |
| 14 | 21.08 |
| 21 | 27.58 |
| 33 | 35.79 |
| 62 | 53.98 |

TABLE 6C-continued

| G6.31 Release | |
|---|---|
| Time/d | Release/% |
| 70 | 58.42 |
| 125 | 75.87 |
| 186 | 93.18 |

Example 7A

Preparation of Cross-Linked HA RabFab Gel

Preparation of RabFab-linker conjugate was performed according to the procedures described in example 3A, 3B, 3C and 3D. Concentration of the RabFab-linker monoconjugate was performed according to the procedure described in Example 3E except that the conjugate was concentrated to a concentration of 46 mg/mL due to which the protein content within the final gel is approx. 30 mg/mL.

Conjugation of RabFab-linker conjugate to maleimide functionalized HA was performed according to the procedure described in Example 4A. 5502 μL of the RabFab-linker conjugate were mixed with 1804 μL of 10 mM histidine, 150 mM NaCl, 0.01% Tween 20 pH 5.5 buffer. 289 μL of 10 mM histidine, 150 mM NaCl, 0.2% Tween 20 pH 5.5 were added. 1124 μL of HA-maleimide f5 solution (30 mg/mL content of a 116 kDa HA with a maleimide content of 0.24 mmol/g) were added. The resulting solution was mixed well and allowed to incubate for 4 hours at ambient temperature.

Preparation of the cross-linked HA RabFab gel was obtained according to the procedure described in Example 4B. To 8691 μL of the RabFab-linker-HA conjugate 869 μL of HA-thiol f6 solution (22.6 mg/mL content of a 116 kDa HA with a thiol content of 0.096 mmol/g) was added. The solution was mixed well and drawn into a 10 mL syringe equipped with a 18 G blunt cannula. The solution was quickly filled into 48 1 mL Luer Lock syringes using the syringe tip for filling. A screw cap was mounted on the syringes and they were allowed to incubate for about 24 h in an upright position at ambient temperature. The syringes were subsequently incubated at 5° C. for three weeks. The cross-linking reaction was completed in the syringes to yield cross-linked HA gel RabFab conjugate ml.

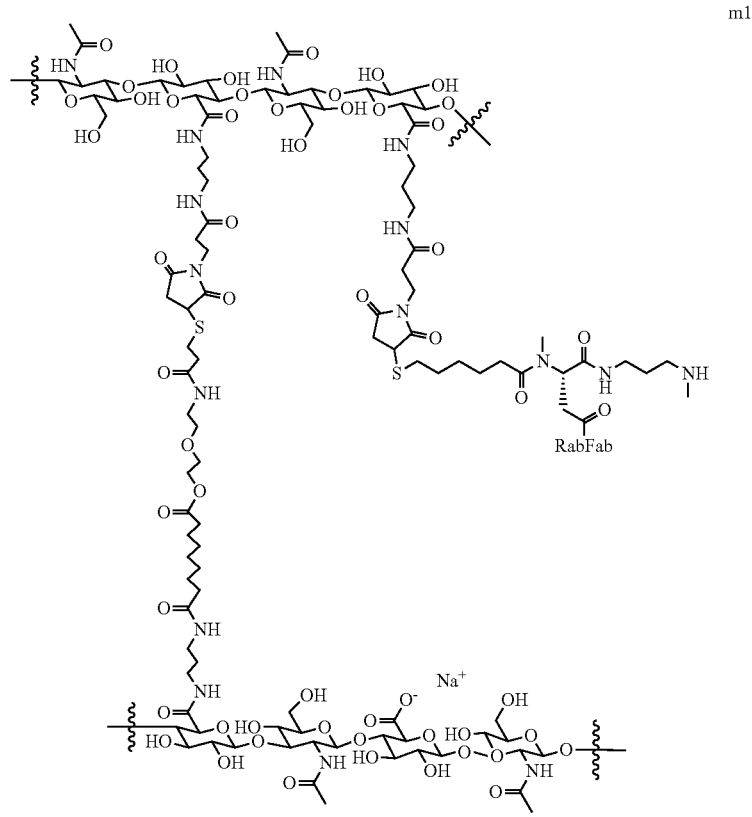

m1

Example 7B

Preparation of Carboxyfluorescein Labeled HA Placebo Gel

Preparation of amine functionalized HA was obtained according to the procedure described in Example 2A. To obtain the HA variant with a higher degree of amine functionalization, 1.00 g of 116 kDa HA were dissolved in 125 mL of 100 MES, 0.4 M 1,3-diaminopropane buffer pH 5.5 and 1.15 g (7.48 mmol) of HOBt and 444.6 mg (2.32 mmol) of EDC were used. Subsequent carboxyfluorescein and maleimide labelling was obtained by dissolving 463 mg of the above mentioned amine functionalized HA in 46 mL of 100 mM HEPES buffer pH 7.4 followed by addition of 1.5 mL of a 5(6)—Carboxyfluorescein N-succinimidyl ester solution (5.28 mg/mL in acetonitrile). After one hour incubation under stirring at ambient temperature, a freshly prepared solution of 396 mg of 3-maleimidopropionic acid NHS ester in 24 mL acetonitrile was added to the solution. After one additional hour of incubation under stirring at ambient temperature, the workup of the reaction mixture was performed according to the procedure described in Example 2B.

Preparation of carboxyfluorescein labeled HA gel was obtained according to the following procedure: 140.6 mg of the carboxyfluorescein labelled maleimide functionalized HA was dissolved in 6580 µL of 10 mM histidine, 150 mM NaCl, 0.01% Tween 20 pH 5.5 buffer. 82.8 mg of the thiol functionalized HA were dissolved in 2946 µL of 10 mM histidine, 150 mM NaCl, 0.01% Tween 20 pH 5.5 buffer. 57.6 mg of 2-mercaptoethanol were dissolved in 6216 µL of 10 mM histidine, 150 mM NaCl, 0.01% Tween 20 pH 5.5 buffer. 500 µL of this 2-mercaptoethanol solution were transferred into a new vial and diluted with 49.5 mL of 10 mM histidine, 150 mM NaCl, 0.01% Tween 20 pH 5.5 buffer. 121.5 mg of native 116 kDa HA were dissolved in 8433 µL of the diluted 2-mercaptoethanol solution. 8433 µL of this solution were transferred into a new vial and 2568 µL of the maleimide HA solution were added. The resulting solution was briefly shaken, centrifuged and allowed to incubate for 2 hours at ambient temperature. 10 mL of this solution were transferred into a new vial and 1 mL of the thiol HA solution was added. The solution was mixed well and drawn into a 10 mL syringe equipped with a 18 G blunt cannula. The solution was quickly filled into 34 1 mL Luer Lock syringes using the syringe tip for filling and applying a fill volume of approx. 300 µL per syringe. A screw cap was mounted on the syringes and they were allowed to incubate for about 24 h in an upright position at ambient temperature. The syringes were subsequently incubated at 5° C. for three weeks. The cross-linking reaction was completed in the syringes to yield cross-linked, carboxyfluorescein labelled HA placebo gel m2.

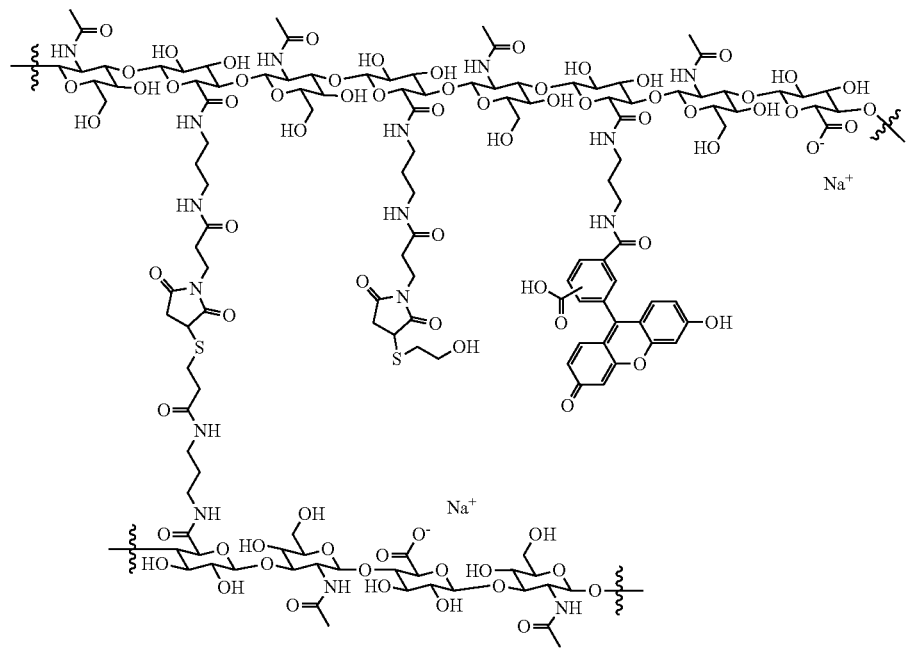

m2

Example 7C

In Vivo Release Kinetics from Cross-Linked HA RabFab Gels

The cross-linked HA RabFab gel was administered to naive New Zealand White (NZW) rabbits via a single bilateral intravitreal injection to the rabbits followed by up to 60 days of observation. Topical antibiotic (tobramicin ophthalmic ointment) was applied to both eyes twice on the day before treatment, immediately following the injection, and twice on the day following the injection, with the exception of animals sent to necropsy on Days 1 and 2. Prior to dosing, mydriatic drops (1% tropicamide) were applied to each eye for full pupil dilation. Animals were sedated with isoflurane/oxygen gas prior to and during the procedure. Alcaine (0.5%) was also applied to each eye prior to injection. The conjunctivae was flushed with benzalkonium chloride (Zephiran™) diluted in sterile water, U.S.P. to 1:10,000 (v/v).

The cross-linked HA RabFab gel was administered by a single 30 µL intravitreal injection (0.3 mg dose) to both eyes in all animals. Doses were administered by a board-certified veterinary ophthalmologist using 1 mL Luer Lock syringes with a 25-gauge×½" needle. In order to mimic clinical dosing, eyes were dosed in the infero-temporal quadrants, i.e. in 5 o'clock and 7 o'clock positions for the left and right eyes, respectively (when facing the animal). The eyes were examined by slit-lamp biomicroscopy and/or indirect ophthalmoscopy immediately following treatment.

All animals underwent exsanguination by incision of the axillary or femoral arteries following anesthesia by intravenous injection of sodium pentobarbital. Aqueous humor, vitreous humor and retina tissue were collected, snap frozen in liquid nitrogen and stored at −80° C. Determination of vitreous concentrations of test article was by antigen-binding ELISA. Values below the LLOQ were not used in pharmacokinetic analysis or for graphical or summary purposes.

The ELISA analysis was performed using a target-coat method. In this assay, the target-coat was phosphorylated cMet peptide conjugated to KLH (P-cMet peptide, from Yenzym, South San Francisco, Calif.). For preparation of assay plates, lyophilized P-cMet peptide was reconstituted with 300 µl of buffer and further diluted to 1:200 in 0.05M sodium bicarbonate buffer. The diluted P-cMet peptide (100 pi/well) was added to a 96 well microtiter plate (Nunc, Thermo Scientific, Rockford, Ill.) and incubated overnight at 2-8° C. After incubation the plate was washed three times with 400 µl of wash buffer (BA029), followed by blocking, with assay diluent (wash buffer containing 0.5% bovine serum albumin and 0.05% Proclin). The standard curve was prepared by diluting Rabbit Fab (Genentech, South San Francisco, Calif.) to 200 ng/ml and then 1:2 serial dilution in assay diluent. The controls were diluted 1:100 in assay diluent. Each sample was diluted to the quantitative range of assay using assay diluent. All samples, controls and standards were added to the plate at 100 µl and incubated at room temperature for 2 hrs. with gentle agitation. After incubation and washing, 100 µl of the detection antibody (mouse anti-rabbit light chain-HRP, SouthernBiotech, Birmingham, Ala.) was added per well, after a 1/4,000 dilution in assay diluent. Plates were then incubated for 1 hr. at room temperature with gentle agitation. After additional washing, 100 µl of HRP substrate (3,3',5,5'-tetramethylbenzidine, TMB, from Kirkegard & Perry Laboratory, Gaithersburg, Md.) was added to each well, followed by 15 min incubation at room temperature with gentle agitation. The reaction was stopped with 100 µl of 1M phosphoric acid. The plate was read at 450 nm for detection and 630 nm for reference wavelength (SpectraMax 384-plus; Molecular Devices, Sunnyvale, Calif.). The optical density values of the standards were plotted using a four-parameter logistic curve-fitting software (Softmax, Molecular Devices), from which concentration values for controls and test samples were derived by extrapolation.

Figure 12:
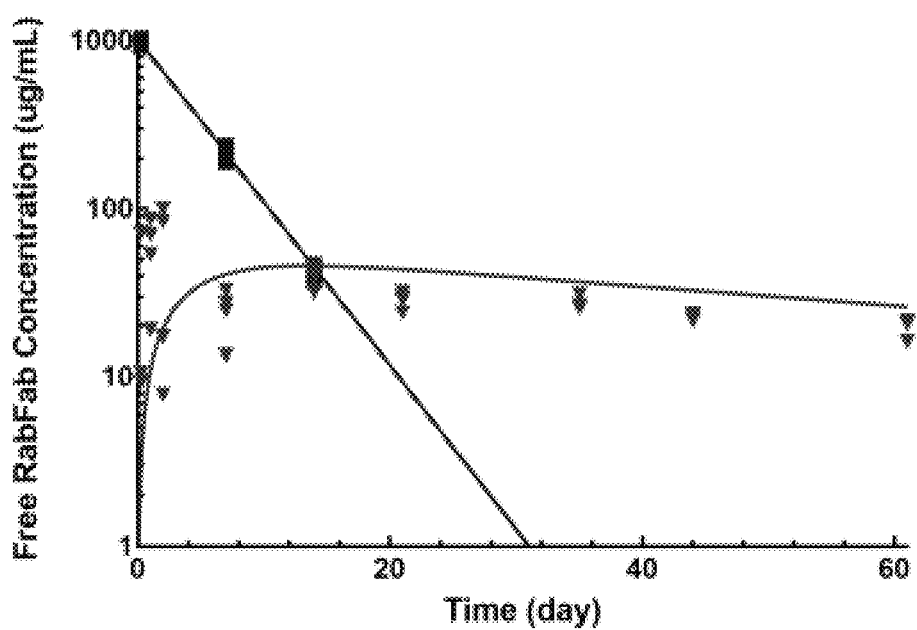
FIG. 12 shows RabFab vitreal PK following release from cross-linked HA RabFab in NZW Rabbits (red points and line) compared to that of free RabFab (blue points and line).

Concentrations in the vitreous were determined by antigen-binding ELISA as described above and plotted as a function of time. Figure. 12 shows a graph summarizing the vitreal concentrations as a function of time post-injection. The free RabFab following IVT administration at presented in blue, while that from release from the cross-linked-HA are presented in red. The points are the individual observed data while the lines are model predictions of the expected vitreal concentrations based on known PK parameters for free Fab in the vitreous, the in vitro release of the reversible prodrug linker, and the pH and temperature of the rabbit vitreous. These data were subjected to a non-compartmental analysis to obtain pharmacokinetic (PK) parameters.

The pharmacokinetic parameters were determined by non-compartmental analysis with nominal time and dose (Phoenix WinNonlin, Pharsight Corp, Mountain View, Calif.). PK parameters calculated using a non-compartmental analysis are summarized in Table 2.

TABLE 1

PK parameter estimates from the NZW Rabbit PK Study

|  | Cmax (ug/mL) | AUCall (day*ug/mL) | CL (mL/day) | Vss (mL) |
|---|---|---|---|---|
| Vitreous | 1030 | 5360 | 0.271 | 0.812 |
| Aqueous | 4.50 | 148 | 5.16 | 403 |
| Serum | 0.147 | 2.32 | 1260 | 19000 |

RabFab vitreal PK following release from cross-linked HA RabFab in NZW Rabbits is consistent with predictions based on in vitro release. Initial higher concentrations are due to the dose solution containing ~3.6% Free Fab and ~4.9% Free Fab-HA species. Release half-life in rabbit vitreous fluid is estimated to be 53 days.

The terminal half-life of free Fab in vitreous is equal to the half-life of the reversible prodrug linker. This means that once dynamics of drug release from HA and subsequent elimination from vitreous reach equilibrium, the effective elimination half-life of active drug in vitreous will be 53/3.2=16.5 times longer compared to that typically observed following an IVT injection of free Fab.

Example 5E

Absence of Significant Fragmentation or Particle Movement in NHP Eye

Two cynomolgus monkeys were administered bilaterally a single ITV administration of placebo cross-linked HA gel-Fluorescein (50 uL/eye) in the inferior temporal quadrant. The animals were observed for 30 days for clinical observations, body weight changes, food consumption and ocular observations (IOP, biomicroscopic (slit lamp) and funduscopic examinations. In addition the location and cohesiveness of the material was monitored over the same period using gonioscopy, gonioimaging, fundus imaging using a confocal scanning laser ophthalmoscope and fluorometry using a Fluoroton.

Figure 13A:
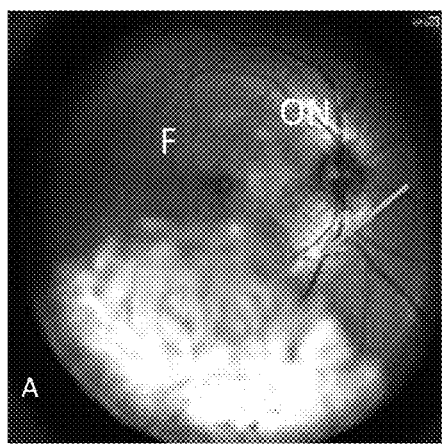
FIGS. 13A and 13B are illustrations showing minimal fragmentation and particle movement of cross-linked HA hydrogel placebo in NHP eye.
Figure 13B:
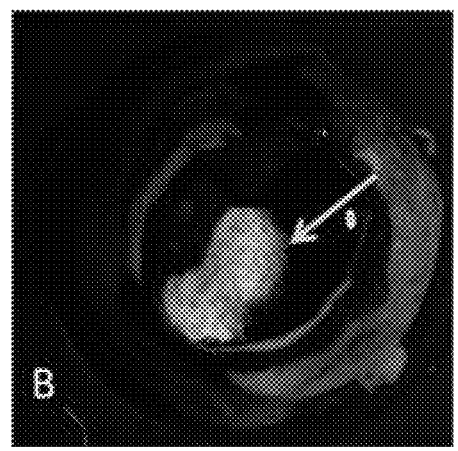

FIG. 13A is a representative cSLO image taken at day 15. The TA (arrow) remains in the inferior vitreous and does not obscure the fovea (F) or optic disc (ON). FIG. 13B is an image taken at necropsy with cobalt blue light following removal of the anterior segment and lens. Note the TA (arrow) remains cohesive. As can be seen, the placebo cross-linked HA gel m2 showed minimal fragmentation and movement after 30 days.

Example 7F

Cross-Linked HA RabFab Gel Tolerability Study in Rabbit

Figure 14:
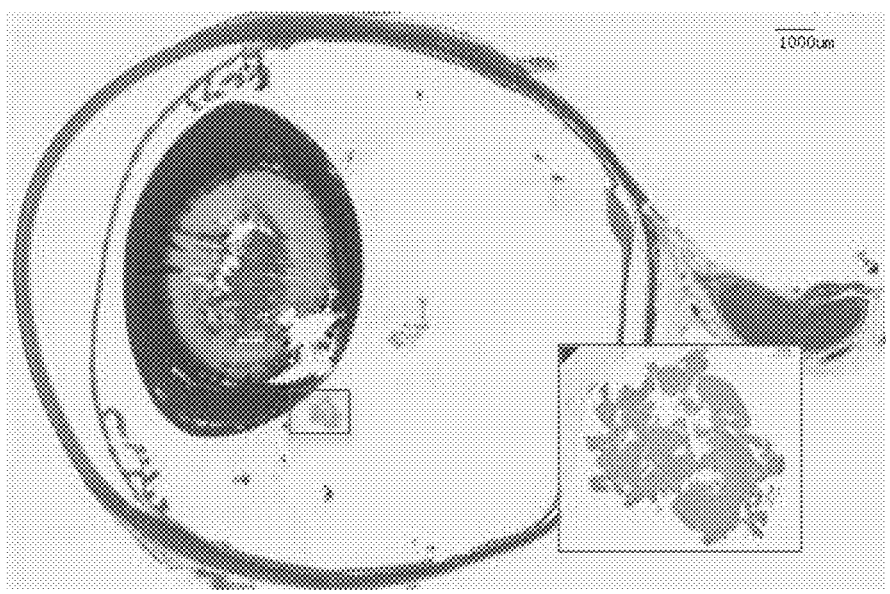
FIG. 14 illustrates tolerability in rabbit eye of cross-linked HA hydrogel Rabfab conjugate.

Three New Zealand White rabbits were administered bilaterally a single ITV administration of cross-linked -HA-RabFab gel (50 µL/eye) in the inferior temporal quadrant. The animals were observed for 60 days for clinical observations, body weight changes, food consumption and ocular observations (IOP, biomicroscopic (slit lamp) and funduscopic examinations). Serum samples were taken for ADA and TK. At necropsy, the eyes were removed and processed for histopathology. FIG. 14 shows a histology section. As can be seen, cross-linked -HA-RabFab gel was well tolerated in a 2-month study. No cellular infiltrate, no inflammatory reaction, and no foreign body reaction were observed (6 eyes).

Example 7G

Cross-Linked HA G6.31 AARR Gel Tolerability Study in Cynomolgus Macaques

Two cynomolgus macaques were administered bilaterally a single ITV injection of cross-linked HA gel conjugated to the anti-VEGF Fab, 66.31 AARR (50 µL/ eye; 1.92 mg Fab/eye) in the inferior temporal quadrant. The animals were observed for 3 months (92 days) for clinical observations, body weight changes, food consumption, and ocular observations (IOP, biomicroscopic (slit lamp) and funduscopic examinations). The location and cohesiveness of the material was monitored over the same period using gonioscopy and gonioimaging Serum samples were taken for ADA and TK assessment and eyes were assessed by histopathology at 3 months.

Figure 15:
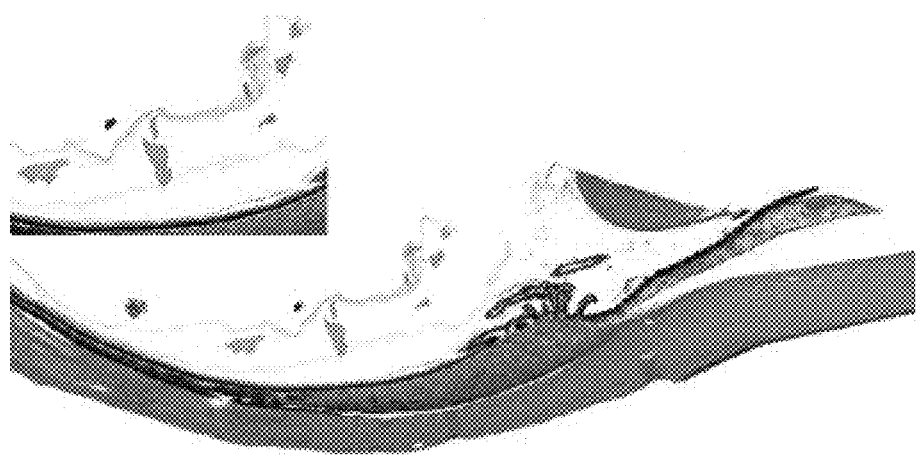
FIG. 15 illustrates tolerability in cymolgus macaque eye of cross-linked HA G6.3.1 AAR conjugate.

The hydrogel remained cohesive and in the inferior vitreous throughout the period of assessment. No significant in-life inflammation was noted despite the induction of ADA in both animals by day 28. There were no test article related changes in clinical observation, qualitative food consumption, and body weights. FIG. 15 shows a superoinferior histology section of the inferior calotte of the eye that contains the test article. As can be seen cross-linked-HA-G6.31 AARR gel was well tolerated in a 3-month study. No cellular infiltrate, no inflammatory reaction, and no foreign body reaction were observed (4 eyes).

Compared to PEG-based particulate hydrogel conjugated to ranibizumab, cross-linked-HA-G6.31 AARR gel displays a superior safety profile. When injected into the inferior vitreous cavity, cross-linked-HA-G6.31 AARR gel does not move and remains below the visual axis and thus is not expected to interfere with patient vision. Conversely, PEG-based particulate hydrogels moved freely within the vitreous cavity.

Cross-linked-HA-G6.31 AARR gel remains cohesive and does not form significant numbers of free particulate-like fragments thus limiting the risk of blockage of the outflow. A fraction of the PEG-based particulate hydrogel. was observed in the anterior chamber of cyaomolgus monkey eyes.

Example 8

Exemplary Optimized Anti-VEGF Antibodies for Use in the Antibody Conjugates of the Invention Any of the optimized anti-VEGF antibodies described in this Example can be used to prepare antibody conjugates as described in Examples 3A through 4D above]. For example, any optimized anti-VEGF antibody described in International Patent Application No. PCT/US2016/053454 can be used. Table 3 describes exemplary optimized anti-VEGF antibodies that can be used, as well as the amino acid sequences of the VH and VL domains for each antibody. Table 4 describes the VL HVR amino acid sequences for the anti-VEGF antibodies described in Table 3. Table 5 describes the VH HVR amino acid sequences for the anti-VEGF antibodies described in Table 3. In particular embodiments, the anti-VEGF antibody G6.31 AARR (also referred to herein as "G6.31.AARR") is used.

TABLE 3

VH and VL amino acid sequences for exemplary anti-VEGF antibodies

| Antibody Name | Variant VH (SEQ ID NO) | Variant VL (SEQ ID NO) |
|---|---|---|
| G6.31 WT | G6.31 WT (SEQ ID NO: 42) | G6.31 WT (SEQ ID NO: 38) |
| LC-N94A | G6.31 WT (SEQ ID NO: 42) | N94A (SEQ ID NO: 41) |
| LC-N94A.LC-F83A | G6.31 WT (SEQ ID NO: 42) | N94A.F83A (SEQ ID NO: 12) |
| LC-N94A.LC-F83A.HC-A40E.HC-T57E (G6.31 AAEE) | A40E.T57E (SEQ ID NO: 40) | N94A.F83A (SEQ ID NO: 12) |
| N94A.F83A.N82aR.Y58R (G6.31 AARR) | N82aR.Y58R (SEQ ID NO: 11) | N94A.F83A (SEQ ID NO: 12) |
| HCcombo | HCcombo (SEQ ID NO: 33) | G6.31 WT (SEQ ID NO: 38) |
| HCLC2 | HCcombo (SEQ ID NO: 33) | LCcombo2 (SEQ ID NO: 35) |
| HCLC4 | HCcombo (SEQ ID NO: 33) | LCcombo4 (SEQ ID NO: 37) |
| HCLC5 | HCcombo (SEQ ID NO: 33) | N94A.F83A (SEQ ID NO: 12) |
| HCLC3 | HCcombo (SEQ ID NO: 33) | LCcombo3 (SEQ ID NO: 36) |
| HCLC1 | HCcombo (SEQ ID NO: 33) | LCcombo1 (SEQ ID NO: 34) |
| R19HCcombo | R19HCcombo (SEQ ID NO: 51) | G6.31 WT (SEQ ID NO: 38) |
| R19HCLC2 | R19HCcombo (SEQ ID NO: 51) | LCcombo2 (SEQ ID NO: 35) |
| R19HCLC4 | R19HCcombo (SEQ ID NO: 51) | LCcombo4 (SEQ ID NO: 37) |
| R19HCLC5 | R19HCcombo (SEQ ID NO: 51) | N94A.F83A (SEQ ID NO: 12) |

TABLE 4

VL HVR Sequences for Antibodies from Table 3

| Antibody Name | HVR-L1 | HVR-L2 | HVR-L3 |
|---|---|---|---|
| G6.31 WT | RASQDVSTAVA (SEQ ID NO: 8) | SASFLYS (SEQ ID NO: 9) | QQGYGNPFT (SEQ ID NO: 23) |
| LC-N94A | RASQDVSTAVA (SEQ ID NO: 8) | SASFLYS (SEQ ID NO: 9) | QQGYGAPFT (SEQ ID NO: 10) |
| LC-N94A.LC-F83A | RASQDVSTAVA (SEQ ID NO: 8) | SASFLYS (SEQ ID NO: 9) | QQGYGAPFT (SEQ ID NO: 10) |
| LC-N94A.LC-F83A.HC-A40E.HC-T57E (G6.31 AAEE) | RASQDVSTAVA (SEQ ID NO: 8) | SASFLYS (SEQ ID NO: 9) | QQGYGAPFT (SEQ ID NO: 10) |
| N94A.F83A.N82aR.Y58R (G6.31 AARR) | RASQDVSTAVA (SEQ ID NO: 8) | SASFLYS (SEQ ID NO: 9) | QQGYGAPFT (SEQ ID NO: 10) |
| HCcombo | RASQDVSTAVA (SEQ ID NO: 8) | SASFLYS (SEQ ID NO: 9) | QQGYGNPFT (SEQ ID NO: 23) |
| HCLC2 | RASQDVSTAVA (SEQ ID NO: 8) | SASFLYS (SEQ ID NO: 9) | QQGYGAPFT (SEQ ID NO: 10) |
| HCLC4 | RASQDVSTAVA (SEQ ID NO: 8) | SASFLYS (SEQ ID NO: 9) | QQGYGAPFT (SEQ ID NO: 10) |
| HCLC5 | RASQDVSTAVA (SEQ ID NO: 8) | SASFLYS (SEQ ID NO: 9) | QQGYGAPFT (SEQ ID NO: 10) |
| HCLC3 | RASQDVSTAVA (SEQ ID NO: 8) | SASFLYS (SEQ ID NO: 9) | QQGYGAPFT (SEQ ID NO: 10) |
| HCLC1 | RASQDVSTAVA (SEQ ID NO: 8) | SASFLYS (SEQ ID NO: 9) | QQGYGAPFT (SEQ ID NO: 10) |
| R19HCcombo | RASQDVSTAVA (SEQ ID NO: 8) | SASFLYS (SEQ ID NO: 9) | QQGYGNPFT (SEQ ID NO: 23) |
| R19HCLC2 | RASQDVSTAVA (SEQ ID NO: 8) | SASFLYS (SEQ ID NO: 9) | QQGYGAPFT (SEQ ID NO: 10) |
| R19HCLC4 | RASQDVSTAVA (SEQ ID NO: 8) | SASFLYS (SEQ ID NO: 9) | QQGYGAPFT (SEQ ID NO: 10) |
| R19HCLC5 | RASQDVSTAVA (SEQ ID NO: 8) | SASFLYS (SEQ ID NO: 9) | QQGYGAPFT (SEQ ID NO: 10) |

TABLE 5

VH HVR Sequences for Antibodies from Table 3

| Antibody Name | HVR-H1 | HVR-H2 | HVR-H3 |
|---|---|---|---|
| G6.31 WT | DYWIH (SEQ ID NO: 1) | GITPAGGYTYY ADSVKG (SEQ ID NO: 53) | FVFFLPYAMDY (SEQ ID NO: 3) |
| LC-N94A | DYWIH (SEQ ID NO: 1) | GITPAGGYTYY ADSVKG (SEQ ID NO: 53) | FVFFLPYAMDY (SEQ ID NO: 3) |
| LC-N94A.LC-F83A | DYWIH (SEQ ID NO: 1) | GITPAGGYTYY ADSVKG (SEQ ID NO: 53) | FVFFLPYAMDY (SEQ ID NO: 3) |
| LC-N94A.LC-F83A.HC-A40E.HC-T57E (G6.31 AAEE) | DYWIH (SEQ ID NO: 1) | GITPAGGYEYY ADSVKG (SEQ ID NO: 21) | FVFFLPYAMDY (SEQ ID NO: 3) |
| N94A.F83A.N82aR.Y58R (G6.31 AARR) | DYWIH (SEQ ID NO: 1) | GITPAGGYTRY ADSVKG (SEQ ID NO: 7) | FVFFLPYAMDY (SEQ ID NO: 3) |
| HCcombo | DYWIH (SEQ ID NO: 1) | GITPAGGYEYY ADSVEG (SEQ ID NO: 22) | FVFFLPYAMDY (SEQ ID NO: 3) |
| HCLC2 | DYWIH (SEQ ID NO: 1) | GITPAGGYEYY ADSVEG (SEQ ID NO: 22) | FVFFLPYAMDY (SEQ ID NO: 3) |
| HCLC4 | DYWIH (SEQ ID NO: 1) | GITPAGGYEYY ADSVEG (SEQ ID NO: 22) | FVFFLPYAMDY (SEQ ID NO: 3) |
| HCLC5 | DYWIH (SEQ ID NO: 1) | GITPAGGYEYY ADSVEG (SEQ ID NO: 22) | FVFFLPYAMDY (SEQ ID NO: 3) |
| HCLC3 | DYWIH (SEQ ID NO: 1) | GITPAGGYEYY ADSVEG (SEQ ID NO: 22) | FVFFLPYAMDY (SEQ ID NO: 3) |
| HCLC1 | DYWIH (SEQ ID NO: 1) | GITPAGGYEYY ADSVEG (SEQ ID NO: 22) | FVFFLPYAMDY (SEQ ID NO: 3) |
| R19HCcombo | DYWIH (SEQ ID NO: 1) | GITPAGGYEYY ADSVEG (SEQ ID NO: 22) | FVFFLPYAMDY (SEQ ID NO: 3) |
| R19HCLC2 | DYWIH (SEQ ID NO: 1) | GITPAGGYEYY ADSVEG (SEQ ID NO: 22) | FVFFLPYAMDY (SEQ ID NO: 3) |
| R19HCLC4 | DYWIH (SEQ ID NO: 1) | GITPAGGYEYY ADSVEG (SEQ ID NO: 22) | FVFFLPYAMDY (SEQ ID NO: 3) |
| R19HCLC5 | DYWIH (SEQ ID NO: 1) | GITPAGGYEYY ADSVEG (SEQ ID NO: 22) | FVFFLPYAMDY (SEQ ID NO: 3) |

The upper hinge region of the Fab heavy chain of any of the antibodies listed above, for example, G6.31 AARR, can be mutated to remove reactivity to anti-IgG1 hinge autoantibodies that has been reported in the literature. See, e.g., Brerski et al., *J. Immunol.* 181:3183-3192, 2008 and Brerski et al., *mAbs* 2:3, 212-220, 2010. Thus, the C-terminal amino acid of G6.31 AARR heavy chain can be either a T (wild-type (WT) version) or L (variant version that lacks reactivity to anti-human IgG Fab). The full-length heavy chain amino acid sequence of wild-type G6.31 AARR is SEQ ID NO: 48. The full-length heavy chain amino acid sequence of the variant version that lacks reactivity to anti-human IgG Fab is SEQ ID NO: 49. The full-length light chain amino acid sequence for both G6.31 AARR and the variant version that lacks reactivity to anti-human IgG Fab is SEQ ID NO: 50.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cross-linked hyaluronic acid (HA)-drug hydrogel conjugate comprising a plurality of hyaluronic acid polymers 2A and a plurality of hyaluronic acid polymers 2B, wherein:

each 2A comprises a plurality of linearly connected units, the units consisting essentially of:

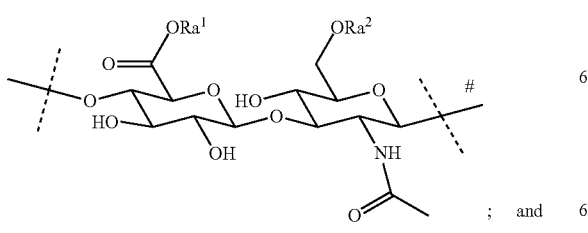

; and

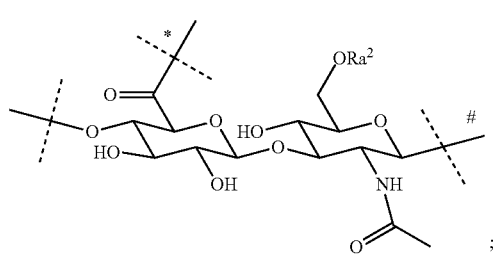

;

each 2B comprises a plurality of linearly connected units, the units consisting essentially of:

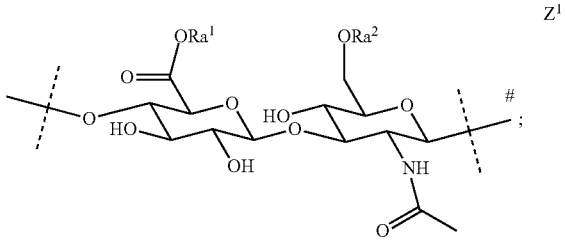

;

-continued $Z^2$

[chemical structure showing Drug-L² attached via L⁴ to a disaccharide unit with ORa² and NH-acetyl groups]

; and $Z^4$

[chemical structure showing * attached via L⁴ to a disaccharide unit with ORa² and NH-acetyl groups]

;

wherein
  an unmarked dashed line indicates a point of attachment to an adjacent unit at a dashed line marked with #, or to a hydrogen within each 2A or 2B polymer,
  a dashed line marked with # indicates a point of attachment to an adjacent unit at an unmarked dashed line, or to a hydroxyl within each 2A or 2B polymer; and
  a dashed line marked with * indicates a point of cross-linking attachment via thiol-maleimide chemistry between a unit ($Z^3$) of 2A and a unit ($Z^4$) of 2B, such that at least one 2A is cross-linked to at least one 2B;
  Drug is a therapeutic agent;
  $Ra^1$ and $Ra^2$ are each independently hydrogen; $C_{1-4}$ alkyl; an alkali metal ion, an ammonium ion, or an alkaline earth metal ion;
  $L^2$ is a reversible prodrug linker;
  $L^4$ is a single chemical bond or a biodegradable spacer and is the same or different in ($Z^2$) and ($Z^4$);
  2A comprises a total of s units wherein s is from 25 to 2500, wherein;
    the number of ($Z^1$) units in 2A is from about 0.8s to about 0.99s, and
    the number of ($Z^3$) units is from about 0.1s to about 0.01s;
  2B comprises a total of t units wherein t is from 25 to 2500, wherein;
    the number of ($Z^1$) units in 2B is from about 0.75t to about 0.94t;
    the combined number of ($Z^2$) and ($Z^4$) units consists of about 0.14t to about 0.06t;
  the number of ($Z^2$) units is at least 0.01t; and
  the number of ($Z^4$) units is at least 0.01t; and
  wherein Drug is only coupled to polymer 2B.

2. The hydrogel conjugate of claim 1, wherein the reversible prodrug linker $L^2$ coupling the drug to spacer $L^4$ has formula (XIIa):

XIIa

[chemical structure of formula XIIa]

wherein:
  the dashed line indicates the attachment to a nitrogen of a drug compound by forming an amide bond;
  —X— is —C($R^4R^{4a}$)—; —N($R^4$)—; —O—; —C($R^4R^{4a}$)—C($R^5R^{5a}$)—; —C($R^5R^{5a}$)—C($R^4R^{4a}$)—; —C($R^4R^{4a}$)—N($R^6$)—; —N($R^6$)—C($R^4R^{4a}$)—; —C($R^4R^{4a}$)—O—; —O—C($R^4R^{4a}$)—; or —C($R^7R^{7a}$)—;
  $X^1$ is C; or S(O);
  —$X^2$— is —C($R^8R^{8a}$)—; or —C($R^8R^{8a}$)—C($R^9R^{9a}$)—;
  =$X^3$ is =O; =S; or =N—CN;
  —$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H; and $C_{1-6}$ alkyl;
  —$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;
  —$R^7$ is —N($R^{10}R^{10a}$); or —$NR^{10}$—(C=O)—$R^{11}$;
  —$R^{7a}$, —$R^{10}$, —$R^{11}$ are independently —H; or $C_{1-10}$ alkyl;
  optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/—$R^{9a}$ form a chemical bond;
  optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;
  optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring A;
  optionally, $R^3$/$R^{3a}$ are joined together with the nitrogen atom to which they are attached to form a 3- to 10-membered heterocycle;
  Ring A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and
  wherein a free group of formula (XIIa) is linked to -$L^4$ provided that the hydrogen marked with the asterisk in formula (XIIa) is not replaced by -$L^4$ or other substituent;
  wherein -$L^4$- is a single chemical bond or a spacer moiety as defined in claim 1.

3. The hydrogel conjugate of claim 2, wherein:
  $X^3$ is =O;
  —$R^1$ and —$R^{1a}$ are each hydrogen;
  —$R^3$ is methyl and $R^{3a}$ is hydrogen; and
  X is —C($R^7R^{7a}$)—; with $R^7$ being $NR^{10}$—(C=O)—$R^{11}$.

4. The hydrogel conjugate of claim 1, wherein the reversible prodrug linker $L^2$ has the formula (VIIa):

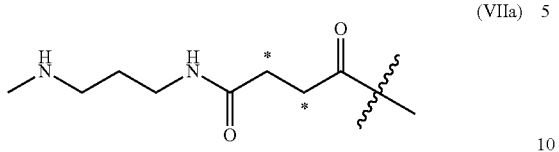
(VIIa)

wherein:
each asterisk is an independent site of attachment to the spacer $L^4$.

5. The hydrogel conjugate of claim 1, wherein the reversible prodrug linker $L^2$ together with spacer $L^4$ has the formula (VIIc):

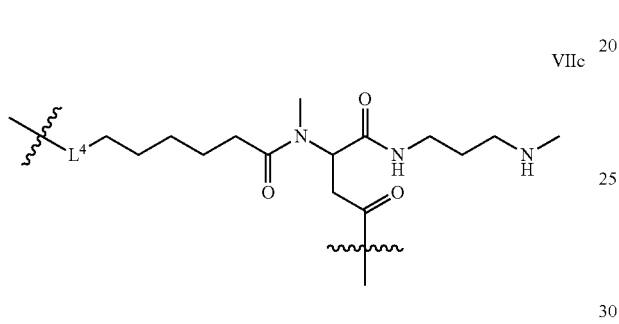
VIIc wherein:
the right-most wavy line is the point of attachment to the nitrogen atom of Drug; and
the left-most wavy line is the point of attachment to a unit ($Z^2$) of hyaluronic acid 2B.

6. The hydrogel conjugate of claim 1, wherein:
the spacer $L^4$ connecting hyaluronic acid polymer 2A to hyaluronic acid polymer 2B has the formula:

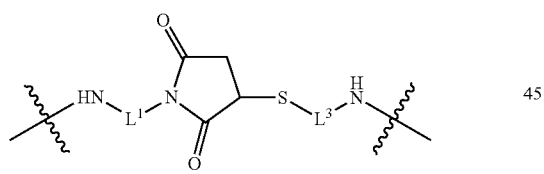

wherein:
the right-most wavy line is the point of attachment to a unit ($Z^3$) on hyaluronic acid polymer 2A; and
the left-most wavy line is the point of attachment to a unit ($Z^4$) on hyaluronic acid polymer 2B;
the spacer $L^4$ joining reversible prodrug linker $L^2$ to hyaluronic acid polymer 2B has the formula

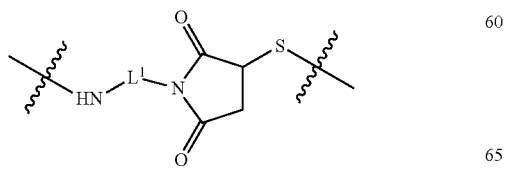

wherein:
the right-most wavy line is the point of attachment to $L^2$; and
the left-most wavy line is the point of attachment to a unit ($Z^2$) on hyaluronic acid polymer 2B;
wherein:
$L^1$ is a spacer; and
$L^3$ is a biodegradable spacer.

7. The hydrogel conjugate of claim 1, wherein:
unit ($Z^4$) is

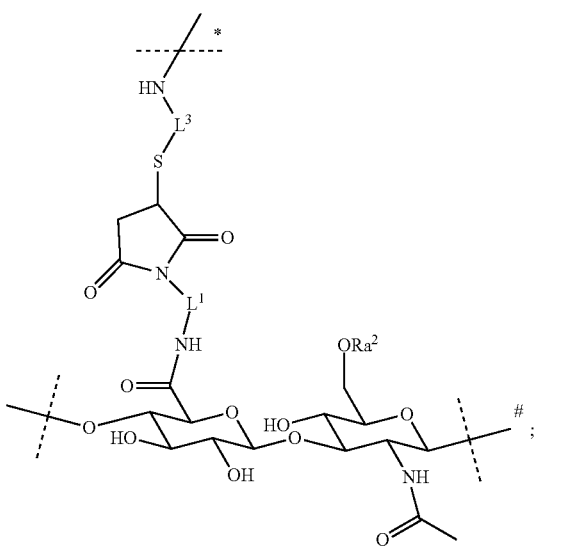
$Z^4$ and
unit ($Z^2$) is

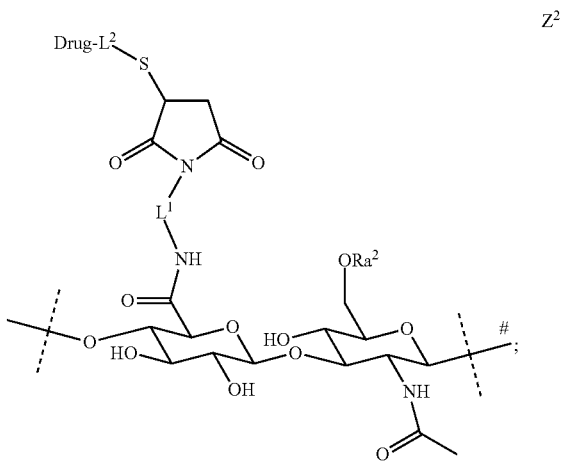
$Z^2$ wherein:

L¹ is a spacer;

L³ is a biodegradable spacer; and 2A, 2B, Drug, $R^{a1}$, $R^{a2}$, $R^{a3}$, $R^{a4}$, $L^2$, $(Z^1)$, $(Z^2)$, $(Z^3)$ and $(Z^4)$ are as defined in claim 1.

8. The hydrogel conjugate of claim 1, wherein the spacer $L^4$ connecting hyaluronic acid polymer 2A to hyaluronic acid polymer 2B has the formula:

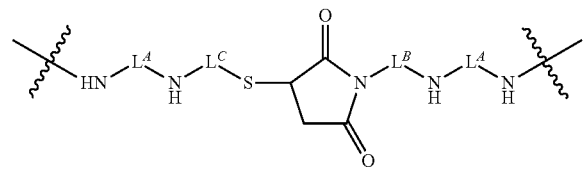

wherein:
  the right-most wavy line is the point of attachment to a unit $(Z^4)$ on hyaluronic acid polymer 2B; and
  the left-most wavy line is the point of attachment to a unit $(Z^3)$ on hyaluronic acid polymer 2A;
and the spacer $L^4$ joining reversible prodrug linker $L^2$ to hyaluronic acid polymer 2A has the formula

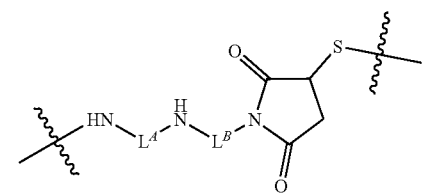

wherein:
  the right-most wavy line is the point of attachment to $L^2$; and
  the left-most wavy line is the point of attachment to a unit $(Z^2)$ on hyaluronic acid polymer 2B;
wherein:
  $L^A$ is a spacer;
  $L^B$ is a spacer; and
  $L^C$ is a biodegradable spacer.

9. The hydrogel conjugate of claim 8, wherein $L^A$ is substituted and/or interrupted $C_{1-10}$ alkylene.

10. The hydrogel conjugate of claim 8, wherein $L^A$ is linear $C_{2-4}$ alkylene.

11. The hydrogel conjugate of claim 8, wherein $L^B$ is linear —(O)—$C_{1-5}$ alkylene.

12. The hydrogel conjugate of claim 8, wherein $L^C$ is:

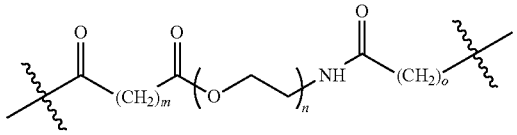

wherein m is from 0 to 10, n is from 1 to 4, and o is from 1 to 4.

13. The hydrogel conjugate of claim 12, wherein $L^C$ is:

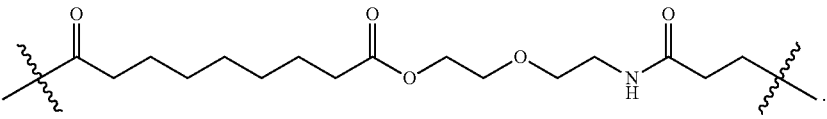 [SMILES: *CCC(=O)NCCOCCOC(=O)CCCCCCCC(*)=O]

14. The hydrogel conjugate of claim 8, wherein the drug is an antibody.

15. The hydrogel conjugate of claim 14, wherein the antibody is a VEGF antagonist.

16. The hydrogel conjugate of claim 15, wherein the antibody is an anti-VEGF antibody fragment.

17. The hydrogel conjugate of claim 16, wherein the antibody fragment is a Fab antibody fragment.

18. The hydrogel conjugate of claim 17, wherein the Fab antibody fragment is ranibizumab.

19. The hydrogel conjugate of claim 14, wherein the antibody-hydrogel conjugate has an ocular effective half-life increased relative to a reference antibody that is not covalently attached to the hydrogel.

20. The hydrogel conjugate of claim 19, wherein the ocular effective half-life is increased at least about 2-fold relative to the reference antibody.

21. The hydrogel conjugate of claim 20, wherein the ocular effective half-life is increased at least about 2.5-fold relative to the reference antibody.

22. The hydrogel conjugate of claim 21, wherein the ocular effective half-life is increased at least about 3-fold relative to the reference antibody.

23. The hydrogel conjugate of claim 22, wherein the ocular effective half-life is increased at least about 3.5-fold relative to the reference antibody.

24. The hydrogel conjugate of claim 23, wherein the ocular effective half-life is increased at least about 4-fold relative to the reference antibody.

25. The hydrogel conjugate of claim 24, wherein the ocular effective half-life is increased at least about 5-fold relative to the reference antibody.

26. The hydrogel conjugate of claim 25, wherein the ocular effective half-life is increased at least about 6-fold relative to the reference antibody.

27. The hydrogel conjugate of claim 19, wherein the ocular effective half-life is a vitreal effective half-life.

28. The hydrogel conjugate of claim 19, wherein the reference antibody is identical to the antibody used in the hydrogel conjugate.

* * * * *

UNITED STATES PATENT AND TRADEMARK OFFICE
CERTIFICATE OF CORRECTION

PATENT NO. : 11,642,415 B2
APPLICATION NO. : 16/575749
DATED : May 9, 2023
INVENTOR(S) : Sebastian Stark et al.

Page 1 of 1

It is certified that error appears in the above-identified patent and that said Letters Patent is hereby corrected as shown below:

In the Claims

At Column 223, Claim number 2, Line number 66, please replace "the drug" with "the Drug".

At Column 224, Claim number 2, Line number 12, please replace "a drug compound" with "the Drug".

At Column 224, Claim number 2, Line number 29, please replace "N" with "the N atom".

At Column 224, Claim number 2, Line number 30, please replace "SP$^3$" with "sp$^3$".

At Column 224, Claim number 2, Line number 32, please replace "-R$^{10}$, -R$^{11}$" with "-R$^{10}$, -R$^{10a}$, -R$^{11}$".

At Column 224, Claim number 2, Line number 47, please replace "R$^3$/R$^{3a}$" with "-R$^3$/R$^{3a}$-".

At Column 224, Claim number 3, Line number 63, please replace "X$^3$" with "=X$^3$".

At Column 224, Claim number 3, Line number 65, please replace "R$^{3a}$" with "-R$^{3a}$".

At Column 224, Claim number 3, Line number 66, please replace "X" and "R$^7$ being NR$^{10}$-(C=O)-R$^{11}$" with "-X-" and "-R$^7$ being -NR$^{10}$-(C=O)-R$^{11}$" respectively.

At Column 224, Claim number 3, Line number 66, please insert the expression --wherein -R$^{10}$ and -R$^{11}$ are independently of each other C$^{1-10}$ alkyl, and with R$^{7a}$ being hydrogen--.

At Column 227, Claim number 7, between Line numbers 5 and 6, please replace "2A, 2B, Drug, R$^{a1}$, R$^{a2}$, R$^{a3}$, L$^2$, (Z$^1$), (Z$^2$), (Z$^3$) and (Z$^4$)" with "Drug, R$^{a2}$, L$^2$, (Z$^2$) and (Z$^4$)".

Signed and Sealed this
Sixth Day of February, 2024

*Katherine Kelly Vidal*
Katherine Kelly Vidal
*Director of the United States Patent and Trademark Office*

SEQUENCE LISTING

<160> NUMBER OF SEQ ID NOS: 66

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Synthetic Construct"

```
<400> SEQUENCE: 1

Asp Tyr Trp Ile His
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Synthetic Construct"
<220> FEATURE:
<221> NAME/KEY: VARIANT
<222> LOCATION: (2)..(2)
<223> OTHER INFORMATION: /replace="His"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (8)..(8)
<223> OTHER INFORMATION: /replace="Lys"
<220> FEATURE:
<221> NAME/KEY: VARIANT
<222> LOCATION: (9)..(9)
<223> OTHER INFORMATION: /replace="Glu"
<220> FEATURE:
<221> NAME/KEY: VARIANT
<222> LOCATION: (10)..(10)
<223> OTHER INFORMATION: /replace="Tyr" or "Gln" or "Glu"
<220> FEATURE:
<221> NAME/KEY: VARIANT
<222> LOCATION: (12)..(12)
<223> OTHER INFORMATION: /replace="Glu"
<220> FEATURE:
<221> NAME/KEY: VARIANT
<222> LOCATION: (16)..(16)
<223> OTHER INFORMATION: /replace="Glu"
<220> FEATURE:
<221> NAME/KEY: VARIANT
<222> LOCATION: (17)..(17)
<223> OTHER INFORMATION: /replace="Glu"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 2

Gly Ile Thr Pro Ala Gly Gly Tyr Thr Arg Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 3

Phe Val Phe Phe Leu Pro Tyr Ala Met Asp Tyr
1               5                   10

<210> SEQ ID NO 4
<211> LENGTH: 11
<212> TYPE: PRT
<213> ORGANISM: Artificial Sequence
```

```
<220> FEATURE:
<221> NAME/KEY: source
<223> OTHER INFORMATION: /note="Synthetic Construct"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 4

Arg Ala Ser Gln Asp Val Ser Thr Ala Val Ala
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Synthetic Construct"
<220> FEATURE:
<221> NAME/KEY: VARIANT
<222> LOCATION: (1)..(1)
<223> OTHER INFORMATION: /replace="Met"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Synthetic Construct"
<220> FEATURE:
<221> NAME/KEY: VARIANT
<222> LOCATION: (1)..(1)
<223> OTHER INFORMATION: /replace="Asn" or "Thr"
<220> FEATURE:
<221> NAME/KEY: VARIANT
<222> LOCATION: (6)..(6)
<223> OTHER INFORMATION: /replace="Asn" or "Gln" or "Arg"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 6

Gln Gln Gly Tyr Gly Ala Pro Phe Thr
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Synthetic Construct"
```

<400> SEQUENCE: 7

Gly Ile Thr Pro Ala Gly Gly Tyr Thr Arg Tyr Ala Asp Ser Val Lys
1               5                   10                  15

Gly

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 8

Arg Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 10

Gln Gln Gly Tyr Gly Ala Pro Phe Thr
1               5

<210> SEQ ID NO 11
<211> LENGTH: 120
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

```
Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 13
<211> LENGTH: 30
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser
            20                  25                  30

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 14

Trp Val Arg Gln Ala Pro Gly Lys Gly Leu Glu Trp Val Ala
1               5                   10

<210> SEQ ID NO 15
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"
```

```
<400> SEQUENCE: 15

Arg Phe Thr Ile Ser Ala Asp Thr Ser Lys Asn Thr Ala Tyr Leu Gln
1               5                   10                  15

Met Arg Ser Leu Arg Ala Glu Asp Thr Ala Val Tyr Tyr Cys Ala Arg
            20                  25                  30

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 16

Trp Gly Gln Gly Thr Leu Val Thr Val Ser Ser
1               5                   10

<210> SEQ ID NO 17
<211> LENGTH: 23
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 18

Trp Tyr Gln Gln Lys Pro Gly Lys Ala Pro Lys Leu Leu Ile Tyr
1               5                   10                  15

<210> SEQ ID NO 19
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 19

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ala Ala Thr Tyr Tyr Cys
            20                  25                  30

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Synthetic Construct"
```

```
<400> SEQUENCE: 20

Phe Gly Gln Gly Thr Lys Val Glu Ile Lys
1               5                   10

<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 21

Gly Ile Thr Pro Ala Gly Gly Tyr Glu Tyr Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 22

Gly Ile Thr Pro Ala Gly Gly Tyr Glu Tyr Tyr Ala Asp Ser Val Glu
1               5                   10                  15

Gly

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 23

Gln Gln Gly Tyr Gly Asn Pro Phe Thr
1               5

<210> SEQ ID NO 24
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 24

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 25
<211> LENGTH: 23
<212> TYPE: PRT
<213> ORGANISM: Artificial Sequence
<220> FEATURE:
<221> NAME/KEY: source
<223> OTHER INFORMATION: /note="Synthetic Construct"
```

<400> SEQUENCE: 25

Asp Ile Gln Met Thr Gln Ser Pro Glu Ser Leu Ser Ala Ser Val Gly
1               5                   10                  15

Asp Glu Val Thr Ile Thr Cys
            20

<210> SEQ ID NO 26
<211> LENGTH: 23
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 26

Asp Ile Gln Met Thr Gln Ser Pro Ser Ser Leu Ser Ala Ser Val Gly
1               5                   10                  15

Asp Glu Val Thr Ile Thr Cys
            20

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 27

Trp Tyr Gln Gln Lys Pro Gly Glu Ala Pro Lys Leu Leu Ile Tyr
1               5                   10                  15

<210> SEQ ID NO 28
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 28

Gly Val Pro Ser Arg Phe Ser Gly Ser Gly Ser Gly Thr Asp Phe Thr
1               5                   10                  15

Leu Thr Ile Glu Ser Leu Gln Pro Glu Asp Ala Ala Thr Tyr Tyr Cys
            20                  25                  30

<210> SEQ ID NO 29
<211> LENGTH: 30
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 29

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser
            20                  25                  30

<210> SEQ ID NO 30
<211> LENGTH: 14
<212> TYPE: PRT
<213> ORGANISM: Artificial Sequence

```
<220> FEATURE:
<221> NAME/KEY: source
<223> OTHER INFORMATION: /note="Synthetic Construct"

<400> SEQUENCE: 30

Trp Val Arg Gln Glu Pro Gly Glu Gly Leu Glu Trp Val Ala
1               5                   10

<210> SEQ ID NO 31
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 31

Arg Phe Thr Ile Ser Ala Asp Thr Ser Glu Asn Thr Ala Tyr Leu Gln
1               5                   10                  15

Met Asn Glu Leu Arg Ala Glu Asp Thr Ala Val Tyr Tyr Cys Ala Arg
            20                  25                  30

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 32

Trp Gly Gln Gly Glu Leu Val Thr Val Ser Ser
1               5                   10

<210> SEQ ID NO 33
<211> LENGTH: 120
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 33

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser Asp Tyr
            20                  25                  30

Trp Ile His Trp Val Arg Gln Glu Pro Gly Glu Gly Leu Glu Trp Val
        35                  40                  45

Ala Gly Ile Thr Pro Ala Gly Gly Tyr Glu Tyr Tyr Ala Asp Ser Val
    50                  55                  60

Glu Gly Arg Phe Thr Ile Ser Ala Asp Thr Ser Glu Asn Thr Ala Tyr
65                  70                  75                  80

Leu Gln Met Asn Glu Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Glu Leu Val Thr Val Ser Ser
        115                 120

<210> SEQ ID NO 34
<211> LENGTH: 107
<212> TYPE: PRT
```

```
<213> ORGANISM: Artificial Sequence
<220> FEATURE:
<221> NAME/KEY: source
<223> OTHER INFORMATION: /note="Synthetic Construct"

<400> SEQUENCE: 34

Asp Ile Gln Met Thr Gln Ser Pro Glu Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 35

Asp Ile Gln Met Thr Gln Ser Pro Ser Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Glu Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Glu Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 36

Asp Ile Gln Met Thr Gln Ser Pro Glu Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Glu Ala Pro Lys Leu Leu Ile
        35                  40                  45
```

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                    85                  90                  95

Thr Phe Gly Gln Gly Thr Lys Val Glu Ile Lys
                100                 105

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 37

Asp Ile Gln Met Thr Gln Ser Pro Ser Ser Leu Ser Ala Ser Val Gly
  1               5                  10                  15

Asp Glu Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                    85                  90                  95

Thr Phe Gly Gln Gly Thr Lys Val Glu Ile Lys
                100                 105

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 38

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Gly Asn Pro Phe
                    85                  90                  95

Thr Phe Gly Gln Gly Thr Lys Val Glu Ile Lys
                100                 105

<210> SEQ ID NO 39

```
<211> LENGTH: 14
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 39

Trp Val Arg Gln Glu Pro Gly Lys Gly Leu Glu Trp Val Ala
1               5                   10

<210> SEQ ID NO 40
<211> LENGTH: 120
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Glu Pro Gly Lys Gly Leu Glu Trp Val
        35                  40                  45

Ala Gly Ile Thr Pro Ala Gly Gly Tyr Glu Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 41
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105
```

```
<210> SEQ ID NO 42
<211> LENGTH: 120
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 43
<211> LENGTH: 227
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His
225

<210> SEQ ID NO 44
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 44

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ser Ala Thr Tyr Tyr Cys
                20                  25                  30

<210> SEQ ID NO 45
<211> LENGTH: 23
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 45

Asp Ile Gln Met Thr Gln Ser Pro Ser Ser Leu Ser Ala Ser Val Gly
1               5                   10                  15

Asp Arg Val Thr Ile Asp Cys
                20

<210> SEQ ID NO 46
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 46

Asp Ile Gln Met Thr Gln Ser Pro Ser Ser Leu Ser Ala Ser Val Gly
1               5                   10                  15

Asp Arg Val Thr Ile Asp Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Tyr Gly Ala Pro Phe
                85                  90                  95

Thr Phe Gly Gln Gly Thr Lys Val Glu Ile Lys
            100                 105

<210> SEQ ID NO 47
<211> LENGTH: 232
<212> TYPE: PRT
<213> ORGANISM: Homo sapiens

<400> SEQUENCE: 47

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 48
<211> LENGTH: 228
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225

<210> SEQ ID NO 49
<211> LENGTH: 228
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Leu
225

<210> SEQ ID NO 50
<211> LENGTH: 214
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 120
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 51

Glu Glu Gln Leu Val Glu Gly Gly Gly Leu Val Gln Pro Gly Glu
1               5                   10                  15

Ser Leu Arg Leu Ser Cys Ala Ala Ser Gly Phe Glu Ile Ser Asp Tyr
            20                  25                  30
```

Trp Ile His Trp Val Arg Gln Glu Pro Gly Glu Gly Leu Glu Trp Val
            35                  40                  45

Ala Gly Ile Thr Pro Ala Gly Gly Tyr Glu Tyr Tyr Ala Asp Ser Val
    50                  55                  60

Glu Gly Arg Phe Thr Ile Ser Ala Asp Thr Ser Glu Asn Thr Ala Tyr
65                  70                  75                  80

Leu Gln Met Asn Glu Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Glu Leu Val Thr Val Ser Ser
            115                 120

<210> SEQ ID NO 52
<211> LENGTH: 30
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 52

Glu Glu Gln Leu Val Glu Gly Gly Gly Leu Val Gln Pro Gly Glu
1               5                   10                  15

Ser Leu Arg Leu Ser Cys Ala Ala Ser Gly Phe Glu Ile Ser
            20                  25                  30

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 53

Gly Ile Thr Pro Ala Gly Gly Tyr Thr Tyr Tyr Ala Asp Ser Val Lys
1               5                   10                  15

Gly

<210> SEQ ID NO 54
<211> LENGTH: 32
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 54

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 55

Phe Gly Gln Gly Thr Lys Val Glu Val Lys
1               5                   10

<210> SEQ ID NO 56
<211> LENGTH: 34
<212> TYPE: DNA
<213> ORGANISM: Artificial Sequence
<220> FEATURE:
<221> NAME/KEY: source
<223> OTHER INFORMATION: /note="Synthetic Construct"

<400> SEQUENCE: 56
catcagatgg cgggaagatg aagacagatg gtgc                          34

<210> SEQ ID NO 57
<211> LENGTH: 23
<212> TYPE: DNA
<213> ORGANISM: Artificial Sequence
<220> FEATURE:
<221> NAME/KEY: source
<223> OTHER INFORMATION: /note="Synthetic Construct"

<400> SEQUENCE: 57
gccatccaga tgacccagtc tcc                                      23

<210> SEQ ID NO 58
<211> LENGTH: 19
<212> TYPE: DNA
<213> ORGANISM: Artificial Sequence
<220> FEATURE:
<221> NAME/KEY: source
<223> OTHER INFORMATION: /note="Synthetic Construct"

<400> SEQUENCE: 58
ggctgcacca tctgtcttc                                           19

<210> SEQ ID NO 59
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Gly Asn Pro Phe
                85                  90                  95

Thr Phe Gly Gln Gly Thr Lys Val Glu Ile Lys
            100                 105

<210> SEQ ID NO 60

```
<211> LENGTH: 107
<212> TYPE: PRT
<213> ORGANISM: Artificial Sequence
<220> FEATURE:
<221> NAME/KEY: source
<223> OTHER INFORMATION: /note="Synthetic Construct"

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Gly Ala Pro Phe
                85                  90                  95

Thr Phe Gly Gln Gly Thr Lys Val Glu Ile Lys
            100                 105

<210> SEQ ID NO 61
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Tyr Tyr Met His
1               5

<210> SEQ ID NO 62
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Trp Ile Asn Pro Asn Ser Gly Gly Thr Asn Tyr Ala Gln Lys Phe Gln
1               5                   10                  15

Gly

<210> SEQ ID NO 63
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Pro Asn Pro Tyr Tyr Tyr Asp Ser Ser Gly Tyr Tyr Tyr Pro Gly
1               5                   10                  15

Ala Phe Asp Ile
            20
```

```
<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Gly Asn Asn Ile Gly Ser Lys Ser Val His
1               5                   10

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Asp Asp Ser Asp Arg Pro Ser
1               5

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gln Val Trp Asp Ser Ser Ser Asp His Trp Val
1               5                   10
```